US012332243B2

(12) United States Patent
Shih et al.

(10) Patent No.: US 12,332,243 B2
(45) Date of Patent: Jun. 17, 2025

(54) METHODS OF DETECTING ALLOANTIBODIES USING HLA AND NON-HLA ANTIGENS

(71) Applicant: One Lambda, Inc., West Hills, CA (US)

(72) Inventors: Neng Jen Remi Shih, Winnetka, CA (US); Jar-How Lee, Los Angeles, CA (US); Rui Pei, West Hills, CA (US)

(73) Assignee: One Lambda, Inc., West Hills, CA (US)

( * ) Notice: Subject to any disclaimer, the term of this patent is extended or adjusted under 35 U.S.C. 154(b) by 719 days.

(21) Appl. No.: 16/796,032

(22) Filed: Feb. 20, 2020

(65) Prior Publication Data

US 2020/0363411 A1 Nov. 19, 2020

Related U.S. Application Data

(63) Continuation of application No. 15/273,027, filed on Sep. 22, 2016, now abandoned.

(60) Provisional application No. 62/222,614, filed on Sep. 23, 2015.

(51) Int. Cl.
*G01N 33/564* (2006.01)
*C07K 14/47* (2006.01)
*C07K 14/72* (2006.01)
*C07K 14/74* (2006.01)
*G01N 33/543* (2006.01)
(Continued)

(52) U.S. Cl.
CPC .......... *G01N 33/564* (2013.01); *C07K 14/47* (2013.01); *C07K 14/4703* (2013.01); *C07K 14/70539* (2013.01); *C07K 14/723* (2013.01); *G01N 33/54313* (2013.01); *G01N 33/54353* (2013.01); *G01N 33/58* (2013.01); *G01N 33/582* (2013.01); *G01N 33/6854* (2013.01); *G01N 2333/70503* (2013.01); *G01N 2333/70539* (2013.01); *G01N 2800/245* (2013.01)

(58) Field of Classification Search
CPC .......... G01N 33/564; G01N 33/54313; G01N 33/54353; G01N 33/58; G01N 33/582; G01N 33/6854; G01N 2333/70539; G01N 2800/245
See application file for complete search history.

(56) References Cited

U.S. PATENT DOCUMENTS 5,223,397 A 6/1993 Pouletty
6,150,122 A * 11/2000 Lee .................. G01N 33/54313
435/7.92
6,514,714 B1 2/2003 Lee et al.
(Continued)

FOREIGN PATENT DOCUMENTS

WO WO-9014363 A1 11/1990
WO WO-0037940 A1 6/2000

OTHER PUBLICATIONS

Li et al. (Differential Immunogenicity and Clinical Relevance of Kidney Compartment Specific Antigens after Renal Transplantation. Journal of Proteosome Research 9: 6715-6721 (2010).*
(Continued)

*Primary Examiner* — Gailene Gabel
(74) *Attorney, Agent, or Firm* — BakerHostetler

(57) ABSTRACT

Described herein are materials and methods for detecting alloantibodies using both HLA and non-HLA antigens in a single assay.

14 Claims, 6 Drawing Sheets

Specification includes a Sequence Listing.

(51) Int. Cl.
G01N 33/58 (2006.01)
G01N 33/68 (2006.01)

(56) References Cited

U.S. PATENT DOCUMENTS

| | | | |
|---|---|---|---|
| 7,132,245 B2 | 11/2006 | Rose et al. | |
| 8,039,225 B2 | 10/2011 | Wilkes et al. | |
| 8,425,877 B2 | 4/2013 | Schulze-Forster et al. | |
| 8,501,427 B2 | 8/2013 | Morgan et al. | |
| 8,592,164 B2 | 11/2013 | Schulze-Forster et al. | |
| 2007/0037195 A1 | 2/2007 | Ho | |
| 2009/0142762 A1* | 6/2009 | Lee | G01N 33/56977 |
| | | | 435/6.11 |
| 2010/0143374 A1 | 6/2010 | Hutton et al. | |
| 2011/0039281 A1 | 2/2011 | Nunez Roldan et al. | |
| 2011/0177534 A1 | 7/2011 | Salant et al. | |
| 2012/0077689 A1 | 3/2012 | Sarwal et al. | |
| 2013/0004978 A1 | 1/2013 | Hebert et al. | |

OTHER PUBLICATIONS

Qin et al. Antibodies Against Nucleolin in Recipients of Organ Transplants. Transplantation 92 (7): 829-836 (Oct. 2011).*
Karpinski et al. Flow Cytometric Crossmatching in Primary Renal Transplant Recipients with a Negative Anti-Human Globulin Enhanced Cytotoxicity Crossmatch. J Am Soc Nephrol 12: 2807-2814 (2001).*
Prigent et al. From Donor to Recipient: Current Questions Relating to Humoral Alloimmunization. Antibodies 3: 130-152 (2014).*
Dinavahi et al. Antibodies Reactive to Non-HLA Antigens in Transplant Glomerulopathy. J Am Soc Nephrol 22 (6): 1168-1178 (Jun. 2011).*
Valenzuela et al. Antibodies in Transplantation: The Effects of HLA and Non-HLA Antibody Binding and Mechanisms of Injury, Methods Mol Biol. 1034: 1-26 (2013).*
Banasik et al. Non-HLA Antibodies: Angiotensin II Type 1 Receptor (Anti-ETAR) Are Associated with Renal Allograft Injury and Graft Loss. Transplantation Proceedings 48: 2818-2821 (2011).*
Acevedo et al., Antibodies against heterogeneous nuclear ribonucleoprotein Kin patients with cardiac allograft vasculopathy, J. Heart Lung Transplant., 30(9):1051-9 (2011 ).
Alvarez-Marquez et al., Donor-specific antibodies against HLA, MICA, and GSTT1 in patients with allograft rejection and C4d deposition in renal biopsies, Transplantation, 87(1):94-9 (2009).
Angaswamy et al., Immune responses to collagen-IV and fibronectin in renal transplant recipients with transplant glomerulopathy, Am. J. Transplant., 14(3):685-93 (2014).
Ationu, Identification of endothelial antigens relevant to transplant coronary artery disease from a human endothelial cell eDNA expression library, Int. J. Mol. Med., 1 (6):1007-10 (1998).
Banasik et al., The impact of non-HLA antibodies directed against endothelin-1 type A receptors (ETAR) on early renal transplant outcomes, Transpl. Immunol., 30(1):24-9 (2014).
Bates et al., High diversity of non-human leukocyte antigens in transplant-associated coronary artery disease, Transplantation, 75(8):1347-50 (2003).
Brucato et al., Pregnancy outcomes in patients with autoimmune diseases and anti-Ro/SSA antibodies, Clin. Rev. Allergy Immunol., 40(1):27-41 (2011).
Cardinal et al., Antiperlecan antibodies are novel accelerators of immune-mediated vascular injury, Am. J. Transplant., 13(4):861-74 (2013).
Colvin, Antibody-mediated renal allograft rejection: diagnosis and pathogenesis, J. Am. Soc. Nephrol., 18(4):1046-56 (2007).
Dinavahi et al., Antibodies reactive to non-HLA antigens in transplant glomerulopathy, J. Am. Soc. Nephrol., 22(6):1168-78 (2011).
Dragon-Durey et al., Autoantibodies against complement components and functional consequences, Mol. Immunol., 56(3):213-21 (2013).
Fortin et al., Complement factor H deficiency in acute allograft glomerulopathy and post-transplant hemolytic uremic syndrome, Am. J. Transplant., 4(2):270-3 (2004).
Frengen et al., Demonstration and minimization of serum interference in flow cytometric two-site immunoassays, Clin. Chem., 40(3):420-5 (1994).
Joosten et al., Antibody response against the glomerular basement membrane protein agrin in patients with transplant qlomerulopathy, Am. J. Transplant, 5(2):383-93 (2005).
Jurecevic et al., Antivimentin antibodies are an independent predictor of transplant-associated coronary artery disease after cardiac transplantation, Transplantation, 71 (7):886-92 (2001).
Karasawa et al., Peroxiredoxin 2 is a novel autoantigen for anti-endothelial cell antibodies in systemic vasculitis, Clin. Exp. Immunol., 161 (3):459-70 (2010).
Khandelwal et al., Outcomes of renal transplant in patients with anti-complement factor H antibody-associated hemolytic uremic syndrome, Pediatr. Transplant., 18(5):E134-9 (2014).
Kohler, G. et al., "Continuous cultures of fused cells secreting antibody of predefined specificity", Nature, vol. 256, Aug. 7, 1975, 495-497.
Lawson et al., Anti-intercellular adhesion molecule-1 antibodies in sera of heart transplant recipients: a role in endothelial cell activation, Transplantation, 80(2):264-71 (2005).
Li et al., Differential immunogenicity and clinical relevance of kidney compartment specific antigens after renal transplantation, J. Proteome Res., 9(12):6715-21 (2010).
Marsh et al., "Nomenclature for factors of the HLA system", 2000, Hum. Immunol., vol. 62, No. 4, 2001, pp. 419-468.
Porcheray et al., B-cell immunity in the context of T-cell tolerance after combined kidney and bone marrow transplantation in humans, Am. J. Transplant., 9(9):2126-35 (2009).
Qin et al., Antibodies against nucleolin in recipients of organ transplants, Transplantation, 92(7):829-35 (2011).
Ringers et al., Pretransplantation GAD-autoantibody status to guide prophylactic antibody induction therapy in simultaneous pancreas and kidney transplantation, Transplantation, 96(8):745-52 (2013).
Robinson et al., Autoimmune disease risk variant of IFIH1 is associated with increased sensitivity to IFN-a and seroloQic autoimmunity in lupus patients, J. Immunol., 187(3):1298-303 (2011).
Sfar et al., The PTPN22 C1858T (R620W) functional polymorphism in kidney transplantation, Transplant. Proc., 41 (2):657-9 (2009).
Shirai et al., A novel autoantibody against fibronectin leucine-rich transmembrane protein 2 expressed on the endothelial cell surface identified by retroviral vector system in systemic lupus erythematosus, Arthritis Res. Ther., 14(4):R157 (2012).
Shroyer et al., A rapid flow cytometry assay for HLA antibody detection using a pooled cell panel covering 14 serological crossreacting groups, Transplantation, 59(4):626-30 (1995).
Sigdel et al., Moving beyond HLA: a review of nHLA antibodies in organ transplantation, Hum. Immunol., 74(11):1486-90 (2013).
Sigdel et al., Non-HLA antibodies to immunogenic epitopes predict the evolution of chronic renal allograft injury, J. Am. Soc. Nephrol., 23(4):750-63 (2012).
Sonkar et al., Evaluation of serum tumor necrosis factor alpha and its correlation with histology in chronic kidney disease, stable renal transplant and rejection cases, Saudi J. Kidney Dis. Transpl., 20(6):1000-4 (2009).
Steubl et al., C-terminal agrin fragment—a new fast biomarker for kidney function in renal transplant recipients, Am. J. Neprhol., 38(6):501-8 (2013).
Sumitran-Holgersson et al., A novel mechanism of liver allograft rejection facilitated by antibodies to liver sinusoidal endothelial cells, Hepatology, 40(5):1211-21 (2004).
Sumitran-Holgersson, Relevance of MICA and other non-HLA antibodies in clinical transplantation, Curr. Opin. Immunol., 20(5):607-13 (2008).
Sumitran-Karuppan et al., The use of magnetic beads coated with soluble HLA class I or class II proteins in antibody screening and for specificity determinations of donor-reactive antibodies, Transplantation, 61 (10):1539-45 (1996).

(56) References Cited

OTHER PUBLICATIONS

Tinckam et al., Mechanisms and role of HLA and non-HLA alloantibodies, Clin. J. Am. Soc. Neprhol., 1 (3):404-14 (2006).

Urlaub, G., and Chasin, L.A. "isolation of Chinese Hamster cell mutants deficient in dihydrofotlate reductase activity," Proc. Natl. Acad. Sci. USA 77:4216-4220, National Academy of Sciences (1980).

Wadia et al., Antibodies specifically target AML antigen NuSAP1 after allogeneic bone marrow transplantation, Blood, 115(10):2077-87 (2010).

Wilson et al., A new microsphere-based immunofluorescence assay for antibodies to membraneassociated antigens, J. Immunol. Methods, 107(2):231-7 (1988).

Zaer et al., Antibody screening by enzyme-linked immunosorbent assay using pooled soluble HLA in renal transplant candidates, Transplantation, 63(1):48-51 (1997).

Zhang et al., Non-MHC antigenic targets of the humoral immune response in transplantation, Curr.Opin. Immunol., 22(5):682-8 (2010).

\* cited by examiner

SEQUENCE LISTING

```
<160> NUMBER OF SEQ ID NOS: 74

<210> SEQ ID NO 1
<211> LENGTH: 2067
<212> TYPE: PRT
<213> ORGANISM: Homo sapiens
<300> PUBLICATION INFORMATION:
<308> DATABASE ACCESSION NUMBER: UniProt / O00468
<309> DATABASE ENTRY DATE: 2015-07-22
<313> RELEVANT RESIDUES IN SEQ ID NO: (1)..(2067)

<400> SEQUENCE: 1

Met Ala Gly Arg Ser His Pro Gly Pro Leu Arg Pro Leu Leu Pro Leu
1               5                   10                  15

Leu Val Val Ala Ala Cys Val Leu Pro Gly Ala Gly Gly Thr Cys Pro
                20                  25                  30

Glu Arg Ala Leu Glu Arg Glu Glu Ala Asn Val Val Leu Thr
            35                  40                  45

Gly Thr Val Glu Glu Ile Leu Asn Val Asp Pro Val Gln His Thr Tyr
        50                  55                  60

Ser Cys Lys Val Arg Val Trp Arg Tyr Leu Lys Gly Lys Asp Leu Val
65                  70                  75                  80

Ala Arg Glu Ser Leu Leu Asp Gly Gly Asn Lys Val Val Ile Ser Gly
                85                  90                  95

Phe Gly Asp Pro Leu Ile Cys Asp Asn Gln Val Ser Thr Gly Asp Thr
                100                 105                 110

Arg Ile Phe Phe Val Asn Pro Ala Pro Pro Tyr Leu Trp Pro Ala His
            115                 120                 125

Lys Asn Glu Leu Met Leu Asn Ser Ser Leu Met Arg Ile Thr Leu Arg
        130                 135                 140

Asn Leu Glu Glu Val Glu Phe Cys Val Glu Asp Lys Pro Gly Thr His
145                 150                 155                 160

Phe Thr Pro Val Pro Pro Thr Pro Pro Asp Ala Cys Arg Gly Met Leu
                165                 170                 175

Cys Gly Phe Gly Ala Val Cys Glu Pro Asn Ala Glu Gly Pro Gly Arg
                180                 185                 190

Ala Ser Cys Val Cys Lys Lys Ser Pro Cys Pro Ser Val Val Ala Pro
            195                 200                 205

Val Cys Gly Ser Asp Ala Ser Thr Tyr Ser Asn Glu Cys Glu Leu Gln
        210                 215                 220

Arg Ala Gln Cys Ser Gln Arg Arg Ile Arg Leu Leu Ser Arg Gly
225                 230                 235                 240

Pro Cys Gly Ser Arg Asp Pro Cys Ser Asn Val Thr Cys Ser Phe Gly
                245                 250                 255

Ser Thr Cys Ala Arg Ser Ala Asp Gly Leu Thr Ala Ser Cys Leu Cys
                260                 265                 270

Pro Ala Thr Cys Arg Gly Ala Pro Glu Gly Thr Val Cys Gly Ser Asp
            275                 280                 285
```

-continued

Gly Ala Asp Tyr Pro Gly Glu Cys Gln Leu Leu Arg Arg Ala Cys Ala
290                 295                 300

Arg Gln Glu Asn Val Phe Lys Lys Phe Asp Gly Pro Cys Asp Pro Cys
305                 310                 315                 320

Gln Gly Ala Leu Pro Asp Pro Ser Arg Ser Cys Arg Val Asn Pro Arg
            325                 330                 335

Thr Arg Arg Pro Glu Met Leu Leu Arg Pro Glu Ser Cys Pro Ala Arg
            340                 345                 350

Gln Ala Pro Val Cys Gly Asp Asp Gly Val Thr Tyr Glu Asn Asp Cys
            355                 360                 365

Val Met Gly Arg Ser Gly Ala Ala Arg Gly Leu Leu Leu Gln Lys Val
370                 375                 380

Arg Ser Gly Gln Cys Gln Gly Arg Asp Gln Cys Pro Glu Pro Cys Arg
385                 390                 395                 400

Phe Asn Ala Val Cys Leu Ser Arg Arg Gly Arg Pro Arg Cys Ser Cys
            405                 410                 415

Asp Arg Val Thr Cys Asp Gly Ala Tyr Arg Pro Val Cys Ala Gln Asp
            420                 425                 430

Gly Arg Thr Tyr Asp Ser Asp Cys Trp Arg Gln Gln Ala Glu Cys Arg
            435                 440                 445

Gln Gln Arg Ala Ile Pro Ser Lys His Gln Gly Pro Cys Asp Gln Ala
450                 455                 460

Pro Ser Pro Cys Leu Gly Val Gln Cys Ala Phe Gly Ala Thr Cys Ala
465                 470                 475                 480

Val Lys Asn Gly Gln Ala Ala Cys Glu Cys Leu Gln Ala Cys Ser Ser
            485                 490                 495

Leu Tyr Asp Pro Val Cys Gly Ser Asp Gly Val Thr Tyr Gly Ser Ala
            500                 505                 510

Cys Glu Leu Glu Ala Thr Ala Cys Thr Leu Gly Arg Glu Ile Gln Val
            515                 520                 525

Ala Arg Lys Gly Pro Cys Asp Arg Cys Gly Gln Cys Arg Phe Gly Ala
530                 535                 540

Leu Cys Glu Ala Glu Thr Gly Arg Cys Val Cys Pro Ser Glu Cys Val
545                 550                 555                 560

Ala Leu Ala Gln Pro Val Cys Gly Ser Asp Gly His Thr Tyr Pro Ser
            565                 570                 575

Glu Cys Met Leu His Val His Ala Cys Thr His Gln Ile Ser Leu His
            580                 585                 590

Val Ala Ser Ala Gly Pro Cys Glu Thr Cys Gly Asp Ala Val Cys Ala
595                 600                 605

Phe Gly Ala Val Cys Ser Ala Gly Gln Cys Val Cys Pro Arg Cys Glu
610                 615                 620

His Pro Pro Gly Pro Val Cys Gly Ser Asp Gly Val Thr Tyr Gly
625                 630                 635                 640

Ser Ala Cys Glu Leu Arg Glu Ala Ala Cys Leu Gln Gln Thr Gln Ile
            645                 650                 655

Glu Glu Ala Arg Ala Gly Pro Cys Glu Gln Ala Glu Cys Gly Ser Gly
            660                 665                 670

Gly Ser Gly Ser Gly Glu Asp Gly Asp Cys Glu Gln Leu Cys Arg
            675                 680                 685

Gln Arg Gly Gly Ile Trp Asp Glu Asp Ser Glu Asp Gly Pro Cys Val
690                 695                 700

Cys Asp Phe Ser Cys Gln Ser Val Pro Gly Ser Pro Val Cys Gly Ser

```
                705                 710                 715                 720
Asp Gly Val Thr Tyr Ser Thr Glu Cys Glu Leu Lys Lys Ala Arg Cys
                    725                 730                 735
Glu Ser Gln Arg Gly Leu Tyr Val Ala Ala Gln Gly Ala Cys Arg Gly
                    740                 745                 750
Pro Thr Phe Ala Pro Leu Pro Pro Val Ala Pro Leu His Cys Ala Gln
                    755                 760                 765
Thr Pro Tyr Gly Cys Cys Gln Asp Asn Ile Thr Ala Ala Arg Gly Val
        770                 775                 780
Gly Leu Ala Gly Cys Pro Ser Ala Cys Gln Cys Asn Pro His Gly Ser
785                 790                 795                 800
Tyr Gly Gly Thr Cys Asp Pro Ala Thr Gly Gln Cys Ser Cys Arg Pro
                805                 810                 815
Gly Val Gly Gly Leu Arg Cys Asp Arg Cys Glu Pro Gly Phe Trp Asn
            820                 825                 830
Phe Arg Gly Ile Val Thr Asp Gly Arg Ser Gly Cys Thr Pro Cys Ser
        835                 840                 845
Cys Asp Pro Gln Gly Ala Val Arg Asp Asp Cys Glu Gln Met Thr Gly
    850                 855                 860
Leu Cys Ser Cys Lys Pro Gly Val Ala Gly Pro Lys Cys Gly Gln Cys
865                 870                 875                 880
Pro Asp Gly Arg Ala Leu Gly Pro Ala Gly Cys Glu Ala Asp Ala Ser
                885                 890                 895
Ala Pro Ala Thr Cys Ala Glu Met Arg Cys Glu Phe Gly Ala Arg Cys
                900                 905                 910
Val Glu Glu Ser Gly Ser Ala His Cys Val Cys Pro Met Leu Thr Cys
            915                 920                 925
Pro Glu Ala Asn Ala Thr Lys Val Cys Gly Ser Asp Gly Val Thr Tyr
        930                 935                 940
Gly Asn Glu Cys Gln Leu Lys Thr Ile Ala Cys Arg Gln Gly Leu Gln
945                 950                 955                 960
Ile Ser Ile Gln Ser Leu Gly Pro Cys Gln Glu Ala Val Ala Pro Ser
                965                 970                 975
Thr His Pro Thr Ser Ala Ser Val Thr Val Thr Pro Gly Leu Leu
                980                 985                 990
Leu Ser Gln Ala Leu Pro Ala Pro  Pro Gly Ala Leu Pro  Leu Ala Pro
            995                 1000                1005
Ser Ser  Thr Ala His Ser Gln  Thr Thr Pro Pro  Ser Ser Arg
    1010                1015                1020
Pro Arg  Thr Thr Ala Ser Val  Pro Arg Thr Thr Val  Trp Pro Val
    1025                1030                1035
Leu Thr  Val Pro Pro Thr Ala  Pro Ser Pro Ala Pro  Ser Leu Val
    1040                1045                1050
Ala Ser  Ala Phe Gly Glu Ser  Gly Ser Thr Asp Gly  Ser Ser Asp
    1055                1060                1065
Glu Glu  Leu Ser Gly Asp Gln  Glu Ala Ser Gly  Gly Ser Gly
    1070                1075                1080
Gly Leu  Glu Pro Leu Glu Gly  Ser Ser Val Ala Thr  Pro Gly Pro
    1085                1090                1095
Pro Val  Glu Arg Ala Ser Cys  Tyr Asn Ser Ala Leu  Gly Cys Cys
    1100                1105                1110
Ser Asp  Gly Lys Thr Pro Ser  Leu Asp Ala Glu Gly  Ser Asn Cys
    1115                1120                1125
```

```
Pro Ala Thr Lys Val Phe Gln Gly Val Leu Glu Leu Glu Gly Val
1130                1135                1140

Glu Gly Gln Glu Leu Phe Tyr Thr Pro Glu Met Ala Asp Pro Lys
1145                1150                1155

Ser Glu Leu Phe Gly Glu Thr Ala Arg Ser Ile Glu Ser Thr Leu
1160                1165                1170

Asp Asp Leu Phe Arg Asn Ser Asp Val Lys Lys Asp Phe Arg Ser
1175                1180                1185

Val Arg Leu Arg Asp Leu Gly Pro Gly Lys Ser Val Arg Ala Ile
1190                1195                1200

Val Asp Val His Phe Asp Pro Thr Thr Ala Phe Arg Ala Pro Asp
1205                1210                1215

Val Ala Arg Ala Leu Leu Arg Gln Ile Gln Val Ser Arg Arg Arg
1220                1225                1230

Ser Leu Gly Val Arg Arg Pro Leu Gln Glu His Val Arg Phe Met
1235                1240                1245

Asp Phe Asp Trp Phe Pro Ala Phe Ile Thr Gly Ala Thr Ser Gly
1250                1255                1260

Ala Ile Ala Ala Gly Ala Thr Ala Arg Ala Thr Thr Ala Ser Arg
1265                1270                1275

Leu Pro Ser Ser Ala Val Thr Pro Arg Ala Pro His Pro Ser His
1280                1285                1290

Thr Ser Gln Pro Val Ala Lys Thr Thr Ala Ala Pro Thr Thr Arg
1295                1300                1305

Arg Pro Pro Thr Thr Ala Pro Ser Arg Val Pro Gly Arg Arg Pro
1310                1315                1320

Pro Ala Pro Gln Gln Pro Pro Lys Pro Cys Asp Ser Gln Pro Cys
1325                1330                1335

Phe His Gly Gly Thr Cys Gln Asp Trp Ala Leu Gly Gly Gly Phe
1340                1345                1350

Thr Cys Ser Cys Pro Ala Gly Arg Gly Gly Ala Val Cys Glu Lys
1355                1360                1365

Val Leu Gly Ala Pro Val Pro Ala Phe Glu Gly Arg Ser Phe Leu
1370                1375                1380

Ala Phe Pro Thr Leu Arg Ala Tyr His Thr Leu Arg Leu Ala Leu
1385                1390                1395

Glu Phe Arg Ala Leu Glu Pro Gln Gly Leu Leu Leu Tyr Asn Gly
1400                1405                1410

Asn Ala Arg Gly Lys Asp Phe Leu Ala Leu Ala Leu Leu Asp Gly
1415                1420                1425

Arg Val Gln Leu Arg Phe Asp Thr Gly Ser Gly Pro Ala Val Leu
1430                1435                1440

Thr Ser Ala Val Pro Val Glu Pro Gly Gln Trp His Arg Leu Glu
1445                1450                1455

Leu Ser Arg His Trp Arg Arg Gly Thr Leu Ser Val Asp Gly Glu
1460                1465                1470

Thr Pro Val Leu Gly Glu Ser Pro Ser Gly Thr Asp Gly Leu Asn
1475                1480                1485

Leu Asp Thr Asp Leu Phe Val Gly Gly Val Pro Glu Asp Gln Ala
1490                1495                1500

Ala Val Ala Leu Glu Arg Thr Phe Val Gly Ala Gly Leu Arg Gly
1505                1510                1515
```

```
Cys Ile Arg Leu Leu Asp Val Asn Asn Gln Arg Leu Glu Leu Gly
1520                    1525                1530

Ile Gly Pro Gly Ala Ala Thr Arg Gly Ser Gly Val Gly Glu Cys
1535                    1540                1545

Gly Asp His Pro Cys Leu Pro Asn Pro Cys His Gly Gly Ala Pro
1550                    1555                1560

Cys Gln Asn Leu Glu Ala Gly Arg Phe His Cys Gln Cys Pro Pro
1565                    1570                1575

Gly Arg Val Gly Pro Thr Cys Ala Asp Glu Lys Ser Pro Cys Gln
1580                    1585                1590

Pro Asn Pro Cys His Gly Ala Ala Pro Cys Arg Val Leu Pro Glu
1595                    1600                1605

Gly Gly Ala Gln Cys Glu Cys Pro Leu Gly Arg Glu Gly Thr Phe
1610                    1615                1620

Cys Gln Thr Ala Ser Gly Gln Asp Gly Ser Gly Pro Phe Leu Ala
1625                    1630                1635

Asp Phe Asn Gly Phe Ser His Leu Glu Leu Arg Gly Leu His Thr
1640                    1645                1650

Phe Ala Arg Asp Leu Gly Glu Lys Met Ala Leu Glu Val Val Phe
1655                    1660                1665

Leu Ala Arg Gly Pro Ser Gly Leu Leu Leu Tyr Asn Gly Gln Lys
1670                    1675                1680

Thr Asp Gly Lys Gly Asp Phe Val Ser Leu Ala Leu Arg Asp Arg
1685                    1690                1695

Arg Leu Glu Phe Arg Tyr Asp Leu Gly Lys Gly Ala Ala Val Ile
1700                    1705                1710

Arg Ser Arg Glu Pro Val Thr Leu Gly Ala Trp Thr Arg Val Ser
1715                    1720                1725

Leu Glu Arg Asn Gly Arg Lys Gly Ala Leu Arg Val Gly Asp Gly
1730                    1735                1740

Pro Arg Val Leu Gly Glu Ser Pro Lys Ser Arg Lys Val Pro His
1745                    1750                1755

Thr Val Leu Asn Leu Lys Glu Pro Leu Tyr Val Gly Gly Ala Pro
1760                    1765                1770

Asp Phe Ser Lys Leu Ala Arg Ala Ala Ala Val Ser Ser Gly Phe
1775                    1780                1785

Asp Gly Ala Ile Gln Leu Val Ser Leu Gly Gly Arg Gln Leu Leu
1790                    1795                1800

Thr Pro Glu His Val Leu Arg Gln Val Asp Val Thr Ser Phe Ala
1805                    1810                1815

Gly His Pro Cys Thr Arg Ala Ser Gly His Pro Cys Leu Asn Gly
1820                    1825                1830

Ala Ser Cys Val Pro Arg Glu Ala Ala Tyr Val Cys Leu Cys Pro
1835                    1840                1845

Gly Gly Phe Ser Gly Pro His Cys Glu Lys Gly Leu Val Glu Lys
1850                    1855                1860

Ser Ala Gly Asp Val Asp Thr Leu Ala Phe Asp Gly Arg Thr Phe
1865                    1870                1875

Val Glu Tyr Leu Asn Ala Val Thr Glu Ser Glu Leu Ala Asn Glu
1880                    1885                1890

Ile Pro Val Pro Glu Thr Leu Asp Ser Gly Ala Leu His Glu Lys
1895                    1900                1905

Ala Leu Gln Ser Asn His Phe Glu Leu Ser Leu Arg Thr Glu Ala
```

```
                      1910                1915                1920

Thr Gln Gly Leu Val Leu Trp Ser Gly Lys Ala Thr Glu Arg Ala
    1925                1930                1935

Asp Tyr Val Ala Leu Ala Ile Val Asp Gly His Leu Gln Leu Ser
    1940                1945                1950

Tyr Asn Leu Gly Ser Gln Pro Val Val Leu Arg Ser Thr Val Pro
    1955                1960                1965

Val Asn Thr Asn Arg Trp Leu Arg Val Val Ala His Arg Glu Gln
    1970                1975                1980

Arg Glu Gly Ser Leu Gln Val Gly Asn Glu Ala Pro Val Thr Gly
    1985                1990                1995

Ser Ser Pro Leu Gly Ala Thr Gln Leu Asp Thr Asp Gly Ala Leu
    2000                2005                2010

Trp Leu Gly Gly Leu Pro Glu Leu Pro Val Gly Pro Ala Leu Pro
    2015                2020                2025

Lys Ala Tyr Gly Thr Gly Phe Val Gly Cys Leu Arg Asp Val Val
    2030                2035                2040

Val Gly Arg His Pro Leu His Leu Leu Glu Asp Ala Val Thr Lys
    2045                2050                2055

Pro Glu Leu Arg Pro Cys Pro Thr Pro
    2060                2065

<210> SEQ ID NO 2
<211> LENGTH: 485
<212> TYPE: PRT
<213> ORGANISM: Homo sapiens
<300> PUBLICATION INFORMATION:
<308> DATABASE ACCESSION NUMBER: UniProt / P01019
<309> DATABASE ENTRY DATE: 2015-07-22
<313> RELEVANT RESIDUES IN SEQ ID NO: (1)..(485)

<400> SEQUENCE: 2

Met Arg Lys Arg Ala Pro Gln Ser Glu Met Ala Pro Ala Gly Val Ser
1               5                   10                  15

Leu Arg Ala Thr Ile Leu Cys Leu Leu Ala Trp Ala Gly Leu Ala Ala
                20                  25                  30

Gly Asp Arg Val Tyr Ile His Pro Phe His Leu Val Ile His Asn Glu
            35                  40                  45

Ser Thr Cys Glu Gln Leu Ala Lys Ala Asn Ala Gly Lys Pro Lys Asp
        50                  55                  60

Pro Thr Phe Ile Pro Ala Pro Ile Gln Ala Lys Thr Ser Pro Val Asp
65                  70                  75                  80

Glu Lys Ala Leu Gln Asp Gln Leu Val Leu Val Ala Ala Lys Leu Asp
                85                  90                  95

Thr Glu Asp Lys Leu Arg Ala Ala Met Val Gly Met Leu Ala Asn Phe
            100                 105                 110

Leu Gly Phe Arg Ile Tyr Gly Met His Ser Glu Leu Trp Gly Val Val
        115                 120                 125

His Gly Ala Thr Val Leu Ser Pro Thr Ala Val Phe Gly Thr Leu Ala
    130                 135                 140

Ser Leu Tyr Leu Gly Ala Leu Asp His Thr Ala Asp Arg Leu Gln Ala
145                 150                 155                 160

Ile Leu Gly Val Pro Trp Lys Asp Lys Asn Cys Thr Ser Arg Leu Asp
                165                 170                 175

Ala His Lys Val Leu Ser Ala Leu Gln Ala Val Gln Gly Leu Leu Val
            180                 185                 190
```

Ala Gln Gly Arg Ala Asp Ser Gln Ala Gln Leu Leu Leu Ser Thr Val
            195                 200                 205

Val Gly Val Phe Thr Ala Pro Gly Leu His Leu Lys Gln Pro Phe Val
    210                 215                 220

Gln Gly Leu Ala Leu Tyr Thr Pro Val Val Leu Pro Arg Ser Leu Asp
225                 230                 235                 240

Phe Thr Glu Leu Asp Val Ala Ala Glu Lys Ile Asp Arg Phe Met Gln
                245                 250                 255

Ala Val Thr Gly Trp Lys Thr Gly Cys Ser Leu Met Gly Ala Ser Val
            260                 265                 270

Asp Ser Thr Leu Ala Phe Asn Thr Tyr Val His Phe Gln Gly Lys Met
            275                 280                 285

Lys Gly Phe Ser Leu Leu Ala Glu Pro Gln Glu Phe Trp Val Asp Asn
        290                 295                 300

Ser Thr Ser Val Ser Val Pro Met Leu Ser Gly Met Gly Thr Phe Gln
305                 310                 315                 320

His Trp Ser Asp Ile Gln Asp Asn Phe Ser Val Thr Gln Val Pro Phe
                325                 330                 335

Thr Glu Ser Ala Cys Leu Leu Leu Ile Gln Pro His Tyr Ala Ser Asp
            340                 345                 350

Leu Asp Lys Val Glu Gly Leu Thr Phe Gln Gln Asn Ser Leu Asn Trp
        355                 360                 365

Met Lys Lys Leu Ser Pro Arg Thr Ile His Leu Thr Met Pro Gln Leu
    370                 375                 380

Val Leu Gln Gly Ser Tyr Asp Leu Gln Asp Leu Leu Ala Gln Ala Glu
385                 390                 395                 400

Leu Pro Ala Ile Leu His Thr Glu Leu Asn Leu Gln Lys Leu Ser Asn
                405                 410                 415

Asp Arg Ile Arg Val Gly Glu Val Leu Asn Ser Ile Phe Phe Glu Leu
            420                 425                 430

Glu Ala Asp Glu Arg Glu Pro Thr Glu Ser Thr Gln Gln Leu Asn Lys
        435                 440                 445

Pro Glu Val Leu Glu Val Thr Leu Asn Arg Pro Phe Leu Phe Ala Val
    450                 455                 460

Tyr Asp Gln Ser Ala Thr Ala Leu His Phe Leu Gly Arg Val Ala Asn
465                 470                 475                 480

Pro Leu Ser Thr Ala
                485

<210> SEQ ID NO 3
<211> LENGTH: 201
<212> TYPE: PRT
<213> ORGANISM: Homo sapiens
<300> PUBLICATION INFORMATION:
<308> DATABASE ACCESSION NUMBER: UniProt / P52566
<309> DATABASE ENTRY DATE: 2015-07-22
<313> RELEVANT RESIDUES IN SEQ ID NO: (1)..(201)

<400> SEQUENCE: 3

Met Thr Glu Lys Ala Pro Glu Pro His Val Glu Glu Asp Asp Asp
1               5                   10                  15

Glu Leu Asp Ser Lys Leu Asn Tyr Lys Pro Pro Pro Gln Lys Ser Leu
                20                  25                  30

Lys Glu Leu Gln Glu Met Asp Lys Asp Asp Glu Ser Leu Ile Lys Tyr
            35                  40                  45

```
Lys Lys Thr Leu Leu Gly Asp Gly Pro Val Val Thr Asp Pro Lys Ala
 50                  55                  60

Pro Asn Val Val Thr Arg Leu Thr Leu Val Cys Glu Ser Ala Pro
 65                  70                  75                  80

Gly Pro Ile Thr Met Asp Leu Thr Gly Asp Leu Glu Ala Leu Lys Lys
                     85                  90                  95

Glu Thr Ile Val Leu Lys Glu Gly Ser Glu Tyr Arg Val Lys Ile His
                100                 105                 110

Phe Lys Val Asn Arg Asp Ile Val Ser Gly Leu Lys Tyr Val Gln His
                115                 120                 125

Thr Tyr Arg Thr Gly Val Lys Val Asp Lys Ala Thr Phe Met Val Gly
    130                 135                 140

Ser Tyr Gly Pro Arg Pro Glu Glu Tyr Glu Phe Leu Thr Pro Val Glu
145                 150                 155                 160

Glu Ala Pro Lys Gly Met Leu Ala Arg Gly Thr Tyr His Asn Lys Ser
                165                 170                 175

Phe Phe Thr Asp Asp Lys Gln Asp His Leu Ser Trp Glu Trp Asn
                180                 185                 190

Leu Ser Ile Lys Lys Glu Trp Thr Glu
        195                 200

<210> SEQ ID NO 4
<211> LENGTH: 199
<212> TYPE: PRT
<213> ORGANISM: Homo sapiens
<300> PUBLICATION INFORMATION:
<308> DATABASE ACCESSION NUMBER: UniProt / Q9NWT8
<309> DATABASE ENTRY DATE: 2015-07-22
<313> RELEVANT RESIDUES IN SEQ ID NO: (1)..(199)

<400> SEQUENCE: 4

Met Leu Leu Gly Arg Leu Thr Ser Gln Leu Leu Arg Ala Val Pro Trp
  1               5                  10                  15

Ala Gly Gly Arg Pro Pro Trp Pro Val Ser Gly Val Leu Gly Ser Arg
                 20                  25                  30

Val Cys Gly Pro Leu Tyr Ser Thr Ser Pro Ala Gly Pro Gly Arg Ala
             35                  40                  45

Ala Ser Leu Pro Arg Lys Gly Ala Gln Leu Glu Leu Glu Glu Met Leu
 50                  55                  60

Val Pro Arg Lys Met Ser Val Ser Pro Leu Glu Ser Trp Leu Thr Ala
 65                  70                  75                  80

Arg Cys Phe Leu Pro Arg Leu Asp Thr Gly Thr Ala Gly Thr Val Ala
                 85                  90                  95

Pro Pro Gln Ser Tyr Gln Cys Pro Pro Ser Gln Ile Gly Glu Gly Ala
                100                 105                 110

Glu Gln Gly Asp Glu Gly Val Ala Asp Ala Pro Gln Ile Gln Cys Lys
            115                 120                 125

Asn Val Leu Lys Ile Arg Arg Arg Lys Met Asn His His Lys Tyr Arg
        130                 135                 140

Lys Leu Val Lys Lys Thr Arg Phe Leu Arg Arg Lys Val Gln Glu Gly
145                 150                 155                 160

Arg Leu Arg Arg Lys Gln Ile Lys Phe Glu Lys Asp Leu Arg Arg Ile
                165                 170                 175

Trp Leu Lys Ala Gly Leu Lys Glu Ala Pro Glu Gly Trp Gln Thr Pro
                180                 185                 190

Lys Ile Tyr Leu Arg Gly Lys
```

-continued

```
            195

<210> SEQ ID NO 5
<211> LENGTH: 1744
<212> TYPE: PRT
<213> ORGANISM: Homo sapiens
<300> PUBLICATION INFORMATION:
<308> DATABASE ACCESSION NUMBER: UniProt / P0C0L5
<309> DATABASE ENTRY DATE: 2015-07-22
<313> RELEVANT RESIDUES IN SEQ ID NO: (1)..(1744)

<400> SEQUENCE: 5

Met Arg Leu Leu Trp Gly Leu Ile Trp Ala Ser Ser Phe Phe Thr Leu
1               5                   10                  15

Ser Leu Gln Lys Pro Arg Leu Leu Phe Ser Pro Ser Val Val His
            20                  25                  30

Leu Gly Val Pro Leu Ser Val Gly Val Gln Leu Gln Asp Val Pro Arg
        35                  40                  45

Gly Gln Val Val Lys Gly Ser Val Phe Leu Arg Asn Pro Ser Arg Asn
    50                  55                  60

Asn Val Pro Cys Ser Pro Lys Val Asp Phe Thr Leu Ser Ser Glu Arg
65              70                  75                  80

Asp Phe Ala Leu Leu Ser Leu Gln Val Pro Leu Lys Asp Ala Lys Ser
                85                  90                  95

Cys Gly Leu His Gln Leu Leu Arg Gly Pro Glu Val Gln Leu Val Ala
            100                 105                 110

His Ser Pro Trp Leu Lys Asp Ser Leu Ser Arg Thr Thr Asn Ile Gln
        115                 120                 125

Gly Ile Asn Leu Leu Phe Ser Ser Arg Arg Gly His Leu Phe Leu Gln
    130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
            180                 185                 190

Met Pro Ser Ser Ile Phe Gln Asp Asp Phe Val Ile Pro Asp Ile Ser
        195                 200                 205

Glu Pro Gly Thr Trp Lys Ile Ser Ala Arg Phe Ser Asp Gly Leu Glu
    210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
            260                 265                 270

Gly Lys Pro Val Gln Gly Val Ala Tyr Val Arg Phe Gly Leu Leu Asp
        275                 280                 285

Glu Asp Gly Lys Lys Thr Phe Phe Arg Gly Leu Glu Ser Gln Thr Lys
    290                 295                 300

Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
                325                 330                 335

Arg Leu Tyr Val Ala Ala Ala Ile Ile Glu Ser Pro Gly Gly Glu Met
            340                 345                 350
```

-continued

```
Glu Glu Ala Glu Leu Thr Ser Trp Tyr Phe Val Ser Ser Pro Phe Ser
            355                 360                 365

Leu Asp Leu Ser Lys Thr Lys Arg His Leu Val Pro Gly Ala Pro Phe
        370                 375                 380

Leu Leu Gln Ala Leu Val Arg Glu Met Ser Gly Ser Pro Ala Ser Gly
385                 390                 395                 400

Ile Pro Val Lys Val Ser Ala Thr Val Ser Ser Pro Gly Ser Val Pro
                405                 410                 415

Glu Val Gln Asp Ile Gln Gln Asn Thr Asp Gly Ser Gly Gln Val Ser
            420                 425                 430

Ile Pro Ile Ile Ile Pro Gln Thr Ile Ser Glu Leu Gln Leu Ser Val
            435                 440                 445

Ser Ala Gly Ser Pro His Pro Ala Ile Ala Arg Leu Thr Val Ala Ala
        450                 455                 460

Pro Pro Ser Gly Gly Pro Gly Phe Leu Ser Ile Glu Arg Pro Asp Ser
465                 470                 475                 480

Arg Pro Pro Arg Val Gly Asp Thr Leu Asn Leu Asn Leu Arg Ala Val
                485                 490                 495

Gly Ser Gly Ala Thr Phe Ser His Tyr Tyr Tyr Met Ile Leu Ser Arg
            500                 505                 510

Gly Gln Ile Val Phe Met Asn Arg Glu Pro Lys Arg Thr Leu Thr Ser
            515                 520                 525

Val Ser Val Phe Val Asp His His Leu Ala Pro Ser Phe Tyr Phe Val
        530                 535                 540

Ala Phe Tyr Tyr His Gly Asp His Pro Val Ala Asn Ser Leu Arg Val
545                 550                 555                 560

Asp Val Gln Ala Gly Ala Cys Glu Gly Lys Leu Glu Leu Ser Val Asp
                565                 570                 575

Gly Ala Lys Gln Tyr Arg Asn Gly Glu Ser Val Lys Leu His Leu Glu
            580                 585                 590

Thr Asp Ser Leu Ala Leu Val Ala Leu Gly Ala Leu Asp Thr Ala Leu
        595                 600                 605

Tyr Ala Ala Gly Ser Lys Ser His Lys Pro Leu Asn Met Gly Lys Val
    610                 615                 620

Phe Glu Ala Met Asn Ser Tyr Asp Leu Gly Cys Gly Pro Gly Gly Gly
625                 630                 635                 640

Asp Ser Ala Leu Gln Val Phe Gln Ala Ala Gly Leu Ala Phe Ser Asp
                645                 650                 655

Gly Asp Gln Trp Thr Leu Ser Arg Lys Arg Leu Ser Cys Pro Lys Glu
            660                 665                 670

Lys Thr Thr Arg Lys Lys Arg Asn Val Asn Phe Gln Lys Ala Ile Asn
        675                 680                 685

Glu Lys Leu Gly Gln Tyr Ala Ser Pro Thr Ala Lys Arg Cys Cys Gln
    690                 695                 700

Asp Gly Val Thr Arg Leu Pro Met Met Arg Ser Cys Glu Gln Arg Ala
705                 710                 715                 720

Ala Arg Val Gln Gln Pro Asp Cys Arg Glu Pro Phe Leu Ser Cys Cys
                725                 730                 735

Gln Phe Ala Glu Ser Leu Arg Lys Lys Ser Arg Asp Lys Gly Gln Ala
            740                 745                 750

Gly Leu Gln Arg Ala Leu Glu Ile Leu Gln Glu Glu Asp Leu Ile Asp
        755                 760                 765
```

```
Glu Asp Asp Ile Pro Val Arg Ser Phe Phe Pro Glu Asn Trp Leu Trp
770             775                 780

Arg Val Glu Thr Val Asp Arg Phe Gln Ile Leu Thr Leu Trp Leu Pro
785             790                 795                 800

Asp Ser Leu Thr Thr Trp Glu Ile His Gly Leu Ser Leu Ser Lys Thr
                805                 810                 815

Lys Gly Leu Cys Val Ala Thr Pro Val Gln Leu Arg Val Phe Arg Glu
            820                 825                 830

Phe His Leu His Leu Arg Leu Pro Met Ser Val Arg Arg Phe Glu Gln
            835                 840                 845

Leu Glu Leu Arg Pro Val Leu Tyr Asn Tyr Leu Asp Lys Asn Leu Thr
850                 855                 860

Val Ser Val His Val Ser Pro Val Glu Gly Leu Cys Leu Ala Gly Gly
865                 870                 875                 880

Gly Gly Leu Ala Gln Gln Val Leu Val Pro Ala Gly Ser Ala Arg Pro
                885                 890                 895

Val Ala Phe Ser Val Val Pro Thr Ala Ala Thr Ala Val Ser Leu Lys
                900                 905                 910

Val Val Ala Arg Gly Ser Phe Glu Phe Pro Val Gly Asp Ala Val Ser
            915                 920                 925

Lys Val Leu Gln Ile Glu Lys Glu Gly Ala Ile His Arg Glu Glu Leu
            930                 935                 940

Val Tyr Glu Leu Asn Pro Leu Asp His Arg Gly Arg Thr Leu Glu Ile
945                 950                 955                 960

Pro Gly Asn Ser Asp Pro Asn Met Ile Pro Asp Gly Asp Phe Asn Ser
            965                 970                 975

Tyr Val Arg Val Thr Ala Ser Asp Pro Leu Asp Thr Leu Gly Ser Glu
            980                 985                 990

Gly Ala Leu Ser Pro Gly Gly Val  Ala Ser Leu Leu Arg  Leu Pro Arg
            995                 1000                1005

Gly Cys  Gly Glu Gln Thr Met  Ile Tyr Leu Ala Pro  Thr Leu Ala
    1010                 1015                  1020

Ala Ser  Arg Tyr Leu Asp Lys  Thr Glu Gln Trp Ser  Thr Leu Pro
    1025                 1030                  1035

Pro Glu  Thr Lys Asp His Ala  Val Asp Leu Ile Gln  Lys Gly Tyr
    1040                 1045                  1050

Met Arg  Ile Gln Gln Phe Arg  Lys Ala Asp Gly Ser  Tyr Ala Ala
    1055                 1060                  1065

Trp Leu  Ser Arg Gly Ser Ser  Thr Trp Leu Thr Ala  Phe Val Leu
    1070                 1075                  1080

Lys Val  Leu Ser Leu Ala Gln  Glu Gln Val Gly Gly  Ser Pro Glu
    1085                 1090                  1095

Lys Leu  Gln Glu Thr Ser Asn  Trp Leu Leu Ser Gln  Gln Gln Ala
    1100                 1105                  1110

Asp Gly  Ser Phe Gln Asp Leu  Ser Pro Val Ile His  Arg Ser Met
    1115                 1120                  1125

Gln Gly  Gly Leu Val Gly Asn  Asp Glu Thr Val Ala  Leu Thr Ala
    1130                 1135                  1140

Phe Val  Thr Ile Ala Leu His  His Gly Leu Ala Val  Phe Gln Asp
    1145                 1150                  1155

Glu Gly  Ala Glu Pro Leu Lys  Gln Arg Val Glu Ala  Ser Ile Ser
    1160                 1165                  1170

Lys Ala  Ser Ser Phe Leu Gly  Glu Lys Ala Ser Ala  Gly Leu Leu
```

```
                    1175                1180                1185
        Gly Ala His Ala Ala Ile Thr Ala Tyr Ala Leu Thr Leu Thr
                1190                1195                1200
        Lys Ala Pro Ala Asp Leu Arg Gly Val Ala His Asn Asn Leu Met
                1205                1210                1215
        Ala Met Ala Gln Glu Thr Gly Asp Asn Leu Tyr Trp Gly Ser Val
                1220                1225                1230
        Thr Gly Ser Gln Ser Asn Ala Val Ser Pro Thr Pro Ala Pro Arg
                1235                1240                1245
        Asn Pro Ser Asp Pro Met Pro Gln Ala Pro Ala Leu Trp Ile Glu
                1250                1255                1260
        Thr Thr Ala Tyr Ala Leu Leu His Leu Leu Leu His Glu Gly Lys
                1265                1270                1275
        Ala Glu Met Ala Asp Gln Ala Ala Ala Trp Leu Thr Arg Gln Gly
                1280                1285                1290
        Ser Phe Gln Gly Gly Phe Arg Ser Thr Gln Asp Thr Val Ile Ala
                1295                1300                1305
        Leu Asp Ala Leu Ser Ala Tyr Trp Ile Ala Ser His Thr Thr Glu
                1310                1315                1320
        Glu Arg Gly Leu Asn Val Thr Leu Ser Ser Thr Gly Arg Asn Gly
                1325                1330                1335
        Phe Lys Ser His Ala Leu Gln Leu Asn Asn Arg Gln Ile Arg Gly
                1340                1345                1350
        Leu Glu Glu Glu Leu Gln Phe Ser Leu Gly Ser Lys Ile Asn Val
                1355                1360                1365
        Lys Val Gly Gly Asn Ser Lys Gly Thr Leu Lys Val Leu Arg Thr
                1370                1375                1380
        Tyr Asn Val Leu Asp Met Lys Asn Thr Thr Cys Gln Asp Leu Gln
                1385                1390                1395
        Ile Glu Val Thr Val Lys Gly His Val Glu Tyr Thr Met Glu Ala
                1400                1405                1410
        Asn Glu Asp Tyr Glu Asp Tyr Glu Tyr Asp Glu Leu Pro Ala Lys
                1415                1420                1425
        Asp Asp Pro Asp Ala Pro Leu Gln Pro Val Thr Pro Leu Gln Leu
                1430                1435                1440
        Phe Glu Gly Arg Arg Asn Arg Arg Arg Glu Ala Pro Lys Val
                1445                1450                1455
        Val Glu Glu Gln Glu Ser Arg Val His Tyr Thr Val Cys Ile Trp
                1460                1465                1470
        Arg Asn Gly Lys Val Gly Leu Ser Gly Met Ala Ile Ala Asp Val
                1475                1480                1485
        Thr Leu Leu Ser Gly Phe His Ala Leu Arg Ala Asp Leu Glu Lys
                1490                1495                1500
        Leu Thr Ser Leu Ser Asp Arg Tyr Val Ser His Phe Glu Thr Glu
                1505                1510                1515
        Gly Pro His Val Leu Leu Tyr Phe Asp Ser Val Pro Thr Ser Arg
                1520                1525                1530
        Glu Cys Val Gly Phe Glu Ala Val Gln Glu Val Pro Val Gly Leu
                1535                1540                1545
        Val Gln Pro Ala Ser Ala Thr Leu Tyr Asp Tyr Tyr Asn Pro Glu
                1550                1555                1560
        Arg Arg Cys Ser Val Phe Tyr Gly Ala Pro Ser Lys Ser Arg Leu
                1565                1570                1575
```

-continued

```
Leu Ala Thr Leu Cys Ser Ala Glu Val Cys Gln Cys Ala Glu Gly
    1580            1585                1590

Lys Cys Pro Arg Gln Arg Arg Ala Leu Glu Arg Gly Leu Gln Asp
    1595            1600                1605

Glu Asp Gly Tyr Arg Met Lys Phe Ala Cys Tyr Tyr Pro Arg Val
    1610            1615                1620

Glu Tyr Gly Phe Gln Val Lys Val Leu Arg Glu Asp Ser Arg Ala
    1625            1630                1635

Ala Phe Arg Leu Phe Glu Thr Lys Ile Thr Gln Val Leu His Phe
    1640            1645                1650

Thr Lys Asp Val Lys Ala Ala Ala Asn Gln Met Arg Asn Phe Leu
    1655            1660                1665

Val Arg Ala Ser Cys Arg Leu Arg Leu Glu Pro Gly Lys Glu Tyr
    1670            1675                1680

Leu Ile Met Gly Leu Asp Gly Ala Thr Tyr Asp Leu Glu Gly His
    1685            1690                1695

Pro Gln Tyr Leu Leu Asp Ser Asn Ser Trp Ile Glu Glu Met Pro
    1700            1705                1710

Ser Glu Arg Leu Cys Arg Ser Thr Arg Gln Arg Ala Ala Cys Ala
    1715            1720                1725

Gln Leu Asn Asp Phe Leu Gln Glu Tyr Gly Thr Gln Gly Cys Gln
    1730            1735                1740

Val

<210> SEQ ID NO 6
<211> LENGTH: 559
<212> TYPE: PRT
<213> ORGANISM: Homo sapiens
<300> PUBLICATION INFORMATION:
<308> DATABASE ACCESSION NUMBER: UniProt / Q13112
<309> DATABASE ENTRY DATE: 2015-07-22
<313> RELEVANT RESIDUES IN SEQ ID NO: (1)..(559)

<400> SEQUENCE: 6

Met Lys Val Ile Thr Cys Glu Ile Ala Trp His Asn Lys Glu Pro Val
1               5                   10                  15

Tyr Ser Leu Asp Phe Gln His Gly Thr Ala Gly Arg Ile His Arg Leu
                20                  25                  30

Ala Ser Ala Gly Val Asp Thr Asn Val Arg Ile Trp Lys Val Glu Lys
            35                  40                  45

Gly Pro Asp Gly Lys Ala Ile Val Glu Phe Leu Ser Asn Leu Ala Arg
        50                  55                  60

His Thr Lys Ala Val Asn Val Val Arg Phe Ser Pro Thr Gly Glu Ile
65                  70                  75                  80

Leu Ala Ser Gly Gly Asp Asp Ala Val Ile Leu Leu Trp Lys Val Asn
                85                  90                  95

Asp Asn Lys Glu Pro Glu Gln Ile Ala Phe Gln Asp Glu Asp Glu Ala
                100                 105                 110

Gln Leu Asn Lys Glu Asn Trp Thr Val Val Lys Thr Leu Arg Gly His
            115                 120                 125

Leu Glu Asp Val Tyr Asp Ile Cys Trp Ala Thr Asp Gly Asn Leu Met
        130                 135                 140

Ala Ser Ala Ser Val Asp Asn Thr Ala Ile Ile Trp Asp Val Ser Lys
145                 150                 155                 160

Gly Gln Lys Ile Ser Ile Phe Asn Glu His Lys Ser Tyr Val Gln Gly
```

```
                    165                 170                 175
Val Thr Trp Asp Pro Leu Gly Gln Tyr Val Ala Thr Leu Ser Cys Asp
                180                 185                 190
Arg Val Leu Arg Val Tyr Ser Ile Gln Lys Arg Val Ala Phe Asn
            195                 200                 205
Val Ser Lys Met Leu Ser Gly Ile Gly Ala Glu Glu Ala Arg Ser
        210                 215                 220
Tyr Arg Met Phe His Asp Asp Ser Met Lys Ser Phe Arg Arg Leu
225                 230                 235                 240
Ser Phe Thr Pro Asp Gly Ser Leu Leu Leu Thr Pro Ala Gly Cys Val
                245                 250                 255
Glu Ser Gly Glu Asn Val Met Asn Thr Thr Tyr Val Phe Ser Arg Lys
            260                 265                 270
Asn Leu Lys Arg Pro Ile Ala His Leu Pro Cys Pro Gly Lys Ala Thr
        275                 280                 285
Leu Ala Val Arg Cys Cys Pro Val Tyr Phe Glu Leu Arg Pro Val Val
290                 295                 300
Glu Thr Gly Val Glu Leu Met Ser Leu Pro Tyr Arg Leu Val Phe Ala
305                 310                 315                 320
Val Ala Ser Glu Asp Ser Val Leu Leu Tyr Asp Thr Gln Gln Ser Phe
                325                 330                 335
Pro Phe Gly Tyr Val Ser Asn Ile His Tyr His Thr Leu Ser Asp Ile
            340                 345                 350
Ser Trp Ser Ser Asp Gly Ala Phe Leu Ala Ile Ser Thr Asp Gly
        355                 360                 365
Tyr Cys Ser Phe Val Thr Phe Glu Lys Asp Glu Leu Gly Ile Pro Leu
370                 375                 380
Lys Glu Lys Pro Val Leu Asn Met Arg Thr Pro Asp Thr Ala Lys Lys
385                 390                 395                 400
Thr Lys Ser Gln Thr His Arg Gly Ser Ser Pro Gly Pro Arg Pro Val
                405                 410                 415
Glu Gly Thr Pro Ala Ser Arg Thr Gln Asp Pro Ser Pro Gly Thr
            420                 425                 430
Thr Pro Pro Gln Ala Arg Gln Ala Pro Ala Pro Thr Val Ile Arg Asp
        435                 440                 445
Pro Pro Ser Ile Thr Pro Ala Val Lys Ser Pro Leu Pro Gly Pro Ser
        450                 455                 460
Glu Glu Lys Thr Leu Gln Pro Ser Ser Gln Asn Thr Lys Ala His Pro
465                 470                 475                 480
Ser Arg Arg Val Thr Leu Asn Thr Leu Gln Ala Trp Ser Lys Thr Thr
                485                 490                 495
Pro Arg Arg Ile Asn Leu Thr Pro Leu Lys Thr Asp Thr Pro Pro Ser
            500                 505                 510
Ser Val Pro Thr Ser Val Ile Ser Thr Pro Ser Thr Glu Glu Ile Gln
        515                 520                 525
Ser Glu Thr Pro Gly Asp Ala Gln Gly Ser Pro Pro Glu Leu Lys Arg
        530                 535                 540
Pro Arg Leu Asp Glu Asn Lys Gly Gly Thr Glu Ser Leu Asp Pro
545                 550                 555

<210> SEQ ID NO 7
<211> LENGTH: 94
<212> TYPE: PRT
<213> ORGANISM: Homo sapiens
```

```
<300> PUBLICATION INFORMATION:
<308> DATABASE ACCESSION NUMBER: UniProt / O14625
<309> DATABASE ENTRY DATE: 2015-06-24
<313> RELEVANT RESIDUES IN SEQ ID NO: (1)..(94)

<400> SEQUENCE: 7

Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
    50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
                85                  90

<210> SEQ ID NO 8
<211> LENGTH: 125
<212> TYPE: PRT
<213> ORGANISM: Homo sapiens
<300> PUBLICATION INFORMATION:
<308> DATABASE ACCESSION NUMBER: UniProt / Q07325
<309> DATABASE ENTRY DATE: 2015-07-22
<313> RELEVANT RESIDUES IN SEQ ID NO: (1)..(125)

<400> SEQUENCE: 8

Met Lys Lys Ser Gly Val Leu Phe Leu Leu Gly Ile Ile Leu Leu Val
1               5                   10                  15

Leu Ile Gly Val Gln Gly Thr Pro Val Val Arg Lys Gly Arg Cys Ser
            20                  25                  30

Cys Ile Ser Thr Asn Gln Gly Thr Ile His Leu Gln Ser Leu Lys Asp
        35                  40                  45

Leu Lys Gln Phe Ala Pro Ser Pro Ser Cys Glu Lys Ile Glu Ile Ile
    50                  55                  60

Ala Thr Leu Lys Asn Gly Val Gln Thr Cys Leu Asn Pro Asp Ser Ala
65                  70                  75                  80

Asp Val Lys Glu Leu Ile Lys Lys Trp Glu Lys Gln Val Ser Gln Lys
                85                  90                  95

Lys Lys Gln Lys Asn Gly Lys Lys His Gln Lys Lys Lys Val Leu Lys
            100                 105                 110

Val Arg Lys Ser Gln Arg Ser Arg Gln Lys Lys Thr Thr
            115                 120                 125

<210> SEQ ID NO 9
<211> LENGTH: 165
<212> TYPE: PRT
<213> ORGANISM: Homo sapiens
<300> PUBLICATION INFORMATION:
<308> DATABASE ACCESSION NUMBER: UniProt / P62937
<309> DATABASE ENTRY DATE: 2015-07-22
<313> RELEVANT RESIDUES IN SEQ ID NO: (1)..(165)

<400> SEQUENCE: 9

Met Val Asn Pro Thr Val Phe Phe Asp Ile Ala Val Asp Gly Glu Pro
1               5                   10                  15

Leu Gly Arg Val Ser Phe Glu Leu Phe Ala Asp Lys Val Pro Lys Thr
            20                  25                  30
```

Ala Glu Asn Phe Arg Ala Leu Ser Thr Gly Glu Lys Gly Phe Gly Tyr
             35                  40                  45

Lys Gly Ser Cys Phe His Arg Ile Ile Pro Gly Phe Met Cys Gln Gly
 50                  55                  60

Gly Asp Phe Thr Arg His Asn Gly Thr Gly Lys Ser Ile Tyr Gly
 65                  70                  75                  80

Glu Lys Phe Glu Asp Glu Asn Phe Ile Leu Lys His Thr Gly Pro Gly
                     85                  90                  95

Ile Leu Ser Met Ala Asn Ala Gly Pro Asn Thr Asn Gly Ser Gln Phe
                100                 105                 110

Phe Ile Cys Thr Ala Lys Thr Glu Trp Leu Asp Gly Lys His Val Val
                115                 120                 125

Phe Gly Lys Val Lys Glu Gly Met Asn Ile Val Glu Ala Met Glu Arg
130                 135                 140

Phe Gly Ser Arg Asn Gly Lys Thr Ser Lys Lys Ile Thr Ile Ala Asp
145                 150                 155                 160

Cys Gly Gln Leu Glu
                165

<210> SEQ ID NO 10
<211> LENGTH: 585
<212> TYPE: PRT
<213> ORGANISM: Homo sapiens
<300> PUBLICATION INFORMATION:
<308> DATABASE ACCESSION NUMBER: UniProt / Q9BY44
<309> DATABASE ENTRY DATE: 2015-07-22
<313> RELEVANT RESIDUES IN SEQ ID NO: (1)..(585)

<400> SEQUENCE: 10

Met Ala Pro Ser Thr Pro Leu Leu Thr Val Arg Gly Ser Glu Gly Leu
1               5                   10                  15

Tyr Met Val Asn Gly Pro Pro His Phe Thr Glu Ser Thr Val Phe Pro
                20                  25                  30

Arg Glu Ser Gly Lys Asn Cys Lys Val Cys Ile Phe Ser Lys Asp Gly
                35                  40                  45

Thr Leu Phe Ala Trp Gly Asn Gly Glu Lys Val Asn Ile Ile Ser Val
 50                  55                  60

Thr Asn Lys Gly Leu Leu His Ser Phe Asp Leu Leu Lys Ala Val Cys
 65                  70                  75                  80

Leu Glu Phe Ser Pro Lys Asn Thr Val Leu Ala Thr Trp Gln Pro Tyr
                     85                  90                  95

Thr Thr Ser Lys Asp Gly Thr Ala Gly Ile Pro Asn Leu Gln Leu Tyr
                100                 105                 110

Asp Val Lys Thr Gly Thr Cys Leu Lys Ser Phe Ile Gln Lys Lys Met
                115                 120                 125

Gln Asn Trp Cys Pro Ser Trp Ser Glu Asp Glu Thr Leu Cys Ala Arg
130                 135                 140

Asn Val Asn Asn Glu Val His Phe Phe Glu Asn Asn Phe Asn Thr
145                 150                 155                 160

Ile Ala Asn Lys Leu His Leu Gln Lys Ile Asn Asp Phe Val Leu Ser
                165                 170                 175

Pro Gly Pro Gln Pro Tyr Lys Val Ala Val Tyr Val Pro Gly Ser Lys
                180                 185                 190

Gly Ala Pro Ser Phe Val Arg Leu Tyr Gln Tyr Pro Asn Phe Ala Gly
                195                 200                 205

Pro His Ala Ala Leu Ala Asn Lys Ser Phe Phe Lys Ala Asp Lys Val

```
            210                 215                 220
Thr Met Leu Trp Asn Lys Lys Ala Thr Ala Val Leu Ile Ala Ser
225                 230                 235                 240

Thr Asp Val Asp Lys Thr Gly Ala Ser Tyr Tyr Gly Glu Gln Thr Leu
                245                 250                 255

His Tyr Ile Ala Thr Asn Gly Glu Ser Ala Val Val Gln Leu Pro Lys
                260                 265                 270

Asn Gly Pro Ile Tyr Asp Val Val Trp Asn Ser Ser Thr Glu Phe
                275                 280                 285

Cys Ala Val Tyr Gly Phe Met Pro Ala Lys Ala Thr Ile Phe Asn Leu
290                 295                 300

Lys Cys Asp Pro Val Phe Asp Phe Gly Thr Gly Pro Arg Asn Ala Ala
305                 310                 315                 320

Tyr Tyr Ser Pro His Gly His Ile Leu Val Leu Ala Gly Phe Gly Asn
                325                 330                 335

Leu Arg Gly Gln Met Glu Val Trp Asp Val Lys Asn Tyr Lys Leu Ile
                340                 345                 350

Ser Lys Pro Val Ala Ser Asp Ser Thr Tyr Phe Ala Trp Cys Pro Asp
                355                 360                 365

Gly Glu His Ile Leu Thr Ala Thr Cys Ala Pro Arg Leu Arg Val Asn
370                 375                 380

Asn Gly Tyr Lys Ile Trp His Tyr Thr Gly Ser Ile Leu His Lys Tyr
385                 390                 395                 400

Asp Val Pro Ser Asn Ala Glu Leu Trp Gln Val Ser Trp Gln Pro Phe
                405                 410                 415

Leu Asp Gly Ile Phe Pro Ala Lys Thr Ile Thr Tyr Gln Ala Val Pro
                420                 425                 430

Ser Glu Val Pro Asn Glu Pro Lys Val Ala Thr Ala Tyr Arg Pro
                435                 440                 445

Pro Ala Leu Arg Asn Lys Pro Ile Thr Asn Ser Lys Leu His Glu Glu
450                 455                 460

Glu Pro Pro Gln Asn Met Lys Pro Gln Ser Gly Asn Asp Lys Pro Leu
465                 470                 475                 480

Ser Lys Thr Ala Leu Lys Asn Gln Arg Lys His Glu Ala Lys Lys Ala
                485                 490                 495

Ala Lys Gln Glu Ala Arg Ser Asp Lys Ser Pro Asp Leu Ala Pro Thr
                500                 505                 510

Pro Ala Pro Gln Ser Thr Pro Arg Asn Thr Val Ser Gln Ser Ile Ser
                515                 520                 525

Gly Asp Pro Glu Ile Asp Lys Lys Ile Lys Asn Leu Lys Lys Lys Leu
530                 535                 540

Lys Ala Ile Glu Gln Leu Lys Glu Gln Ala Ala Thr Gly Lys Gln Leu
545                 550                 555                 560

Glu Lys Asn Gln Leu Glu Lys Ile Gln Lys Glu Thr Ala Leu Leu Gln
                565                 570                 575

Glu Leu Glu Asp Leu Glu Leu Gly Ile
                580                 585

<210> SEQ ID NO 11
<211> LENGTH: 434
<212> TYPE: PRT
<213> ORGANISM: Homo sapiens
<300> PUBLICATION INFORMATION:
<308> DATABASE ACCESSION NUMBER: UniProt / P06733
<309> DATABASE ENTRY DATE: 2015-07-22
```

<313> RELEVANT RESIDUES IN SEQ ID NO: (1)..(434)

<400> SEQUENCE: 11

Met Ser Ile Leu Lys Ile His Ala Arg Glu Ile Phe Asp Ser Arg Gly
1               5                   10                  15

Asn Pro Thr Val Glu Val Asp Leu Phe Thr Ser Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Asn Asp Lys Thr Arg Tyr Met Gly Lys Gly Val Ser Lys
    50                  55                  60

Ala Val Glu His Ile Asn Lys Thr Ile Ala Pro Ala Leu Val Ser Lys
65                  70                  75                  80

Lys Leu Asn Val Thr Glu Gln Glu Lys Ile Asp Lys Leu Met Ile Glu
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Val Glu Lys Gly Val
        115                 120                 125

Pro Leu Tyr Arg His Ile Ala Asp Leu Ala Gly Asn Ser Glu Val Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Ala
                165                 170                 175

Asn Phe Arg Glu Ala Met Arg Ile Gly Ala Glu Val Tyr His Asn Leu
            180                 185                 190

Lys Asn Val Ile Lys Glu Lys Tyr Gly Lys Asp Ala Thr Asn Val Gly
        195                 200                 205

Asp Glu Gly Gly Phe Ala Pro Asn Ile Leu Glu Asn Lys Glu Gly Leu
    210                 215                 220

Glu Leu Leu Lys Thr Ala Ile Gly Lys Ala Gly Tyr Thr Asp Lys Val
225                 230                 235                 240

Val Ile Gly Met Asp Val Ala Ala Ser Glu Phe Phe Arg Ser Gly Lys
                245                 250                 255

Tyr Asp Leu Asp Phe Lys Ser Pro Asp Asp Pro Ser Arg Tyr Ile Ser
            260                 265                 270

Pro Asp Gln Leu Ala Asp Leu Tyr Lys Ser Phe Ile Lys Asp Tyr Pro
        275                 280                 285

Val Val Ser Ile Glu Asp Pro Phe Asp Gln Asp Trp Gly Ala Trp
    290                 295                 300

Gln Lys Phe Thr Ala Ser Ala Gly Ile Gln Val Val Gly Asp Asp Leu
305                 310                 315                 320

Thr Val Thr Asn Pro Lys Arg Ile Ala Lys Ala Val Asn Glu Lys Ser
                325                 330                 335

Cys Asn Cys Leu Leu Leu Lys Val Asn Gln Ile Gly Ser Val Thr Glu
            340                 345                 350

Ser Leu Gln Ala Cys Lys Leu Ala Gln Ala Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

```
Ser Glu Arg Leu Ala Lys Tyr Asn Gln Leu Arg Ile Glu Glu Glu
            405                 410                 415

Leu Gly Ser Lys Ala Lys Phe Ala Gly Arg Asn Phe Asn Pro Leu
            420                 425                 430

Ala Lys

<210> SEQ ID NO 12
<211> LENGTH: 585
<212> TYPE: PRT
<213> ORGANISM: Homo sapiens
<300> PUBLICATION INFORMATION:
<308> DATABASE ACCESSION NUMBER: UniProt / Q05329
<309> DATABASE ENTRY DATE: 2015-07-22
<313> RELEVANT RESIDUES IN SEQ ID NO: (1)..(585)

<400> SEQUENCE: 12

Met Ala Ser Pro Gly Ser Gly Phe Trp Ser Phe Gly Ser Glu Asp Gly
  1               5                  10                  15

Ser Gly Asp Ser Glu Asn Pro Gly Thr Ala Arg Ala Trp Cys Gln Val
             20                  25                  30

Ala Gln Lys Phe Thr Gly Gly Ile Gly Asn Lys Leu Cys Ala Leu Leu
         35                  40                  45

Tyr Gly Asp Ala Glu Lys Pro Ala Glu Ser Gly Gly Ser Gln Pro Pro
     50                  55                  60

Arg Ala Ala Ala Arg Lys Ala Ala Cys Ala Cys Asp Gln Lys Pro Cys
 65                  70                  75                  80

Ser Cys Ser Lys Val Asp Val Asn Tyr Ala Phe Leu His Ala Thr Asp
                 85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
    130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
    210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
    290                 295                 300

Asp Glu Arg Gly Lys Met Ile Pro Ser Asp Leu Glu Arg Arg Ile Leu
305                 310                 315                 320
```

-continued

Glu Ala Lys Gln Lys Gly Phe Val Pro Phe Leu Val Ser Ala Thr Ala
            325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
            355                 360                 365

Gly Gly Leu Leu Met Ser Arg Lys His Lys Trp Lys Leu Ser Gly Val
    370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
            405                 410                 415

Asn Cys Asn Gln Met His Ala Ser Tyr Leu Phe Gln Gln Asp Lys His
            420                 425                 430

Tyr Asp Leu Ser Tyr Asp Thr Gly Asp Lys Ala Leu Gln Cys Gly Arg
            435                 440                 445

His Val Asp Val Phe Lys Leu Trp Leu Met Trp Arg Ala Lys Gly Thr
    450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
            500                 505                 510

Leu Arg Thr Leu Glu Asp Asn Glu Glu Arg Met Ser Arg Leu Ser Lys
            515                 520                 525

Val Ala Pro Val Ile Lys Ala Arg Met Met Glu Tyr Gly Thr Thr Met
            530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
            580                 585

<210> SEQ ID NO 13
<211> LENGTH: 211
<212> TYPE: PRT
<213> ORGANISM: Homo sapiens
<300> PUBLICATION INFORMATION:
<308> DATABASE ACCESSION NUMBER: UniProt / P39905
<309> DATABASE ENTRY DATE: 2015-07-22
<313> RELEVANT RESIDUES IN SEQ ID NO: (1)..(211)

<400> SEQUENCE: 13

Met Lys Leu Trp Asp Val Val Ala Val Cys Leu Val Leu Leu His Thr
1               5                   10                  15

Ala Ser Ala Phe Pro Leu Pro Ala Gly Lys Arg Pro Pro Glu Ala Pro
            20                  25                  30

Ala Glu Asp Arg Ser Leu Gly Arg Arg Arg Ala Pro Phe Ala Leu Ser
        35                  40                  45

Ser Asp Ser Asn Met Pro Glu Asp Tyr Pro Asp Gln Phe Asp Asp Val
    50                  55                  60

Met Asp Phe Ile Gln Ala Thr Ile Lys Arg Leu Lys Arg Ser Pro Asp
65                  70                  75                  80

```
Lys Gln Met Ala Val Leu Pro Arg Arg Glu Arg Asn Arg Gln Ala Ala
                85                  90                  95

Ala Ala Asn Pro Glu Asn Ser Arg Gly Lys Gly Arg Gly Gln Arg
            100                 105                 110

Gly Lys Asn Arg Gly Cys Val Leu Thr Ala Ile His Leu Asn Val Thr
            115                 120                 125

Asp Leu Gly Leu Gly Tyr Glu Thr Lys Glu Glu Leu Ile Phe Arg Tyr
            130                 135                 140

Cys Ser Gly Ser Cys Asp Ala Ala Glu Thr Thr Tyr Asp Lys Ile Leu
145                 150                 155                 160

Lys Asn Leu Ser Arg Asn Arg Arg Leu Val Ser Asp Lys Val Gly Gln
                165                 170                 175

Ala Cys Cys Arg Pro Ile Ala Phe Asp Asp Asp Leu Ser Phe Leu Asp
            180                 185                 190

Asp Asn Leu Val Tyr His Ile Leu Arg Lys His Ser Ala Lys Arg Cys
            195                 200                 205

Gly Cys Ile
        210

<210> SEQ ID NO 14
<211> LENGTH: 463
<212> TYPE: PRT
<213> ORGANISM: Homo sapiens
<300> PUBLICATION INFORMATION:
<308> DATABASE ACCESSION NUMBER: UniProt / P61978
<309> DATABASE ENTRY DATE: 2015-07-22
<313> RELEVANT RESIDUES IN SEQ ID NO: (1)..(463)

<400> SEQUENCE: 14

Met Glu Thr Glu Gln Pro Glu Glu Thr Phe Pro Asn Thr Glu Thr Asn
1               5                   10                  15

Gly Glu Phe Gly Lys Arg Pro Ala Glu Asp Met Glu Glu Glu Gln Ala
                20                  25                  30

Phe Lys Arg Ser Arg Asn Thr Asp Glu Met Val Glu Leu Arg Ile Leu
            35                  40                  45

Leu Gln Ser Lys Asn Ala Gly Ala Val Ile Gly Lys Gly Gly Lys Asn
50                  55                  60

Ile Lys Ala Leu Arg Thr Asp Tyr Asn Ala Ser Val Ser Val Pro Asp
65                  70                  75                  80

Ser Ser Gly Pro Glu Arg Ile Leu Ser Ile Ser Ala Asp Ile Glu Thr
                85                  90                  95

Ile Gly Glu Ile Leu Lys Lys Ile Ile Pro Thr Leu Glu Glu Gly Leu
            100                 105                 110

Gln Leu Pro Ser Pro Thr Ala Thr Ser Gln Leu Pro Leu Glu Ser Asp
            115                 120                 125

Ala Val Glu Cys Leu Asn Tyr Gln His Tyr Lys Gly Ser Asp Phe Asp
            130                 135                 140

Cys Glu Leu Arg Leu Leu Ile His Gln Ser Leu Ala Gly Gly Ile Ile
145                 150                 155                 160

Gly Val Lys Gly Ala Lys Ile Lys Glu Leu Arg Glu Asn Thr Gln Thr
                165                 170                 175

Thr Ile Lys Leu Phe Gln Glu Cys Cys Pro His Ser Thr Asp Arg Val
            180                 185                 190

Val Leu Ile Gly Gly Lys Pro Asp Arg Val Val Glu Cys Ile Lys Ile
            195                 200                 205

Ile Leu Asp Leu Ile Ser Glu Ser Pro Ile Lys Gly Arg Ala Gln Pro
```

-continued

```
                210                 215                 220
Tyr Asp Pro Asn Phe Tyr Asp Glu Thr Tyr Asp Tyr Gly Gly Phe Thr
225                 230                 235                 240

Met Met Phe Asp Asp Arg Arg Gly Arg Pro Val Gly Phe Pro Met Arg
                245                 250                 255

Gly Arg Gly Gly Phe Asp Arg Met Pro Pro Gly Arg Gly Arg Pro
            260                 265                 270

Met Pro Pro Ser Arg Arg Asp Tyr Asp Asp Met Ser Pro Arg Arg Gly
                275                 280                 285

Pro Pro Pro Pro Pro Gly Arg Gly Gly Arg Gly Gly Ser Arg Ala
    290                 295                 300

Arg Asn Leu Pro Leu Pro Pro Pro Pro Arg Gly Gly Asp Leu
305                 310                 315                 320

Met Ala Tyr Asp Arg Arg Gly Arg Pro Gly Asp Arg Tyr Asp Gly Met
                325                 330                 335

Val Gly Phe Ser Ala Asp Glu Thr Trp Asp Ser Ala Ile Asp Thr Trp
                340                 345                 350

Ser Pro Ser Glu Trp Gln Met Ala Tyr Glu Pro Gln Gly Gly Ser Gly
                355                 360                 365

Tyr Asp Tyr Ser Tyr Ala Gly Gly Arg Gly Ser Tyr Gly Asp Leu Gly
                370                 375                 380

Gly Pro Ile Ile Thr Thr Gln Val Thr Ile Pro Lys Asp Leu Ala Gly
385                 390                 395                 400

Ser Ile Ile Gly Lys Gly Gly Gln Arg Ile Lys Gln Ile Arg His Glu
                405                 410                 415

Ser Gly Ala Ser Ile Lys Ile Asp Glu Pro Leu Glu Gly Ser Glu Asp
                420                 425                 430

Arg Ile Ile Thr Ile Thr Gly Thr Gln Asp Gln Ile Gln Asn Ala Gln
                435                 440                 445

Tyr Leu Leu Gln Asn Ser Val Lys Gln Tyr Ser Gly Lys Phe Phe
    450                 455                 460

<210> SEQ ID NO 15
<211> LENGTH: 532
<212> TYPE: PRT
<213> ORGANISM: Homo sapiens
<300> PUBLICATION INFORMATION:
<308> DATABASE ACCESSION NUMBER: UniProt / P05362
<309> DATABASE ENTRY DATE: 2015-07-22
<313> RELEVANT RESIDUES IN SEQ ID NO: (1)..(532)

<400> SEQUENCE: 15

Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
                20                  25                  30

Pro Ser Lys Val Ile Leu Pro Arg Gly Gly Ser Val Leu Val Thr Cys
            35                  40                  45

Ser Thr Ser Cys Asp Gln Pro Lys Leu Leu Gly Ile Glu Thr Pro Leu
50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
            100                 105                 110
```

```
Pro Glu Arg Val Glu Leu Ala Pro Leu Pro Ser Trp Gln Pro Val Gly
            115                 120                 125

Lys Asn Leu Thr Leu Arg Cys Gln Val Glu Gly Gly Ala Pro Arg Ala
130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
            195                 200                 205

Leu Gln Thr Phe Val Leu Pro Ala Thr Pro Pro Gln Leu Val Ser Pro
        210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
            260                 265                 270

Lys Ala Ser Val Ser Val Thr Ala Glu Asp Glu Gly Thr Gln Arg Leu
            275                 280                 285

Thr Cys Ala Val Ile Leu Gly Asn Gln Ser Gln Glu Thr Leu Gln Thr
        290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
            340                 345                 350

Arg Ala Gln Leu Leu Leu Lys Ala Thr Pro Glu Asp Asn Gly Arg Ser
            355                 360                 365

Phe Ser Cys Ser Ala Thr Leu Glu Val Ala Gly Gln Leu Ile His Lys
        370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
                405                 410                 415

Pro Met Cys Gln Ala Trp Gly Asn Pro Leu Pro Glu Leu Lys Cys Leu
            420                 425                 430

Lys Asp Gly Thr Phe Pro Leu Pro Ile Gly Glu Ser Val Thr Val Thr
            435                 440                 445

Arg Asp Leu Glu Gly Thr Tyr Leu Cys Arg Ala Arg Ser Thr Gln Gly
        450                 455                 460

Glu Val Thr Arg Lys Val Thr Val Asn Val Leu Ser Pro Arg Tyr Glu
465                 470                 475                 480

Ile Val Ile Ile Thr Val Val Ala Ala Ala Val Ile Met Gly Thr Ala
                485                 490                 495

Gly Leu Ser Thr Tyr Leu Tyr Asn Arg Gln Arg Lys Ile Lys Lys Tyr
            500                 505                 510

Arg Leu Gln Gln Ala Gln Lys Gly Thr Pro Met Lys Pro Asn Thr Gln
            515                 520                 525
```

```
Ala Thr Pro Pro
        530
```

<210> SEQ ID NO 16
<211> LENGTH: 785
<212> TYPE: PRT
<213> ORGANISM: Homo sapiens
<300> PUBLICATION INFORMATION:
<308> DATABASE ACCESSION NUMBER: UniProt / Q16666
<309> DATABASE ENTRY DATE: 2015-07-22
<313> RELEVANT RESIDUES IN SEQ ID NO: (1)..(785)

<400> SEQUENCE: 16

```
Met Gly Lys Lys Tyr Lys Asn Ile Val Leu Leu Lys Gly Leu Glu Val
1               5                   10                  15

Ile Asn Asp Tyr His Phe Arg Met Val Lys Ser Leu Leu Ser Asn Asp
            20                  25                  30

Leu Lys Leu Asn Leu Lys Met Arg Glu Glu Tyr Asp Lys Ile Gln Ile
        35                  40                  45

Ala Asp Leu Met Glu Glu Lys Phe Arg Gly Asp Ala Gly Leu Gly Lys
    50                  55                  60

Leu Ile Lys Ile Phe Glu Asp Ile Pro Thr Leu Glu Asp Leu Ala Glu
65                  70                  75                  80

Thr Leu Lys Lys Glu Lys Leu Lys Val Lys Gly Pro Ala Leu Ser Arg
                85                  90                  95

Lys Arg Lys Lys Glu Val Asp Ala Thr Ser Pro Ala Pro Ser Thr Ser
            100                 105                 110

Ser Thr Val Lys Thr Glu Gly Ala Glu Ala Thr Pro Gly Ala Gln Lys
        115                 120                 125

Arg Lys Lys Ser Thr Lys Glu Lys Ala Gly Pro Lys Gly Ser Lys Val
    130                 135                 140

Ser Glu Glu Gln Thr Gln Pro Pro Ser Pro Ala Gly Ala Gly Met Ser
145                 150                 155                 160

Thr Ala Met Gly Arg Ser Pro Ser Pro Lys Thr Ser Leu Ser Ala Pro
                165                 170                 175

Pro Asn Ser Ser Ser Thr Glu Asn Pro Lys Thr Val Ala Lys Cys Gln
            180                 185                 190

Val Thr Pro Arg Arg Asn Val Leu Gln Lys Arg Pro Val Ile Val Lys
        195                 200                 205

Val Leu Ser Thr Thr Lys Pro Phe Glu Tyr Glu Thr Pro Glu Met Glu
    210                 215                 220

Lys Lys Ile Met Phe His Ala Thr Val Ala Thr Gln Thr Gln Phe Phe
225                 230                 235                 240

His Val Lys Val Leu Asn Thr Ser Leu Lys Glu Lys Phe Asn Gly Lys
                245                 250                 255

Lys Ile Ile Ile Ile Ser Asp Tyr Leu Glu Tyr Asp Ser Leu Leu Glu
            260                 265                 270

Val Asn Glu Glu Ser Thr Val Ser Glu Ala Gly Pro Asn Gln Thr Phe
        275                 280                 285

Glu Val Pro Asn Lys Ile Ile Asn Arg Ala Lys Glu Thr Leu Lys Ile
    290                 295                 300

Asp Ile Leu His Lys Gln Ala Ser Gly Asn Ile Val Tyr Gly Val Phe
305                 310                 315                 320

Met Leu His Lys Lys Thr Val Asn Gln Lys Thr Thr Ile Tyr Glu Ile
                325                 330                 335

Gln Asp Asp Arg Gly Lys Met Asp Val Val Gly Thr Gly Gln Cys His
```

```
                  340                 345                 350
Asn Ile Pro Cys Glu Glu Gly Asp Lys Leu Gln Leu Phe Cys Phe Arg
            355                 360                 365
Leu Arg Lys Lys Asn Gln Met Ser Lys Leu Ile Ser Glu Met His Ser
        370                 375                 380
Phe Ile Gln Ile Lys Lys Thr Asn Pro Arg Asn Asn Asp Pro Lys
385                 390                 395                 400
Ser Met Lys Leu Pro Gln Glu Gln Arg Gln Leu Pro Tyr Pro Ser Glu
            405                 410                 415
Ala Ser Thr Thr Phe Pro Glu Ser His Leu Arg Thr Pro Gln Met Pro
        420                 425                 430
Pro Thr Thr Pro Ser Ser Phe Thr Lys Lys Ser Glu Asp Thr
    435                 440                 445
Ile Ser Lys Met Asn Asp Phe Met Arg Met Gln Ile Leu Lys Glu Gly
    450                 455                 460
Ser His Phe Pro Gly Pro Phe Met Thr Ser Ile Gly Pro Ala Glu Ser
465                 470                 475                 480
His Pro His Thr Pro Gln Met Pro Pro Ser Thr Pro Ser Ser Ser Phe
            485                 490                 495
Leu Thr Thr Lys Ser Glu Asp Thr Ile Ser Lys Met Asn Asp Phe Met
        500                 505                 510
Arg Met Gln Ile Leu Lys Glu Gly Ser His Phe Pro Gly Pro Phe Met
    515                 520                 525
Thr Ser Ile Gly Pro Ala Glu Ser His Pro His Thr Pro Gln Met Pro
    530                 535                 540
Pro Ser Thr Pro Ser Ser Ser Phe Leu Thr Thr Leu Lys Pro Arg Leu
545                 550                 555                 560
Lys Thr Glu Pro Glu Glu Val Ser Ile Glu Asp Ser Ala Gln Ser Asp
            565                 570                 575
Leu Lys Glu Val Met Val Leu Asn Ala Thr Glu Ser Phe Val Tyr Glu
        580                 585                 590
Pro Lys Glu Gln Lys Lys Met Phe His Ala Thr Val Ala Thr Glu Asn
    595                 600                 605
Glu Val Phe Arg Val Lys Val Phe Asn Ile Asp Leu Lys Glu Lys Phe
    610                 615                 620
Thr Pro Lys Lys Ile Ile Ala Ile Ala Asn Tyr Val Cys Arg Asn Gly
625                 630                 635                 640
Phe Leu Glu Val Tyr Pro Phe Thr Leu Val Ala Asp Val Asn Ala Asp
            645                 650                 655
Arg Asn Met Glu Ile Pro Lys Gly Leu Ile Arg Ser Ala Ser Val Thr
        660                 665                 670
Pro Lys Ile Asn Gln Leu Cys Ser Gln Thr Lys Gly Ser Phe Val Asn
    675                 680                 685
Gly Val Phe Glu Val His Lys Lys Asn Val Arg Gly Glu Phe Thr Tyr
    690                 695                 700
Tyr Glu Ile Gln Asp Asn Thr Gly Lys Met Glu Val Val His Gly
705                 710                 715                 720
Arg Leu Thr Thr Ile Asn Cys Glu Glu Gly Asp Lys Leu Lys Leu Thr
            725                 730                 735
Cys Phe Glu Leu Ala Pro Lys Ser Gly Asn Thr Gly Glu Leu Arg Ser
        740                 745                 750
Val Ile His Ser His Ile Lys Val Ile Lys Thr Arg Lys Asn Lys Lys
    755                 760                 765
```

```
Asp Ile Leu Asn Pro Asp Ser Ser Met Glu Thr Ser Pro Asp Phe Phe
        770                 775                 780

Phe
785

<210> SEQ ID NO 17
<211> LENGTH: 166
<212> TYPE: PRT
<213> ORGANISM: Homo sapiens
<300> PUBLICATION INFORMATION:
<308> DATABASE ACCESSION NUMBER: UniProt / P17803
<309> DATABASE ENTRY DATE: 2015-07-22
<313> RELEVANT RESIDUES IN SEQ ID NO: (1)..(166)

<400> SEQUENCE: 17

Met Ser Tyr Thr Thr Tyr Phe Leu Ala Phe Gln Leu Cys Val Thr Leu
1               5                   10                  15

Cys Phe Ser Gly Ser Tyr Cys Gln Ala Pro Phe Phe Lys Glu Ile Thr
            20                  25                  30

Ile Leu Lys Asp Tyr Phe Asn Ala Ser Thr Ser Asp Val Pro Asn Gly
        35                  40                  45

Gly Pro Leu Phe Leu Glu Ile Leu Lys Asn Trp Lys Glu Glu Ser Asp
    50                  55                  60

Lys Lys Ile Ile Gln Ser Gln Ile Val Ser Phe Tyr Phe Lys Phe Phe
65                  70                  75                  80

Glu Ile Phe Lys Asp Asn Gln Ala Ile Gln Arg Ser Met Asp Val Ile
                85                  90                  95

Lys Gln Asp Met Phe Gln Arg Phe Leu Asn Gly Ser Ser Gly Lys Leu
            100                 105                 110

Asn Asp Phe Glu Lys Leu Ile Lys Ile Pro Val Asp Asn Leu Gln Ile
        115                 120                 125

Gln Arg Lys Ala Ile Ser Glu Leu Ile Lys Val Met Asn Asp Leu Ser
    130                 135                 140

Pro Arg Ser Asn Leu Arg Lys Arg Lys Arg Ser Gln Thr Met Phe Gln
145                 150                 155                 160

Gly Gln Arg Ala Ser Lys
                165

<210> SEQ ID NO 18
<211> LENGTH: 272
<212> TYPE: PRT
<213> ORGANISM: Homo sapiens
<300> PUBLICATION INFORMATION:
<308> DATABASE ACCESSION NUMBER: UniProt / P01589
<309> DATABASE ENTRY DATE: 2015-07-22
<313> RELEVANT RESIDUES IN SEQ ID NO: (1)..(272)

<400> SEQUENCE: 18

Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
            20                  25                  30

His Ala Thr Phe Lys Ala Met Ala Tyr Lys Glu Gly Thr Met Leu Asn
        35                  40                  45

Cys Glu Cys Lys Arg Gly Phe Arg Arg Ile Lys Ser Gly Ser Leu Tyr
    50                  55                  60

Met Leu Cys Thr Gly Asn Ser Ser His Ser Ser Trp Asp Asn Gln Cys
65                  70                  75                  80
```

-continued

```
Gln Cys Thr Ser Ser Ala Thr Arg Asn Thr Thr Lys Gln Val Thr Pro
                 85                  90                  95
Gln Pro Glu Glu Gln Lys Glu Arg Lys Thr Thr Glu Met Gln Ser Pro
            100                 105                 110
Met Gln Pro Val Asp Gln Ala Ser Leu Pro Gly His Cys Arg Glu Pro
            115                 120                 125
Pro Pro Trp Glu Asn Glu Ala Thr Glu Arg Ile Tyr His Phe Val Val
        130                 135                 140
Gly Gln Met Val Tyr Tyr Gln Cys Val Gln Gly Tyr Arg Ala Leu His
145                 150                 155                 160
Arg Gly Pro Ala Glu Ser Val Cys Lys Met Thr His Gly Lys Thr Arg
                165                 170                 175
Trp Thr Gln Pro Gln Leu Ile Cys Thr Gly Glu Met Glu Thr Ser Gln
            180                 185                 190
Phe Pro Gly Glu Glu Lys Pro Gln Ala Ser Pro Glu Gly Arg Pro Glu
        195                 200                 205
Ser Glu Thr Ser Cys Leu Val Thr Thr Thr Asp Phe Gln Ile Gln Thr
    210                 215                 220
Glu Met Ala Ala Thr Met Glu Thr Ser Ile Phe Thr Thr Glu Tyr Gln
225                 230                 235                 240
Val Ala Val Ala Gly Cys Val Phe Leu Leu Ile Ser Val Leu Leu Leu
                245                 250                 255
Ser Gly Leu Thr Trp Gln Arg Arg Gln Arg Lys Ser Arg Arg Thr Ile
            260                 265                 270
```

<210> SEQ ID NO 19
<211> LENGTH: 459
<212> TYPE: PRT
<213> ORGANISM: Homo sapiens
<300> PUBLICATION INFORMATION:
<308> DATABASE ACCESSION NUMBER: UniProt / P16871
<309> DATABASE ENTRY DATE: 2015-07-22
<313> RELEVANT RESIDUES IN SEQ ID NO: (1)..(459)

<400> SEQUENCE: 19

```
Met Thr Ile Leu Gly Thr Thr Phe Gly Met Val Phe Ser Leu Leu Gln
1               5                   10                  15
Val Val Ser Gly Glu Ser Gly Tyr Ala Gln Asn Gly Asp Leu Glu Asp
            20                  25                  30
Ala Glu Leu Asp Asp Tyr Ser Phe Ser Cys Tyr Ser Gln Leu Glu Val
        35                  40                  45
Asn Gly Ser Gln His Ser Leu Thr Cys Ala Phe Glu Asp Pro Asp Val
    50                  55                  60
Asn Thr Thr Asn Leu Glu Phe Glu Ile Cys Gly Ala Leu Val Glu Val
65                  70                  75                  80
Lys Cys Leu Asn Phe Arg Lys Leu Gln Glu Ile Tyr Phe Ile Glu Thr
                85                  90                  95
Lys Lys Phe Leu Leu Ile Gly Lys Ser Asn Ile Cys Val Lys Val Gly
            100                 105                 110
Glu Lys Ser Leu Thr Cys Lys Lys Ile Asp Leu Thr Thr Ile Val Lys
        115                 120                 125
Pro Glu Ala Pro Phe Asp Leu Ser Val Ile Tyr Arg Glu Gly Ala Asn
    130                 135                 140
Asp Phe Val Val Thr Phe Asn Thr Ser His Leu Gln Lys Lys Tyr Val
145                 150                 155                 160
Lys Val Leu Met His Asp Val Ala Tyr Arg Gln Glu Lys Asp Glu Asn
```

```
                165                 170                 175
Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
    210                 215                 220

Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
            245                 250                 255

Val Ile Leu Ala Cys Val Leu Trp Lys Lys Arg Ile Lys Pro Ile Val
        260                 265                 270

Trp Pro Ser Leu Pro Asp His Lys Lys Thr Leu Glu His Leu Cys Lys
    275                 280                 285

Lys Pro Arg Lys Asn Leu Asn Val Ser Phe Asn Pro Glu Ser Phe Leu
290                 295                 300

Asp Cys Gln Ile His Arg Val Asp Asp Ile Gln Ala Arg Asp Glu Val
305                 310                 315                 320

Glu Gly Phe Leu Gln Asp Thr Phe Pro Gln Gln Leu Glu Glu Ser Glu
            325                 330                 335

Lys Gln Arg Leu Gly Gly Asp Val Gln Ser Pro Asn Cys Pro Ser Glu
        340                 345                 350

Asp Val Val Ile Thr Pro Glu Ser Phe Gly Arg Asp Ser Ser Leu Thr
    355                 360                 365

Cys Leu Ala Gly Asn Val Ser Ala Cys Asp Ala Pro Ile Leu Ser Ser
370                 375                 380

Ser Arg Ser Leu Asp Cys Arg Glu Ser Gly Lys Asn Gly Pro His Val
385                 390                 395                 400

Tyr Gln Asp Leu Leu Leu Ser Leu Gly Thr Thr Asn Ser Thr Leu Pro
            405                 410                 415

Pro Pro Phe Ser Leu Gln Ser Gly Ile Leu Thr Leu Asn Pro Val Ala
        420                 425                 430

Gln Gly Gln Pro Ile Leu Thr Ser Leu Gly Ser Asn Gln Glu Glu Ala
    435                 440                 445

Tyr Val Thr Met Ser Ser Phe Tyr Gln Asn Gln
    450                 455

<210> SEQ ID NO 20
<211> LENGTH: 110
<212> TYPE: PRT
<213> ORGANISM: Homo sapiens
<300> PUBLICATION INFORMATION:
<308> DATABASE ACCESSION NUMBER: UniProt / P01308
<309> DATABASE ENTRY DATE: 2015-07-22
<313> RELEVANT RESIDUES IN SEQ ID NO: (1)..(110)

<400> SEQUENCE: 20

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60
```

-continued

Gln Val Glu Leu Gly Gly Pro Gly Ala Gly Ser Leu Gln Pro Leu
65                  70                  75                  80

Ala Leu Glu Gly Ser Leu Gln Lys Arg Gly Ile Val Glu Cys Cys
                85                  90                  95

Thr Ser Ile Cys Ser Leu Tyr Gln Leu Glu Asn Tyr Cys Asn
            100                 105                 110

<210> SEQ ID NO 21
<211> LENGTH: 711
<212> TYPE: PRT
<213> ORGANISM: Homo sapiens
<300> PUBLICATION INFORMATION:
<308> DATABASE ACCESSION NUMBER: UniProt / Q92945
<309> DATABASE ENTRY DATE: 2015-07-22
<313> RELEVANT RESIDUES IN SEQ ID NO: (1)..(459)

<400> SEQUENCE: 21

Met Ser Asp Tyr Ser Thr Gly Gly Pro Pro Pro Gly Pro Pro Pro
1               5                   10                  15

Ala Gly Gly Gly Gly Gly Ala Gly Gly Ala Gly Gly Gly Pro Pro
                20                  25                  30

Gly Pro Pro Gly Ala Gly Asp Arg Gly Gly Gly Pro Gly Gly Gly
            35                  40                  45

Gly Pro Gly Gly Gly Ser Ala Gly Gly Pro Ser Gln Pro Pro Gly
        50                  55                  60

Gly Gly Pro Gly Ile Arg Lys Asp Ala Phe Ala Asp Ala Val Gln
65                  70                  75                  80

Ala Arg Gln Ile Ala Ala Lys Ile Gly Gly Asp Ala Ala Thr Thr Val
                85                  90                  95

Asn Asn Ser Thr Pro Asp Phe Gly Phe Gly Gly Gln Lys Arg Gln Leu
                100                 105                 110

Glu Asp Gly Asp Gln Pro Glu Ser Lys Lys Leu Ala Ser Gln Gly Asp
            115                 120                 125

Ser Ile Ser Ser Gln Leu Gly Pro Ile His Pro Pro Pro Arg Thr Ser
        130                 135                 140

Met Thr Glu Glu Tyr Arg Val Pro Asp Gly Met Val Gly Leu Ile Ile
145                 150                 155                 160

Gly Arg Gly Gly Glu Gln Ile Asn Lys Ile Gln Gln Asp Ser Gly Cys
                165                 170                 175

Lys Val Gln Ile Ser Pro Asp Ser Gly Gly Leu Pro Glu Arg Ser Val
                180                 185                 190

Ser Leu Thr Gly Ala Pro Glu Ser Val Gln Lys Ala Lys Met Met Leu
            195                 200                 205

Asp Asp Ile Val Ser Arg Gly Arg Gly Gly Pro Pro Gly Gln Phe His
        210                 215                 220

Asp Asn Ala Asn Gly Gly Gln Asn Gly Thr Val Gln Glu Ile Met Ile
225                 230                 235                 240

Pro Ala Gly Lys Ala Gly Leu Val Ile Gly Lys Gly Gly Glu Thr Ile
                245                 250                 255

Lys Gln Leu Gln Glu Arg Ala Gly Val Lys Met Ile Leu Ile Gln Asp
                260                 265                 270

Gly Ser Gln Asn Thr Asn Val Asp Lys Pro Leu Arg Ile Ile Gly Asp
            275                 280                 285

Pro Tyr Lys Val Gln Gln Ala Cys Glu Met Val Met Asp Ile Leu Arg
        290                 295                 300

-continued

```
Glu Arg Asp Gln Gly Gly Phe Gly Asp Arg Asn Glu Tyr Gly Ser Arg
305                 310                 315                 320

Ile Gly Gly Gly Ile Asp Val Pro Val Pro Arg His Ser Val Gly Val
                325                 330                 335

Val Ile Gly Arg Ser Gly Glu Met Ile Lys Lys Ile Gln Asn Asp Ala
            340                 345                 350

Gly Val Arg Ile Gln Phe Lys Gln Asp Asp Gly Thr Gly Pro Glu Lys
        355                 360                 365

Ile Ala His Ile Met Gly Pro Pro Asp Arg Cys Glu His Ala Ala Arg
    370                 375                 380

Ile Ile Asn Asp Leu Leu Gln Ser Leu Arg Ser Gly Pro Pro Gly Pro
385                 390                 395                 400

Pro Gly Gly Pro Gly Met Pro Pro Gly Arg Gly Arg Gly Arg Gly
                405                 410                 415

Gln Gly Asn Trp Gly Pro Pro Gly Gly Glu Met Thr Phe Ser Ile Pro
                420                 425                 430

Thr His Lys Cys Gly Leu Val Ile Gly Arg Gly Gly Glu Asn Val Lys
            435                 440                 445

Ala Ile Asn Gln Gln Thr Gly Ala Phe Val Glu Ile Ser Arg Gln Leu
450                 455                 460

Pro Pro Asn Gly Asp Pro Asn Phe Lys Leu Phe Ile Ile Arg Gly Ser
465                 470                 475                 480

Pro Gln Gln Ile Asp His Ala Lys Gln Leu Ile Glu Glu Lys Ile Glu
                485                 490                 495

Gly Pro Leu Cys Pro Val Gly Pro Gly Pro Gly Gly Pro Gly Pro Ala
            500                 505                 510

Gly Pro Met Gly Pro Phe Asn Pro Gly Pro Phe Asn Gln Gly Pro Pro
            515                 520                 525

Gly Ala Pro Pro His Ala Gly Gly Pro Pro His Gln Tyr Pro Pro
        530                 535                 540

Gln Gly Trp Gly Asn Thr Tyr Pro Gln Trp Gln Pro Pro Ala Pro His
545                 550                 555                 560

Asp Pro Ser Lys Ala Ala Ala Ala Ala Asp Pro Asn Ala Ala Trp
                565                 570                 575

Ala Ala Tyr Tyr Ser His Tyr Tyr Gln Gln Pro Pro Gly Pro Val Pro
            580                 585                 590

Gly Pro Ala Pro Ala Pro Ala Ala Pro Pro Ala Gln Gly Glu Pro Pro
        595                 600                 605

Gln Pro Pro Pro Thr Gly Gln Ser Asp Tyr Thr Lys Ala Trp Glu Glu
610                 615                 620

Tyr Tyr Lys Lys Ile Gly Gln Gln Pro Gln Gln Pro Gly Ala Pro Pro
625                 630                 635                 640

Gln Gln Asp Tyr Thr Lys Ala Trp Glu Glu Tyr Tyr Lys Lys Gln Ala
                645                 650                 655

Gln Val Ala Thr Gly Gly Gly Pro Gly Ala Pro Pro Gly Ser Gln Pro
            660                 665                 670

Asp Tyr Ser Ala Ala Trp Ala Glu Tyr Tyr Arg Gln Gln Ala Ala Tyr
            675                 680                 685

Tyr Gly Gln Thr Pro Gly Pro Gly Gly Pro Gln Pro Pro Thr Gln
            690                 695                 700

Gln Gly Gln Gln Gln Ala Gln
705                 710
```

-continued

```
<210> SEQ ID NO 22
<211> LENGTH: 664
<212> TYPE: PRT
<213> ORGANISM: Homo sapiens
<300> PUBLICATION INFORMATION:
<308> DATABASE ACCESSION NUMBER: UniProt / P02545
<309> DATABASE ENTRY DATE: 2015-07-22
<313> RELEVANT RESIDUES IN SEQ ID NO: (1)..(664)

<400> SEQUENCE: 22

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
                20                  25                  30

Glu Asp Leu Gln Glu Leu Asn Asp Arg Leu Ala Val Tyr Ile Asp Arg
            35                  40                  45

Val Arg Ser Leu Glu Thr Glu Asn Ala Gly Leu Arg Leu Arg Ile Thr
50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
            115                 120                 125

Ala Ala Gln Ala Arg Leu Lys Asp Leu Glu Ala Leu Leu Asn Ser Lys
130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365
```

-continued

```
Leu Asp Met Glu Ile His Ala Tyr Arg Lys Leu Leu Glu Gly Glu
    370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Ser Val Thr
                405                 410                 415

Lys Lys Arg Lys Leu Glu Ser Thr Glu Ser Arg Ser Ser Phe Ser Gln
                420                 425                 430

His Ala Arg Thr Ser Gly Arg Val Ala Val Glu Glu Val Asp Glu Glu
                435                 440                 445

Gly Lys Phe Val Arg Leu Arg Asn Lys Ser Asn Glu Asp Gln Ser Met
450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Pro Thr Asp Leu
                500                 505                 510

Val Trp Lys Ala Gln Asn Thr Trp Gly Cys Gly Asn Ser Leu Arg Thr
                515                 520                 525

Ala Leu Ile Asn Ser Thr Gly Glu Glu Val Ala Met Arg Lys Leu Val
530                 535                 540

Arg Ser Val Thr Val Val Glu Asp Asp Glu Asp Glu Asp Gly Asp Asp
545                 550                 555                 560

Leu Leu His His His His Gly Ser His Cys Ser Ser Ser Gly Asp Pro
                565                 570                 575

Ala Glu Tyr Asn Leu Arg Ser Arg Thr Val Leu Cys Gly Thr Cys Gly
                580                 585                 590

Gln Pro Ala Asp Lys Ala Ser Ala Ser Gly Ser Gly Ala Gln Val Gly
                595                 600                 605

Gly Pro Ile Ser Ser Gly Ser Ser Ala Ser Ser Val Thr Val Thr Arg
                610                 615                 620

Ser Tyr Arg Ser Val Gly Gly Ser Gly Gly Gly Ser Phe Gly Asp Asn
625                 630                 635                 640

Leu Val Thr Arg Ser Tyr Leu Leu Gly Asn Ser Ser Pro Arg Thr Gln
                645                 650                 655

Ser Pro Gln Asn Cys Ser Ile Met
                660
```

<210> SEQ ID NO 23
<211> LENGTH: 586
<212> TYPE: PRT
<213> ORGANISM: Homo sapiens
<300> PUBLICATION INFORMATION:
<308> DATABASE ACCESSION NUMBER: UniProt / P20700
<309> DATABASE ENTRY DATE: 2015-07-22
<313> RELEVANT RESIDUES IN SEQ ID NO: (1)..(586)

<400> SEQUENCE: 23

```
Met Ala Thr Ala Thr Pro Val Pro Pro Arg Met Gly Ser Arg Ala Gly
1               5                   10                  15

Gly Pro Thr Thr Pro Leu Ser Pro Thr Arg Leu Ser Arg Leu Gln Glu
                20                  25                  30

Lys Glu Glu Leu Arg Glu Leu Asn Asp Arg Leu Ala Val Tyr Ile Asp
                35                  40                  45
```

```
Lys Val Arg Ser Leu Glu Thr Glu Asn Ser Ala Leu Gln Leu Gln Val
 50                  55                  60

Thr Glu Arg Glu Val Arg Gly Arg Glu Leu Thr Gly Leu Lys Ala
 65                  70                  75                  80

Leu Tyr Glu Thr Glu Leu Ala Asp Ala Arg Arg Ala Leu Asp Asp Thr
                 85                  90                  95

Ala Arg Glu Arg Ala Lys Leu Gln Ile Glu Leu Gly Lys Cys Lys Ala
                100                 105                 110

Glu His Asp Gln Leu Leu Leu Asn Tyr Ala Lys Lys Glu Ser Asp Leu
                115                 120                 125

Asn Gly Ala Gln Ile Lys Leu Arg Glu Tyr Glu Ala Ala Leu Asn Ser
            130                 135                 140

Lys Asp Ala Ala Leu Ala Thr Ala Leu Gly Asp Lys Lys Ser Leu Glu
145                 150                 155                 160

Gly Asp Leu Glu Asp Leu Lys Asp Gln Ile Ala Gln Leu Glu Ala Ser
                165                 170                 175

Leu Ala Ala Ala Lys Lys Gln Leu Ala Asp Glu Thr Leu Leu Lys Val
                180                 185                 190

Asp Leu Glu Asn Arg Cys Gln Ser Leu Thr Glu Asp Leu Glu Phe Arg
            195                 200                 205

Lys Ser Met Tyr Glu Glu Ile Asn Glu Thr Arg Arg Lys His Glu
210                 215                 220

Thr Arg Leu Val Glu Val Asp Ser Gly Arg Gln Ile Glu Tyr Glu Tyr
225                 230                 235                 240

Lys Leu Ala Gln Ala Leu His Glu Met Arg Glu Gln His Asp Ala Gln
                245                 250                 255

Val Arg Leu Tyr Lys Glu Glu Leu Glu Gln Thr Tyr His Ala Lys Leu
            260                 265                 270

Glu Asn Ala Arg Leu Ser Ser Glu Met Asn Thr Ser Thr Val Asn Ser
            275                 280                 285

Ala Arg Glu Glu Leu Met Glu Ser Arg Met Arg Ile Glu Ser Leu Ser
            290                 295                 300

Ser Gln Leu Ser Asn Leu Gln Lys Glu Ser Arg Ala Cys Leu Glu Arg
305                 310                 315                 320

Ile Gln Glu Leu Glu Asp Leu Leu Ala Lys Glu Lys Asp Asn Ser Arg
                325                 330                 335

Arg Met Leu Thr Asp Lys Glu Arg Glu Met Ala Glu Ile Arg Asp Gln
            340                 345                 350

Met Gln Gln Leu Asn Asp Tyr Glu Gln Leu Leu Asp Val Lys Leu
            355                 360                 365

Ala Leu Asp Met Glu Ile Ser Ala Tyr Arg Lys Leu Leu Glu Gly Glu
370                 375                 380

Glu Glu Arg Leu Lys Leu Ser Pro Ser Pro Ser Ser Arg Val Thr Val
385                 390                 395                 400

Ser Arg Ala Ser Ser Ser Arg Ser Val Arg Thr Thr Arg Gly Lys Arg
                405                 410                 415

Lys Arg Val Asp Val Glu Glu Ser Glu Ala Ser Ser Val Ser Ile
            420                 425                 430

Ser His Ser Ala Ser Ala Thr Gly Asn Val Cys Ile Glu Glu Ile Asp
            435                 440                 445

Val Asp Gly Lys Phe Ile Arg Leu Lys Asn Thr Ser Glu Gln Asp Gln
450                 455                 460

Pro Met Gly Gly Trp Glu Met Ile Arg Lys Ile Gly Asp Thr Ser Val
```

```
            465                 470                 475                 480

Ser Tyr Lys Tyr Thr Ser Arg Tyr Val Leu Lys Ala Gly Gln Thr Val
                    485                 490                 495

Thr Ile Trp Ala Ala Asn Ala Gly Val Thr Ala Ser Pro Pro Thr Asp
                    500                 505                 510

Leu Ile Trp Lys Asn Gln Asn Ser Trp Gly Thr Gly Glu Asp Val Lys
                    515                 520                 525

Val Ile Leu Lys Asn Ser Gln Gly Glu Glu Val Ala Gln Arg Ser Thr
                    530                 535                 540

Val Phe Lys Thr Thr Ile Pro Glu Glu Glu Glu Glu Glu Glu Glu Ala
    545                 550                 555                 560

Ala Gly Val Val Val Glu Glu Glu Leu Phe His Gln Gln Gly Thr Pro
                    565                 570                 575

Arg Ala Ser Asn Arg Ser Cys Ala Ile Met
                    580                 585

<210> SEQ ID NO 24
<211> LENGTH: 923
<212> TYPE: PRT
<213> ORGANISM: Homo sapiens
<300> PUBLICATION INFORMATION:
<308> DATABASE ACCESSION NUMBER: UniProt / O14786
<309> DATABASE ENTRY DATE: 2015-07-22
<313> RELEVANT RESIDUES IN SEQ ID NO: (1)..(923)

<400> SEQUENCE: 24

Met Glu Arg Gly Leu Pro Leu Leu Cys Ala Val Leu Ala Leu Val Leu
    1               5                   10                  15

Ala Pro Ala Gly Ala Phe Arg Asn Asp Lys Cys Gly Asp Thr Ile Lys
                    20                  25                  30

Ile Glu Ser Pro Gly Tyr Leu Thr Ser Pro Gly Tyr Pro His Ser Tyr
                    35                  40                  45

His Pro Ser Glu Lys Cys Glu Trp Leu Ile Gln Ala Pro Asp Pro Tyr
                    50                  55                  60

Gln Arg Ile Met Ile Asn Phe Asn Pro His Phe Asp Leu Glu Asp Arg
    65                  70                  75                  80

Asp Cys Lys Tyr Asp Tyr Val Glu Val Phe Asp Gly Glu Asn Glu Asn
                    85                  90                  95

Gly His Phe Arg Gly Lys Phe Cys Gly Lys Ile Ala Pro Pro Pro Val
                    100                 105                 110

Val Ser Ser Gly Pro Phe Leu Phe Ile Lys Phe Val Ser Asp Tyr Glu
                    115                 120                 125

Thr His Gly Ala Gly Phe Ser Ile Arg Tyr Glu Ile Phe Lys Arg Gly
                    130                 135                 140

Pro Glu Cys Ser Gln Asn Tyr Thr Thr Pro Ser Gly Val Ile Lys Ser
    145                 150                 155                 160

Pro Gly Phe Pro Glu Lys Tyr Pro Asn Ser Leu Glu Cys Thr Tyr Ile
                    165                 170                 175

Val Phe Val Pro Lys Met Ser Glu Ile Ile Leu Glu Phe Glu Ser Phe
                    180                 185                 190

Asp Leu Glu Pro Asp Ser Asn Pro Pro Gly Gly Met Phe Cys Arg Tyr
                    195                 200                 205

Asp Arg Leu Glu Ile Trp Asp Gly Phe Pro Asp Val Gly Pro His Ile
                    210                 215                 220

Gly Arg Tyr Cys Gly Gln Lys Thr Pro Gly Arg Ile Arg Ser Ser Ser
    225                 230                 235                 240
```

-continued

```
Gly Ile Leu Ser Met Val Phe Tyr Thr Asp Ser Ala Ile Ala Lys Glu
                245                 250                 255
Gly Phe Ser Ala Asn Tyr Ser Val Leu Gln Ser Ser Val Ser Glu Asp
                260                 265                 270
Phe Lys Cys Met Glu Ala Leu Gly Met Glu Ser Gly Ile His Ser
                275                 280                 285
Asp Gln Ile Thr Ala Ser Ser Gln Tyr Ser Thr Asn Trp Ser Ala Glu
                290                 295                 300
Arg Ser Arg Leu Asn Tyr Pro Glu Asn Gly Trp Thr Pro Gly Glu Asp
305                 310                 315                 320
Ser Tyr Arg Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
                340                 345                 350
Tyr Tyr Val Lys Thr Tyr Lys Ile Asp Val Ser Ser Asn Gly Glu Asp
                355                 360                 365
Trp Ile Thr Ile Lys Glu Gly Asn Lys Pro Val Leu Phe Gln Gly Asn
                370                 375                 380
Thr Asn Pro Thr Asp Val Val Ala Val Phe Pro Lys Pro Leu Ile
385                 390                 395                 400
Thr Arg Phe Val Arg Ile Lys Pro Ala Thr Trp Glu Thr Gly Ile Ser
                405                 410                 415
Met Arg Phe Glu Val Tyr Gly Cys Lys Ile Thr Asp Tyr Pro Cys Ser
                420                 425                 430
Gly Met Leu Gly Met Val Ser Gly Leu Ile Ser Asp Ser Gln Ile Thr
                435                 440                 445
Ser Ser Asn Gln Gly Asp Arg Asn Trp Met Pro Glu Asn Ile Arg Leu
                450                 455                 460
Val Thr Ser Arg Ser Gly Trp Ala Leu Pro Pro Ala Pro His Ser Tyr
465                 470                 475                 480
Ile Asn Glu Trp Leu Gln Ile Asp Leu Gly Glu Glu Lys Ile Val Arg
                485                 490                 495
Gly Ile Ile Ile Gln Gly Gly Lys His Arg Glu Asn Lys Val Phe Met
                500                 505                 510
Arg Lys Phe Lys Ile Gly Tyr Ser Asn Asn Gly Ser Asp Trp Lys Met
                515                 520                 525
Ile Met Asp Asp Ser Lys Arg Lys Ala Lys Ser Phe Glu Gly Asn Asn
530                 535                 540
Asn Tyr Asp Thr Pro Glu Leu Arg Thr Phe Pro Ala Leu Ser Thr Arg
545                 550                 555                 560
Phe Ile Arg Ile Tyr Pro Glu Arg Ala Thr His Gly Gly Leu Gly Leu
                565                 570                 575
Arg Met Glu Leu Leu Gly Cys Glu Val Glu Ala Pro Thr Ala Gly Pro
                580                 585                 590
Thr Thr Pro Asn Gly Asn Leu Val Asp Glu Cys Asp Asp Gln Ala
                595                 600                 605
Asn Cys His Ser Gly Thr Gly Asp Asp Phe Gln Leu Thr Gly Gly Thr
                610                 615                 620
Thr Val Leu Ala Thr Glu Lys Pro Thr Val Ile Asp Ser Thr Ile Gln
625                 630                 635                 640
Ser Glu Phe Pro Thr Tyr Gly Phe Asn Cys Glu Phe Gly Trp Gly Ser
                645                 650                 655
```

His Lys Thr Phe Cys His Trp Glu His Asp Asn His Val Gln Leu Lys
                660                 665                 670

Trp Ser Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
    690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Ala Ile Gly His Gln Gly Asp His Trp Lys Glu Gly Arg Val
        755                 760                 765

Leu Leu His Lys Ser Leu Lys Leu Tyr Gln Val Ile Phe Glu Gly Glu
    770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
            820                 825                 830

Tyr Glu Gly Glu Gly Glu Asp Lys Asn Ile Ser Arg Lys Pro Gly
        835                 840                 845

Asn Val Leu Lys Thr Leu Asp Pro Ile Leu Ile Thr Ile Ala Met
850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
            900                 905                 910

Lys Leu Asn Thr Gln Ser Thr Tyr Ser Glu Ala
        915                 920

<210> SEQ ID NO 25
<211> LENGTH: 441
<212> TYPE: PRT
<213> ORGANISM: Homo sapiens
<300> PUBLICATION INFORMATION:
<308> DATABASE ACCESSION NUMBER: UniProt / Q9BXS6
<309> DATABASE ENTRY DATE: 2015-07-22
<313> RELEVANT RESIDUES IN SEQ ID NO: (1)..(441)

<400> SEQUENCE: 25

Met Ile Ile Pro Ser Leu Glu Glu Leu Asp Ser Leu Lys Tyr Ser Asp
1               5                   10                  15

Leu Gln Asn Leu Ala Lys Ser Leu Gly Leu Arg Ala Asn Leu Arg Ala
            20                  25                  30

Thr Lys Leu Leu Lys Ala Leu Lys Gly Tyr Ile Lys His Glu Ala Arg
        35                  40                  45

Lys Gly Asn Glu Asn Gln Asp Glu Ser Gln Thr Ser Ala Ser Ser Cys
    50                  55                  60

Asp Glu Thr Glu Ile Gln Ile Ser Asn Gln Glu Glu Ala Glu Arg Gln
65                  70                  75                  80

Pro Leu Gly His Val Thr Lys Thr Arg Arg Arg Cys Lys Thr Val Arg 85                  90                  95
Val Asp Pro Asp Ser Gln Gln Asn His Ser Glu Ile Lys Ile Ser Asn
                100                 105                 110

Pro Thr Glu Phe Gln Asn His Glu Lys Gln Glu Ser Gln Asp Leu Arg
            115                 120                 125

Ala Thr Ala Lys Val Pro Ser Pro Asp Glu His Gln Glu Ala Glu
        130                 135                 140

Asn Ala Val Ser Ser Gly Asn Arg Asp Ser Lys Val Pro Ser Glu Gly
145                 150                 155                 160

Lys Lys Ser Leu Tyr Thr Asp Glu Ser Ser Lys Pro Gly Lys Asn Lys
                165                 170                 175

Arg Thr Ala Ile Thr Thr Pro Asn Phe Lys Lys Leu His Glu Ala His
                180                 185                 190

Phe Lys Glu Met Glu Ser Ile Asp Gln Tyr Ile Glu Arg Lys Lys Lys
            195                 200                 205

His Phe Glu Glu His Asn Ser Met Asn Glu Leu Lys Gln Gln Pro Ile
        210                 215                 220

Asn Lys Gly Gly Val Arg Thr Pro Val Pro Arg Gly Arg Leu Ser
225                 230                 235                 240

Val Ala Ser Thr Pro Ile Ser Gln Arg Arg Ser Gln Gly Arg Ser Cys
                245                 250                 255

Gly Pro Ala Ser Gln Ser Thr Leu Gly Leu Lys Gly Ser Leu Lys Arg
                260                 265                 270

Ser Ala Ile Ser Ala Ala Lys Thr Gly Val Arg Phe Ser Ala Ala Thr
            275                 280                 285

Lys Asp Asn Glu His Lys Arg Ser Leu Thr Lys Thr Pro Ala Arg Lys
        290                 295                 300

Ser Ala His Val Thr Val Ser Gly Gly Thr Pro Lys Gly Glu Ala Val
305                 310                 315                 320

Leu Gly Thr His Lys Leu Lys Thr Ile Thr Gly Asn Ser Ala Ala Val
                325                 330                 335

Ile Thr Pro Phe Lys Leu Thr Thr Glu Ala Thr Gln Thr Pro Val Ser
                340                 345                 350

Asn Lys Lys Pro Val Phe Asp Leu Lys Ala Ser Leu Ser Arg Pro Leu
            355                 360                 365

Asn Tyr Glu Pro His Lys Gly Lys Leu Lys Pro Trp Gly Gln Ser Lys
        370                 375                 380

Glu Asn Asn Tyr Leu Asn Gln His Val Asn Arg Ile Asn Phe Tyr Lys
385                 390                 395                 400

Lys Thr Tyr Lys Gln Pro His Leu Gln Thr Lys Glu Glu Arg Lys
                405                 410                 415

Lys Arg Glu Gln Glu Arg Lys Glu Lys Ala Lys Val Leu Gly Met
            420                 425                 430

Arg Arg Gly Leu Ile Leu Ala Glu Asp
        435                 440

<210> SEQ ID NO 26
<211> LENGTH: 394
<212> TYPE: PRT
<213> ORGANISM: Homo sapiens
<300> PUBLICATION INFORMATION:
<308> DATABASE ACCESSION NUMBER: UniProt / Q9UQ80
<309> DATABASE ENTRY DATE: 2015-07-22
<313> RELEVANT RESIDUES IN SEQ ID NO: (1)..(394)

<400> SEQUENCE: 26

```
Met Ser Gly Glu Asp Glu Gln Gln Glu Gln Thr Ile Ala Glu Asp Leu
1               5                   10                  15

Val Val Thr Lys Tyr Lys Met Gly Gly Asp Ile Ala Asn Arg Val Leu
            20                  25                  30

Arg Ser Leu Val Glu Ala Ser Ser Gly Val Ser Val Leu Ser Leu
        35                  40                  45

Cys Glu Lys Gly Asp Ala Met Ile Met Glu Glu Thr Gly Lys Ile Phe
    50                  55                  60

Lys Lys Glu Lys Glu Met Lys Lys Gly Ile Ala Phe Pro Thr Ser Ile
65                  70                  75                  80

Ser Val Asn Asn Cys Val Cys His Phe Ser Pro Leu Lys Ser Asp Gln
            85                  90                  95

Asp Tyr Ile Leu Lys Glu Gly Asp Leu Val Lys Ile Asp Leu Gly Val
            100                 105                 110

His Val Asp Gly Phe Ile Ala Asn Val Ala His Thr Phe Val Val Asp
            115                 120                 125

Val Ala Gln Gly Thr Gln Val Thr Gly Arg Lys Ala Asp Val Ile Lys
        130                 135                 140

Ala Ala His Leu Cys Ala Glu Ala Ala Leu Arg Leu Val Lys Pro Gly
145                 150                 155                 160

Asn Gln Asn Thr Gln Val Thr Glu Ala Trp Asn Lys Val Ala His Ser
                165                 170                 175

Phe Asn Cys Thr Pro Ile Glu Gly Met Leu Ser His Gln Leu Lys Gln
            180                 185                 190

His Val Ile Asp Gly Glu Lys Thr Ile Ile Gln Asn Pro Thr Asp Gln
            195                 200                 205

Gln Lys Lys Asp His Glu Lys Ala Glu Phe Glu Val His Glu Val Tyr
        210                 215                 220

Ala Val Asp Val Leu Val Ser Ser Gly Glu Gly Lys Ala Lys Asp Ala
225                 230                 235                 240

Gly Gln Arg Thr Thr Ile Tyr Lys Arg Asp Pro Ser Lys Gln Tyr Gly
                245                 250                 255

Leu Lys Met Lys Thr Ser Arg Ala Phe Phe Ser Glu Val Glu Arg Arg
                260                 265                 270

Phe Asp Ala Met Pro Phe Thr Leu Arg Ala Phe Glu Asp Glu Lys Lys
            275                 280                 285

Ala Arg Met Gly Val Val Glu Cys Ala Lys His Glu Leu Leu Gln Pro
            290                 295                 300

Phe Asn Val Leu Tyr Glu Lys Glu Gly Glu Phe Val Ala Gln Phe Lys
305                 310                 315                 320

Phe Thr Val Leu Leu Met Pro Asn Gly Pro Met Arg Ile Thr Ser Gly
                325                 330                 335

Pro Phe Glu Pro Asp Leu Tyr Lys Ser Glu Met Glu Val Gln Asp Ala
            340                 345                 350

Glu Leu Lys Ala Leu Leu Gln Ser Ala Ser Arg Lys Thr Gln Lys
                355                 360                 365

Lys Lys Lys Lys Ala Ser Lys Thr Ala Glu Asn Ala Thr Ser Gly
    370                 375                 380

Glu Thr Leu Glu Glu Asn Glu Ala Gly Asp
385                 390

<210> SEQ ID NO 27
<211> LENGTH: 198
```

<212> TYPE: PRT
<213> ORGANISM: Homo sapiens
<300> PUBLICATION INFORMATION:
<308> DATABASE ACCESSION NUMBER: UniProt / P32119
<309> DATABASE ENTRY DATE: 2015-07-22
<313> RELEVANT RESIDUES IN SEQ ID NO: (1)..(198)

<400> SEQUENCE: 27

```
Met Ala Ser Gly Asn Ala Arg Ile Gly Lys Pro Ala Pro Asp Phe Lys
1               5                   10                  15

Ala Thr Ala Val Val Asp Gly Ala Phe Lys Glu Val Lys Leu Ser Asp
            20                  25                  30

Tyr Lys Gly Lys Tyr Val Val Leu Phe Phe Tyr Pro Leu Asp Phe Thr
        35                  40                  45

Phe Val Cys Pro Thr Glu Ile Ile Ala Phe Ser Asn Arg Ala Glu Asp
50                  55                  60

Phe Arg Lys Leu Gly Cys Glu Val Leu Gly Val Ser Val Asp Ser Gln
65                  70                  75                  80

Phe Thr His Leu Ala Trp Ile Asn Thr Pro Arg Lys Glu Gly Gly Leu
                85                  90                  95

Gly Pro Leu Asn Ile Pro Leu Leu Ala Asp Val Thr Arg Arg Leu Ser
            100                 105                 110

Glu Asp Tyr Gly Val Leu Lys Thr Asp Glu Gly Ile Ala Tyr Arg Gly
        115                 120                 125

Leu Phe Ile Ile Asp Gly Lys Gly Val Leu Arg Gln Ile Thr Val Asn
130                 135                 140

Asp Leu Pro Val Gly Arg Ser Val Asp Glu Ala Leu Arg Leu Val Gln
145                 150                 155                 160

Ala Phe Gln Tyr Thr Asp Glu His Gly Glu Val Cys Pro Ala Gly Trp
                165                 170                 175

Lys Pro Gly Ser Asp Thr Ile Lys Pro Asn Val Asp Asp Ser Lys Glu
            180                 185                 190

Tyr Phe Ser Lys His Asn
        195
```

<210> SEQ ID NO 28
<211> LENGTH: 592
<212> TYPE: PRT
<213> ORGANISM: Homo sapiens
<300> PUBLICATION INFORMATION:
<308> DATABASE ACCESSION NUMBER: UniProt / Q05513
<309> DATABASE ENTRY DATE: 2015-07-22
<313> RELEVANT RESIDUES IN SEQ ID NO: (1)..(592)

<400> SEQUENCE: 28

```
Met Pro Ser Arg Thr Gly Pro Lys Met Glu Gly Ser Gly Gly Arg Val
1               5                   10                  15

Arg Leu Lys Ala His Tyr Gly Gly Asp Ile Phe Ile Thr Ser Val Asp
            20                  25                  30

Ala Ala Thr Thr Phe Glu Glu Leu Cys Glu Glu Val Arg Asp Met Cys
        35                  40                  45

Arg Leu His Gln Gln His Pro Leu Thr Leu Lys Trp Val Asp Ser Glu
50                  55                  60

Gly Asp Pro Cys Thr Val Ser Ser Gln Met Glu Leu Glu Glu Ala Phe
65                  70                  75                  80

Arg Leu Ala Arg Gln Cys Arg Asp Glu Gly Leu Ile Ile His Val Phe
                85                  90                  95

Pro Ser Thr Pro Glu Gln Pro Gly Leu Pro Cys Pro Gly Glu Asp Lys
```

```
                100                 105                 110
Ser Ile Tyr Arg Arg Gly Ala Arg Arg Trp Arg Lys Leu Tyr Arg Ala
            115                 120                 125

Asn Gly His Leu Phe Gln Ala Lys Arg Phe Asn Arg Arg Ala Tyr Cys
130                 135                 140

Gly Gln Cys Ser Glu Arg Ile Trp Gly Leu Ala Arg Gln Gly Tyr Arg
145                 150                 155                 160

Cys Ile Asn Cys Lys Leu Leu Val His Lys Arg Cys His Gly Leu Val
                165                 170                 175

Pro Leu Thr Cys Arg Lys His Met Asp Ser Val Met Pro Ser Gln Glu
            180                 185                 190

Pro Pro Val Asp Asp Lys Asn Glu Asp Ala Asp Leu Pro Ser Glu Glu
        195                 200                 205

Thr Asp Gly Ile Ala Tyr Ile Ser Ser Ser Arg Lys His Asp Ser Ile
    210                 215                 220

Lys Asp Asp Ser Glu Asp Leu Lys Pro Val Ile Asp Gly Met Asp Gly
225                 230                 235                 240

Ile Lys Ile Ser Gln Gly Leu Gly Leu Gln Asp Phe Asp Leu Ile Arg
                245                 250                 255

Val Ile Gly Arg Gly Ser Tyr Ala Lys Val Leu Leu Val Arg Leu Lys
            260                 265                 270

Lys Asn Asp Gln Ile Tyr Ala Met Lys Val Val Lys Lys Glu Leu Val
        275                 280                 285

His Asp Asp Glu Asp Ile Asp Trp Val Gln Thr Glu Lys His Val Phe
    290                 295                 300

Glu Gln Ala Ser Ser Asn Pro Phe Leu Val Gly Leu His Ser Cys Phe
305                 310                 315                 320

Gln Thr Thr Ser Arg Leu Phe Leu Val Ile Glu Tyr Val Asn Gly Gly
                325                 330                 335

Asp Leu Met Phe His Met Gln Arg Gln Arg Lys Leu Pro Glu Glu His
            340                 345                 350

Ala Arg Phe Tyr Ala Ala Glu Ile Cys Ile Ala Leu Asn Phe Leu His
        355                 360                 365

Glu Arg Gly Ile Ile Tyr Arg Asp Leu Lys Leu Asp Asn Val Leu Leu
    370                 375                 380

Asp Ala Asp Gly His Ile Lys Leu Thr Asp Tyr Gly Met Cys Lys Glu
385                 390                 395                 400

Gly Leu Gly Pro Gly Asp Thr Thr Ser Thr Phe Cys Gly Thr Pro Asn
                405                 410                 415

Tyr Ile Ala Pro Glu Ile Leu Arg Gly Glu Glu Tyr Gly Phe Ser Val
            420                 425                 430

Asp Trp Trp Ala Leu Gly Val Leu Met Phe Glu Met Met Ala Gly Arg
        435                 440                 445

Ser Pro Phe Asp Ile Ile Thr Asp Asn Pro Asp Met Asn Thr Glu Asp
    450                 455                 460

Tyr Leu Phe Gln Val Ile Leu Glu Lys Pro Ile Arg Ile Pro Arg Phe
465                 470                 475                 480

Leu Ser Val Lys Ala Ser His Val Leu Lys Gly Phe Leu Asn Lys Asp
                485                 490                 495

Pro Lys Glu Arg Leu Gly Cys Arg Pro Gln Thr Gly Phe Ser Asp Ile
            500                 505                 510

Lys Ser His Ala Phe Phe Arg Ser Ile Asp Trp Asp Leu Leu Glu Lys
        515                 520                 525
```

-continued

```
Lys Gln Ala Leu Pro Pro Phe Gln Pro Gln Ile Thr Asp Asp Tyr Gly
            530                 535                 540

Leu Asp Asn Phe Asp Thr Gln Phe Thr Ser Glu Pro Val Gln Leu Thr
545                 550                 555                 560

Pro Asp Asp Glu Asp Ala Ile Lys Arg Ile Asp Gln Ser Glu Phe Glu
                565                 570                 575

Gly Phe Glu Tyr Ile Asn Pro Leu Leu Leu Ser Thr Glu Glu Ser Val
            580                 585                 590
```

<210> SEQ ID NO 29
<211> LENGTH: 256
<212> TYPE: PRT
<213> ORGANISM: Homo sapiens
<300> PUBLICATION INFORMATION:
<308> DATABASE ACCESSION NUMBER: UniProt / Q9NP55
<309> DATABASE ENTRY DATE: 2015-07-22
<313> RELEVANT RESIDUES IN SEQ ID NO: (1)..(256)

<400> SEQUENCE: 29

```
Met Phe Gln Thr Gly Gly Leu Ile Val Phe Tyr Gly Leu Leu Ala Gln
1               5                   10                  15

Thr Met Ala Gln Phe Gly Gly Leu Pro Val Pro Leu Asp Gln Thr Leu
            20                  25                  30

Pro Leu Asn Val Asn Pro Ala Leu Pro Leu Ser Pro Thr Gly Leu Ala
        35                  40                  45

Gly Ser Leu Thr Asn Ala Leu Ser Asn Gly Leu Leu Ser Gly Gly Leu
    50                  55                  60

Leu Gly Ile Leu Glu Asn Leu Pro Leu Leu Asp Ile Leu Lys Pro Gly
65                  70                  75                  80

Gly Gly Thr Ser Gly Gly Leu Leu Gly Gly Leu Leu Gly Lys Val Thr
                85                  90                  95

Ser Val Ile Pro Gly Leu Asn Asn Ile Ile Asp Ile Lys Val Thr Asp
            100                 105                 110

Pro Gln Leu Leu Glu Leu Gly Leu Val Gln Ser Pro Asp Gly His Arg
        115                 120                 125

Leu Tyr Val Thr Ile Pro Leu Gly Ile Lys Leu Gln Val Asn Thr Pro
    130                 135                 140

Leu Val Gly Ala Ser Leu Leu Arg Leu Ala Val Lys Leu Asp Ile Thr
145                 150                 155                 160

Ala Glu Ile Leu Ala Val Arg Asp Lys Gln Glu Arg Ile His Leu Val
                165                 170                 175

Leu Gly Asp Cys Thr His Ser Pro Gly Ser Leu Gln Ile Ser Leu Leu
            180                 185                 190

Asp Gly Leu Gly Pro Leu Pro Ile Gln Gly Leu Leu Asp Ser Leu Thr
        195                 200                 205

Gly Ile Leu Asn Lys Val Leu Pro Glu Leu Val Gln Gly Asn Val Cys
    210                 215                 220

Pro Leu Val Asn Glu Val Leu Arg Gly Leu Asp Ile Thr Leu Val His
225                 230                 235                 240

Asp Ile Val Asn Met Leu Ile His Gly Leu Gln Phe Val Ile Lys Val
                245                 250                 255
```

<210> SEQ ID NO 30
<211> LENGTH: 418
<212> TYPE: PRT
<213> ORGANISM: Homo sapiens
<300> PUBLICATION INFORMATION:

<308> DATABASE ACCESSION NUMBER: UniProt / P43686
<309> DATABASE ENTRY DATE: 2015-07-22
<313> RELEVANT RESIDUES IN SEQ ID NO: (1)..(418)

<400> SEQUENCE: 30

```
Met Glu Glu Ile Gly Ile Leu Val Lys Ala Gln Asp Glu Ile Pro
1               5                   10                  15

Ala Leu Ser Val Ser Arg Pro Gln Thr Gly Leu Ser Phe Leu Gly Pro
                20                  25                  30

Glu Pro Glu Asp Leu Glu Asp Leu Tyr Ser Arg Tyr Lys Lys Leu Gln
            35                  40                  45

Gln Glu Leu Glu Phe Leu Glu Val Gln Glu Glu Tyr Ile Lys Asp Glu
50                  55                  60

Gln Lys Asn Leu Lys Lys Glu Phe Leu His Ala Gln Glu Glu Val Lys
65                  70                  75                  80

Arg Ile Gln Ser Ile Pro Leu Val Ile Gly Gln Phe Leu Glu Ala Val
                85                  90                  95

Asp Gln Asn Thr Ala Ile Val Gly Ser Thr Thr Gly Ser Asn Tyr Tyr
            100                 105                 110

Val Arg Ile Leu Ser Thr Ile Asp Arg Glu Leu Leu Lys Pro Asn Ala
        115                 120                 125

Ser Val Ala Leu His Lys His Ser Asn Ala Leu Val Asp Val Leu Pro
    130                 135                 140

Pro Glu Ala Asp Ser Ser Ile Met Met Leu Thr Ser Asp Gln Lys Pro
145                 150                 155                 160

Asp Val Met Tyr Ala Asp Ile Gly Gly Met Asp Ile Gln Lys Gln Glu
                165                 170                 175

Val Arg Glu Ala Val Glu Leu Pro Leu Thr His Phe Glu Leu Tyr Lys
            180                 185                 190

Gln Ile Gly Ile Asp Pro Pro Arg Gly Val Leu Met Tyr Gly Pro Pro
        195                 200                 205

Gly Cys Gly Lys Thr Met Leu Ala Lys Ala Val Ala His His Thr Thr
210                 215                 220

Ala Ala Phe Ile Arg Val Val Gly Ser Glu Phe Val Gln Lys Tyr Leu
225                 230                 235                 240

Gly Glu Gly Pro Arg Met Val Arg Asp Val Phe Arg Leu Ala Lys Glu
                245                 250                 255

Asn Ala Pro Ala Ile Ile Phe Ile Asp Glu Ile Asp Ala Ile Ala Thr
            260                 265                 270

Lys Arg Phe Asp Ala Gln Thr Gly Ala Asp Arg Glu Val Gln Arg Ile
        275                 280                 285

Leu Leu Glu Leu Leu Asn Gln Met Asp Gly Phe Asp Gln Asn Val Asn
290                 295                 300

Val Lys Val Ile Met Ala Thr Asn Arg Ala Asp Thr Leu Asp Pro Ala
305                 310                 315                 320

Leu Leu Arg Pro Gly Arg Leu Asp Arg Lys Ile Glu Phe Pro Leu Pro
                325                 330                 335

Asp Arg Arg Gln Lys Arg Leu Ile Phe Ser Thr Ile Thr Ser Lys Met
            340                 345                 350

Asn Leu Ser Glu Glu Val Asp Leu Glu Asp Tyr Val Ala Arg Pro Asp
        355                 360                 365

Lys Ile Ser Gly Ala Asp Ile Asn Ser Ile Cys Gln Glu Ser Gly Met
370                 375                 380

Leu Ala Val Arg Glu Asn Arg Tyr Ile Val Leu Ala Lys Asp Phe Glu
```

-continued

```
                385                 390                 395                 400
Lys Ala Tyr Lys Thr Val Ile Lys Lys Asp Glu Gln Glu His Glu Phe
                    405                 410                 415
Tyr Lys

<210> SEQ ID NO 31
<211> LENGTH: 979
<212> TYPE: PRT
<213> ORGANISM: Homo sapiens
<300> PUBLICATION INFORMATION:
<308> DATABASE ACCESSION NUMBER: UniProt / Q16849
<309> DATABASE ENTRY DATE: 2015-07-22
<313> RELEVANT RESIDUES IN SEQ ID NO: (1)..(979)

<400> SEQUENCE: 31

Met Arg Arg Pro Arg Pro Gly Gly Leu Gly Gly Ser Gly Gly Leu
1               5                   10                  15

Arg Leu Leu Leu Cys Leu Leu Leu Ser Ser Arg Pro Gly Gly Cys
                    20                  25                  30

Ser Ala Val Ser Ala His Gly Cys Leu Phe Asp Arg Arg Leu Cys Ser
                35                  40                  45

His Leu Glu Val Cys Ile Gln Asp Gly Leu Phe Gly Gln Cys Gln Val
    50                  55                  60

Gly Val Gly Gln Ala Arg Pro Leu Leu Gln Val Thr Ser Pro Val Leu
65                  70                  75                  80

Gln Arg Leu Gln Gly Val Leu Arg Gln Leu Met Ser Gln Gly Leu Ser
                    85                  90                  95

Trp His Asp Asp Leu Thr Gln Tyr Val Ile Ser Gln Glu Met Glu Arg
                100                 105                 110

Ile Pro Arg Leu Arg Pro Pro Glu Pro Arg Pro Arg Asp Arg Ser Gly
                115                 120                 125

Leu Ala Pro Lys Arg Pro Gly Pro Ala Gly Glu Leu Leu Leu Gln Asp
    130                 135                 140

Ile Pro Thr Gly Ser Ala Pro Ala Ala Gln His Arg Leu Pro Gln Pro
145                 150                 155                 160

Pro Val Gly Lys Gly Gly Ala Gly Ala Ser Ser Ser Leu Ser Pro Leu
                    165                 170                 175

Gln Ala Glu Leu Leu Pro Pro Leu Leu Glu His Leu Leu Leu Pro Pro
                180                 185                 190

Gln Pro Pro His Pro Ser Leu Ser Tyr Glu Pro Ala Leu Leu Gln Pro
                195                 200                 205

Tyr Leu Phe His Gln Phe Gly Ser Arg Asp Gly Ser Arg Val Ser Glu
    210                 215                 220

Gly Ser Pro Gly Met Val Ser Val Gly Pro Leu Pro Lys Ala Glu Ala
225                 230                 235                 240

Pro Ala Leu Phe Ser Arg Thr Ala Ser Lys Gly Ile Phe Gly Asp His
                    245                 250                 255

Pro Gly His Ser Tyr Gly Asp Leu Pro Gly Pro Ser Pro Ala Gln Leu
                260                 265                 270

Phe Gln Asp Ser Gly Leu Leu Tyr Leu Ala Gln Glu Leu Pro Ala Pro
                275                 280                 285

Ser Arg Ala Arg Val Pro Arg Leu Pro Glu Gln Gly Ser Ser Ser Arg
    290                 295                 300

Ala Glu Asp Ser Pro Glu Gly Tyr Glu Lys Glu Gly Leu Gly Asp Arg
305                 310                 315                 320
```

-continued

```
Gly Glu Lys Pro Ala Ser Pro Ala Val Gln Pro Asp Ala Ala Leu Gln
            325                 330                 335

Arg Leu Ala Ala Val Leu Ala Gly Tyr Gly Val Glu Leu Arg Gln Leu
            340                 345                 350

Thr Pro Glu Gln Leu Ser Thr Leu Leu Thr Leu Leu Gln Leu Leu Pro
            355                 360                 365

Lys Gly Ala Gly Arg Asn Pro Gly Gly Val Val Asn Val Gly Ala Asp
            370                 375                 380

Ile Lys Lys Thr Met Glu Gly Pro Val Glu Gly Arg Asp Thr Ala Glu
385                 390                 395                 400

Leu Pro Ala Arg Thr Ser Pro Met Pro Gly His Pro Thr Ala Ser Pro
            405                 410                 415

Thr Ser Ser Glu Val Gln Gln Val Pro Ser Pro Val Ser Ser Glu Pro
            420                 425                 430

Pro Lys Ala Ala Arg Pro Pro Val Thr Pro Val Leu Leu Glu Lys Lys
            435                 440                 445

Ser Pro Leu Gly Gln Ser Gln Pro Thr Val Ala Gly Gln Pro Ser Ala
            450                 455                 460

Arg Pro Ala Ala Glu Glu Tyr Gly Tyr Ile Val Thr Asp Gln Lys Pro
465                 470                 475                 480

Leu Ser Leu Ala Ala Gly Val Lys Leu Leu Glu Ile Leu Ala Glu His
            485                 490                 495

Val His Met Ser Ser Gly Ser Phe Ile Asn Ile Ser Val Val Gly Pro
            500                 505                 510

Ala Leu Thr Phe Arg Ile Arg His Asn Glu Gln Asn Leu Ser Leu Ala
            515                 520                 525

Asp Val Thr Gln Gln Ala Gly Leu Val Lys Ser Glu Leu Glu Ala Gln
            530                 535                 540

Thr Gly Leu Gln Ile Leu Gln Thr Gly Val Gly Gln Arg Glu Glu Ala
545                 550                 555                 560

Ala Ala Val Leu Pro Gln Thr Ala His Ser Thr Ser Pro Met Arg Ser
            565                 570                 575

Val Leu Leu Thr Leu Val Ala Leu Ala Gly Val Ala Gly Leu Leu Val
            580                 585                 590

Ala Leu Ala Val Ala Leu Cys Val Arg Gln His Ala Arg Gln Gln Asp
            595                 600                 605

Lys Glu Arg Leu Ala Ala Leu Gly Pro Glu Gly Ala His Gly Asp Thr
            610                 615                 620

Thr Phe Glu Tyr Gln Asp Leu Cys Arg Gln His Met Ala Thr Lys Ser
625                 630                 635                 640

Leu Phe Asn Arg Ala Glu Gly Pro Pro Glu Pro Ser Arg Val Ser Ser
            645                 650                 655

Val Ser Ser Gln Phe Ser Asp Ala Ala Gln Ala Ser Pro Ser Ser His
            660                 665                 670

Ser Ser Thr Pro Ser Trp Cys Glu Glu Pro Ala Gln Ala Asn Met Asp
            675                 680                 685

Ile Ser Thr Gly His Met Ile Leu Ala Tyr Met Glu Asp His Leu Arg
            690                 695                 700

Asn Arg Asp Arg Leu Ala Lys Glu Trp Gln Ala Leu Cys Ala Tyr Gln
705                 710                 715                 720

Ala Glu Pro Asn Thr Cys Ala Thr Ala Gln Gly Glu Gly Asn Ile Lys
            725                 730                 735

Lys Asn Arg His Pro Asp Phe Leu Pro Tyr Asp His Ala Arg Ile Lys
```

```
                740                 745                 750
Leu Lys Val Glu Ser Ser Pro Ser Arg Ser Asp Tyr Ile Asn Ala Ser
            755                 760                 765

Pro Ile Ile Glu His Asp Pro Arg Met Pro Ala Tyr Ile Ala Thr Gln
        770                 775                 780

Gly Pro Leu Ser His Thr Ile Ala Asp Phe Trp Gln Met Val Trp Glu
785                 790                 795                 800

Ser Gly Cys Thr Val Ile Val Met Leu Thr Pro Leu Val Glu Asp Gly
                805                 810                 815

Val Lys Gln Cys Asp Arg Tyr Trp Pro Asp Glu Gly Ala Ser Leu Tyr
            820                 825                 830

His Val Tyr Glu Val Asn Leu Val Ser Glu His Ile Trp Cys Glu Asp
        835                 840                 845

Phe Leu Val Arg Ser Phe Tyr Leu Lys Asn Val Gln Thr Gln Glu Thr
    850                 855                 860

Arg Thr Leu Thr Gln Phe His Phe Leu Ser Trp Pro Ala Glu Gly Thr
865                 870                 875                 880

Pro Ala Ser Thr Arg Pro Leu Leu Asp Phe Arg Arg Lys Val Asn Lys
                885                 890                 895

Cys Tyr Arg Gly Arg Ser Cys Pro Ile Ile Val His Cys Ser Asp Gly
            900                 905                 910

Ala Gly Arg Thr Gly Thr Tyr Ile Leu Ile Asp Met Val Leu Asn Arg
        915                 920                 925

Met Ala Lys Gly Val Lys Glu Ile Asp Ile Ala Ala Thr Leu Glu His
    930                 935                 940

Val Arg Asp Gln Arg Pro Gly Leu Val Arg Ser Lys Asp Gln Phe Glu
945                 950                 955                 960

Phe Ala Leu Thr Ala Val Ala Glu Glu Val Asn Ala Ile Leu Lys Ala
                965                 970                 975

Leu Pro Gln

<210> SEQ ID NO 32
<211> LENGTH: 807
<212> TYPE: PRT
<213> ORGANISM: Homo sapiens
<300> PUBLICATION INFORMATION:
<308> DATABASE ACCESSION NUMBER: UniProt / Q9Y2R2
<309> DATABASE ENTRY DATE: 2015-07-22
<313> RELEVANT RESIDUES IN SEQ ID NO: (1)..(807)

<400> SEQUENCE: 32

Met Asp Gln Arg Glu Ile Leu Gln Lys Phe Leu Asp Glu Ala Gln Ser
1               5                   10                  15

Lys Lys Ile Thr Lys Glu Glu Phe Ala Asn Glu Phe Leu Lys Leu Lys
            20                  25                  30

Arg Gln Ser Thr Lys Tyr Lys Ala Asp Lys Thr Tyr Pro Thr Thr Val
        35                  40                  45

Ala Glu Lys Pro Lys Asn Ile Lys Lys Asn Arg Tyr Lys Asp Ile Leu
    50                  55                  60

Pro Tyr Asp Tyr Ser Arg Val Glu Leu Ser Leu Ile Thr Ser Asp Glu
65                  70                  75                  80

Asp Ser Ser Tyr Ile Asn Ala Asn Phe Ile Lys Gly Val Tyr Gly Pro
                85                  90                  95

Lys Ala Tyr Ile Ala Thr Gln Gly Pro Leu Ser Thr Thr Leu Leu Asp
            100                 105                 110
```

```
Phe Trp Arg Met Ile Trp Glu Tyr Ser Val Leu Ile Ile Val Met Ala
            115                 120                 125
Cys Met Glu Tyr Glu Met Gly Lys Lys Cys Glu Arg Tyr Trp Ala
    130                 135                 140
Glu Pro Gly Glu Met Gln Leu Glu Phe Gly Pro Phe Ser Val Ser Cys
145                 150                 155                 160
Glu Ala Glu Lys Arg Lys Ser Asp Tyr Ile Ile Arg Thr Leu Lys Val
                165                 170                 175
Lys Phe Asn Ser Glu Thr Arg Thr Ile Tyr Gln Phe His Tyr Lys Asn
                180                 185                 190
Trp Pro Asp His Asp Val Pro Ser Ser Ile Asp Pro Ile Leu Glu Leu
                195                 200                 205
Ile Trp Asp Val Arg Cys Tyr Gln Glu Asp Asp Ser Val Pro Ile Cys
    210                 215                 220
Ile His Cys Ser Ala Gly Cys Gly Arg Thr Gly Val Ile Cys Ala Ile
225                 230                 235                 240
Asp Tyr Thr Trp Met Leu Leu Lys Asp Gly Ile Ile Pro Glu Asn Phe
                245                 250                 255
Ser Val Phe Ser Leu Ile Arg Glu Met Arg Thr Gln Arg Pro Ser Leu
                260                 265                 270
Val Gln Thr Gln Glu Gln Tyr Glu Leu Val Tyr Asn Ala Val Leu Glu
    275                 280                 285
Leu Phe Lys Arg Gln Met Asp Val Ile Arg Asp Lys His Ser Gly Thr
    290                 295                 300
Glu Ser Gln Ala Lys His Cys Ile Pro Glu Lys Asn His Thr Leu Gln
305                 310                 315                 320
Ala Asp Ser Tyr Ser Pro Asn Leu Pro Lys Ser Thr Thr Lys Ala Ala
                325                 330                 335
Lys Met Met Asn Gln Gln Arg Thr Lys Met Glu Ile Lys Glu Ser Ser
                340                 345                 350
Ser Phe Asp Phe Arg Thr Ser Glu Ile Ser Ala Lys Glu Glu Leu Val
                355                 360                 365
Leu His Pro Ala Lys Ser Ser Thr Ser Phe Asp Phe Leu Glu Leu Asn
    370                 375                 380
Tyr Ser Phe Asp Lys Asn Ala Asp Thr Thr Met Lys Trp Gln Thr Lys
385                 390                 395                 400
Ala Phe Pro Ile Val Gly Glu Pro Leu Gln Lys His Gln Ser Leu Asp
                405                 410                 415
Leu Gly Ser Leu Leu Phe Glu Gly Cys Ser Asn Ser Lys Pro Val Asn
                420                 425                 430
Ala Ala Gly Arg Tyr Phe Asn Ser Lys Val Pro Ile Thr Arg Thr Lys
                435                 440                 445
Ser Thr Pro Phe Glu Leu Ile Gln Gln Arg Glu Thr Lys Glu Val Asp
    450                 455                 460
Ser Lys Glu Asn Phe Ser Tyr Leu Glu Ser Gln Pro His Asp Ser Cys
465                 470                 475                 480
Phe Val Glu Met Gln Ala Gln Lys Val Met His Val Ser Ser Ala Glu
                485                 490                 495
Leu Asn Tyr Ser Leu Pro Tyr Asp Ser Lys His Gln Ile Arg Asn Ala
                500                 505                 510
Ser Asn Val Lys His His Asp Ser Ser Ala Leu Gly Val Tyr Ser Tyr
                515                 520                 525
Ile Pro Leu Val Glu Asn Pro Tyr Phe Ser Ser Trp Pro Pro Ser Gly
```

```
                530             535             540
Thr Ser Ser Lys Met Ser Leu Asp Leu Pro Glu Lys Gln Asp Gly Thr
545                 550                 555                 560

Val Phe Pro Ser Ser Leu Leu Pro Thr Ser Thr Ser Leu Phe Ser
                565                 570                 575

Tyr Tyr Asn Ser His Asp Ser Leu Ser Leu Asn Ser Pro Thr Asn Ile
                580                 585                 590

Ser Ser Leu Leu Asn Gln Glu Ser Ala Val Leu Ala Thr Ala Pro Arg
            595                 600                 605

Ile Asp Asp Glu Ile Pro Pro Leu Pro Val Arg Thr Pro Glu Ser
            610                 615                 620

Phe Ile Val Val Glu Glu Ala Gly Glu Phe Ser Pro Asn Val Pro Lys
625                 630                 635                 640

Ser Leu Ser Ser Ala Val Lys Val Lys Ile Gly Thr Ser Leu Glu Trp
                645                 650                 655

Gly Gly Thr Ser Glu Pro Lys Lys Phe Asp Asp Ser Val Ile Leu Arg
                660                 665                 670

Pro Ser Lys Ser Val Lys Leu Arg Ser Pro Lys Ser Glu Leu His Gln
            675                 680                 685

Asp Arg Ser Ser Pro Pro Pro Leu Pro Glu Arg Thr Leu Glu Ser
            690                 695                 700

Phe Phe Leu Ala Asp Glu Asp Cys Met Gln Ala Gln Ser Ile Glu Thr
705                 710                 715                 720

Tyr Ser Thr Ser Tyr Pro Asp Thr Met Glu Asn Ser Thr Ser Ser Lys
                725                 730                 735

Gln Thr Leu Lys Thr Pro Gly Lys Ser Phe Thr Arg Ser Lys Ser Leu
                740                 745                 750

Lys Ile Leu Arg Asn Met Lys Lys Ser Ile Cys Asn Ser Cys Pro Pro
            755                 760                 765

Asn Lys Pro Ala Glu Ser Val Gln Ser Asn Asn Ser Ser Ser Phe Leu
            770                 775                 780

Asn Phe Gly Phe Ala Asn Arg Phe Ser Lys Pro Lys Gly Pro Arg Asn
785                 790                 795                 800

Pro Pro Pro Thr Trp Asn Ile
                805

<210> SEQ ID NO 33
<211> LENGTH: 248
<212> TYPE: PRT
<213> ORGANISM: Homo sapiens
<300> PUBLICATION INFORMATION:
<308> DATABASE ACCESSION NUMBER: UniProt / P18124
<309> DATABASE ENTRY DATE: 2015-07-22
<313> RELEVANT RESIDUES IN SEQ ID NO: (1)..(248)

<400> SEQUENCE: 33

Met Glu Gly Val Glu Glu Lys Lys Lys Glu Val Pro Ala Val Pro Glu
1               5                   10                  15

Thr Leu Lys Lys Lys Arg Arg Asn Phe Ala Glu Leu Lys Ile Lys Arg
                20                  25                  30

Leu Arg Lys Lys Phe Ala Gln Lys Met Leu Arg Lys Ala Arg Arg Lys
                35                  40                  45

Leu Ile Tyr Glu Lys Ala Lys His Tyr His Lys Glu Tyr Arg Gln Met
            50                  55                  60

Tyr Arg Thr Glu Ile Arg Met Ala Arg Met Ala Arg Lys Ala Gly Asn
65                  70                  75                  80
```

```
Phe Tyr Val Pro Ala Glu Pro Lys Leu Ala Phe Val Ile Arg Ile Arg
                85                  90                  95

Gly Ile Asn Gly Val Ser Pro Lys Val Arg Lys Val Leu Gln Leu Leu
            100                 105                 110

Arg Leu Arg Gln Ile Phe Asn Gly Thr Phe Val Lys Leu Asn Lys Ala
            115                 120                 125

Ser Ile Asn Met Leu Arg Ile Val Glu Pro Tyr Ile Ala Trp Gly Tyr
130                 135                 140

Pro Asn Leu Lys Ser Val Asn Glu Leu Ile Tyr Lys Arg Gly Tyr Gly
145                 150                 155                 160

Lys Ile Asn Lys Lys Arg Ile Ala Leu Thr Asp Asn Ala Leu Ile Ala
                165                 170                 175

Arg Ser Leu Gly Lys Tyr Gly Ile Ile Cys Met Glu Asp Leu Ile His
            180                 185                 190

Glu Ile Tyr Thr Val Gly Lys Arg Phe Lys Glu Ala Asn Asn Phe Leu
            195                 200                 205

Trp Pro Phe Lys Leu Ser Ser Pro Arg Gly Gly Met Lys Lys Lys Thr
        210                 215                 220

Thr His Phe Val Glu Gly Gly Asp Ala Gly Asn Arg Glu Asp Gln Ile
225                 230                 235                 240

Asn Arg Leu Ile Arg Arg Met Asn
                245

<210> SEQ ID NO 34
<211> LENGTH: 313
<212> TYPE: PRT
<213> ORGANISM: Homo sapiens
<300> PUBLICATION INFORMATION:
<308> DATABASE ACCESSION NUMBER: UniProt / Q5MJ70
<309> DATABASE ENTRY DATE: 2015-07-22
<313> RELEVANT RESIDUES IN SEQ ID NO: (1)..(313)

<400> SEQUENCE: 34

Met Arg His Asn Gln Met Cys Cys Glu Thr Pro Pro Thr Val Thr Val
1               5                   10                  15

Tyr Val Lys Ser Gly Ser Asn Arg Ser His Gln Pro Lys Lys Pro Ile
            20                  25                  30

Thr Leu Lys Arg Pro Ile Cys Lys Asp Asn Trp Gln Ala Phe Glu Lys
        35                  40                  45

Asn Thr His Asn Asn Asn Lys Ser Lys Arg Pro Lys Gly Pro Cys Leu
    50                  55                  60

Val Ile Gln Arg Gln Asp Met Thr Ala Phe Phe Lys Leu Phe Asp Asp
65                  70                  75                  80

Asp Leu Ile Gln Asp Phe Leu Trp Met Asp Cys Cys Cys Lys Ile Ala
                85                  90                  95

Asp Lys Tyr Leu Leu Ala Met Thr Phe Val Tyr Phe Lys Arg Ala Lys
            100                 105                 110

Phe Thr Ile Ser Glu His Thr Arg Ile Asn Phe Phe Ile Ala Leu Tyr
            115                 120                 125

Leu Ala Asn Thr Val Glu Glu Asp Glu Glu Thr Lys Tyr Glu Ile
        130                 135                 140

Phe Pro Trp Ala Leu Gly Lys Asn Trp Arg Lys Leu Phe Pro Asn Phe
145                 150                 155                 160

Leu Lys Leu Arg Asp Gln Leu Trp Asp Arg Ile Asp Tyr Arg Ala Ile
                165                 170                 175
```

```
Val Ser Arg Arg Cys Cys Glu Glu Val Met Ala Ile Ala Pro Thr His
            180                 185                 190

Tyr Ile Trp Gln Arg Glu Arg Ser Val His His Ser Gly Ala Val Arg
            195                 200                 205

Asn Tyr Asn Arg Asp Glu Val Gln Leu Pro Arg Gly Pro Ser Ala Thr
            210                 215                 220

Pro Val Asp Cys Ser Leu Cys Gly Lys Lys Arg Arg Tyr Val Arg Leu
225                 230                 235                 240

Gly Leu Ser Ser Ser Ser Leu Ser Ser His Thr Ala Gly Val Thr
            245                 250                 255

Glu Lys His Ser Gln Asp Ser Tyr Asn Ser Leu Ser Met Asp Ile Ile
            260                 265                 270

Gly Asp Pro Ser Gln Ala Tyr Thr Gly Ser Glu Val Val Asn Asp His
            275                 280                 285

Gln Ser Asn Lys Gly Lys Lys Thr Asn Phe Leu Lys Lys Asp Lys Ser
            290                 295                 300

Met Glu Trp Phe Thr Gly Ser Glu Glu
305                 310
```

<210> SEQ ID NO 35
<211> LENGTH: 233
<212> TYPE: PRT
<213> ORGANISM: Homo sapiens
<300> PUBLICATION INFORMATION:
<308> DATABASE ACCESSION NUMBER: UniProt / P01375
<309> DATABASE ENTRY DATE: 2015-07-22
<313> RELEVANT RESIDUES IN SEQ ID NO: (1)..(233)

<400> SEQUENCE: 35

```
Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
            115                 120                 125

Glu Gly Leu Tyr Leu Ile Tyr Ser Gln Val Leu Phe Lys Gly Gln Gly
            130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
            195                 200                 205

Ser Ala Glu Ile Asn Arg Pro Asp Tyr Leu Asp Phe Ala Glu Ser Gly
```

```
                210                 215                 220
Gln Val Tyr Phe Gly Ile Ile Ala Leu
225                 230
```

<210> SEQ ID NO 36
<211> LENGTH: 175
<212> TYPE: PRT
<213> ORGANISM: Homo sapiens
<300> PUBLICATION INFORMATION:
<308> DATABASE ACCESSION NUMBER: UniProt / Q06141
<309> DATABASE ENTRY DATE: 2015-07-22
<313> RELEVANT RESIDUES IN SEQ ID NO: (1)..(175)

<400> SEQUENCE: 36

```
Met Leu Pro Pro Met Ala Leu Pro Ser Val Ser Trp Met Leu Leu Ser
1               5                   10                  15

Cys Leu Met Leu Leu Ser Gln Val Gln Gly Glu Glu Pro Gln Arg Glu
                20                  25                  30

Leu Pro Ser Ala Arg Ile Arg Cys Pro Lys Gly Ser Lys Ala Tyr Gly
            35                  40                  45

Ser His Cys Tyr Ala Leu Phe Leu Ser Pro Lys Ser Trp Thr Asp Ala
        50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
                100                 105                 110

Thr Glu Pro Asn Gly Glu Gly Trp Glu Trp Ser Ser Ser Asp Val Met
            115                 120                 125

Asn Tyr Phe Ala Trp Glu Arg Asn Pro Ser Thr Ile Ser Ser Pro Gly
        130                 135                 140

His Cys Ala Ser Leu Ser Arg Ser Thr Ala Phe Leu Arg Trp Lys Asp
145                 150                 155                 160

Tyr Asn Cys Asn Val Arg Leu Pro Tyr Val Cys Lys Phe Thr Asp
                165                 170                 175
```

<210> SEQ ID NO 37
<211> LENGTH: 1342
<212> TYPE: PRT
<213> ORGANISM: Homo sapiens
<300> PUBLICATION INFORMATION:
<308> DATABASE ACCESSION NUMBER: UniProt / P21860
<309> DATABASE ENTRY DATE: 2015-07-22
<313> RELEVANT RESIDUES IN SEQ ID NO: (1)..(1342)

<400> SEQUENCE: 37

```
Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
                20                  25                  30

Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu
        50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95
```

```
Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
            130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
            165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
            195                 200                 205

Ile Cys Ala Pro Gln Cys Asn Gly His Cys Phe Gly Pro Asn Pro Asn
            210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
            245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
            275                 280                 285

Ser Cys Pro His Asn Phe Val Val Asp Gln Thr Ser Cys Val Arg Ala
            290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
            325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
            370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
            405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
            435                 440                 445

Ile Ser Ala Gly Arg Ile Tyr Ile Ser Ala Asn Arg Gln Leu Cys Tyr
            450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
            485                 490                 495

Gly Lys Val Cys Asp Pro Leu Cys Ser Ser Gly Gly Cys Trp Gly Pro
            500                 505                 510
```

```
Gly Pro Gly Gln Cys Leu Ser Cys Arg Asn Tyr Ser Arg Gly Gly Val
        515                 520                 525

Cys Val Thr His Cys Asn Phe Leu Asn Gly Glu Pro Arg Glu Phe Ala
        530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
                580                 585                 590

Val Leu Gly Ala Lys Gly Pro Ile Tyr Lys Tyr Pro Asp Val Gln Asn
            595                 600                 605

Glu Cys Arg Pro Cys His Glu Asn Cys Thr Gln Gly Cys Lys Gly Pro
        610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
        675                 680                 685

Pro Leu Asp Pro Ser Glu Lys Ala Asn Lys Val Leu Ala Arg Ile Phe
        690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
    770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Asn Trp Gly Val
                805                 810                 815

Gln Ile Ala Lys Gly Met Tyr Tyr Leu Glu Glu His Gly Met Val His
        820                 825                 830

Arg Asn Leu Ala Ala Arg Asn Val Leu Leu Lys Ser Pro Ser Gln Val
835                 840                 845

Gln Val Ala Asp Phe Gly Val Ala Asp Leu Leu Pro Pro Asp Asp Lys
    850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
                900                 905                 910

Ala Gly Leu Arg Leu Ala Glu Val Pro Asp Leu Leu Glu Lys Gly Glu
        915                 920                 925

Arg Leu Ala Gln Pro Gln Ile Cys Thr Ile Asp Val Tyr Met Val Met
```

```
                    930             935             940
Val Lys Cys Trp Met Ile Asp Glu Asn Ile Arg Pro Thr Phe Lys Glu
945                 950             955             960

Leu Ala Asn Glu Phe Thr Arg Met Ala Arg Asp Pro Pro Arg Tyr Leu
                965             970             975

Val Ile Lys Arg Glu Ser Gly Pro Gly Ile Ala Pro Gly Pro Glu Pro
            980             985             990

His Gly Leu Thr Asn Lys Lys Leu Glu Glu Val Glu Leu Glu Pro Glu
        995             1000            1005

Leu Asp Leu Asp Leu Asp Leu Glu Ala Glu Glu Asp Asn Leu Ala
    1010            1015            1020

Thr Thr Thr Leu Gly Ser Ala Leu Ser Leu Pro Val Gly Thr Leu
    1025            1030            1035

Asn Arg Pro Arg Gly Ser Gln Ser Leu Leu Ser Pro Ser Ser Gly
    1040            1045            1050

Tyr Met Pro Met Asn Gln Gly Asn Leu Gly Glu Ser Cys Gln Glu
    1055            1060            1065

Ser Ala Val Ser Gly Ser Ser Glu Arg Cys Pro Arg Pro Val Ser
    1070            1075            1080

Leu His Pro Met Pro Arg Gly Cys Leu Ala Ser Glu Ser Ser Glu
    1085            1090            1095

Gly His Val Thr Gly Ser Glu Ala Glu Leu Gln Glu Lys Val Ser
    1100            1105            1110

Met Cys Arg Ser Arg Ser Arg Ser Arg Ser Pro Arg Pro Arg Gly
    1115            1120            1125

Asp Ser Ala Tyr His Ser Gln Arg His Ser Leu Leu Thr Pro Val
    1130            1135            1140

Thr Pro Leu Ser Pro Pro Gly Leu Glu Glu Glu Asp Val Asn Gly
    1145            1150            1155

Tyr Val Met Pro Asp Thr His Leu Lys Gly Thr Pro Ser Ser Arg
    1160            1165            1170

Glu Gly Thr Leu Ser Ser Val Gly Leu Ser Ser Val Leu Gly Thr
    1175            1180            1185

Glu Glu Glu Asp Glu Asp Glu Glu Tyr Glu Tyr Met Asn Arg Arg
    1190            1195            1200

Arg Arg His Ser Pro Pro His Pro Pro Arg Pro Ser Ser Leu Glu
    1205            1210            1215

Glu Leu Gly Tyr Glu Tyr Met Asp Val Gly Ser Asp Leu Ser Ala
    1220            1225            1230

Ser Leu Gly Ser Thr Gln Ser Cys Pro Leu His Pro Val Pro Ile
    1235            1240            1245

Met Pro Thr Ala Gly Thr Thr Pro Asp Glu Asp Tyr Glu Tyr Met
    1250            1255            1260

Asn Arg Gln Arg Asp Gly Gly Gly Pro Gly Gly Asp Tyr Ala Ala
    1265            1270            1275

Met Gly Ala Cys Pro Ala Ser Glu Gln Gly Tyr Glu Glu Met Arg
    1280            1285            1290

Ala Phe Gln Gly Pro Gly His Gln Ala Pro His Val His Tyr Ala
    1295            1300            1305

Arg Leu Lys Thr Leu Arg Ser Leu Glu Ala Thr Asp Ser Ala Phe
    1310            1315            1320

Asp Asn Pro Asp Tyr Trp His Ser Arg Leu Phe Pro Lys Ala Asn
    1325            1330            1335
```

-continued

Ala Gln Arg Thr
     1340

<210> SEQ ID NO 38
<211> LENGTH: 472
<212> TYPE: PRT
<213> ORGANISM: Homo sapiens
<300> PUBLICATION INFORMATION:
<308> DATABASE ACCESSION NUMBER: UniProt / P16671
<309> DATABASE ENTRY DATE: 2015-07-22
<313> RELEVANT RESIDUES IN SEQ ID NO: (1)..(472)

<400> SEQUENCE: 38

Met Gly Cys Asp Arg Asn Cys Gly Leu Ile Ala Gly Ala Val Ile Gly
1               5                   10                  15

Ala Val Leu Ala Val Phe Gly Gly Ile Leu Met Pro Val Gly Asp Leu
            20                  25                  30

Leu Ile Gln Lys Thr Ile Lys Lys Gln Val Val Leu Glu Glu Gly Thr
        35                  40                  45

Ile Ala Phe Lys Asn Trp Val Lys Thr Gly Thr Glu Val Tyr Arg Gln
    50                  55                  60

Phe Trp Ile Phe Asp Val Gln Asn Pro Gln Glu Val Met Met Asn Ser
65                  70                  75                  80

Ser Asn Ile Gln Val Lys Gln Arg Gly Pro Tyr Thr Tyr Arg Val Arg
                85                  90                  95

Phe Leu Ala Lys Glu Asn Val Thr Gln Asp Ala Glu Asp Asn Thr Val
            100                 105                 110

Ser Phe Leu Gln Pro Asn Gly Ala Ile Phe Glu Pro Ser Leu Ser Val
        115                 120                 125

Gly Thr Glu Ala Asp Asn Phe Thr Val Leu Asn Leu Ala Val Ala Ala
    130                 135                 140

Ala Ser His Ile Tyr Gln Asn Gln Phe Val Gln Met Ile Leu Asn Ser
145                 150                 155                 160

Leu Ile Asn Lys Ser Lys Ser Ser Met Phe Gln Val Arg Thr Leu Arg
                165                 170                 175

Glu Leu Leu Trp Gly Tyr Arg Asp Pro Phe Leu Ser Leu Val Pro Tyr
            180                 185                 190

Pro Val Thr Thr Thr Val Gly Leu Phe Tyr Pro Tyr Asn Asn Thr Ala
        195                 200                 205

Asp Gly Val Tyr Lys Val Phe Asn Gly Lys Asp Asn Ile Ser Lys Val
    210                 215                 220

Ala Ile Ile Asp Thr Tyr Lys Gly Lys Arg Asn Leu Ser Tyr Trp Glu
225                 230                 235                 240

Ser His Cys Asp Met Ile Asn Gly Thr Asp Ala Ala Ser Phe Pro Pro
                245                 250                 255

Phe Val Glu Lys Ser Gln Val Leu Gln Phe Phe Ser Ser Asp Ile Cys
            260                 265                 270

Arg Ser Ile Tyr Ala Val Phe Glu Ser Asp Val Asn Leu Lys Gly Ile
        275                 280                 285

Pro Val Tyr Arg Phe Val Leu Pro Ser Lys Ala Phe Ala Ser Pro Val
    290                 295                 300

Glu Asn Pro Asp Asn Tyr Cys Phe Cys Thr Glu Lys Ile Ile Ser Lys
305                 310                 315                 320

Asn Cys Thr Ser Tyr Gly Val Leu Asp Ile Ser Lys Cys Lys Glu Gly
                325                 330                 335

```
Arg Pro Val Tyr Ile Ser Leu Pro His Phe Leu Tyr Ala Ser Pro Asp
            340                 345                 350

Val Ser Glu Pro Ile Asp Gly Leu Asn Pro Asn Glu Glu Glu His Arg
        355                 360                 365

Thr Tyr Leu Asp Ile Glu Pro Ile Thr Gly Phe Thr Leu Gln Phe Ala
    370                 375                 380

Lys Arg Leu Gln Val Asn Leu Leu Val Lys Pro Ser Glu Lys Ile Gln
385                 390                 395                 400

Val Leu Lys Asn Leu Lys Arg Asn Tyr Ile Val Pro Ile Leu Trp Leu
                405                 410                 415

Asn Glu Thr Gly Thr Ile Gly Asp Glu Lys Ala Asn Met Phe Arg Ser
            420                 425                 430

Gln Val Thr Gly Lys Ile Asn Leu Leu Gly Leu Ile Glu Met Ile Leu
        435                 440                 445

Leu Ser Val Gly Val Val Met Phe Val Ala Phe Met Ile Ser Tyr Cys
    450                 455                 460

Ala Cys Arg Ser Lys Thr Ile Lys
465                 470

<210> SEQ ID NO 39
<211> LENGTH: 710
<212> TYPE: PRT
<213> ORGANISM: Homo sapiens
<300> PUBLICATION INFORMATION:
<308> DATABASE ACCESSION NUMBER: UniProt / P19338
<309> DATABASE ENTRY DATE: 2015-07-22
<313> RELEVANT RESIDUES IN SEQ ID NO: (1)..(710)

<400> SEQUENCE: 39

Met Val Lys Leu Ala Lys Ala Gly Lys Asn Gln Gly Asp Pro Lys Lys
1               5                   10                  15

Met Ala Pro Pro Lys Glu Val Glu Glu Asp Ser Glu Asp Glu Glu
            20                  25                  30

Met Ser Glu Asp Glu Glu Asp Ser Ser Gly Glu Glu Val Val Ile
        35                  40                  45

Pro Gln Lys Lys Gly Lys Ala Ala Thr Ser Ala Lys Lys Val
    50                  55                  60

Val Val Ser Pro Thr Lys Val Ala Val Thr Pro Ala Lys Lys
65                  70                  75                  80

Ala Ala Val Thr Pro Gly Lys Lys Ala Ala Thr Pro Ala Lys Lys
                85                  90                  95

Thr Val Thr Pro Ala Lys Ala Val Thr Thr Pro Gly Lys Lys Gly Ala
            100                 105                 110

Thr Pro Gly Lys Ala Leu Val Ala Thr Pro Gly Lys Lys Gly Ala Ala
        115                 120                 125

Ile Pro Ala Lys Gly Ala Lys Asn Gly Lys Asn Ala Lys Lys Glu Asp
    130                 135                 140

Ser Asp Glu Glu Asp Asp Ser Glu Glu Asp Glu Glu Asp Asp
145                 150                 155                 160

Glu Asp Glu Asp Glu Asp Glu Ile Glu Pro Ala Ala Met Lys
                165                 170                 175

Ala Ala Ala Ala Pro Ala Ser Glu Asp Glu Asp Asp Glu Asp Asp
            180                 185                 190

Glu Asp Asp Glu Asp Asp Asp Glu Glu Asp Asp Ser Glu Glu
        195                 200                 205

Glu Ala Met Glu Thr Thr Pro Ala Lys Gly Lys Lys Ala Ala Lys Val
```

```
                210                 215                 220
Val Pro Val Lys Ala Lys Asn Val Ala Glu Asp Glu Asp Glu Glu
225                 230                 235                 240

Asp Asp Glu Asp Glu Asp Asp Asp Glu Asp Asp Glu Asp Asp
                245                 250                 255

Asp Asp Glu Asp Asp Glu Glu Glu Glu Glu Glu Glu Glu Pro
                260                 265                 270

Val Lys Glu Ala Pro Gly Lys Arg Lys Glu Met Ala Lys Gln Lys
                275                 280                 285

Ala Ala Pro Glu Ala Lys Lys Gln Lys Val Glu Gly Thr Glu Pro Thr
        290                 295                 300

Thr Ala Phe Asn Leu Phe Val Gly Asn Leu Asn Phe Asn Lys Ser Ala
305                 310                 315                 320

Pro Glu Leu Lys Thr Gly Ile Ser Asp Val Phe Ala Lys Asn Asp Leu
                325                 330                 335

Ala Val Val Asp Val Arg Ile Gly Met Thr Arg Lys Phe Gly Tyr Val
                340                 345                 350

Asp Phe Glu Ser Ala Glu Asp Leu Glu Lys Ala Leu Glu Leu Thr Gly
                355                 360                 365

Leu Lys Val Phe Gly Asn Glu Ile Lys Leu Glu Lys Pro Lys Gly Lys
                370                 375                 380

Asp Ser Lys Lys Glu Arg Asp Ala Arg Thr Leu Leu Ala Lys Asn Leu
385                 390                 395                 400

Pro Tyr Lys Val Thr Gln Asp Glu Leu Lys Glu Val Phe Glu Asp Ala
                405                 410                 415

Ala Glu Ile Arg Leu Val Ser Lys Asp Gly Lys Ser Lys Gly Ile Ala
                420                 425                 430

Tyr Ile Glu Phe Lys Thr Glu Ala Asp Ala Glu Lys Thr Phe Glu Glu
                435                 440                 445

Lys Gln Gly Thr Glu Ile Asp Gly Arg Ser Ile Ser Leu Tyr Tyr Thr
                450                 455                 460

Gly Glu Lys Gly Gln Asn Gln Asp Tyr Arg Gly Gly Lys Asn Ser Thr
465                 470                 475                 480

Trp Ser Gly Glu Ser Lys Thr Leu Val Leu Ser Asn Leu Ser Tyr Ser
                485                 490                 495

Ala Thr Glu Glu Thr Leu Gln Glu Val Phe Glu Lys Ala Thr Phe Ile
                500                 505                 510

Lys Val Pro Gln Asn Gln Asn Gly Lys Ser Lys Gly Tyr Ala Phe Ile
                515                 520                 525

Glu Phe Ala Ser Phe Glu Asp Ala Lys Glu Ala Leu Asn Ser Cys Asn
                530                 535                 540

Lys Arg Glu Ile Glu Gly Arg Ala Ile Arg Leu Glu Leu Gln Gly Pro
545                 550                 555                 560

Arg Gly Ser Pro Asn Ala Arg Ser Gln Pro Ser Lys Thr Leu Phe Val
                565                 570                 575

Lys Gly Leu Ser Glu Asp Thr Thr Glu Glu Thr Leu Lys Glu Ser Phe
                580                 585                 590

Asp Gly Ser Val Arg Ala Arg Ile Val Thr Asp Arg Glu Thr Gly Ser
                595                 600                 605

Ser Lys Gly Phe Gly Phe Val Asp Phe Asn Ser Glu Glu Asp Ala Lys
                610                 615                 620

Ala Ala Lys Glu Ala Met Glu Asp Gly Glu Ile Asp Gly Asn Lys Val
625                 630                 635                 640
```

-continued

```
Thr Leu Asp Trp Ala Lys Pro Lys Gly Glu Gly Gly Phe Gly Gly Arg
                645                 650                 655
Gly Gly Gly Arg Gly Gly Phe Gly Gly Arg Gly Gly Arg Gly Gly
            660                 665                 670
Arg Gly Gly Phe Gly Gly Arg Gly Arg Gly Gly Phe Gly Gly Arg Gly
            675                 680                 685
Gly Phe Arg Gly Gly Arg Gly Gly Gly Asp His Lys Pro Gln Gly
        690                 695                 700
Lys Lys Thr Lys Phe Glu
705                 710

<210> SEQ ID NO 40
<211> LENGTH: 303
<212> TYPE: PRT
<213> ORGANISM: Homo sapiens
<300> PUBLICATION INFORMATION:
<308> DATABASE ACCESSION NUMBER: UniProt / Q9BY49
<309> DATABASE ENTRY DATE: 2015-07-22
<313> RELEVANT RESIDUES IN SEQ ID NO: (1)..(303)

<400> SEQUENCE: 40

Met Ala Ser Trp Ala Lys Gly Arg Ser Tyr Leu Ala Pro Gly Leu Leu
1               5                   10                  15
Gln Gly Gln Val Ala Ile Val Thr Gly Gly Ala Thr Gly Ile Gly Lys
            20                  25                  30
Ala Ile Val Lys Glu Leu Leu Glu Leu Gly Ser Asn Val Val Ile Ala
        35                  40                  45
Ser Arg Lys Leu Glu Arg Leu Lys Ser Ala Ala Asp Glu Leu Gln Ala
    50                  55                  60
Asn Leu Pro Pro Thr Lys Gln Ala Arg Val Ile Pro Ile Gln Cys Asn
65                  70                  75                  80
Ile Arg Asn Glu Glu Glu Val Asn Asn Leu Val Lys Ser Thr Leu Asp
                85                  90                  95
Thr Phe Gly Lys Ile Asn Phe Leu Val Asn Asn Gly Gly Gln Phe
            100                 105                 110
Leu Ser Pro Ala Glu His Ile Ser Lys Gly Trp His Ala Val Leu
        115                 120                 125
Glu Thr Asn Leu Thr Gly Thr Phe Tyr Met Cys Lys Ala Val Tyr Ser
    130                 135                 140
Ser Trp Met Lys Glu His Gly Gly Ser Ile Val Asn Ile Ile Val Pro
145                 150                 155                 160
Thr Lys Ala Gly Phe Pro Leu Ala Val His Ser Gly Ala Ala Arg Ala
                165                 170                 175
Gly Val Tyr Asn Leu Thr Lys Ser Leu Ala Leu Glu Trp Ala Cys Ser
            180                 185                 190
Gly Ile Arg Ile Asn Cys Val Ala Pro Gly Val Ile Tyr Ser Gln Thr
        195                 200                 205
Ala Val Glu Asn Tyr Gly Ser Trp Gly Gln Ser Phe Phe Glu Gly Ser
    210                 215                 220
Phe Gln Lys Ile Pro Ala Lys Arg Ile Gly Val Pro Glu Glu Val Ser
225                 230                 235                 240
Ser Val Val Cys Phe Leu Leu Ser Pro Ala Ala Ser Phe Ile Thr Gly
                245                 250                 255
Gln Ser Val Asp Val Asp Gly Gly Arg Ser Leu Tyr Thr His Ser Tyr
            260                 265                 270
```

```
Glu Val Pro Asp His Asp Asn Trp Pro Lys Gly Ala Gly Asp Leu Ser
                275                 280                 285

Val Val Lys Lys Met Lys Glu Thr Phe Lys Glu Lys Ala Lys Leu
    290                 295                 300

<210> SEQ ID NO 41
<211> LENGTH: 475
<212> TYPE: PRT
<213> ORGANISM: Homo sapiens
<300> PUBLICATION INFORMATION:
<308> DATABASE ACCESSION NUMBER: UniProt / P19474
<309> DATABASE ENTRY DATE: 2015-07-22
<313> RELEVANT RESIDUES IN SEQ ID NO: (1)..(475)

<400> SEQUENCE: 41

Met Ala Ser Ala Ala Arg Leu Thr Met Met Trp Glu Val Thr Cys
1               5                   10                  15

Pro Ile Cys Leu Asp Pro Phe Val Glu Pro Val Ser Ile Glu Cys Gly
                20                  25                  30

His Ser Phe Cys Gln Glu Cys Ile Ser Gln Val Gly Lys Gly Gly Gly
            35                  40                  45

Ser Val Cys Pro Val Cys Arg Gln Arg Phe Leu Leu Lys Asn Leu Arg
    50                  55                  60

Pro Asn Arg Gln Leu Ala Asn Met Val Asn Asn Leu Lys Glu Ile Ser
65                  70                  75                  80

Gln Glu Ala Arg Glu Gly Thr Gln Gly Glu Arg Cys Ala Val His Gly
                85                  90                  95

Glu Arg Leu His Leu Phe Cys Glu Lys Asp Gly Lys Ala Leu Cys Trp
            100                 105                 110

Val Cys Ala Gln Ser Arg Lys His Arg Asp His Ala Met Val Pro Leu
        115                 120                 125

Glu Glu Ala Ala Gln Glu Tyr Gln Glu Lys Leu Gln Val Ala Leu Gly
    130                 135                 140

Glu Leu Arg Arg Lys Gln Glu Leu Ala Glu Lys Leu Glu Val Glu Ile
145                 150                 155                 160

Ala Ile Lys Arg Ala Asp Trp Lys Lys Thr Val Glu Thr Gln Lys Ser
                165                 170                 175

Arg Ile His Ala Glu Phe Val Gln Gln Lys Asn Phe Leu Val Glu Glu
            180                 185                 190

Glu Gln Arg Gln Leu Gln Glu Leu Glu Lys Asp Glu Arg Glu Gln Leu
        195                 200                 205

Arg Ile Leu Gly Glu Lys Glu Ala Lys Leu Ala Gln Gln Ser Gln Ala
    210                 215                 220

Leu Gln Glu Leu Ile Ser Glu Leu Asp Arg Arg Cys His Ser Ser Ala
225                 230                 235                 240

Leu Glu Leu Leu Gln Glu Val Ile Ile Val Leu Glu Arg Ser Glu Ser
                245                 250                 255

Trp Asn Leu Lys Asp Leu Asp Ile Thr Ser Pro Glu Leu Arg Ser Val
            260                 265                 270

Cys His Val Pro Gly Leu Lys Lys Met Leu Arg Thr Cys Ala Val His
        275                 280                 285

Ile Thr Leu Asp Pro Asp Thr Ala Asn Pro Trp Leu Ile Leu Ser Glu
    290                 295                 300

Asp Arg Arg Gln Val Arg Leu Gly Asp Thr Gln Gln Ser Ile Pro Gly
305                 310                 315                 320

Asn Glu Glu Arg Phe Asp Ser Tyr Pro Met Val Leu Gly Ala Gln His
```

```
                    325                 330                 335
Phe His Ser Gly Lys His Tyr Trp Glu Val Asp Val Thr Gly Lys Glu
                340                 345                 350

Ala Trp Asp Leu Gly Val Cys Arg Asp Ser Val Arg Arg Lys Gly His
            355                 360                 365

Phe Leu Leu Ser Ser Lys Ser Gly Phe Trp Thr Ile Trp Leu Trp Asn
        370                 375                 380

Lys Gln Lys Tyr Glu Ala Gly Thr Tyr Pro Gln Thr Pro Leu His Leu
385                 390                 395                 400

Gln Val Pro Pro Cys Gln Val Gly Ile Phe Leu Asp Tyr Glu Ala Gly
                405                 410                 415

Met Val Ser Phe Tyr Asn Ile Thr Asp His Gly Ser Leu Ile Tyr Ser
            420                 425                 430

Phe Ser Glu Cys Ala Phe Thr Gly Pro Leu Arg Pro Phe Phe Ser Pro
        435                 440                 445

Gly Phe Asn Asp Gly Lys Asn Thr Ala Pro Leu Thr Leu Cys Pro
450                 455                 460

Leu Asn Ile Gly Ser Gln Gly Ser Thr Asp Tyr
465                 470                 475

<210> SEQ ID NO 42
<211> LENGTH: 261
<212> TYPE: PRT
<213> ORGANISM: Homo sapiens
<300> PUBLICATION INFORMATION:
<308> DATABASE ACCESSION NUMBER: UniProt / P25789
<309> DATABASE ENTRY DATE: 2015-07-22
<313> RELEVANT RESIDUES IN SEQ ID NO: (1)..(261)

<400> SEQUENCE: 42

Met Ser Arg Arg Tyr Asp Ser Arg Thr Thr Ile Phe Ser Pro Glu Gly
1               5                   10                  15

Arg Leu Tyr Gln Val Glu Tyr Ala Met Glu Ala Ile Gly His Ala Gly
                20                  25                  30

Thr Cys Leu Gly Ile Leu Ala Asn Asp Gly Val Leu Leu Ala Ala Glu
            35                  40                  45

Arg Arg Asn Ile His Lys Leu Leu Asp Glu Val Phe Phe Ser Glu Lys
        50                  55                  60

Ile Tyr Lys Leu Asn Glu Asp Met Ala Cys Ser Val Ala Gly Ile Thr
65                  70                  75                  80

Ser Asp Ala Asn Val Leu Thr Asn Glu Leu Arg Leu Ile Ala Gln Arg
                85                  90                  95

Tyr Leu Leu Gln Tyr Gln Glu Pro Ile Pro Cys Glu Gln Leu Val Thr
            100                 105                 110

Ala Leu Cys Asp Ile Lys Gln Ala Tyr Thr Gln Phe Gly Gly Lys Arg
        115                 120                 125

Pro Phe Gly Val Ser Leu Leu Tyr Ile Gly Trp Asp Lys His Tyr Gly
    130                 135                 140

Phe Gln Leu Tyr Gln Ser Asp Pro Ser Gly Asn Tyr Gly Gly Trp Lys
145                 150                 155                 160

Ala Thr Cys Ile Gly Asn Asn Ser Ala Ala Val Ser Met Leu Lys
                165                 170                 175

Gln Asp Tyr Lys Glu Gly Glu Met Thr Leu Lys Ser Ala Leu Ala Leu
            180                 185                 190

Ala Ile Lys Val Leu Asn Lys Thr Met Asp Val Ser Lys Leu Ser Ala
        195                 200                 205
```

```
Glu Lys Val Glu Ile Ala Thr Leu Thr Arg Glu Asn Gly Lys Thr Val
    210                 215                 220

Ile Arg Val Leu Lys Gln Lys Glu Val Glu Gln Leu Ile Lys Lys His
225                 230                 235                 240

Glu Glu Glu Glu Ala Lys Ala Glu Arg Glu Lys Lys Glu Lys Glu Gln
                245                 250                 255

Lys Glu Lys Asp Lys
            260
```

<210> SEQ ID NO 43
<211> LENGTH: 295
<212> TYPE: PRT
<213> ORGANISM: Homo sapiens
<300> PUBLICATION INFORMATION:
<308> DATABASE ACCESSION NUMBER: UniProt / P13726
<309> DATABASE ENTRY DATE: 2015-07-22
<313> RELEVANT RESIDUES IN SEQ ID NO: (1)..(295)

<400> SEQUENCE: 43

```
Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
                20                  25                  30

Ser Gly Thr Thr Asn Thr Val Ala Ala Tyr Asn Leu Thr Trp Lys Ser
            35                  40                  45

Thr Asn Phe Lys Thr Ile Leu Glu Trp Glu Pro Lys Pro Val Asn Gln
        50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
                100                 105                 110

Gly Asn Val Glu Ser Thr Gly Ser Ala Gly Glu Pro Leu Tyr Glu Asn
            115                 120                 125

Ser Pro Glu Phe Thr Pro Tyr Leu Glu Thr Asn Leu Gly Gln Pro Thr
        130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
                180                 185                 190

Ser Ser Ser Gly Lys Lys Thr Ala Lys Thr Asn Thr Asn Glu Phe Leu
            195                 200                 205

Ile Asp Val Asp Lys Gly Glu Asn Tyr Cys Phe Ser Val Gln Ala Val
        210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
                260                 265                 270

Ser Leu His Lys Cys Arg Lys Ala Gly Val Gly Gln Ser Trp Lys Glu
        275                 280                 285
```

-continued

```
Asn Ser Pro Leu Asn Val Ser
    290                 295

<210> SEQ ID NO 44
<211> LENGTH: 538
<212> TYPE: PRT
<213> ORGANISM: Homo sapiens
<300> PUBLICATION INFORMATION:
<308> DATABASE ACCESSION NUMBER: UniProt / P10155
<309> DATABASE ENTRY DATE: 2015-07-22
<313> RELEVANT RESIDUES IN SEQ ID NO: (1)..(538)

<400> SEQUENCE: 44

Met Glu Glu Ser Val Asn Gln Met Gln Pro Leu Asn Glu Lys Gln Ile
1               5                   10                  15

Ala Asn Ser Gln Asp Gly Tyr Val Trp Gln Val Thr Asp Met Asn Arg
            20                  25                  30

Leu His Arg Phe Leu Cys Phe Gly Ser Glu Gly Gly Thr Tyr Tyr Ile
        35                  40                  45

Lys Glu Gln Lys Leu Gly Leu Glu Asn Ala Glu Ala Leu Ile Arg Leu
    50                  55                  60

Ile Glu Asp Gly Arg Gly Cys Glu Val Ile Gln Glu Ile Lys Ser Phe
65                  70                  75                  80

Ser Gln Glu Gly Arg Thr Thr Lys Gln Glu Pro Met Leu Phe Ala Leu
                85                  90                  95

Ala Ile Cys Ser Gln Cys Ser Asp Ile Ser Thr Lys Gln Ala Ala Phe
            100                 105                 110

Lys Ala Val Ser Glu Val Cys Arg Ile Pro Thr His Leu Phe Thr Phe
        115                 120                 125

Ile Gln Phe Lys Lys Asp Leu Lys Glu Ser Met Lys Cys Gly Met Trp
    130                 135                 140

Gly Arg Ala Leu Arg Lys Ala Ile Ala Asp Trp Tyr Asn Glu Lys Gly
145                 150                 155                 160

Gly Met Ala Leu Ala Leu Ala Val Thr Lys Tyr Lys Gln Arg Asn Gly
                165                 170                 175

Trp Ser His Lys Asp Leu Leu Arg Leu Ser His Leu Lys Pro Ser Ser
            180                 185                 190

Glu Gly Leu Ala Ile Val Thr Lys Tyr Ile Thr Lys Gly Trp Lys Glu
        195                 200                 205

Val His Glu Leu Tyr Lys Glu Lys Ala Leu Ser Val Glu Thr Glu Lys
    210                 215                 220

Leu Leu Lys Tyr Leu Glu Ala Val Glu Lys Val Lys Arg Thr Arg Asp
225                 230                 235                 240

Glu Leu Glu Val Ile His Leu Ile Glu Glu His Arg Leu Val Arg Glu
                245                 250                 255

His Leu Leu Thr Asn His Leu Lys Ser Lys Glu Val Trp Lys Ala Leu
            260                 265                 270

Leu Gln Glu Met Pro Leu Thr Ala Leu Leu Arg Asn Leu Gly Lys Met
        275                 280                 285

Thr Ala Asn Ser Val Leu Glu Pro Gly Asn Ser Glu Val Ser Leu Val
    290                 295                 300

Cys Glu Lys Leu Cys Asn Glu Lys Leu Leu Lys Ala Arg Ile His
305                 310                 315                 320

Pro Phe His Ile Leu Ile Ala Leu Glu Thr Tyr Lys Thr Gly His Gly
                325                 330                 335

Leu Arg Gly Lys Leu Lys Trp Arg Pro Asp Glu Glu Ile Leu Lys Ala
```

```
                340                 345                 350
Leu Asp Ala Ala Phe Tyr Lys Thr Phe Lys Thr Val Glu Pro Thr Gly
            355                 360                 365

Lys Arg Phe Leu Leu Ala Val Asp Val Ser Ala Ser Met Asn Gln Arg
        370                 375                 380

Val Leu Gly Ser Ile Leu Asn Ala Ser Thr Val Ala Ala Met Cys
385                 390                 395                 400

Met Val Val Thr Arg Thr Glu Lys Asp Ser Tyr Val Val Ala Phe Ser
                405                 410                 415

Asp Glu Met Val Pro Cys Pro Val Thr Thr Asp Met Thr Leu Gln Gln
            420                 425                 430

Val Leu Met Ala Met Ser Gln Ile Pro Ala Gly Gly Thr Asp Cys Ser
        435                 440                 445

Leu Pro Met Ile Trp Ala Gln Lys Thr Asn Thr Pro Ala Asp Val Phe
    450                 455                 460

Ile Val Phe Thr Asp Asn Glu Thr Phe Ala Gly Gly Val His Pro Ala
465                 470                 475                 480

Ile Ala Leu Arg Glu Tyr Arg Lys Lys Met Asp Ile Pro Ala Lys Leu
                485                 490                 495

Ile Val Cys Gly Met Thr Ser Asn Gly Phe Thr Ile Ala Asp Pro Asp
            500                 505                 510

Asp Arg Gly Met Leu Asp Met Cys Gly Phe Asp Thr Gly Ala Leu Asp
        515                 520                 525

Val Ile Arg Asn Phe Thr Leu Asp Met Ile
    530                 535

<210> SEQ ID NO 45
<211> LENGTH: 1025
<212> TYPE: PRT
<213> ORGANISM: Homo sapiens
<300> PUBLICATION INFORMATION:
<308> DATABASE ACCESSION NUMBER: UniProt / Q9BYX4
<309> DATABASE ENTRY DATE: 2015-07-22
<313> RELEVANT RESIDUES IN SEQ ID NO: (1)..(1025)

<400> SEQUENCE: 45

Met Ser Asn Gly Tyr Ser Thr Asp Glu Asn Phe Arg Tyr Leu Ile Ser
1               5                   10                  15

Cys Phe Arg Ala Arg Val Lys Met Tyr Ile Gln Val Glu Pro Val Leu
            20                  25                  30

Asp Tyr Leu Thr Phe Leu Pro Ala Glu Val Lys Glu Gln Ile Gln Arg
        35                  40                  45

Thr Val Ala Thr Ser Gly Asn Met Gln Ala Val Glu Leu Leu Leu Ser
    50                  55                  60

Thr Leu Glu Lys Gly Val Trp His Leu Gly Trp Thr Arg Glu Phe Val
65                  70                  75                  80

Glu Ala Leu Arg Arg Thr Gly Ser Pro Leu Ala Ala Arg Tyr Met Asn
                85                  90                  95

Pro Glu Leu Thr Asp Leu Pro Ser Pro Ser Phe Glu Asn Ala His Asp
            100                 105                 110

Glu Tyr Leu Gln Leu Leu Asn Leu Leu Gln Pro Thr Leu Val Asp Lys
        115                 120                 125

Leu Leu Val Arg Asp Val Leu Asp Lys Cys Met Glu Glu Glu Leu Leu
    130                 135                 140

Thr Ile Glu Asp Arg Asn Arg Ile Ala Ala Ala Glu Asn Asn Gly Asn
145                 150                 155                 160
```

```
Glu Ser Gly Val Arg Glu Leu Leu Lys Arg Ile Val Gln Lys Glu Asn
                165                 170                 175
Trp Phe Ser Ala Phe Leu Asn Val Leu Arg Gln Thr Gly Asn Asn Glu
            180                 185                 190
Leu Val Gln Glu Leu Thr Gly Ser Asp Cys Ser Glu Ser Asn Ala Glu
        195                 200                 205
Ile Glu Asn Leu Ser Gln Val Asp Gly Pro Gln Val Glu Glu Gln Leu
    210                 215                 220
Leu Ser Thr Thr Val Gln Pro Asn Leu Glu Lys Val Trp Gly Met
225                 230                 235                 240
Glu Asn Asn Ser Ser Glu Ser Ser Phe Ala Asp Ser Ser Val Val Ser
                245                 250                 255
Glu Ser Asp Thr Ser Leu Ala Glu Gly Ser Val Ser Cys Leu Asp Glu
            260                 265                 270
Ser Leu Gly His Asn Ser Asn Met Gly Ser Asp Ser Gly Thr Met Gly
        275                 280                 285
Ser Asp Ser Asp Glu Glu Asn Val Ala Ala Arg Ala Ser Pro Glu Pro
    290                 295                 300
Glu Leu Gln Leu Arg Pro Tyr Gln Met Glu Val Ala Gln Pro Ala Leu
305                 310                 315                 320
Glu Gly Lys Asn Ile Ile Ile Cys Leu Pro Thr Gly Ser Gly Lys Thr
                325                 330                 335
Arg Val Ala Val Tyr Ile Ala Lys Asp His Leu Asp Lys Lys Lys Lys
            340                 345                 350
Ala Ser Glu Pro Gly Lys Val Ile Val Leu Val Asn Lys Val Leu Leu
        355                 360                 365
Val Glu Gln Leu Phe Arg Lys Glu Phe Gln Pro Phe Leu Lys Lys Trp
    370                 375                 380
Tyr Arg Val Ile Gly Leu Ser Gly Asp Thr Gln Leu Lys Ile Ser Phe
385                 390                 395                 400
Pro Glu Val Val Lys Ser Cys Asp Ile Ile Ile Ser Thr Ala Gln Ile
                405                 410                 415
Leu Glu Asn Ser Leu Leu Asn Leu Glu Asn Gly Glu Asp Ala Gly Val
            420                 425                 430
Gln Leu Ser Asp Phe Ser Leu Ile Ile Ile Asp Glu Cys His His Thr
        435                 440                 445
Asn Lys Glu Ala Val Tyr Asn Asn Ile Met Arg His Tyr Leu Met Gln
        450                 455                 460
Lys Leu Lys Asn Asn Arg Leu Lys Lys Glu Asn Lys Pro Val Ile Pro
465                 470                 475                 480
Leu Pro Gln Ile Leu Gly Leu Thr Ala Ser Pro Gly Val Gly Gly Ala
                485                 490                 495
Thr Lys Gln Ala Lys Ala Glu Glu His Ile Leu Lys Leu Cys Ala Asn
            500                 505                 510
Leu Asp Ala Phe Thr Ile Lys Thr Val Lys Glu Asn Leu Asp Gln Leu
        515                 520                 525
Lys Asn Gln Ile Gln Glu Pro Cys Lys Lys Phe Ala Ile Ala Asp Ala
    530                 535                 540
Thr Arg Glu Asp Pro Phe Lys Glu Lys Leu Leu Glu Ile Met Thr Arg
545                 550                 555                 560
Ile Gln Thr Tyr Cys Gln Met Ser Pro Met Ser Asp Phe Gly Thr Gln
                565                 570                 575
```

```
Pro Tyr Glu Gln Trp Ala Ile Gln Met Glu Lys Lys Ala Ala Lys Glu
            580                 585                 590

Gly Asn Arg Lys Glu Arg Val Cys Ala Glu His Leu Arg Lys Tyr Asn
        595                 600                 605

Glu Ala Leu Gln Ile Asn Asp Thr Ile Arg Met Ile Asp Ala Tyr Thr
    610                 615                 620

His Leu Glu Thr Phe Tyr Asn Glu Glu Lys Asp Lys Lys Phe Ala Val
625                 630                 635                 640

Ile Glu Asp Asp Ser Asp Glu Gly Gly Asp Glu Tyr Cys Asp Gly
                645                 650                 655

Asp Glu Asp Glu Asp Asp Leu Lys Lys Pro Lys Leu Asp Glu Thr
            660                 665                 670

Asp Arg Phe Leu Met Thr Leu Phe Glu Asn Asn Lys Met Leu Lys
        675                 680                 685

Arg Leu Ala Glu Asn Pro Glu Tyr Glu Asn Glu Lys Leu Thr Lys Leu
    690                 695                 700

Arg Asn Thr Ile Met Glu Gln Tyr Thr Arg Thr Glu Glu Ser Ala Arg
705                 710                 715                 720

Gly Ile Ile Phe Thr Lys Thr Arg Gln Ser Ala Tyr Ala Leu Ser Gln
                725                 730                 735

Trp Ile Thr Glu Asn Glu Lys Phe Ala Glu Val Gly Val Lys Ala His
            740                 745                 750

His Leu Ile Gly Ala Gly His Ser Ser Glu Phe Lys Pro Met Thr Gln
        755                 760                 765

Asn Glu Gln Lys Glu Val Ile Ser Lys Phe Arg Thr Gly Lys Ile Asn
    770                 775                 780

Leu Leu Ile Ala Thr Thr Val Ala Glu Glu Gly Leu Asp Ile Lys Glu
785                 790                 795                 800

Cys Asn Ile Val Ile Arg Tyr Gly Leu Val Thr Asn Glu Ile Ala Met
                805                 810                 815

Val Gln Ala Arg Gly Arg Ala Arg Ala Asp Glu Ser Thr Tyr Val Leu
            820                 825                 830

Val Ala His Ser Gly Ser Gly Val Ile Glu His Glu Thr Val Asn Asp
        835                 840                 845

Phe Arg Glu Lys Met Met Tyr Lys Ala Ile His Cys Val Gln Asn Met
    850                 855                 860

Lys Pro Glu Glu Tyr Ala His Lys Ile Leu Glu Leu Gln Met Gln Ser
865                 870                 875                 880

Ile Met Glu Lys Lys Met Lys Thr Lys Arg Asn Ile Ala Lys His Tyr
                885                 890                 895

Lys Asn Asn Pro Ser Leu Ile Thr Phe Leu Cys Lys Asn Cys Ser Val
            900                 905                 910

Leu Ala Cys Ser Gly Glu Asp Ile His Val Ile Glu Lys Met His His
        915                 920                 925

Val Asn Met Thr Pro Glu Phe Lys Glu Leu Tyr Ile Val Arg Glu Asn
    930                 935                 940

Lys Ala Leu Gln Lys Lys Cys Ala Asp Tyr Gln Ile Asn Gly Glu Ile
945                 950                 955                 960

Ile Cys Lys Cys Gly Gln Ala Trp Gly Thr Met Met Val His Lys Gly
                965                 970                 975

Leu Asp Leu Pro Cys Leu Lys Ile Arg Asn Phe Val Val Phe Lys
            980                 985                 990

Asn Asn Ser Thr Lys Lys Gln Tyr  Lys Lys Trp Val Glu  Leu Pro Ile
```

```
                995              1000             1005
Thr Phe Pro Asn Leu Asp Tyr Ser Glu Cys Cys Leu Phe Ser Asp
        1010             1015             1020

Glu Asp
1025

<210> SEQ ID NO 46
<211> LENGTH: 451
<212> TYPE: PRT
<213> ORGANISM: Homo sapiens
<300> PUBLICATION INFORMATION:
<308> DATABASE ACCESSION NUMBER: UniProt / Q71U36
<309> DATABASE ENTRY DATE: 2015-07-22
<313> RELEVANT RESIDUES IN SEQ ID NO: (1)..(451)

<400> SEQUENCE: 46

Met Arg Glu Cys Ile Ser Ile His Val Gly Gln Ala Gly Val Gln Ile
1               5                   10                  15

Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Gly Asp Asp Ser
        35                  40                  45

Phe Asn Thr Phe Phe Ser Glu Thr Gly Ala Gly Lys His Val Pro Arg
    50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Ile Asp Leu Val Leu Asp Arg Ile Arg Lys Leu Ala Asp Gln
        115                 120                 125

Cys Thr Gly Leu Gln Gly Phe Leu Val Phe His Ser Phe Gly Gly Gly
    130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ser Ile Tyr Pro Ala Pro Gln
                165                 170                 175

Val Ser Thr Ala Val Val Glu Pro Tyr Asn Ser Ile Leu Thr Thr His
            180                 185                 190

Thr Thr Leu Glu His Ser Asp Cys Ala Phe Met Val Asp Asn Glu Ala
        195                 200                 205

Ile Tyr Asp Ile Cys Arg Arg Asn Leu Asp Ile Glu Arg Pro Thr Tyr
    210                 215                 220

Thr Asn Leu Asn Arg Leu Ile Gly Gln Ile Val Ser Ser Ile Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Pro Leu Ala Thr Tyr
            260                 265                 270

Ala Pro Val Ile Ser Ala Glu Lys Ala Tyr His Glu Gln Leu Ser Val
        275                 280                 285

Ala Glu Ile Thr Asn Ala Cys Phe Glu Pro Ala Asn Gln Met Val Lys
    290                 295                 300

Cys Asp Pro Arg His Gly Lys Tyr Met Ala Cys Cys Leu Leu Tyr Arg
305                 310                 315                 320
```

```
Gly Asp Val Val Pro Lys Asp Val Asn Ala Ile Ala Thr Ile Lys
            325                 330                 335

Thr Lys Arg Thr Ile Gln Phe Val Asp Trp Cys Pro Thr Gly Phe Lys
        340                 345                 350

Val Gly Ile Asn Tyr Gln Pro Pro Thr Val Val Pro Gly Gly Asp Leu
            355                 360                 365

Ala Lys Val Gln Arg Ala Val Cys Met Leu Ser Asn Thr Thr Ala Ile
    370                 375                 380

Ala Glu Ala Trp Ala Arg Leu Asp His Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Met Ala Ala Leu Glu Lys Asp Tyr
            420                 425                 430

Glu Glu Val Gly Val Asp Ser Val Glu Gly Glu Gly Glu Glu Glu Gly
            435                 440                 445

Glu Glu Tyr
    450

<210> SEQ ID NO 47
<211> LENGTH: 451
<212> TYPE: PRT
<213> ORGANISM: Homo sapiens
<300> PUBLICATION INFORMATION:
<308> DATABASE ACCESSION NUMBER: UniProt / P68363
<309> DATABASE ENTRY DATE: 2015-07-22
<313> RELEVANT RESIDUES IN SEQ ID NO: (1)..(451)

<400> SEQUENCE: 47

Met Arg Glu Cys Ile Ser Ile His Val Gly Gln Ala Gly Val Gln Ile
1               5                   10                  15

Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Gly Asp Asp Ser
        35                  40                  45

Phe Asn Thr Phe Phe Ser Glu Thr Gly Ala Gly Lys His Val Pro Arg
    50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Ile Asp Leu Val Leu Asp Arg Ile Arg Lys Leu Ala Asp Gln
        115                 120                 125

Cys Thr Gly Leu Gln Gly Phe Leu Val Phe His Ser Phe Gly Gly Gly
    130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ser Ile Tyr Pro Ala Pro Gln
                165                 170                 175

Val Ser Thr Ala Val Val Glu Pro Tyr Asn Ser Ile Leu Thr Thr His
            180                 185                 190

Thr Thr Leu Glu His Ser Asp Cys Ala Phe Met Val Asp Asn Glu Ala
        195                 200                 205
```

```
Ile Tyr Asp Ile Cys Arg Arg Asn Leu Asp Ile Glu Arg Pro Thr Tyr
    210                 215                 220

Thr Asn Leu Asn Arg Leu Ile Ser Gln Ile Val Ser Ser Ile Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Pro Leu Ala Thr Tyr
        260                 265                 270

Ala Pro Val Ile Ser Ala Glu Lys Ala Tyr His Glu Gln Leu Ser Val
            275                 280                 285

Ala Glu Ile Thr Asn Ala Cys Phe Glu Pro Ala Asn Gln Met Val Lys
290                 295                 300

Cys Asp Pro Arg His Gly Lys Tyr Met Ala Cys Cys Leu Leu Tyr Arg
305                 310                 315                 320

Gly Asp Val Val Pro Lys Asp Val Asn Ala Ala Ile Ala Thr Ile Lys
                325                 330                 335

Thr Lys Arg Ser Ile Gln Phe Val Asp Trp Cys Pro Thr Gly Phe Lys
            340                 345                 350

Val Gly Ile Asn Tyr Gln Pro Pro Thr Val Val Pro Gly Gly Asp Leu
        355                 360                 365

Ala Lys Val Gln Arg Ala Val Cys Met Leu Ser Asn Thr Thr Ala Ile
370                 375                 380

Ala Glu Ala Trp Ala Arg Leu Asp His Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Met Ala Ala Leu Glu Lys Asp Tyr
            420                 425                 430

Glu Glu Val Gly Val Asp Ser Val Glu Gly Glu Gly Glu Glu Glu Gly
        435                 440                 445

Glu Glu Tyr
    450

<210> SEQ ID NO 48
<211> LENGTH: 449
<212> TYPE: PRT
<213> ORGANISM: Homo sapiens
<300> PUBLICATION INFORMATION:
<308> DATABASE ACCESSION NUMBER: UniProt / Q9BQE3
<309> DATABASE ENTRY DATE: 2015-07-22
<313> RELEVANT RESIDUES IN SEQ ID NO: (1)..(449)

<400> SEQUENCE: 48

Met Arg Glu Cys Ile Ser Ile His Val Gly Gln Ala Gly Val Gln Ile
1               5                   10                  15

Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Gly Asp Asp Ser
        35                  40                  45

Phe Asn Thr Phe Phe Ser Glu Thr Gly Ala Gly Lys His Val Pro Arg
    50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
```

```
            100                 105                 110
Glu Ile Ile Asp Leu Val Leu Asp Arg Ile Arg Lys Leu Ala Asp Gln
            115                 120                 125
Cys Thr Gly Leu Gln Gly Phe Leu Val Phe His Ser Phe Gly Gly Gly
            130                 135                 140
Thr Gly Ser Gly Phe Thr Ser Leu Leu Met Glu Arg Leu Ser Val Asp
145                 150                 155                 160
Tyr Gly Lys Lys Ser Lys Leu Glu Phe Ser Ile Tyr Pro Ala Pro Gln
                165                 170                 175
Val Ser Thr Ala Val Val Glu Pro Tyr Asn Ser Ile Leu Thr Thr His
                180                 185                 190
Thr Thr Leu Glu His Ser Asp Cys Ala Phe Met Val Asp Asn Glu Ala
            195                 200                 205
Ile Tyr Asp Ile Cys Arg Arg Asn Leu Asp Ile Glu Arg Pro Thr Tyr
            210                 215                 220
Thr Asn Leu Asn Arg Leu Ile Ser Gln Ile Val Ser Ser Ile Thr Ala
225                 230                 235                 240
Ser Leu Arg Phe Asp Gly Ala Leu Asn Val Asp Leu Thr Glu Phe Gln
                245                 250                 255
Thr Asn Leu Val Pro Tyr Pro Arg Ile His Phe Pro Leu Ala Thr Tyr
                260                 265                 270
Ala Pro Val Ile Ser Ala Glu Lys Ala Tyr His Glu Gln Leu Thr Val
            275                 280                 285
Ala Glu Ile Thr Asn Ala Cys Phe Glu Pro Ala Asn Gln Met Val Lys
            290                 295                 300
Cys Asp Pro Arg His Gly Lys Tyr Met Ala Cys Cys Leu Leu Tyr Arg
305                 310                 315                 320
Gly Asp Val Val Pro Lys Asp Val Asn Ala Ala Ile Ala Thr Ile Lys
                325                 330                 335
Thr Lys Arg Thr Ile Gln Phe Val Asp Trp Cys Pro Thr Gly Phe Lys
                340                 345                 350
Val Gly Ile Asn Tyr Gln Pro Pro Thr Val Val Pro Gly Gly Asp Leu
            355                 360                 365
Ala Lys Val Gln Arg Ala Val Cys Met Leu Ser Asn Thr Thr Ala Val
            370                 375                 380
Ala Glu Ala Trp Ala Arg Leu Asp His Lys Phe Asp Leu Met Tyr Ala
385                 390                 395                 400
Lys Arg Ala Phe Val His Trp Tyr Val Gly Glu Gly Met Glu Glu Gly
                405                 410                 415
Glu Phe Ser Glu Ala Arg Glu Asp Met Ala Ala Leu Glu Lys Asp Tyr
                420                 425                 430
Glu Glu Val Gly Ala Asp Ser Ala Asp Gly Glu Asp Glu Gly Glu Glu
            435                 440                 445
Tyr

<210> SEQ ID NO 49
<211> LENGTH: 444
<212> TYPE: PRT
<213> ORGANISM: Homo sapiens
<300> PUBLICATION INFORMATION:
<308> DATABASE ACCESSION NUMBER: UniProt / P07437
<309> DATABASE ENTRY DATE: 2015-07-22
<313> RELEVANT RESIDUES IN SEQ ID NO: (1)..(444)

<400> SEQUENCE: 49
```

```
Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Asp Arg Ile Ser
            35                  40                  45

Val Tyr Tyr Asn Glu Ala Thr Gly Gly Lys Tyr Val Pro Arg Ala Ile
50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
                100                 105                 110

Val Asp Ser Val Leu Asp Val Val Arg Lys Glu Ala Glu Ser Cys Asp
            115                 120                 125

Cys Leu Gln Gly Phe Gln Leu Thr His Ser Leu Gly Gly Gly Thr Gly
        130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Leu Thr Thr Pro Thr Tyr Gly Asp
    210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Val Phe Asp Ala Lys Asn Met Met Ala Ala Cys Asp
    290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ala Val Thr Phe Ile
        355                 360                 365

Gly Asn Ser Thr Ala Ile Gln Glu Leu Phe Lys Arg Ile Ser Glu Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
```

```
                        420               425               430
Glu Glu Asp Phe Gly Glu Glu Ala Glu Glu Glu Ala
            435               440

<210> SEQ ID NO 50
<211> LENGTH: 4391
<212> TYPE: PRT
<213> ORGANISM: Homo sapiens
<300> PUBLICATION INFORMATION:
<308> DATABASE ACCESSION NUMBER: UniProt / P98160
<309> DATABASE ENTRY DATE: 2015-07-22
<313> RELEVANT RESIDUES IN SEQ ID NO: (1)..(4391)

<400> SEQUENCE: 50

Met Gly Trp Arg Ala Ala Gly Ala Leu Leu Ala Leu Leu Leu His
1               5                   10                  15

Gly Arg Leu Leu Ala Val Thr His Gly Leu Arg Ala Tyr Asp Gly Leu
            20                  25                  30

Ser Leu Pro Glu Asp Ile Glu Thr Val Thr Ala Ser Gln Met Arg Trp
            35                  40                  45

Thr His Ser Tyr Leu Ser Asp Asp Glu Asp Met Leu Ala Asp Ser Ile
        50                  55                  60

Ser Gly Asp Asp Leu Gly Ser Gly Asp Leu Gly Ser Gly Asp Phe Gln
65                  70                  75                  80

Met Val Tyr Phe Arg Ala Leu Val Asn Phe Thr Arg Ser Ile Glu Tyr
                85                  90                  95

Ser Pro Gln Leu Glu Asp Ala Gly Ser Arg Glu Phe Arg Glu Val Ser
            100                 105                 110

Glu Ala Val Val Asp Thr Leu Glu Ser Glu Tyr Leu Lys Ile Pro Gly
            115                 120                 125

Asp Gln Val Val Ser Val Val Phe Ile Lys Glu Leu Asp Gly Trp Val
        130                 135                 140

Phe Val Glu Leu Asp Val Gly Ser Glu Gly Asn Ala Asp Gly Ala Gln
145                 150                 155                 160

Ile Gln Glu Met Leu Leu Arg Val Ile Ser Ser Gly Ser Val Ala Ser
                165                 170                 175

Tyr Val Thr Ser Pro Gln Gly Phe Gln Phe Arg Arg Leu Gly Thr Val
            180                 185                 190

Pro Gln Phe Pro Arg Ala Cys Thr Glu Ala Glu Phe Ala Cys His Ser
            195                 200                 205

Tyr Asn Glu Cys Val Ala Leu Glu Tyr Arg Cys Asp Arg Arg Pro Asp
        210                 215                 220

Cys Arg Asp Met Ser Asp Glu Leu Asn Cys Glu Glu Pro Val Leu Gly
225                 230                 235                 240

Ile Ser Pro Thr Phe Ser Leu Leu Val Glu Thr Thr Ser Leu Pro Pro
                245                 250                 255

Arg Pro Glu Thr Thr Ile Met Arg Gln Pro Pro Val Thr His Ala Pro
            260                 265                 270

Gln Pro Leu Leu Pro Gly Ser Val Arg Pro Leu Pro Cys Gly Pro Gln
            275                 280                 285

Glu Ala Ala Cys Arg Asn Gly His Cys Ile Pro Arg Asp Tyr Leu Cys
        290                 295                 300

Asp Gly Gln Glu Asp Cys Glu Asp Gly Ser Asp Glu Leu Asp Cys Gly
305                 310                 315                 320

Pro Pro Pro Pro Cys Glu Pro Asn Glu Phe Pro Cys Gly Asn Gly His
                325                 330                 335
```

```
Cys Ala Leu Lys Leu Trp Arg Cys Asp Gly Asp Phe Asp Cys Glu Asp
            340                 345                 350

Arg Thr Asp Glu Ala Asn Cys Pro Thr Lys Arg Pro Glu Glu Val Cys
            355                 360                 365

Gly Pro Thr Gln Phe Arg Cys Val Ser Thr Asn Met Cys Ile Pro Ala
            370                 375                 380

Ser Phe His Cys Asp Glu Glu Ser Asp Cys Pro Asp Arg Ser Asp Glu
385                 390                 395                 400

Phe Gly Cys Met Pro Pro Gln Val Val Thr Pro Pro Arg Glu Ser Ile
                405                 410                 415

Gln Ala Ser Arg Gly Gln Thr Val Thr Phe Thr Cys Val Ala Ile Gly
            420                 425                 430

Val Pro Thr Pro Ile Ile Asn Trp Arg Leu Asn Trp Gly His Ile Pro
            435                 440                 445

Ser His Pro Arg Val Thr Val Thr Ser Glu Gly Gly Arg Gly Thr Leu
        450                 455                 460

Ile Ile Arg Asp Val Lys Glu Ser Asp Gln Gly Ala Tyr Thr Cys Glu
465                 470                 475                 480

Ala Met Asn Ala Arg Gly Met Val Phe Gly Ile Pro Asp Gly Val Leu
                485                 490                 495

Glu Leu Val Pro Gln Arg Gly Pro Cys Pro Asp Gly His Phe Tyr Leu
            500                 505                 510

Glu His Ser Ala Ala Cys Leu Pro Cys Phe Cys Phe Gly Ile Thr Ser
        515                 520                 525

Val Cys Gln Ser Thr Arg Arg Phe Arg Asp Gln Ile Arg Leu Arg Phe
    530                 535                 540

Asp Gln Pro Asp Asp Phe Lys Gly Val Asn Val Thr Met Pro Ala Gln
545                 550                 555                 560

Pro Gly Thr Pro Pro Leu Ser Ser Thr Gln Leu Gln Ile Asp Pro Ser
                565                 570                 575

Leu His Glu Phe Gln Leu Val Asp Leu Ser Arg Arg Phe Leu Val His
            580                 585                 590

Asp Ser Phe Trp Ala Leu Pro Glu Gln Phe Leu Gly Asn Lys Val Asp
            595                 600                 605

Ser Tyr Gly Gly Ser Leu Arg Tyr Asn Val Arg Tyr Glu Leu Ala Arg
        610                 615                 620

Gly Met Leu Glu Pro Val Gln Arg Pro Asp Val Val Leu Met Gly Ala
625                 630                 635                 640

Gly Tyr Arg Leu Leu Ser Arg Gly His Thr Pro Thr Gln Pro Gly Ala
                645                 650                 655

Leu Asn Gln Arg Gln Val Gln Phe Ser Glu Glu His Trp Val His Glu
            660                 665                 670

Ser Gly Arg Pro Val Gln Arg Ala Glu Leu Leu Gln Val Leu Gln Ser
        675                 680                 685

Leu Glu Ala Val Leu Ile Gln Thr Val Tyr Asn Thr Lys Met Ala Ser
    690                 695                 700

Val Gly Leu Ser Asp Ile Ala Met Asp Thr Thr Val Thr His Ala Thr
705                 710                 715                 720

Ser His Gly Arg Ala His Ser Val Glu Glu Cys Arg Cys Pro Ile Gly
                725                 730                 735

Tyr Ser Gly Leu Ser Cys Glu Ser Cys Asp Ala His Phe Thr Arg Val
            740                 745                 750
```

```
Pro Gly Gly Pro Tyr Leu Gly Thr Cys Ser Gly Cys Asn Cys Asn Gly
            755                 760                 765

His Ala Ser Ser Cys Asp Pro Val Tyr Gly His Cys Leu Asn Cys Gln
    770                 775                 780

His Asn Thr Glu Gly Pro Gln Cys Asn Lys Cys Lys Ala Gly Phe Phe
785                 790                 795                 800

Gly Asp Ala Met Lys Ala Thr Ala Thr Ser Cys Arg Pro Cys Pro Cys
                805                 810                 815

Pro Tyr Ile Asp Ala Ser Arg Arg Phe Ser Asp Thr Cys Phe Leu Asp
            820                 825                 830

Thr Asp Gly Gln Ala Thr Cys Asp Ala Cys Ala Pro Gly Tyr Thr Gly
            835                 840                 845

Arg Arg Cys Glu Ser Cys Ala Pro Gly Tyr Glu Gly Asn Pro Ile Gln
            850                 855                 860

Pro Gly Gly Lys Cys Arg Pro Val Asn Gln Glu Ile Val Arg Cys Asp
865                 870                 875                 880

Glu Arg Gly Ser Met Gly Thr Ser Gly Glu Ala Cys Arg Cys Lys Asn
                885                 890                 895

Asn Val Val Gly Arg Leu Cys Asn Glu Cys Ala Asp Gly Ser Phe His
            900                 905                 910

Leu Ser Thr Arg Asn Pro Asp Gly Cys Leu Lys Cys Phe Cys Met Gly
            915                 920                 925

Val Ser Arg His Cys Thr Ser Ser Ser Trp Ser Arg Ala Gln Leu His
            930                 935                 940

Gly Ala Ser Glu Glu Pro Gly His Phe Ser Leu Thr Asn Ala Ala Ser
945                 950                 955                 960

Thr His Thr Thr Asn Glu Gly Ile Phe Ser Pro Thr Pro Gly Glu Leu
                965                 970                 975

Gly Phe Ser Ser Phe His Arg Leu Leu Ser Gly Pro Tyr Phe Trp Ser
            980                 985                 990

Leu Pro Ser Arg Phe Leu Gly Asp Lys Val Thr Ser Tyr Gly Gly Glu
            995                 1000                1005

Leu Arg Phe Thr Val Thr Gln Arg Ser Gln Pro Gly Ser Thr Pro
    1010                1015                1020

Leu His Gly Gln Pro Leu Val Val Leu Gln Gly Asn Asn Ile Ile
    1025                1030                1035

Leu Glu His His Val Ala Gln Glu Pro Ser Pro Gly Gln Pro Ser
    1040                1045                1050

Thr Phe Ile Val Pro Phe Arg Glu Gln Ala Trp Gln Arg Pro Asp
    1055                1060                1065

Gly Gln Pro Ala Thr Arg Glu His Leu Leu Met Ala Leu Ala Gly
    1070                1075                1080

Ile Asp Thr Leu Leu Ile Arg Ala Ser Tyr Ala Gln Gln Pro Ala
    1085                1090                1095

Glu Ser Arg Val Ser Gly Ile Ser Met Asp Val Ala Val Pro Glu
    1100                1105                1110

Glu Thr Gly Gln Asp Pro Ala Leu Glu Val Glu Gln Cys Ser Cys
    1115                1120                1125

Pro Pro Gly Tyr Arg Gly Pro Ser Cys Gln Asp Cys Asp Thr Gly
    1130                1135                1140

Tyr Thr Arg Thr Pro Ser Gly Leu Tyr Leu Gly Thr Cys Glu Arg
    1145                1150                1155

Cys Ser Cys His Gly His Ser Glu Ala Cys Glu Pro Glu Thr Gly
```

```
                    1160                1165                1170
Ala Cys Gln Gly Cys Gln His His Thr Glu Gly Pro Arg Cys Glu
    1175                1180                1185
Gln Cys Gln Pro Gly Tyr Tyr Gly Asp Ala Gln Arg Gly Thr Pro
    1190                1195                1200
Gln Asp Cys Gln Leu Cys Pro Cys Tyr Gly Asp Pro Ala Ala Gly
    1205                1210                1215
Gln Ala Ala His Thr Cys Phe Leu Asp Thr Asp Gly His Pro Thr
    1220                1225                1230
Cys Asp Ala Cys Ser Pro Gly His Ser Gly Arg His Cys Glu Arg
    1235                1240                1245
Cys Ala Pro Gly Tyr Tyr Gly Asn Pro Ser Gln Gly Gln Pro Cys
    1250                1255                1260
Gln Arg Asp Ser Gln Val Pro Gly Pro Ile Gly Cys Asn Cys Asp
    1265                1270                1275
Pro Gln Gly Ser Val Ser Ser Gln Cys Asp Ala Ala Gly Gln Cys
    1280                1285                1290
Gln Cys Lys Ala Gln Val Glu Gly Leu Thr Cys Ser His Cys Arg
    1295                1300                1305
Pro His His Phe His Leu Ser Ala Ser Asn Pro Asp Gly Cys Leu
    1310                1315                1320
Pro Cys Phe Cys Met Gly Ile Thr Gln Gln Cys Ala Ser Ser Ala
    1325                1330                1335
Tyr Thr Arg His Leu Ile Ser Thr His Phe Ala Pro Gly Asp Phe
    1340                1345                1350
Gln Gly Phe Ala Leu Val Asn Pro Gln Arg Asn Ser Arg Leu Thr
    1355                1360                1365
Gly Glu Phe Thr Val Glu Pro Val Pro Glu Gly Ala Gln Leu Ser
    1370                1375                1380
Phe Gly Asn Phe Ala Gln Leu Gly His Glu Ser Phe Tyr Trp Gln
    1385                1390                1395
Leu Pro Glu Thr Tyr Gln Gly Asp Lys Val Ala Ala Tyr Gly Gly
    1400                1405                1410
Lys Leu Arg Tyr Thr Leu Ser Tyr Thr Ala Gly Pro Gln Gly Ser
    1415                1420                1425
Pro Leu Ser Asp Pro Asp Val Gln Ile Thr Gly Asn Asn Ile Met
    1430                1435                1440
Leu Val Ala Ser Gln Pro Ala Leu Gln Gly Pro Glu Arg Arg Ser
    1445                1450                1455
Tyr Glu Ile Met Phe Arg Glu Glu Phe Trp Arg Arg Pro Asp Gly
    1460                1465                1470
Gln Pro Ala Thr Arg Glu His Leu Leu Met Ala Leu Ala Asp Leu
    1475                1480                1485
Asp Glu Leu Leu Ile Arg Ala Thr Phe Ser Ser Val Pro Leu Ala
    1490                1495                1500
Ala Ser Ile Ser Ala Val Ser Leu Glu Val Ala Gln Pro Gly Pro
    1505                1510                1515
Ser Asn Arg Pro Arg Ala Leu Glu Val Glu Glu Cys Arg Cys Pro
    1520                1525                1530
Pro Gly Tyr Ile Gly Leu Ser Cys Gln Asp Cys Ala Pro Gly Tyr
    1535                1540                1545
Thr Arg Thr Gly Ser Gly Leu Tyr Leu Gly His Cys Glu Leu Cys
    1550                1555                1560
```

-continued

```
Glu Cys Asn Gly His Ser Asp Leu Cys His Pro Glu Thr Gly Ala
1565                1570                1575

Cys Ser Gln Cys Gln His Asn Ala Ala Gly Glu Phe Cys Glu Leu
1580                1585                1590

Cys Ala Pro Gly Tyr Tyr Gly Asp Ala Thr Ala Gly Thr Pro Glu
1595                1600                1605

Asp Cys Gln Pro Cys Ala Cys Pro Leu Thr Asn Pro Glu Asn Met
1610                1615                1620

Phe Ser Arg Thr Cys Glu Ser Leu Gly Ala Gly Gly Tyr Arg Cys
1625                1630                1635

Thr Ala Cys Glu Pro Gly Tyr Thr Gly Gln Tyr Cys Glu Gln Cys
1640                1645                1650

Gly Pro Gly Tyr Val Gly Asn Pro Ser Val Gln Gly Gly Gln Cys
1655                1660                1665

Leu Pro Glu Thr Asn Gln Ala Pro Leu Val Val Glu Val His Pro
1670                1675                1680

Ala Arg Ser Ile Val Pro Gln Gly Gly Ser His Ser Leu Arg Cys
1685                1690                1695

Gln Val Ser Gly Ser Pro Pro His Tyr Phe Tyr Trp Ser Arg Glu
1700                1705                1710

Asp Gly Arg Pro Val Pro Ser Gly Thr Gln Gln Arg His Gln Gly
1715                1720                1725

Ser Glu Leu His Phe Pro Ser Val Gln Pro Ser Asp Ala Gly Val
1730                1735                1740

Tyr Ile Cys Thr Cys Arg Asn Leu His Gln Ser Asn Thr Ser Arg
1745                1750                1755

Ala Glu Leu Leu Val Thr Glu Ala Pro Ser Lys Pro Ile Thr Val
1760                1765                1770

Thr Val Glu Glu Gln Arg Ser Gln Ser Val Arg Pro Gly Ala Asp
1775                1780                1785

Val Thr Phe Ile Cys Thr Ala Lys Ser Lys Ser Pro Ala Tyr Thr
1790                1795                1800

Leu Val Trp Thr Arg Leu His Asn Gly Lys Leu Pro Thr Arg Ala
1805                1810                1815

Met Asp Phe Asn Gly Ile Leu Thr Ile Arg Asn Val Gln Leu Ser
1820                1825                1830

Asp Ala Gly Thr Tyr Val Cys Thr Gly Ser Asn Met Phe Ala Met
1835                1840                1845

Asp Gln Gly Thr Ala Thr Leu His Val Gln Ala Ser Gly Thr Leu
1850                1855                1860

Ser Ala Pro Val Val Ser Ile His Pro Pro Gln Leu Thr Val Gln
1865                1870                1875

Pro Gly Gln Leu Ala Glu Phe Arg Cys Ser Ala Thr Gly Ser Pro
1880                1885                1890

Thr Pro Thr Leu Glu Trp Thr Gly Gly Pro Gly Gly Gln Leu Pro
1895                1900                1905

Ala Lys Ala Gln Ile His Gly Gly Ile Leu Arg Leu Pro Ala Val
1910                1915                1920

Glu Pro Thr Asp Gln Ala Gln Tyr Leu Cys Arg Ala His Ser Ser
1925                1930                1935

Ala Gly Gln Gln Val Ala Arg Ala Val Leu His Val His Gly Gly
1940                1945                1950
```

```
Gly Gly Pro Arg Val Gln Val Ser Pro Glu Arg Thr Gln Val His
    1955                1960                1965

Ala Gly Arg Thr Val Arg Leu Tyr Cys Arg Ala Ala Gly Val Pro
    1970                1975                1980

Ser Ala Thr Ile Thr Trp Arg Lys Glu Gly Gly Ser Leu Pro Pro
    1985                1990                1995

Gln Ala Arg Ser Glu Arg Thr Asp Ile Ala Thr Leu Leu Ile Pro
    2000                2005                2010

Ala Ile Thr Thr Ala Asp Ala Gly Phe Tyr Leu Cys Val Ala Thr
    2015                2020                2025

Ser Pro Ala Gly Thr Ala Gln Ala Arg Ile Gln Val Val Val Leu
    2030                2035                2040

Ser Ala Ser Asp Ala Ser Pro Pro Val Lys Ile Glu Ser Ser
    2045                2050                2055

Ser Pro Ser Val Thr Glu Gly Gln Thr Leu Asp Leu Asn Cys Val
    2060                2065                2070

Val Ala Gly Ser Ala His Ala Gln Val Thr Trp Tyr Arg Arg Gly
    2075                2080                2085

Gly Ser Leu Pro Pro His Thr Gln Val His Gly Ser Arg Leu Arg
    2090                2095                2100

Leu Pro Gln Val Ser Pro Ala Asp Ser Gly Glu Tyr Val Cys Arg
    2105                2110                2115

Val Glu Asn Gly Ser Gly Pro Lys Glu Ala Ser Ile Thr Val Ser
    2120                2125                2130

Val Leu His Gly Thr His Ser Gly Pro Ser Tyr Thr Pro Val Pro
    2135                2140                2145

Gly Ser Thr Arg Pro Ile Arg Ile Glu Pro Ser Ser Ser His Val
    2150                2155                2160

Ala Glu Gly Gln Thr Leu Asp Leu Asn Cys Val Val Pro Gly Gln
    2165                2170                2175

Ala His Ala Gln Val Thr Trp His Lys Arg Gly Gly Ser Leu Pro
    2180                2185                2190

Ala Arg His Gln Thr His Gly Ser Leu Leu Arg Leu His Gln Val
    2195                2200                2205

Thr Pro Ala Asp Ser Gly Glu Tyr Val Cys His Val Val Gly Thr
    2210                2215                2220

Ser Gly Pro Leu Glu Ala Ser Val Leu Val Thr Ile Glu Ala Ser
    2225                2230                2235

Val Ile Pro Gly Pro Ile Pro Pro Val Arg Ile Glu Ser Ser Ser
    2240                2245                2250

Ser Thr Val Ala Glu Gly Gln Thr Leu Asp Leu Ser Cys Val Val
    2255                2260                2265

Ala Gly Gln Ala His Ala Gln Val Thr Trp Tyr Lys Arg Gly Gly
    2270                2275                2280

Ser Leu Pro Ala Arg His Gln Val Arg Gly Ser Arg Leu Tyr Ile
    2285                2290                2295

Phe Gln Ala Ser Pro Ala Asp Ala Gly Gln Tyr Val Cys Arg Ala
    2300                2305                2310

Ser Asn Gly Met Glu Ala Ser Ile Thr Val Thr Val Thr Gly Thr
    2315                2320                2325

Gln Gly Ala Asn Leu Ala Tyr Pro Ala Gly Ser Thr Gln Pro Ile
    2330                2335                2340

Arg Ile Glu Pro Ser Ser Ser Gln Val Ala Glu Gly Gln Thr Leu
```

-continued

```
            2345                2350                2355
Asp Leu Asn Cys Val Val Pro Gly Gln Ser His Ala Gln Val Thr
            2360                2365                2370
Trp His Lys Arg Gly Gly Ser Leu Pro Val Arg His Gln Thr His
            2375                2380                2385
Gly Ser Leu Leu Arg Leu Tyr Gln Ala Ser Pro Ala Asp Ser Gly
            2390                2395                2400
Glu Tyr Val Cys Arg Val Leu Gly Ser Ser Val Pro Leu Glu Ala
            2405                2410                2415
Ser Val Leu Val Thr Ile Glu Pro Ala Gly Ser Val Pro Ala Leu
            2420                2425                2430
Gly Val Thr Pro Thr Val Arg Ile Glu Ser Ser Ser Gln Val
            2435                2440                2445
Ala Glu Gly Gln Thr Leu Asp Leu Asn Cys Leu Val Ala Gly Gln
            2450                2455                2460
Ala His Ala Gln Val Thr Trp His Lys Arg Gly Gly Ser Leu Pro
            2465                2470                2475
Ala Arg His Gln Val His Gly Ser Arg Leu Arg Leu Leu Gln Val
            2480                2485                2490
Thr Pro Ala Asp Ser Gly Glu Tyr Val Cys Arg Val Val Gly Ser
            2495                2500                2505
Ser Gly Thr Gln Glu Ala Ser Val Leu Val Thr Ile Gln Gln Arg
            2510                2515                2520
Leu Ser Gly Ser His Ser Gln Gly Val Ala Tyr Pro Val Arg Ile
            2525                2530                2535
Glu Ser Ser Ser Ala Ser Leu Ala Asn Gly His Thr Leu Asp Leu
            2540                2545                2550
Asn Cys Leu Val Ala Ser Gln Ala Pro His Thr Ile Thr Trp Tyr
            2555                2560                2565
Lys Arg Gly Gly Ser Leu Pro Ser Arg His Gln Ile Val Gly Ser
            2570                2575                2580
Arg Leu Arg Ile Pro Gln Val Thr Pro Ala Asp Ser Gly Glu Tyr
            2585                2590                2595
Val Cys His Val Ser Asn Gly Ala Gly Ser Arg Glu Thr Ser Leu
            2600                2605                2610
Ile Val Thr Ile Gln Gly Ser Gly Ser Ser His Val Pro Ser Val
            2615                2620                2625
Ser Pro Pro Ile Arg Ile Glu Ser Ser Ser Pro Thr Val Val Glu
            2630                2635                2640
Gly Gln Thr Leu Asp Leu Asn Cys Val Val Ala Arg Gln Pro Gln
            2645                2650                2655
Ala Ile Ile Thr Trp Tyr Lys Arg Gly Gly Ser Leu Pro Ser Arg
            2660                2665                2670
His Gln Thr His Gly Ser His Leu Arg Leu His Gln Met Ser Val
            2675                2680                2685
Ala Asp Ser Gly Glu Tyr Val Cys Arg Ala Asn Asn Asn Ile Asp
            2690                2695                2700
Ala Leu Glu Ala Ser Ile Val Ile Ser Val Ser Pro Ser Ala Gly
            2705                2710                2715
Ser Pro Ser Ala Pro Gly Ser Ser Met Pro Ile Arg Ile Glu Ser
            2720                2725                2730
Ser Ser Ser His Val Ala Glu Gly Glu Thr Leu Asp Leu Asn Cys
            2735                2740                2745
```

```
Val Val Pro Gly Gln Ala His Ala Gln Val Thr Trp His Lys Arg
    2750                2755                2760

Gly Gly Ser Leu Pro Ser His His Gln Thr Arg Gly Ser Arg Leu
    2765                2770                2775

Arg Leu His His Val Ser Pro Ala Asp Ser Gly Glu Tyr Val Cys
    2780                2785                2790

Arg Val Met Gly Ser Ser Gly Pro Leu Glu Ala Ser Val Leu Val
    2795                2800                2805

Thr Ile Glu Ala Ser Gly Ser Ser Ala Val His Val Pro Ala Pro
    2810                2815                2820

Gly Gly Ala Pro Pro Ile Arg Ile Glu Pro Ser Ser Ser Arg Val
    2825                2830                2835

Ala Glu Gly Gln Thr Leu Asp Leu Lys Cys Val Val Pro Gly Gln
    2840                2845                2850

Ala His Ala Gln Val Thr Trp His Lys Arg Gly Gly Asn Leu Pro
    2855                2860                2865

Ala Arg His Gln Val His Gly Pro Leu Leu Arg Leu Asn Gln Val
    2870                2875                2880

Ser Pro Ala Asp Ser Gly Glu Tyr Ser Cys Gln Val Thr Gly Ser
    2885                2890                2895

Ser Gly Thr Leu Glu Ala Ser Val Leu Val Thr Ile Glu Pro Ser
    2900                2905                2910

Ser Pro Gly Pro Ile Pro Ala Pro Gly Leu Ala Gln Pro Ile Tyr
    2915                2920                2925

Ile Glu Ala Ser Ser Ser His Val Thr Glu Gly Gln Thr Leu Asp
    2930                2935                2940

Leu Asn Cys Val Val Pro Gly Gln Ala His Ala Gln Val Thr Trp
    2945                2950                2955

Tyr Lys Arg Gly Gly Ser Leu Pro Ala Arg His Gln Thr His Gly
    2960                2965                2970

Ser Gln Leu Arg Leu His Leu Val Ser Pro Ala Asp Ser Gly Glu
    2975                2980                2985

Tyr Val Cys Arg Ala Ala Ser Gly Pro Gly Pro Glu Gln Glu Ala
    2990                2995                3000

Ser Phe Thr Val Thr Val Pro Pro Ser Glu Gly Ser Ser Tyr Arg
    3005                3010                3015

Leu Arg Ser Pro Val Ile Ser Ile Asp Pro Pro Ser Ser Thr Val
    3020                3025                3030

Gln Gln Gly Gln Asp Ala Ser Phe Lys Cys Leu Ile His Asp Gly
    3035                3040                3045

Ala Ala Pro Ile Ser Leu Glu Trp Lys Thr Arg Asn Gln Glu Leu
    3050                3055                3060

Glu Asp Asn Val His Ile Ser Pro Asn Gly Ser Ile Ile Thr Ile
    3065                3070                3075

Val Gly Thr Arg Pro Ser Asn His Gly Thr Tyr Arg Cys Val Ala
    3080                3085                3090

Ser Asn Ala Tyr Gly Val Ala Gln Ser Val Val Asn Leu Ser Val
    3095                3100                3105

His Gly Pro Pro Thr Val Ser Val Leu Pro Glu Gly Pro Val Trp
    3110                3115                3120

Val Lys Val Gly Lys Ala Val Thr Leu Glu Cys Val Ser Ala Gly
    3125                3130                3135
```

```
Glu Pro Arg Ser Ser Ala Arg Trp Thr Arg Ile Ser Ser Thr Pro
    3140                3145                3150

Ala Lys Leu Glu Gln Arg Thr Tyr Gly Leu Met Asp Ser His Ala
    3155                3160                3165

Val Leu Gln Ile Ser Ser Ala Lys Pro Ser Asp Ala Gly Thr Tyr
    3170                3175                3180

Val Cys Leu Ala Gln Asn Ala Leu Gly Thr Ala Gln Lys Gln Val
    3185                3190                3195

Glu Val Ile Val Asp Thr Gly Ala Met Ala Pro Gly Ala Pro Gln
    3200                3205                3210

Val Gln Ala Glu Glu Ala Glu Leu Thr Val Glu Ala Gly His Thr
    3215                3220                3225

Ala Thr Leu Arg Cys Ser Ala Thr Gly Ser Pro Ala Pro Thr Ile
    3230                3235                3240

His Trp Ser Lys Leu Arg Ser Pro Leu Pro Trp Gln His Arg Leu
    3245                3250                3255

Glu Gly Asp Thr Leu Ile Ile Pro Arg Val Ala Gln Gln Asp Ser
    3260                3265                3270

Gly Gln Tyr Ile Cys Asn Ala Thr Ser Pro Ala Gly His Ala Glu
    3275                3280                3285

Ala Thr Ile Ile Leu His Val Glu Ser Pro Pro Tyr Ala Thr Thr
    3290                3295                3300

Val Pro Glu His Ala Ser Val Gln Ala Gly Glu Thr Val Gln Leu
    3305                3310                3315

Gln Cys Leu Ala His Gly Thr Pro Pro Leu Thr Phe Gln Trp Ser
    3320                3325                3330

Arg Val Gly Ser Ser Leu Pro Gly Arg Ala Thr Ala Arg Asn Glu
    3335                3340                3345

Leu Leu His Phe Glu Arg Ala Ala Pro Glu Asp Ser Gly Arg Tyr
    3350                3355                3360

Arg Cys Arg Val Thr Asn Lys Val Gly Ser Ala Glu Ala Phe Ala
    3365                3370                3375

Gln Leu Leu Val Gln Gly Pro Pro Gly Ser Leu Pro Ala Thr Ser
    3380                3385                3390

Ile Pro Ala Gly Ser Thr Pro Thr Val Gln Val Thr Pro Gln Leu
    3395                3400                3405

Glu Thr Lys Ser Ile Gly Ala Ser Val Glu Phe His Cys Ala Val
    3410                3415                3420

Pro Ser Asp Arg Gly Thr Gln Leu Arg Trp Phe Lys Glu Gly Gly
    3425                3430                3435

Gln Leu Pro Pro Gly His Ser Val Gln Asp Gly Val Leu Arg Ile
    3440                3445                3450

Gln Asn Leu Asp Gln Ser Cys Gln Gly Thr Tyr Ile Cys Gln Ala
    3455                3460                3465

His Gly Pro Trp Gly Lys Ala Gln Ala Ser Ala Gln Leu Val Ile
    3470                3475                3480

Gln Ala Leu Pro Ser Val Leu Ile Asn Ile Arg Thr Ser Val Gln
    3485                3490                3495

Thr Val Val Val Gly His Ala Val Glu Phe Glu Cys Leu Ala Leu
    3500                3505                3510

Gly Asp Pro Lys Pro Gln Val Thr Trp Ser Lys Val Gly Gly His
    3515                3520                3525

Leu Arg Pro Gly Ile Val Gln Ser Gly Gly Val Val Arg Ile Ala
```

-continued

His Val Glu Leu Ala Asp Ala Gly Gln Tyr Arg Cys Thr Ala Thr
3545                3550                3555

Asn Ala Ala Gly Thr Thr Gln Ser His Val Leu Leu Leu Val Gln
3560                3565                3570

Ala Leu Pro Gln Ile Ser Met Pro Gln Glu Val Arg Val Pro Ala
3575                3580                3585

Gly Ser Ala Ala Val Phe Pro Cys Ile Ala Ser Gly Tyr Pro Thr
3590                3595                3600

Pro Asp Ile Ser Trp Ser Lys Leu Asp Gly Ser Leu Pro Pro Asp
3605                3610                3615

Ser Arg Leu Glu Asn Asn Met Leu Met Leu Pro Ser Val Arg Pro
3620                3625                3630

Gln Asp Ala Gly Thr Tyr Val Cys Thr Ala Thr Asn Arg Gln Gly
3635                3640                3645

Lys Val Lys Ala Phe Ala His Leu Gln Val Pro Glu Arg Val Val
3650                3655                3660

Pro Tyr Phe Thr Gln Thr Pro Tyr Ser Phe Leu Pro Leu Pro Thr
3665                3670                3675

Ile Lys Asp Ala Tyr Arg Lys Phe Glu Ile Lys Ile Thr Phe Arg
3680                3685                3690

Pro Asp Ser Ala Asp Gly Met Leu Leu Tyr Asn Gly Gln Lys Arg
3695                3700                3705

Val Pro Gly Ser Pro Thr Asn Leu Ala Asn Arg Gln Pro Asp Phe
3710                3715                3720

Ile Ser Phe Gly Leu Val Gly Gly Arg Pro Glu Phe Arg Phe Asp
3725                3730                3735

Ala Gly Ser Gly Met Ala Thr Ile Arg His Pro Thr Pro Leu Ala
3740                3745                3750

Leu Gly His Phe His Thr Val Thr Leu Leu Arg Ser Leu Thr Gln
3755                3760                3765

Gly Ser Leu Ile Val Gly Asp Leu Ala Pro Val Asn Gly Thr Ser
3770                3775                3780

Gln Gly Lys Phe Gln Gly Leu Asp Leu Asn Glu Glu Leu Tyr Leu
3785                3790                3795

Gly Gly Tyr Pro Asp Tyr Gly Ala Ile Pro Lys Ala Gly Leu Ser
3800                3805                3810

Ser Gly Phe Ile Gly Cys Val Arg Glu Leu Arg Ile Gln Gly Glu
3815                3820                3825

Glu Ile Val Phe His Asp Leu Asn Leu Thr Ala His Gly Ile Ser
3830                3835                3840

His Cys Pro Thr Cys Arg Asp Arg Pro Cys Gln Asn Gly Gly Gln
3845                3850                3855

Cys His Asp Ser Glu Ser Ser Tyr Val Cys Val Cys Pro Ala
3860                3865                3870

Gly Phe Thr Gly Ser Arg Cys Glu His Ser Gln Ala Leu His Cys
3875                3880                3885

His Pro Glu Ala Cys Gly Pro Asp Ala Thr Cys Val Asn Arg Pro
3890                3895                3900

Asp Gly Arg Gly Tyr Thr Cys Arg Cys His Leu Gly Arg Ser Gly
3905                3910                3915

Leu Arg Cys Glu Glu Gly Val Thr Val Thr Thr Pro Ser Leu Ser
3920                3925                3930

```
Gly Ala Gly Ser Tyr Leu Ala Leu Pro Ala Leu Thr Asn Thr His
    3935                3940                3945

His Glu Leu Arg Leu Asp Val Glu Phe Lys Pro Leu Ala Pro Asp
    3950                3955                3960

Gly Val Leu Leu Phe Ser Gly Gly Lys Ser Gly Pro Val Glu Asp
    3965                3970                3975

Phe Val Ser Leu Ala Met Val Gly Gly His Leu Glu Phe Arg Tyr
    3980                3985                3990

Glu Leu Gly Ser Gly Leu Ala Val Leu Arg Ser Ala Glu Pro Leu
    3995                4000                4005

Ala Leu Gly Arg Trp His Arg Val Ser Ala Glu Arg Leu Asn Lys
    4010                4015                4020

Asp Gly Ser Leu Arg Val Asn Gly Gly Arg Pro Val Leu Arg Ser
    4025                4030                4035

Ser Pro Gly Lys Ser Gln Gly Leu Asn Leu His Thr Leu Leu Tyr
    4040                4045                4050

Leu Gly Gly Val Glu Pro Ser Val Pro Leu Ser Pro Ala Thr Asn
    4055                4060                4065

Met Ser Ala His Phe Arg Gly Cys Val Gly Glu Val Ser Val Asn
    4070                4075                4080

Gly Lys Arg Leu Asp Leu Thr Tyr Ser Phe Leu Gly Ser Gln Gly
    4085                4090                4095

Ile Gly Gln Cys Tyr Asp Ser Ser Pro Cys Glu Arg Gln Pro Cys
    4100                4105                4110

Gln His Gly Ala Thr Cys Met Pro Ala Gly Glu Tyr Glu Phe Gln
    4115                4120                4125

Cys Leu Cys Arg Asp Gly Phe Lys Gly Asp Leu Cys Glu His Glu
    4130                4135                4140

Glu Asn Pro Cys Gln Leu Arg Glu Pro Cys Leu His Gly Gly Thr
    4145                4150                4155

Cys Gln Gly Thr Arg Cys Leu Cys Leu Pro Gly Phe Ser Gly Pro
    4160                4165                4170

Arg Cys Gln Gln Gly Ser Gly His Gly Ile Ala Glu Ser Asp Trp
    4175                4180                4185

His Leu Glu Gly Ser Gly Gly Asn Asp Ala Pro Gly Gln Tyr Gly
    4190                4195                4200

Ala Tyr Phe His Asp Asp Gly Phe Leu Ala Phe Pro Gly His Val
    4205                4210                4215

Phe Ser Arg Ser Leu Pro Glu Val Pro Glu Thr Ile Glu Leu Glu
    4220                4225                4230

Val Arg Thr Ser Thr Ala Ser Gly Leu Leu Leu Trp Gln Gly Val
    4235                4240                4245

Glu Val Gly Glu Ala Gly Gln Gly Lys Asp Phe Ile Ser Leu Gly
    4250                4255                4260

Leu Gln Asp Gly His Leu Val Phe Arg Tyr Gln Leu Gly Ser Gly
    4265                4270                4275

Glu Ala Arg Leu Val Ser Glu Asp Pro Ile Asn Asp Gly Glu Trp
    4280                4285                4290

His Arg Val Thr Ala Leu Arg Glu Gly Arg Arg Gly Ser Ile Gln
    4295                4300                4305

Val Asp Gly Glu Glu Leu Val Ser Gly Arg Ser Pro Gly Pro Asn
    4310                4315                4320
```

-continued

```
Val Ala Val Asn Ala Lys Gly Ser Val Tyr Ile Gly Gly Ala Pro
    4325            4330                    4335

Asp Val Ala Thr Leu Thr Gly Gly Arg Phe Ser Ser Gly Ile Thr
    4340            4345                    4350

Gly Cys Val Lys Asn Leu Val Leu His Ser Ala Arg Pro Gly Ala
    4355            4360                    4365

Pro Pro Pro Gln Pro Leu Asp Leu Gln His Arg Ala Gln Ala Gly
    4370            4375                    4380

Ala Asn Thr Arg Pro Cys Pro Ser
    4385            4390

<210> SEQ ID NO 51
<211> LENGTH: 184
<212> TYPE: PRT
<213> ORGANISM: Homo sapiens
<300> PUBLICATION INFORMATION:
<308> DATABASE ACCESSION NUMBER: UniProt / Q9H875
<309> DATABASE ENTRY DATE: 2015-07-22
<313> RELEVANT RESIDUES IN SEQ ID NO: (1)..(184)

<400> SEQUENCE: 51

Met Ala Ser Pro Ala Ala Ser Ser Val Arg Pro Pro Arg Pro Lys Lys
1               5                   10                  15

Glu Pro Gln Thr Leu Val Ile Pro Lys Asn Ala Ala Glu Glu Gln Lys
            20                  25                  30

Leu Lys Leu Glu Arg Leu Met Lys Asn Pro Asp Lys Ala Val Pro Ile
        35                  40                  45

Pro Glu Lys Met Ser Glu Trp Ala Pro Arg Pro Pro Pro Glu Phe Val
    50                  55                  60

Arg Asp Val Met Gly Ser Ser Ala Gly Ala Gly Ser Gly Glu Phe His
65                  70                  75                  80

Val Tyr Arg His Leu Arg Arg Glu Tyr Gln Arg Gln Asp Tyr Met
                85                  90                  95

Asp Ala Met Ala Glu Lys Gln Lys Leu Asp Ala Glu Phe Gln Lys Arg
            100                 105                 110

Leu Glu Lys Asn Lys Ile Ala Ala Glu Glu Gln Thr Ala Lys Arg Arg
        115                 120                 125

Lys Lys Arg Gln Lys Leu Lys Glu Lys Leu Leu Ala Lys Lys Met
    130                 135                 140

Lys Leu Glu Gln Lys Lys Gln Glu Gly Pro Gly Gln Pro Lys Glu Gln
145                 150                 155                 160

Gly Ser Ser Ser Ala Glu Ala Ser Gly Thr Glu Glu Glu Glu
                165                 170                 175

Val Pro Ser Phe Thr Met Gly Arg
            180

<210> SEQ ID NO 52
<211> LENGTH: 427
<212> TYPE: PRT
<213> ORGANISM: Homo sapiens
<300> PUBLICATION INFORMATION:
<308> DATABASE ACCESSION NUMBER: UniProt / P25101
<309> DATABASE ENTRY DATE: 2015-07-22
<313> RELEVANT RESIDUES IN SEQ ID NO: (1)..(427)

<400> SEQUENCE: 52

Met Glu Thr Leu Cys Leu Arg Ala Ser Phe Trp Leu Ala Leu Val Gly
1               5                   10                  15

Cys Val Ile Ser Asp Asn Pro Glu Arg Tyr Ser Thr Asn Leu Ser Asn
```

```
                20                  25                  30
His Val Asp Asp Phe Thr Thr Phe Arg Gly Thr Glu Leu Ser Phe Leu
                35                  40                  45

Val Thr Thr His Gln Pro Thr Asn Leu Val Leu Pro Ser Asn Gly Ser
 50                  55                  60

Met His Asn Tyr Cys Pro Gln Gln Thr Lys Ile Thr Ser Ala Phe Lys
 65                  70                  75                  80

Tyr Ile Asn Thr Val Ile Ser Cys Thr Ile Phe Ile Val Gly Met Val
                 85                  90                  95

Gly Asn Ala Thr Leu Leu Arg Ile Ile Tyr Gln Asn Lys Cys Met Arg
                100                 105                 110

Asn Gly Pro Asn Ala Leu Ile Ala Ser Leu Ala Leu Gly Asp Leu Ile
                115                 120                 125

Tyr Val Val Ile Asp Leu Pro Ile Asn Val Phe Lys Leu Leu Ala Gly
                130                 135                 140

Arg Trp Pro Phe Asp His Asn Asp Phe Gly Val Phe Leu Cys Lys Leu
145                 150                 155                 160

Phe Pro Phe Leu Gln Lys Ser Ser Val Gly Ile Thr Val Leu Asn Leu
                165                 170                 175

Cys Ala Leu Ser Val Asp Arg Tyr Arg Ala Val Ala Ser Trp Ser Arg
                180                 185                 190

Val Gln Gly Ile Gly Ile Pro Leu Val Thr Ala Ile Glu Ile Val Ser
                195                 200                 205

Ile Trp Ile Leu Ser Phe Ile Leu Ala Ile Pro Glu Ala Ile Gly Phe
                210                 215                 220

Val Met Val Pro Phe Glu Tyr Arg Gly Glu Gln His Lys Thr Cys Met
225                 230                 235                 240

Leu Asn Ala Thr Ser Lys Phe Met Glu Phe Tyr Gln Asp Val Lys Asp
                245                 250                 255

Trp Trp Leu Phe Gly Phe Tyr Phe Cys Met Pro Leu Val Cys Thr Ala
                260                 265                 270

Ile Phe Tyr Thr Leu Met Thr Cys Glu Met Leu Asn Arg Arg Asn Gly
                275                 280                 285

Ser Leu Arg Ile Ala Leu Ser Glu His Leu Lys Gln Arg Arg Glu Val
                290                 295                 300

Ala Lys Thr Val Phe Cys Leu Val Val Ile Phe Ala Leu Cys Trp Phe
305                 310                 315                 320

Pro Leu His Leu Ser Arg Ile Leu Lys Lys Thr Val Tyr Asn Glu Met
                325                 330                 335

Asp Lys Asn Arg Cys Glu Leu Leu Ser Phe Leu Leu Leu Met Asp Tyr
                340                 345                 350

Ile Gly Ile Asn Leu Ala Thr Met Asn Ser Cys Ile Asn Pro Ile Ala
                355                 360                 365

Leu Tyr Phe Val Ser Lys Lys Phe Lys Asn Cys Phe Gln Ser Cys Leu
                370                 375                 380

Cys Cys Cys Cys Tyr Gln Ser Lys Ser Leu Met Thr Ser Val Pro Met
385                 390                 395                 400

Asn Gly Thr Ser Ile Gln Trp Lys Asn His Asp Gln Asn Asn His Asn
                405                 410                 415

Thr Asp Arg Ser Ser His Lys Asp Ser Met Asn
                420                 425

<210> SEQ ID NO 53
```

```
<211> LENGTH: 660
<212> TYPE: PRT
<213> ORGANISM: Homo sapiens
<300> PUBLICATION INFORMATION:
<308> DATABASE ACCESSION NUMBER: UniProt / O43155
<309> DATABASE ENTRY DATE: 2015-07-22
<313> RELEVANT RESIDUES IN SEQ ID NO: (1)..(660)

<400> SEQUENCE: 53
```

| Met | Gly | Leu | Gln | Thr | Thr | Lys | Trp | Pro | Ser | His | Gly | Ala | Phe | Phe | Leu |
|---|---|---|---|---|---|---|---|---|---|---|---|---|---|---|---|
| 1 | | | | 5 | | | | | 10 | | | | | 15 | |

| Lys | Ser | Trp | Leu | Ile | Ile | Ser | Leu | Gly | Leu | Tyr | Ser | Gln | Val | Ser | Lys |
|---|---|---|---|---|---|---|---|---|---|---|---|---|---|---|---|
| | | | 20 | | | | | 25 | | | | | 30 | | |

| Leu | Leu | Ala | Cys | Pro | Ser | Val | Cys | Arg | Cys | Asp | Arg | Asn | Phe | Val | Tyr |
|---|---|---|---|---|---|---|---|---|---|---|---|---|---|---|---|
| | | 35 | | | | | 40 | | | | | 45 | | | |

| Cys | Asn | Glu | Arg | Ser | Leu | Thr | Ser | Val | Pro | Leu | Gly | Ile | Pro | Glu | Gly |
|---|---|---|---|---|---|---|---|---|---|---|---|---|---|---|---|
| | 50 | | | | | 55 | | | | | 60 | | | | |

| Val | Thr | Val | Leu | Tyr | Leu | His | Asn | Asn | Gln | Ile | Asn | Asn | Ala | Gly | Phe |
|---|---|---|---|---|---|---|---|---|---|---|---|---|---|---|---|
| 65 | | | | | 70 | | | | | 75 | | | | | 80 |

| Pro | Ala | Glu | Leu | His | Asn | Val | Gln | Ser | Val | His | Thr | Val | Tyr | Leu | Tyr |
|---|---|---|---|---|---|---|---|---|---|---|---|---|---|---|---|
| | | | | 85 | | | | | 90 | | | | | 95 | |

| Gly | Asn | Gln | Leu | Asp | Glu | Phe | Pro | Met | Asn | Leu | Pro | Lys | Asn | Val | Arg |
|---|---|---|---|---|---|---|---|---|---|---|---|---|---|---|---|
| | | | 100 | | | | | 105 | | | | | 110 | | |

| Val | Leu | His | Leu | Gln | Glu | Asn | Asn | Ile | Gln | Thr | Ile | Ser | Arg | Ala | Ala |
|---|---|---|---|---|---|---|---|---|---|---|---|---|---|---|---|
| | | 115 | | | | | 120 | | | | | 125 | | | |

| Leu | Ala | Gln | Leu | Leu | Lys | Leu | Glu | Glu | Leu | His | Leu | Asp | Asp | Asn | Ser |
|---|---|---|---|---|---|---|---|---|---|---|---|---|---|---|---|
| | 130 | | | | | 135 | | | | | 140 | | | | |

| Ile | Ser | Thr | Val | Gly | Val | Glu | Asp | Gly | Ala | Phe | Arg | Glu | Ala | Ile | Ser |
|---|---|---|---|---|---|---|---|---|---|---|---|---|---|---|---|
| 145 | | | | | 150 | | | | | 155 | | | | | 160 |

| Leu | Lys | Leu | Leu | Phe | Leu | Ser | Lys | Asn | His | Leu | Ser | Ser | Val | Pro | Val |
|---|---|---|---|---|---|---|---|---|---|---|---|---|---|---|---|
| | | | | 165 | | | | | 170 | | | | | 175 | |

| Gly | Leu | Pro | Val | Asp | Leu | Gln | Glu | Leu | Arg | Val | Asp | Glu | Asn | Arg | Ile |
|---|---|---|---|---|---|---|---|---|---|---|---|---|---|---|---|
| | | | 180 | | | | | 185 | | | | | 190 | | |

| Ala | Val | Ile | Ser | Asp | Met | Ala | Phe | Gln | Asn | Leu | Thr | Ser | Leu | Glu | Arg |
|---|---|---|---|---|---|---|---|---|---|---|---|---|---|---|---|
| | | 195 | | | | | 200 | | | | | 205 | | | |

| Leu | Ile | Val | Asp | Gly | Asn | Leu | Leu | Thr | Asn | Lys | Gly | Ile | Ala | Glu | Gly |
|---|---|---|---|---|---|---|---|---|---|---|---|---|---|---|---|
| | 210 | | | | | 215 | | | | | 220 | | | | |

| Thr | Phe | Ser | His | Leu | Thr | Lys | Leu | Lys | Glu | Phe | Ser | Ile | Val | Arg | Asn |
|---|---|---|---|---|---|---|---|---|---|---|---|---|---|---|---|
| 225 | | | | | 230 | | | | | 235 | | | | | 240 |

| Ser | Leu | Ser | His | Pro | Pro | Asp | Leu | Pro | Gly | Thr | His | Leu | Ile | Arg |
|---|---|---|---|---|---|---|---|---|---|---|---|---|---|---|
| | | | | 245 | | | | | 250 | | | | | 255 |

| Leu | Tyr | Leu | Gln | Asp | Asn | Gln | Ile | Asn | His | Ile | Pro | Leu | Thr | Ala | Phe |
|---|---|---|---|---|---|---|---|---|---|---|---|---|---|---|---|
| | | | 260 | | | | | 265 | | | | | 270 | | |

| Ser | Asn | Leu | Arg | Lys | Leu | Glu | Arg | Leu | Asp | Ile | Ser | Asn | Asn | Gln | Leu |
|---|---|---|---|---|---|---|---|---|---|---|---|---|---|---|---|
| | | 275 | | | | | 280 | | | | | 285 | | | |

| Arg | Met | Leu | Thr | Gln | Gly | Val | Phe | Asp | Asn | Leu | Ser | Asn | Leu | Lys | Gln |
|---|---|---|---|---|---|---|---|---|---|---|---|---|---|---|---|
| | 290 | | | | | 295 | | | | | 300 | | | | |

| Leu | Thr | Ala | Arg | Asn | Asn | Pro | Trp | Phe | Cys | Asp | Cys | Ser | Ile | Lys | Trp |
|---|---|---|---|---|---|---|---|---|---|---|---|---|---|---|---|
| 305 | | | | | 310 | | | | | 315 | | | | | 320 |

| Val | Thr | Glu | Trp | Leu | Lys | Tyr | Ile | Pro | Ser | Ser | Leu | Asn | Val | Arg | Gly |
|---|---|---|---|---|---|---|---|---|---|---|---|---|---|---|---|
| | | | | 325 | | | | | 330 | | | | | 335 | |

| Phe | Met | Cys | Gln | Gly | Pro | Glu | Gln | Val | Arg | Gly | Met | Ala | Val | Arg | Glu |
|---|---|---|---|---|---|---|---|---|---|---|---|---|---|---|---|
| | | | 340 | | | | | 345 | | | | | 350 | | |

| Leu | Asn | Met | Asn | Leu | Leu | Ser | Cys | Pro | Thr | Thr | Thr | Pro | Gly | Leu | Pro |
|---|---|---|---|---|---|---|---|---|---|---|---|---|---|---|---|
| | | 355 | | | | | 360 | | | | | 365 | | | |

```
Leu Phe Thr Pro Ala Pro Ser Thr Ala Ser Pro Thr Thr Gln Pro Pro
    370                 375                 380

Thr Leu Ser Ile Pro Asn Pro Ser Arg Ser Tyr Thr Pro Pro Thr Pro
385                 390                 395                 400

Thr Thr Ser Lys Leu Pro Thr Ile Pro Asp Trp Asp Gly Arg Glu Arg
                405                 410                 415

Val Thr Pro Pro Ile Ser Glu Arg Ile Gln Leu Ser Ile His Phe Val
            420                 425                 430

Asn Asp Thr Ser Ile Gln Val Ser Trp Leu Ser Leu Phe Thr Val Met
        435                 440                 445

Ala Tyr Lys Leu Thr Trp Val Lys Met Gly His Ser Leu Val Gly Gly
    450                 455                 460

Ile Val Gln Glu Arg Ile Val Ser Gly Glu Lys Gln His Leu Ser Leu
465                 470                 475                 480

Val Asn Leu Glu Pro Arg Ser Thr Tyr Arg Ile Cys Leu Val Pro Leu
                485                 490                 495

Asp Ala Phe Asn Tyr Arg Ala Val Glu Asp Thr Ile Cys Ser Glu Ala
            500                 505                 510

Thr Thr His Ala Ser Tyr Leu Asn Asn Gly Ser Asn Thr Ala Ser Ser
        515                 520                 525

His Glu Gln Thr Thr Ser His Ser Met Gly Ser Pro Phe Leu Leu Ala
    530                 535                 540

Gly Leu Ile Gly Gly Ala Val Ile Phe Val Leu Val Leu Leu Leu Ser
545                 550                 555                 560

Val Phe Cys Trp His Met His Lys Lys Gly Arg Tyr Thr Ser Gln Lys
                565                 570                 575

Trp Lys Tyr Asn Arg Gly Arg Arg Lys Asp Asp Tyr Cys Glu Ala Gly
            580                 585                 590

Thr Lys Lys Asp Asn Ser Ile Leu Glu Met Thr Glu Thr Ser Phe Gln
        595                 600                 605

Ile Val Ser Leu Asn Asn Asp Gln Leu Leu Lys Gly Asp Phe Arg Leu
    610                 615                 620

Gln Pro Ile Tyr Thr Pro Asn Gly Gly Ile Asn Tyr Thr Asp Cys His
625                 630                 635                 640

Ile Pro Asn Asn Met Arg Tyr Cys Asn Ser Ser Val Pro Asp Leu Glu
                645                 650                 655

His Cys His Thr
            660

<210> SEQ ID NO 54
<211> LENGTH: 466
<212> TYPE: PRT
<213> ORGANISM: Homo sapiens
<300> PUBLICATION INFORMATION:
<308> DATABASE ACCESSION NUMBER: UniProt / P08670
<309> DATABASE ENTRY DATE: 2015-07-22
<313> RELEVANT RESIDUES IN SEQ ID NO: (1)..(466)

<400> SEQUENCE: 54

Met Ser Thr Arg Ser Val Ser Ser Ser Tyr Arg Arg Met Phe Gly
1               5                   10                  15

Gly Pro Gly Thr Ala Ser Arg Pro Ser Ser Ser Arg Ser Tyr Val Thr
            20                  25                  30

Thr Ser Thr Arg Thr Tyr Ser Leu Gly Ser Ala Leu Arg Pro Ser Thr
        35                  40                  45

Ser Arg Ser Leu Tyr Ala Ser Ser Pro Gly Gly Val Tyr Ala Thr Arg
```

```
             50                  55                  60
Ser Ser Ala Val Arg Leu Arg Ser Ser Val Pro Gly Val Arg Leu Leu
 65                  70                  75                  80

Gln Asp Ser Val Asp Phe Ser Leu Ala Asp Ala Ile Asn Thr Glu Phe
                     85                  90                  95

Lys Asn Thr Arg Thr Asn Glu Lys Val Glu Leu Gln Glu Leu Asn Asp
                100                 105                 110

Arg Phe Ala Asn Tyr Ile Asp Lys Val Arg Phe Leu Glu Gln Gln Asn
                115                 120                 125

Lys Ile Leu Leu Ala Glu Leu Glu Gln Leu Lys Gly Gln Gly Lys Ser
130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
                180                 185                 190

Met Leu Gln Arg Glu Glu Ala Glu Asn Thr Leu Gln Ser Phe Arg Gln
                195                 200                 205

Asp Val Asp Asn Ala Ser Leu Ala Arg Leu Asp Leu Glu Arg Lys Val
                210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
                260                 265                 270

Arg Gln Gln Tyr Glu Ser Val Ala Ala Lys Asn Leu Gln Glu Ala Glu
                275                 280                 285

Glu Trp Tyr Lys Ser Lys Phe Ala Asp Leu Ser Glu Ala Ala Asn Arg
                290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
                340                 345                 350

Val Glu Ala Ala Asn Tyr Gln Asp Thr Ile Gly Arg Leu Gln Asp Glu
                355                 360                 365

Ile Gln Asn Met Lys Glu Glu Met Ala Arg His Leu Arg Glu Tyr Gln
                370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
                420                 425                 430

Leu Val Asp Thr His Ser Lys Arg Thr Leu Leu Ile Lys Thr Val Glu
                435                 440                 445

Thr Arg Asp Gly Gln Val Ile Asn Glu Thr Ser Gln His His Asp Asp
450                 455                 460

Leu Glu
465
```

<210> SEQ ID NO 55
<211> LENGTH: 359
<212> TYPE: PRT
<213> ORGANISM: Homo sapiens
<300> PUBLICATION INFORMATION:
<308> DATABASE ACCESSION NUMBER: UniProt / P30556
<309> DATABASE ENTRY DATE: 2015-07-22
<313> RELEVANT RESIDUES IN SEQ ID NO: (1)..(359)

<400> SEQUENCE: 55

Met Ile Leu Asn Ser Ser Thr Glu Asp Gly Ile Lys Arg Ile Gln Asp
1               5                   10                  15

Asp Cys Pro Lys Ala Gly Arg His Asn Tyr Ile Phe Val Met Ile Pro
            20                  25                  30

Thr Leu Tyr Ser Ile Ile Phe Val Val Gly Ile Phe Gly Asn Ser Leu
        35                  40                  45

Val Val Ile Val Ile Tyr Phe Tyr Met Lys Leu Lys Thr Val Ala Ser
    50                  55                  60

Val Phe Leu Leu Asn Leu Ala Leu Ala Asp Leu Cys Phe Leu Leu Thr
65                  70                  75                  80

Leu Pro Leu Trp Ala Val Tyr Thr Ala Met Glu Tyr Arg Trp Pro Phe
                85                  90                  95

Gly Asn Tyr Leu Cys Lys Ile Ala Ser Ala Ser Val Ser Phe Asn Leu
            100                 105                 110

Tyr Ala Ser Val Phe Leu Leu Thr Cys Leu Ser Ile Asp Arg Tyr Leu
        115                 120                 125

Ala Ile Val His Pro Met Lys Ser Arg Leu Arg Arg Thr Met Leu Val
130                 135                 140

Ala Lys Val Thr Cys Ile Ile Ile Trp Leu Leu Ala Gly Leu Ala Ser
145                 150                 155                 160

Leu Pro Ala Ile Ile His Arg Asn Val Phe Phe Ile Glu Asn Thr Asn
                165                 170                 175

Ile Thr Val Cys Ala Phe His Tyr Glu Ser Gln Asn Ser Thr Leu Pro
            180                 185                 190

Ile Gly Leu Gly Leu Thr Lys Asn Ile Leu Gly Phe Leu Phe Pro Phe
        195                 200                 205

Leu Ile Ile Leu Thr Ser Tyr Thr Leu Ile Trp Lys Ala Leu Lys Lys
210                 215                 220

Ala Tyr Glu Ile Gln Lys Asn Lys Pro Arg Asn Asp Asp Ile Phe Lys
225                 230                 235                 240

Ile Ile Met Ala Ile Val Leu Phe Phe Phe Phe Ser Trp Ile Pro His
                245                 250                 255

Gln Ile Phe Thr Phe Leu Asp Val Leu Ile Gln Leu Gly Ile Ile Arg
            260                 265                 270

Asp Cys Arg Ile Ala Asp Ile Val Asp Thr Ala Met Pro Ile Thr Ile
        275                 280                 285

Cys Ile Ala Tyr Phe Asn Asn Cys Leu Asn Pro Leu Phe Tyr Gly Phe
290                 295                 300

Leu Gly Lys Lys Phe Lys Arg Tyr Phe Leu Gln Leu Leu Lys Tyr Ile
305                 310                 315                 320

Pro Pro Lys Ala Lys Ser His Ser Asn Leu Ser Thr Lys Met Ser Thr
                325                 330                 335

Leu Ser Tyr Arg Pro Ser Asp Asn Val Ser Ser Ser Thr Lys Lys Pro
            340                 345                 350

-continued

```
Ala Pro Cys Phe Glu Val Glu
        355

<210> SEQ ID NO 56
<211> LENGTH: 1053
<212> TYPE: PRT
<213> ORGANISM: Homo sapiens
<300> PUBLICATION INFORMATION:
<308> DATABASE ACCESSION NUMBER: UniProt / Q2KHT3
<309> DATABASE ENTRY DATE: 2015-07-22
<313> RELEVANT RESIDUES IN SEQ ID NO: (1)..(1053)

<400> SEQUENCE: 56

Met Phe Gly Arg Ser Arg Ser Trp Val Gly Gly His Gly Lys Thr
1               5                   10                  15

Ser Arg Asn Ile His Ser Leu Asp His Leu Lys Tyr Leu Tyr His Val
                20                  25                  30

Leu Thr Lys Asn Thr Thr Val Thr Glu Gln Asn Arg Asn Leu Leu Val
                35                  40                  45

Glu Thr Ile Arg Ser Ile Thr Glu Ile Leu Ile Trp Gly Asp Gln Asn
        50                  55                  60

Asp Ser Ser Val Phe Asp Phe Phe Leu Glu Lys Asn Met Phe Val Phe
65                  70                  75                  80

Phe Leu Asn Ile Leu Arg Gln Lys Ser Gly Arg Tyr Val Cys Val Gln
                85                  90                  95

Leu Leu Gln Thr Leu Asn Ile Leu Phe Glu Asn Ile Ser His Glu Thr
                100                 105                 110

Ser Leu Tyr Tyr Leu Leu Ser Asn Asn Tyr Val Asn Ser Ile Ile Val
                115                 120                 125

His Lys Phe Asp Phe Ser Asp Glu Glu Ile Met Ala Tyr Tyr Ile Ser
        130                 135                 140

Phe Leu Lys Thr Leu Ser Leu Lys Leu Asn Asn His Thr Val His Phe
145                 150                 155                 160

Phe Tyr Asn Glu His Thr Asn Asp Phe Ala Leu Tyr Thr Glu Ala Ile
                165                 170                 175

Lys Phe Phe Asn His Pro Glu Ser Met Val Arg Ile Ala Val Arg Thr
                180                 185                 190

Ile Thr Leu Asn Val Tyr Lys Val Ser Leu Asp Asn Gln Ala Met Leu
        195                 200                 205

His Tyr Ile Arg Asp Lys Thr Ala Val Pro Tyr Phe Ser Asn Leu Val
        210                 215                 220

Trp Phe Ile Gly Ser His Val Ile Glu Leu Asp Asp Cys Val Gln Thr
225                 230                 235                 240

Asp Glu Glu His Arg Asn Arg Gly Lys Leu Ser Asp Leu Val Ala Glu
                245                 250                 255

His Leu Asp His Leu His Tyr Leu Asn Asp Ile Leu Ile Asn Cys
                260                 265                 270

Glu Phe Leu Asn Asp Val Leu Thr Asp His Leu Leu Asn Arg Leu Phe
                275                 280                 285

Leu Pro Leu Tyr Val Tyr Ser Leu Glu Asn Gln Asp Lys Gly Gly Glu
        290                 295                 300

Arg Pro Lys Ile Ser Leu Pro Val Ser Leu Tyr Leu Ser Gln Val
305                 310                 315                 320

Phe Leu Ile Ile His His Ala Pro Leu Val Asn Ser Leu Ala Glu Val
                325                 330                 335

Ile Leu Asn Gly Asp Leu Ser Glu Met Tyr Ala Lys Thr Glu Gln Asp
```

```
            340                 345                 350
Ile Gln Arg Ser Ser Ala Lys Pro Ser Ile Arg Cys Phe Ile Lys Pro
            355                 360                 365

Thr Glu Thr Leu Glu Arg Ser Leu Glu Met Asn Lys His Lys Gly Lys
            370                 375             380

Arg Arg Val Gln Lys Arg Pro Asn Tyr Lys Asn Val Gly Glu Glu Glu
385                 390                 395                 400

Asp Glu Glu Lys Gly Pro Thr Glu Asp Ala Gln Glu Asp Ala Glu Lys
                405                 410                 415

Ala Lys Gly Thr Glu Gly Gly Ser Lys Gly Ile Lys Thr Ser Gly Glu
            420                 425                 430

Ser Glu Glu Ile Glu Met Val Ile Met Glu Arg Ser Lys Leu Ser Glu
            435                 440                 445

Leu Ala Ala Ser Thr Ser Val Gln Glu Gln Asn Thr Thr Asp Glu Glu
            450                 455                 460

Lys Ser Ala Ala Ala Thr Cys Ser Glu Ser Thr Gln Trp Ser Arg Pro
465                 470                 475                 480

Phe Leu Asp Met Val Tyr His Ala Leu Asp Ser Pro Asp Asp Tyr
                485                 490                 495

His Ala Leu Phe Val Leu Cys Leu Leu Tyr Ala Met Ser His Asn Lys
                500                 505                 510

Gly Met Asp Pro Glu Lys Leu Glu Arg Ile Gln Leu Pro Val Pro Asn
            515                 520                 525

Ala Ala Glu Lys Thr Thr Tyr Asn His Pro Leu Ala Glu Arg Leu Ile
            530                 535                 540

Arg Ile Met Asn Asn Ala Ala Gln Pro Asp Gly Lys Ile Arg Leu Ala
545                 550                 555                 560

Thr Leu Glu Leu Ser Cys Leu Leu Leu Lys Gln Gln Val Leu Met Ser
                565                 570                 575

Ala Gly Cys Ile Met Lys Asp Val His Leu Ala Cys Leu Glu Gly Ala
            580                 585                 590

Arg Glu Glu Ser Val His Leu Val Arg His Phe Tyr Lys Gly Glu Asp
            595                 600                 605

Ile Phe Leu Asp Met Phe Glu Asp Glu Tyr Arg Ser Met Thr Met Lys
            610                 615                 620

Pro Met Asn Val Glu Tyr Leu Met Met Asp Ala Ser Ile Leu Leu Pro
625                 630                 635                 640

Pro Thr Gly Thr Pro Leu Thr Gly Ile Asp Phe Val Lys Arg Leu Pro
                645                 650                 655

Cys Gly Asp Val Glu Lys Thr Arg Arg Ala Ile Arg Val Phe Phe Met
                660                 665                 670

Leu Arg Ser Leu Ser Leu Gln Leu Arg Gly Glu Pro Glu Thr Gln Leu
            675                 680                 685

Pro Leu Thr Arg Glu Glu Asp Leu Ile Lys Thr Asp Asp Val Leu Asp
            690                 695                 700

Leu Asn Asn Ser Asp Leu Ile Ala Cys Thr Val Ile Thr Lys Asp Gly
705                 710                 715                 720

Gly Met Val Gln Arg Phe Leu Ala Val Asp Ile Tyr Gln Met Ser Leu
                725                 730                 735

Val Glu Pro Asp Val Ser Arg Leu Gly Trp Gly Val Val Lys Phe Ala
                740                 745                 750

Gly Leu Leu Gln Asp Met Gln Val Thr Gly Val Glu Asp Asp Ser Arg
            755                 760                 765
```

```
Ala Leu Asn Ile Thr Ile His Lys Pro Ala Ser Ser Pro His Ser Lys
            770                 775                 780
Pro Phe Pro Ile Leu Gln Ala Thr Phe Ile Phe Ser Asp His Ile Arg
    785                 790                 795                 800
Cys Ile Ile Ala Lys Gln Arg Leu Ala Lys Gly Arg Ile Gln Ala Arg
                805                 810                 815
Arg Met Lys Met Gln Arg Ile Ala Ala Leu Leu Asp Leu Pro Ile Gln
            820                 825                 830
Pro Thr Thr Glu Val Leu Gly Phe Gly Leu Gly Ser Ser Thr Ser Thr
                835                 840                 845
Gln His Leu Pro Phe Arg Phe Tyr Asp Gln Gly Arg Arg Gly Ser Ser
    850                 855                 860
Asp Pro Thr Val Gln Arg Ser Val Phe Ala Ser Val Asp Lys Val Pro
865                 870                 875                 880
Gly Phe Ala Val Ala Gln Cys Ile Asn Gln His Ser Ser Pro Ser Leu
                885                 890                 895
Ser Ser Gln Ser Pro Pro Ser Ala Ser Gly Ser Pro Ser Gly Ser Gly
                900                 905                 910
Ser Thr Ser His Cys Asp Ser Gly Gly Thr Ser Ser Ser Ser Thr Pro
                915                 920                 925
Ser Thr Ala Gln Ser Pro Ala Asp Ala Pro Met Ser Pro Glu Leu Pro
            930                 935                 940
Lys Pro His Leu Pro Asp Gln Leu Val Ile Val Asn Glu Thr Glu Ala
945                 950                 955                 960
Asp Ser Lys Pro Ser Lys Asn Val Ala Arg Ser Ala Ala Val Glu Thr
                965                 970                 975
Ala Ser Leu Ser Pro Ser Leu Val Pro Ala Arg Gln Pro Thr Ile Ser
            980                 985                 990
Leu Leu Cys Glu Asp Thr Ala Asp  Thr Leu Ser Val Glu  Ser Leu Thr
            995                 1000                1005
Leu Val  Pro Pro Val Asp Pro  His Ser Leu Arg Ser  Leu Thr Gly
    1010                1015                1020
Met Pro  Pro Leu Ser Thr Pro  Ala Ala Ala Cys Thr  Glu Pro Val
    1025                1030                1035
Gly Glu  Glu Ala Ala Cys Ala  Glu Pro Val Gly Thr  Ala Glu Asp
    1040                1045                1050

<210> SEQ ID NO 57
<211> LENGTH: 1464
<212> TYPE: PRT
<213> ORGANISM: Homo sapiens
<300> PUBLICATION INFORMATION:
<308> DATABASE ACCESSION NUMBER: UniProt / P02452
<309> DATABASE ENTRY DATE: 2015-07-22
<313> RELEVANT RESIDUES IN SEQ ID NO: (1)..(1464)

<400> SEQUENCE: 57

Met Phe Ser Phe Val Asp Leu Arg Leu Leu Leu Leu Leu Ala Ala Thr
1               5                   10                  15
Ala Leu Leu Thr His Gly Gln Glu Glu Gly Gln Val Glu Gly Gln Asp
            20                  25                  30
Glu Asp Ile Pro Pro Ile Thr Cys Val Gln Asn Gly Leu Arg Tyr His
        35                  40                  45
Asp Arg Asp Val Trp Lys Pro Glu Pro Cys Arg Ile Cys Val Cys Asp
    50                  55                  60
```

```
Asn Gly Lys Val Leu Cys Asp Asp Val Ile Cys Asp Glu Thr Lys Asn
 65                  70                  75                  80

Cys Pro Gly Ala Glu Val Pro Glu Gly Glu Cys Cys Pro Val Cys Pro
                 85                  90                  95

Asp Gly Ser Glu Ser Pro Thr Asp Gln Glu Thr Thr Gly Val Glu Gly
            100                 105                 110

Pro Lys Gly Asp Thr Gly Pro Arg Gly Pro Arg Gly Pro Ala Gly Pro
        115                 120                 125

Pro Gly Arg Asp Gly Ile Pro Gly Gln Pro Gly Leu Pro Gly Pro Pro
    130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
            180                 185                 190

Pro Gly Ala Pro Gly Pro Gln Gly Phe Gln Gly Pro Pro Gly Glu Pro
        195                 200                 205

Gly Glu Pro Gly Ala Ser Gly Pro Met Gly Pro Arg Gly Pro Pro Gly
    210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255

Gly Thr Ala Gly Leu Pro Gly Met Lys Gly His Arg Gly Phe Ser Gly
            260                 265                 270

Leu Asp Gly Ala Lys Gly Asp Ala Gly Pro Ala Gly Pro Lys Gly Glu
        275                 280                 285

Pro Gly Ser Pro Gly Glu Asn Gly Ala Pro Gly Gln Met Gly Pro Arg
    290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
            340                 345                 350

Gly Glu Ala Gly Pro Gln Gly Pro Arg Gly Ser Glu Gly Pro Gln Gly
        355                 360                 365

Val Arg Gly Glu Pro Gly Pro Pro Gly Pro Ala Gly Ala Ala Gly Pro
    370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415

Pro Ser Gly Pro Gln Gly Pro Gly Pro Gly Pro Gly Lys Gly Asn
            420                 425                 430

Ser Gly Glu Pro Gly Ala Pro Gly Ser Lys Gly Asp Thr Gly Ala Lys
        435                 440                 445

Gly Glu Pro Gly Pro Val Gly Val Gln Gly Pro Pro Gly Pro Ala Gly
    450                 455                 460

Glu Glu Gly Lys Arg Gly Ala Arg Gly Glu Pro Gly Pro Thr Gly Leu
465                 470                 475                 480

Pro Gly Pro Pro Gly Glu Arg Gly Gly Pro Gly Ser Arg Gly Phe Pro
```

```
                485                 490                 495
Gly Ala Asp Gly Val Ala Gly Pro Lys Gly Pro Ala Gly Glu Arg Gly
            500                 505                 510
Ser Pro Gly Pro Ala Gly Pro Lys Gly Ser Pro Gly Glu Ala Gly Arg
            515                 520                 525
Pro Gly Glu Ala Gly Leu Pro Gly Ala Lys Gly Leu Thr Gly Ser Pro
            530                 535                 540
Gly Ser Pro Gly Pro Asp Gly Lys Thr Gly Pro Pro Gly Pro Ala Gly
545                 550                 555                 560
Gln Asp Gly Arg Pro Gly Pro Gly Pro Pro Gly Ala Arg Gly Gln
            565                 570                 575
Ala Gly Val Met Gly Phe Pro Gly Pro Lys Gly Ala Ala Gly Glu Pro
            580                 585                 590
Gly Lys Ala Gly Glu Arg Gly Val Pro Gly Pro Pro Gly Ala Val Gly
            595                 600                 605
Pro Ala Gly Lys Asp Gly Glu Ala Gly Ala Gln Gly Pro Pro Gly Pro
            610                 615                 620
Ala Gly Pro Ala Gly Glu Arg Gly Glu Gln Gly Pro Ala Gly Ser Pro
625                 630                 635                 640
Gly Phe Gln Gly Leu Pro Gly Pro Ala Gly Pro Pro Gly Glu Ala Gly
                        645                 650                 655
Lys Pro Gly Glu Gln Gly Val Pro Gly Asp Leu Gly Ala Pro Gly Pro
            660                 665                 670
Ser Gly Ala Arg Gly Glu Arg Gly Phe Pro Gly Glu Arg Gly Val Gln
            675                 680                 685
Gly Pro Pro Gly Pro Ala Gly Pro Arg Gly Ala Asn Gly Ala Pro Gly
            690                 695                 700
Asn Asp Gly Ala Lys Gly Asp Ala Gly Ala Pro Gly Ala Pro Gly Ser
705                 710                 715                 720
Gln Gly Ala Pro Gly Leu Gln Gly Met Pro Gly Glu Arg Gly Ala Ala
                        725                 730                 735
Gly Leu Pro Gly Pro Lys Gly Asp Arg Gly Asp Ala Gly Pro Lys Gly
                        740                 745                 750
Ala Asp Gly Ser Pro Gly Lys Asp Gly Val Arg Gly Leu Thr Gly Pro
                        755                 760                 765
Ile Gly Pro Pro Gly Pro Ala Gly Ala Pro Gly Asp Lys Gly Glu Ser
            770                 775                 780
Gly Pro Ser Gly Pro Ala Gly Pro Thr Gly Ala Arg Gly Ala Pro Gly
785                 790                 795                 800
Asp Arg Gly Glu Pro Gly Pro Pro Gly Pro Ala Gly Phe Ala Gly Pro
                        805                 810                 815
Pro Gly Ala Asp Gly Gln Pro Gly Ala Lys Gly Glu Pro Gly Asp Ala
            820                 825                 830
Gly Ala Lys Gly Asp Ala Gly Pro Pro Gly Pro Ala Gly Pro Ala Gly
            835                 840                 845
Pro Pro Gly Pro Ile Gly Asn Val Gly Ala Pro Gly Ala Lys Gly Ala
            850                 855                 860
Arg Gly Ser Ala Gly Pro Pro Gly Ala Thr Gly Phe Pro Gly Ala Ala
865                 870                 875                 880
Gly Arg Val Gly Pro Pro Gly Pro Ser Gly Asn Ala Gly Pro Pro Gly
                        885                 890                 895
Pro Pro Gly Pro Ala Gly Lys Glu Gly Gly Lys Gly Pro Arg Gly Glu
            900                 905                 910
```

-continued

Thr Gly Pro Ala Gly Arg Pro Gly Glu Val Gly Pro Pro Gly Pro Pro
        915                 920                 925

Gly Pro Ala Gly Glu Lys Gly Ser Pro Gly Ala Asp Gly Pro Ala Gly
    930                 935                 940

Ala Pro Gly Thr Pro Gly Pro Gln Gly Ile Ala Gly Gln Arg Gly Val
945                 950                 955                 960

Val Gly Leu Pro Gly Gln Arg Gly Glu Arg Gly Phe Pro Gly Leu Pro
                965                 970                 975

Gly Pro Ser Gly Glu Pro Gly Lys Gln Gly Pro Ser Gly Ala Ser Gly
            980                 985                 990

Glu Arg Gly Pro Pro Gly Pro Met Gly Pro Pro Gly Leu Ala Gly Pro
        995                 1000                1005

Pro Gly Glu Ser Gly Arg Glu Gly Ala Pro Gly Ala Glu Gly Ser
    1010                1015                1020

Pro Gly Arg Asp Gly Ser Pro Gly Ala Lys Gly Asp Arg Gly Glu
    1025                1030                1035

Thr Gly Pro Ala Gly Pro Pro Gly Ala Pro Gly Ala Pro Gly Ala
    1040                1045                1050

Pro Gly Pro Val Gly Pro Ala Gly Lys Ser Gly Asp Arg Gly Glu
    1055                1060                1065

Thr Gly Pro Ala Gly Pro Thr Gly Pro Val Gly Pro Val Gly Ala
    1070                1075                1080

Arg Gly Pro Ala Gly Pro Gln Gly Pro Arg Gly Asp Lys Gly Glu
    1085                1090                1095

Thr Gly Glu Gln Gly Asp Arg Gly Ile Lys Gly His Arg Gly Phe
    1100                1105                1110

Ser Gly Leu Gln Gly Pro Pro Gly Pro Pro Gly Ser Pro Gly Glu
    1115                1120                1125

Gln Gly Pro Ser Gly Ala Ser Gly Pro Ala Gly Pro Arg Gly Pro
    1130                1135                1140

Pro Gly Ser Ala Gly Ala Pro Gly Lys Asp Gly Leu Asn Gly Leu
    1145                1150                1155

Pro Gly Pro Ile Gly Pro Pro Gly Pro Arg Gly Arg Thr Gly Asp
    1160                1165                1170

Ala Gly Pro Val Gly Pro Pro Gly Pro Pro Gly Pro Pro Gly Pro
    1175                1180                1185

Pro Gly Pro Pro Ser Ala Gly Phe Asp Phe Ser Phe Leu Pro Gln
    1190                1195                1200

Pro Pro Gln Glu Lys Ala His Asp Gly Gly Arg Tyr Tyr Arg Ala
    1205                1210                1215

Asp Asp Ala Asn Val Val Arg Asp Arg Asp Leu Glu Val Asp Thr
    1220                1225                1230

Thr Leu Lys Ser Leu Ser Gln Gln Ile Glu Asn Ile Arg Ser Pro
    1235                1240                1245

Glu Gly Ser Arg Lys Asn Pro Ala Arg Thr Cys Arg Asp Leu Lys
    1250                1255                1260

Met Cys His Ser Asp Trp Lys Ser Gly Glu Tyr Trp Ile Asp Pro
    1265                1270                1275

Asn Gln Gly Cys Asn Leu Asp Ala Ile Lys Val Phe Cys Asn Met
    1280                1285                1290

Glu Thr Gly Glu Thr Cys Val Tyr Pro Thr Gln Pro Ser Val Ala
    1295                1300                1305

```
Gln Lys Asn Trp Tyr Ile Ser Lys Asn Pro Lys Asp Lys Arg His
    1310                1315                1320

Val Trp Phe Gly Glu Ser Met Thr Asp Gly Phe Gln Phe Glu Tyr
1325                1330                1335

Gly Gly Gln Gly Ser Asp Pro Ala Asp Val Ala Ile Gln Leu Thr
1340                1345                1350

Phe Leu Arg Leu Met Ser Thr Glu Ala Ser Gln Asn Ile Thr Tyr
1355                1360                1365

His Cys Lys Asn Ser Val Ala Tyr Met Asp Gln Gln Thr Gly Asn
    1370                1375                1380

Leu Lys Lys Ala Leu Leu Leu Gln Gly Ser Asn Glu Ile Glu Ile
    1385                1390                1395

Arg Ala Glu Gly Asn Ser Arg Phe Thr Tyr Ser Val Thr Val Asp
    1400                1405                1410

Gly Cys Thr Ser His Thr Gly Ala Trp Gly Lys Thr Val Ile Glu
    1415                1420                1425

Tyr Lys Thr Thr Lys Thr Ser Arg Leu Pro Ile Ile Asp Val Ala
    1430                1435                1440

Pro Leu Asp Val Gly Ala Pro Asp Gln Glu Phe Gly Phe Asp Val
    1445                1450                1455

Gly Pro Val Cys Phe Leu
    1460

<210> SEQ ID NO 58
<211> LENGTH: 1487
<212> TYPE: PRT
<213> ORGANISM: Homo sapiens
<300> PUBLICATION INFORMATION:
<308> DATABASE ACCESSION NUMBER: UniProt / P02458
<309> DATABASE ENTRY DATE: 2015-07-22
<313> RELEVANT RESIDUES IN SEQ ID NO: (1)..(1487)

<400> SEQUENCE: 58

Met Ile Arg Leu Gly Ala Pro Gln Thr Leu Val Leu Leu Thr Leu Leu
1               5                   10                  15

Val Ala Ala Val Leu Arg Cys Gln Gly Gln Asp Val Gln Glu Ala Gly
                20                  25                  30

Ser Cys Val Gln Asp Gly Gln Arg Tyr Asn Asp Lys Asp Val Trp Lys
            35                  40                  45

Pro Glu Pro Cys Arg Ile Cys Val Cys Asp Thr Gly Thr Val Leu Cys
        50                  55                  60

Asp Asp Ile Ile Cys Glu Asp Val Lys Asp Cys Leu Ser Pro Glu Ile
65                  70                  75                  80

Pro Phe Gly Glu Cys Cys Pro Ile Cys Pro Thr Asp Leu Ala Thr Ala
                85                  90                  95

Ser Gly Gln Pro Gly Pro Lys Gly Gln Lys Gly Glu Pro Gly Asp Ile
            100                 105                 110

Lys Asp Ile Val Gly Pro Lys Gly Pro Pro Gly Pro Gln Gly Pro Ala
        115                 120                 125

Gly Glu Gln Gly Pro Arg Gly Asp Arg Gly Asp Lys Gly Glu Lys Gly
    130                 135                 140

Ala Pro Gly Pro Arg Gly Arg Asp Gly Glu Pro Gly Thr Pro Gly Asn
145                 150                 155                 160

Pro Gly Pro Pro Gly Pro Pro Gly Pro Pro Gly Pro Pro Gly Leu Gly
                165                 170                 175

Gly Asn Phe Ala Ala Gln Met Ala Gly Gly Phe Asp Glu Lys Ala Gly
```

```
                180                 185                 190
Gly Ala Gln Leu Gly Val Met Gln Gly Pro Met Gly Pro Met Gly Pro
            195                 200                 205
Arg Gly Pro Pro Gly Pro Ala Gly Ala Pro Gly Pro Gln Gly Phe Gln
        210                 215                 220
Gly Asn Pro Gly Glu Pro Gly Glu Pro Gly Val Ser Gly Pro Met Gly
225                 230                 235                 240
Pro Arg Gly Pro Pro Gly Pro Pro Gly Lys Pro Gly Asp Asp Gly Glu
                245                 250                 255
Ala Gly Lys Pro Gly Lys Ala Gly Glu Arg Gly Pro Pro Gly Pro Gln
            260                 265                 270
Gly Ala Arg Gly Phe Pro Gly Thr Pro Gly Leu Pro Gly Val Lys Gly
        275                 280                 285
His Arg Gly Tyr Pro Gly Leu Asp Gly Ala Lys Gly Glu Ala Gly Ala
    290                 295                 300
Pro Gly Val Lys Gly Glu Ser Gly Ser Pro Gly Glu Asn Gly Ser Pro
305                 310                 315                 320
Gly Pro Met Gly Pro Arg Gly Leu Pro Gly Glu Arg Gly Arg Thr Gly
                325                 330                 335
Pro Ala Gly Ala Ala Gly Ala Arg Gly Asn Asp Gly Gln Pro Gly Pro
            340                 345                 350
Ala Gly Pro Pro Gly Pro Val Gly Pro Ala Gly Pro Gly Phe Pro
        355                 360                 365
Gly Ala Pro Gly Ala Lys Gly Glu Ala Gly Pro Thr Gly Ala Arg Gly
    370                 375                 380
Pro Glu Gly Ala Gln Gly Pro Arg Gly Glu Pro Gly Thr Pro Gly Ser
385                 390                 395                 400
Pro Gly Pro Ala Gly Ala Ser Gly Asn Pro Gly Thr Asp Gly Ile Pro
                405                 410                 415
Gly Ala Lys Gly Ser Ala Gly Ala Pro Gly Ile Ala Gly Ala Pro Gly
            420                 425                 430
Phe Pro Gly Pro Arg Gly Pro Pro Gly Pro Gln Gly Ala Thr Gly Pro
        435                 440                 445
Leu Gly Pro Lys Gly Gln Thr Gly Glu Pro Gly Ile Ala Gly Phe Lys
    450                 455                 460
Gly Glu Gln Gly Pro Lys Gly Glu Pro Gly Pro Ala Gly Pro Gln Gly
465                 470                 475                 480
Ala Pro Gly Pro Ala Gly Glu Glu Gly Lys Arg Gly Ala Arg Gly Glu
                485                 490                 495
Pro Gly Gly Val Gly Pro Ile Gly Pro Pro Gly Glu Arg Gly Ala Pro
            500                 505                 510
Gly Asn Arg Gly Phe Pro Gly Gln Asp Gly Leu Ala Gly Pro Lys Gly
        515                 520                 525
Ala Pro Gly Glu Arg Gly Pro Ser Gly Leu Ala Gly Pro Lys Gly Ala
    530                 535                 540
Asn Gly Asp Pro Gly Arg Pro Gly Glu Pro Gly Leu Pro Gly Ala Arg
545                 550                 555                 560
Gly Leu Thr Gly Arg Pro Gly Asp Ala Gly Pro Gln Gly Lys Val Gly
                565                 570                 575
Pro Ser Gly Ala Pro Gly Glu Asp Gly Arg Pro Gly Pro Pro Gly Pro
            580                 585                 590
Gln Gly Ala Arg Gly Gln Pro Gly Val Met Gly Phe Pro Gly Pro Lys
        595                 600                 605
```

```
Gly Ala Asn Gly Glu Pro Gly Lys Ala Gly Glu Lys Gly Leu Pro Gly
        610             615             620
Ala Pro Gly Leu Arg Gly Leu Pro Gly Lys Asp Gly Glu Thr Gly Ala
625             630             635             640
Ala Gly Pro Pro Gly Pro Ala Gly Pro Ala Gly Glu Arg Gly Glu Gln
            645             650             655
Gly Ala Pro Gly Pro Ser Gly Phe Gln Gly Leu Pro Gly Pro Pro Gly
            660             665             670
Pro Pro Gly Glu Gly Gly Lys Pro Gly Asp Gln Gly Val Pro Gly Glu
            675             680             685
Ala Gly Ala Pro Gly Leu Val Gly Pro Arg Gly Glu Arg Gly Phe Pro
        690             695             700
Gly Glu Arg Gly Ser Pro Gly Ala Gln Gly Leu Gln Gly Pro Arg Gly
705             710             715             720
Leu Pro Gly Thr Pro Gly Thr Asp Gly Pro Lys Gly Ala Ser Gly Pro
            725             730             735
Ala Gly Pro Pro Gly Ala Gln Gly Pro Pro Gly Leu Gln Gly Met Pro
            740             745             750
Gly Glu Arg Gly Ala Ala Gly Ile Ala Gly Pro Lys Gly Asp Arg Gly
            755             760             765
Asp Val Gly Glu Lys Gly Pro Glu Gly Ala Pro Gly Lys Asp Gly Gly
770             775             780
Arg Gly Leu Thr Gly Pro Ile Gly Pro Pro Gly Pro Ala Gly Ala Asn
785             790             795             800
Gly Glu Lys Gly Glu Val Gly Pro Pro Gly Pro Ala Gly Ser Ala Gly
            805             810             815
Ala Arg Gly Ala Pro Gly Glu Arg Gly Glu Thr Gly Pro Pro Gly Pro
            820             825             830
Ala Gly Phe Ala Gly Pro Pro Gly Ala Asp Gly Gln Pro Gly Ala Lys
            835             840             845
Gly Glu Gln Gly Glu Ala Gly Gln Lys Gly Asp Ala Gly Ala Pro Gly
        850             855             860
Pro Gln Gly Pro Ser Gly Ala Pro Gly Pro Gln Gly Pro Thr Gly Val
865             870             875             880
Thr Gly Pro Lys Gly Ala Arg Gly Ala Gln Gly Pro Pro Gly Ala Thr
            885             890             895
Gly Phe Pro Gly Ala Ala Gly Arg Val Gly Pro Pro Gly Ser Asn Gly
            900             905             910
Asn Pro Gly Pro Pro Gly Pro Pro Gly Pro Ser Gly Lys Asp Gly Pro
            915             920             925
Lys Gly Ala Arg Gly Asp Ser Gly Pro Pro Gly Arg Ala Gly Glu Pro
        930             935             940
Gly Leu Gln Gly Pro Ala Gly Pro Pro Gly Glu Lys Gly Glu Pro Gly
945             950             955             960
Asp Asp Gly Pro Ser Gly Ala Glu Gly Pro Pro Gly Pro Gln Gly Leu
            965             970             975
Ala Gly Gln Arg Gly Ile Val Gly Leu Pro Gly Gln Arg Gly Glu Arg
            980             985             990
Gly Phe Pro Gly Leu Pro Gly Pro Ser Gly Glu Pro Gly Lys Gln Gly
            995             1000            1005
Ala Pro  Gly Ala Ser Gly Asp  Arg Gly Pro Pro Gly  Pro Val Gly
    1010            1015                1020
```

```
Pro Pro Gly Leu Thr Gly Pro Ala Gly Glu Pro Gly Arg Glu Gly
    1025                1030                1035

Ser Pro Gly Ala Asp Gly Pro Pro Gly Arg Asp Gly Ala Ala Gly
    1040                1045                1050

Val Lys Gly Asp Arg Gly Glu Thr Gly Ala Val Gly Ala Pro Gly
    1055                1060                1065

Ala Pro Gly Pro Pro Gly Ser Pro Gly Pro Ala Gly Pro Thr Gly
    1070                1075                1080

Lys Gln Gly Asp Arg Gly Glu Ala Gly Ala Gln Gly Pro Met Gly
    1085                1090                1095

Pro Ser Gly Pro Ala Gly Ala Arg Gly Ile Gln Gly Pro Gln Gly
    1100                1105                1110

Pro Arg Gly Asp Lys Gly Glu Ala Gly Glu Pro Gly Glu Arg Gly
    1115                1120                1125

Leu Lys Gly His Arg Gly Phe Thr Gly Leu Gln Gly Leu Pro Gly
    1130                1135                1140

Pro Pro Gly Pro Ser Gly Asp Gln Gly Ala Ser Gly Pro Ala Gly
    1145                1150                1155

Pro Ser Gly Pro Arg Gly Pro Pro Gly Pro Val Gly Pro Ser Gly
    1160                1165                1170

Lys Asp Gly Ala Asn Gly Ile Pro Gly Pro Ile Gly Pro Pro Gly
    1175                1180                1185

Pro Arg Gly Arg Ser Gly Glu Thr Gly Pro Ala Gly Pro Pro Gly
    1190                1195                1200

Asn Pro Gly Pro Pro Gly Pro Pro Gly Pro Pro Gly Pro Gly Ile
    1205                1210                1215

Asp Met Ser Ala Phe Ala Gly Leu Gly Pro Arg Glu Lys Gly Pro
    1220                1225                1230

Asp Pro Leu Gln Tyr Met Arg Ala Asp Gln Ala Ala Gly Gly Leu
    1235                1240                1245

Arg Gln His Asp Ala Glu Val Asp Ala Thr Leu Lys Ser Leu Asn
    1250                1255                1260

Asn Gln Ile Glu Ser Ile Arg Ser Pro Glu Gly Ser Arg Lys Asn
    1265                1270                1275

Pro Ala Arg Thr Cys Arg Asp Leu Lys Leu Cys His Pro Glu Trp
    1280                1285                1290

Lys Ser Gly Asp Tyr Trp Ile Asp Pro Asn Gln Gly Cys Thr Leu
    1295                1300                1305

Asp Ala Met Lys Val Phe Cys Asn Met Glu Thr Gly Glu Thr Cys
    1310                1315                1320

Val Tyr Pro Asn Pro Ala Asn Val Pro Lys Lys Asn Trp Trp Ser
    1325                1330                1335

Ser Lys Ser Lys Glu Lys Lys His Ile Trp Phe Gly Glu Thr Ile
    1340                1345                1350

Asn Gly Gly Phe His Phe Ser Tyr Gly Asp Asp Asn Leu Ala Pro
    1355                1360                1365

Asn Thr Ala Asn Val Gln Met Thr Phe Leu Arg Leu Leu Ser Thr
    1370                1375                1380

Glu Gly Ser Gln Asn Ile Thr Tyr His Cys Lys Asn Ser Ile Ala
    1385                1390                1395

Tyr Leu Asp Glu Ala Ala Gly Asn Leu Lys Lys Ala Leu Leu Ile
    1400                1405                1410

Gln Gly Ser Asn Asp Val Glu Ile Arg Ala Glu Gly Asn Ser Arg
```

-continued

```
                1415                1420                1425

Phe Thr Tyr Thr Ala Leu Lys Asp Gly Cys Thr Lys His Thr Gly
            1430                1435                1440

Lys Trp Gly Lys Thr Val Ile Glu Tyr Arg Ser Gln Lys Thr Ser
        1445                1450                1455

Arg Leu Pro Ile Ile Asp Ile Ala Pro Met Asp Ile Gly Gly Pro
    1460                1465                1470

Glu Gln Glu Phe Gly Val Asp Ile Gly Pro Val Cys Phe Leu
    1475                1480                1485

<210> SEQ ID NO 59
<211> LENGTH: 1466
<212> TYPE: PRT
<213> ORGANISM: Homo sapiens
<300> PUBLICATION INFORMATION:
<308> DATABASE ACCESSION NUMBER: UniProt / P02461
<309> DATABASE ENTRY DATE: 2015-07-22
<313> RELEVANT RESIDUES IN SEQ ID NO: (1)..(1466)

<400> SEQUENCE: 59

Met Met Ser Phe Val Gln Lys Gly Ser Trp Leu Leu Leu Ala Leu Leu
1               5                   10                  15

His Pro Thr Ile Ile Leu Ala Gln Gln Glu Ala Val Glu Gly Gly Cys
            20                  25                  30

Ser His Leu Gly Gln Ser Tyr Ala Asp Arg Asp Val Trp Lys Pro Glu
        35                  40                  45

Pro Cys Gln Ile Cys Val Cys Asp Ser Gly Ser Val Leu Cys Asp Asp
    50                  55                  60

Ile Ile Cys Asp Asp Gln Glu Leu Asp Cys Pro Asn Pro Glu Ile Pro
65                  70                  75                  80

Phe Gly Glu Cys Cys Ala Val Cys Pro Gln Pro Thr Ala Pro Thr
                85                  90                  95

Arg Pro Pro Asn Gly Gln Gly Pro Gln Gly Pro Lys Gly Asp Pro Gly
            100                 105                 110

Pro Pro Gly Ile Pro Gly Arg Asn Gly Asp Pro Gly Ile Pro Gly Gln
        115                 120                 125

Pro Gly Ser Pro Gly Ser Pro Gly Pro Pro Gly Ile Cys Glu Ser Cys
    130                 135                 140

Pro Thr Gly Pro Gln Asn Tyr Ser Pro Gln Tyr Asp Ser Tyr Asp Val
145                 150                 155                 160

Lys Ser Gly Val Ala Val Gly Gly Leu Ala Gly Tyr Pro Gly Pro Ala
                165                 170                 175

Gly Pro Pro Gly Pro Pro Gly Pro Pro Gly Thr Ser Gly His Pro Gly
            180                 185                 190

Ser Pro Gly Ser Pro Gly Tyr Gln Gly Pro Pro Gly Glu Pro Gly Gln
        195                 200                 205

Ala Gly Pro Ser Gly Pro Pro Gly Pro Pro Gly Ala Ile Gly Pro Ser
    210                 215                 220

Gly Pro Ala Gly Lys Asp Gly Glu Ser Gly Arg Pro Gly Arg Pro Gly
225                 230                 235                 240

Glu Arg Gly Leu Pro Gly Pro Pro Gly Ile Lys Gly Pro Ala Gly Ile
                245                 250                 255

Pro Gly Phe Pro Gly Met Lys Gly His Arg Gly Phe Asp Gly Arg Asn
            260                 265                 270

Gly Glu Lys Gly Glu Thr Gly Ala Pro Gly Leu Lys Gly Glu Asn Gly
        275                 280                 285
```

```
Leu Pro Gly Glu Asn Gly Ala Pro Gly Pro Met Gly Pro Arg Gly Ala
    290                 295                 300

Pro Gly Glu Arg Gly Arg Pro Gly Leu Pro Gly Ala Ala Gly Ala Arg
305                 310                 315                 320

Gly Asn Asp Gly Ala Arg Gly Ser Asp Gly Gln Pro Gly Pro Pro Gly
                325                 330                 335

Pro Pro Gly Thr Ala Gly Phe Pro Gly Ser Pro Gly Ala Lys Gly Glu
                340                 345                 350

Val Gly Pro Ala Gly Ser Pro Gly Ser Asn Gly Ala Pro Gly Gln Arg
                355                 360                 365

Gly Glu Pro Gly Pro Gln Gly His Ala Gly Ala Gln Gly Pro Pro Gly
    370                 375                 380

Pro Pro Gly Ile Asn Gly Ser Pro Gly Gly Lys Gly Glu Met Gly Pro
385                 390                 395                 400

Ala Gly Ile Pro Gly Ala Pro Gly Leu Met Gly Ala Arg Gly Pro Pro
                405                 410                 415

Gly Pro Ala Gly Ala Asn Gly Ala Pro Gly Leu Arg Gly Gly Ala Gly
                420                 425                 430

Glu Pro Gly Lys Asn Gly Ala Lys Gly Glu Pro Gly Pro Arg Gly Glu
    435                 440                 445

Arg Gly Glu Ala Gly Ile Pro Gly Val Pro Gly Ala Lys Gly Glu Asp
    450                 455                 460

Gly Lys Asp Gly Ser Pro Gly Glu Pro Gly Ala Asn Gly Leu Pro Gly
465                 470                 475                 480

Ala Ala Gly Glu Arg Gly Ala Pro Gly Phe Arg Gly Pro Ala Gly Pro
                485                 490                 495

Asn Gly Ile Pro Gly Glu Lys Gly Pro Ala Gly Glu Arg Gly Ala Pro
                500                 505                 510

Gly Pro Ala Gly Pro Arg Gly Ala Ala Gly Glu Pro Gly Arg Asp Gly
                515                 520                 525

Val Pro Gly Gly Pro Gly Met Arg Gly Met Pro Gly Ser Pro Gly Gly
    530                 535                 540

Pro Gly Ser Asp Gly Lys Pro Gly Pro Pro Gly Ser Gln Gly Glu Ser
545                 550                 555                 560

Gly Arg Pro Gly Pro Pro Gly Pro Ser Gly Pro Arg Gly Gln Pro Gly
                565                 570                 575

Val Met Gly Phe Pro Gly Pro Lys Gly Asn Asp Gly Ala Pro Gly Lys
                580                 585                 590

Asn Gly Glu Arg Gly Gly Pro Gly Gly Pro Gly Pro Gln Gly Pro Pro
    595                 600                 605

Gly Lys Asn Gly Glu Thr Gly Pro Gln Gly Pro Pro Gly Pro Thr Gly
    610                 615                 620

Pro Gly Gly Asp Lys Gly Asp Thr Gly Pro Pro Gly Pro Gln Gly Leu
625                 630                 635                 640

Gln Gly Leu Pro Gly Thr Gly Gly Pro Pro Gly Glu Asn Gly Lys Pro
                645                 650                 655

Gly Glu Pro Gly Pro Lys Gly Asp Ala Gly Ala Pro Gly Ala Pro Gly
                660                 665                 670

Gly Lys Gly Asp Ala Gly Ala Pro Gly Glu Arg Gly Pro Pro Gly Leu
                675                 680                 685

Ala Gly Ala Pro Gly Leu Arg Gly Gly Ala Gly Pro Pro Gly Pro Glu
    690                 695                 700
```

-continued

Gly Gly Lys Gly Ala Ala Gly Pro Pro Gly Pro Gly Ala Ala Gly
705                 710                 715                 720

Thr Pro Gly Leu Gln Gly Met Pro Gly Glu Arg Gly Gly Leu Gly Ser
                725                 730                 735

Pro Gly Pro Lys Gly Asp Lys Gly Glu Pro Gly Gly Pro Gly Ala Asp
                740                 745                 750

Gly Val Pro Gly Lys Asp Gly Pro Arg Gly Pro Thr Gly Pro Ile Gly
                755                 760                 765

Pro Pro Gly Pro Ala Gly Gln Pro Gly Asp Lys Gly Glu Gly Gly Ala
                770                 775                 780

Pro Gly Leu Pro Gly Ile Ala Gly Pro Arg Gly Ser Pro Gly Glu Arg
785                 790                 795                 800

Gly Glu Thr Gly Pro Pro Gly Pro Ala Gly Phe Pro Gly Ala Pro Gly
                805                 810                 815

Gln Asn Gly Glu Pro Gly Gly Lys Gly Glu Arg Gly Ala Pro Gly Glu
                820                 825                 830

Lys Gly Glu Gly Gly Pro Pro Gly Val Ala Gly Pro Pro Gly Gly Ser
                835                 840                 845

Gly Pro Ala Gly Pro Pro Gly Pro Gln Gly Val Lys Gly Glu Arg Gly
                850                 855                 860

Ser Pro Gly Gly Pro Gly Ala Ala Gly Phe Pro Gly Ala Arg Gly Leu
865                 870                 875                 880

Pro Gly Pro Pro Gly Ser Asn Gly Asn Pro Gly Pro Pro Gly Pro Ser
                885                 890                 895

Gly Ser Pro Gly Lys Asp Gly Pro Pro Gly Pro Ala Gly Asn Thr Gly
                900                 905                 910

Ala Pro Gly Ser Pro Gly Val Ser Gly Pro Lys Gly Asp Ala Gly Gln
                915                 920                 925

Pro Gly Glu Lys Gly Ser Pro Gly Ala Gln Gly Pro Pro Gly Ala Pro
                930                 935                 940

Gly Pro Leu Gly Ile Ala Gly Ile Thr Gly Ala Arg Gly Leu Ala Gly
945                 950                 955                 960

Pro Pro Gly Met Pro Gly Pro Arg Gly Ser Pro Gly Pro Gln Gly Val
                965                 970                 975

Lys Gly Glu Ser Gly Lys Pro Gly Ala Asn Gly Leu Ser Gly Glu Arg
                980                 985                 990

Gly Pro Pro Gly Pro Gln Gly Leu Pro Gly Leu Ala Gly Thr Ala Gly
                995                 1000                1005

Glu Pro Gly Arg Asp Gly Asn Pro Gly Ser Asp Gly Leu Pro Gly
    1010                1015                1020

Arg Asp Gly Ser Pro Gly Gly Lys Gly Asp Arg Gly Glu Asn Gly
    1025                1030                1035

Ser Pro Gly Ala Pro Gly Ala Pro Gly His Pro Gly Pro Pro Gly
    1040                1045                1050

Pro Val Gly Pro Ala Gly Lys Ser Gly Asp Arg Gly Glu Ser Gly
    1055                1060                1065

Pro Ala Gly Pro Ala Gly Ala Pro Gly Pro Ala Gly Ser Arg Gly
    1070                1075                1080

Ala Pro Gly Pro Gln Gly Pro Arg Gly Asp Lys Gly Glu Thr Gly
    1085                1090                1095

Glu Arg Gly Ala Ala Gly Ile Lys Gly His Arg Gly Phe Pro Gly
    1100                1105                1110

Asn Pro Gly Ala Pro Gly Ser Pro Gly Pro Ala Gly Gln Gln Gly

| | 1115 | | | | 1120 | | | | 1125 | |
|---|---|---|---|---|---|---|---|---|---|---|

Ala Ile Gly Ser Pro Gly Pro Ala Gly Pro Arg Gly Pro Val Gly
    1130                        1135                        1140

Pro Ser Gly Pro Pro Gly Lys Asp Gly Thr Ser Gly His Pro Gly
    1145                        1150                        1155

Pro Ile Gly Pro Pro Gly Pro Arg Gly Asn Arg Gly Glu Arg Gly
    1160                        1165                        1170

Ser Glu Gly Ser Pro Gly His Pro Gly Gln Pro Gly Pro Pro Gly
    1175                        1180                        1185

Pro Pro Gly Ala Pro Gly Pro Cys Cys Gly Gly Val Gly Ala Ala
    1190                        1195                        1200

Ala Ile Ala Gly Ile Gly Gly Glu Lys Ala Gly Gly Phe Ala Pro
    1205                        1210                        1215

Tyr Tyr Gly Asp Glu Pro Met Asp Phe Lys Ile Asn Thr Asp Glu
    1220                        1225                        1230

Ile Met Thr Ser Leu Lys Ser Val Asn Gly Gln Ile Glu Ser Leu
    1235                        1240                        1245

Ile Ser Pro Asp Gly Ser Arg Lys Asn Pro Ala Arg Asn Cys Arg
    1250                        1255                        1260

Asp Leu Lys Phe Cys His Pro Glu Leu Lys Ser Gly Glu Tyr Trp
    1265                        1270                        1275

Val Asp Pro Asn Gln Gly Cys Lys Leu Asp Ala Ile Lys Val Phe
    1280                        1285                        1290

Cys Asn Met Glu Thr Gly Glu Thr Cys Ile Ser Ala Asn Pro Leu
    1295                        1300                        1305

Asn Val Pro Arg Lys His Trp Trp Thr Asp Ser Ser Ala Glu Lys
    1310                        1315                        1320

Lys His Val Trp Phe Gly Glu Ser Met Asp Gly Gly Phe Gln Phe
    1325                        1330                        1335

Ser Tyr Gly Asn Pro Glu Leu Pro Glu Asp Val Leu Asp Val His
    1340                        1345                        1350

Leu Ala Phe Leu Arg Leu Leu Ser Ser Arg Ala Ser Gln Asn Ile
    1355                        1360                        1365

Thr Tyr His Cys Lys Asn Ser Ile Ala Tyr Met Asp Gln Ala Ser
    1370                        1375                        1380

Gly Asn Val Lys Lys Ala Leu Lys Leu Met Gly Ser Asn Glu Gly
    1385                        1390                        1395

Glu Phe Lys Ala Glu Gly Asn Ser Lys Phe Thr Tyr Thr Val Leu
    1400                        1405                        1410

Glu Asp Gly Cys Thr Lys His Thr Gly Glu Trp Ser Lys Thr Val
    1415                        1420                        1425

Phe Glu Tyr Arg Thr Arg Lys Ala Val Arg Leu Pro Ile Val Asp
    1430                        1435                        1440

Ile Ala Pro Tyr Asp Ile Gly Gly Pro Asp Gln Glu Phe Gly Val
    1445                        1450                        1455

Asp Val Gly Pro Val Cys Phe Leu
    1460                        1465

```
<210> SEQ ID NO 60
<211> LENGTH: 1669
<212> TYPE: PRT
<213> ORGANISM: Homo sapiens
<300> PUBLICATION INFORMATION:
<308> DATABASE ACCESSION NUMBER: UniProt / P02462
<309> DATABASE ENTRY DATE: 2015-07-22
```

-continued

<313> RELEVANT RESIDUES IN SEQ ID NO: (1)..(1669)

<400> SEQUENCE: 60

```
Met Gly Pro Arg Leu Ser Val Trp Leu Leu Leu Pro Ala Ala Leu
1               5                   10                  15

Leu Leu His Glu Glu His Ser Arg Ala Ala Lys Gly Gly Cys Ala
            20                  25                  30

Gly Ser Gly Cys Gly Lys Cys Asp Cys His Gly Val Lys Gly Gln Lys
        35                  40                  45

Gly Glu Arg Gly Leu Pro Gly Leu Gln Gly Val Ile Gly Phe Pro Gly
    50                  55                  60

Met Gln Gly Pro Glu Gly Pro Gln Gly Pro Pro Gly Gln Lys Gly Asp
65                  70                  75                  80

Thr Gly Glu Pro Gly Leu Pro Gly Thr Lys Gly Thr Arg Gly Pro Pro
                85                  90                  95

Gly Ala Ser Gly Tyr Pro Gly Asn Pro Gly Leu Pro Gly Ile Pro Gly
                100                 105                 110

Gln Asp Gly Pro Pro Gly Pro Pro Gly Ile Pro Gly Cys Asn Gly Thr
            115                 120                 125

Lys Gly Glu Arg Gly Pro Leu Gly Pro Pro Gly Leu Pro Gly Phe Ala
130                 135                 140

Gly Asn Pro Gly Pro Pro Gly Leu Pro Gly Met Lys Gly Asp Pro Gly
145                 150                 155                 160

Glu Ile Leu Gly His Val Pro Gly Met Leu Leu Lys Gly Glu Arg Gly
                165                 170                 175

Phe Pro Gly Ile Pro Gly Thr Pro Gly Pro Pro Gly Leu Pro Gly Leu
                180                 185                 190

Gln Gly Pro Val Gly Pro Pro Gly Phe Thr Gly Pro Pro Gly Pro Pro
            195                 200                 205

Gly Pro Pro Gly Pro Pro Gly Glu Lys Gly Gln Met Gly Leu Ser Phe
210                 215                 220

Gln Gly Pro Lys Gly Asp Lys Gly Asp Gln Gly Val Ser Gly Pro Pro
225                 230                 235                 240

Gly Val Pro Gly Gln Ala Gln Val Gln Glu Lys Gly Asp Phe Ala Thr
                245                 250                 255

Lys Gly Glu Lys Gly Gln Lys Gly Glu Pro Gly Phe Gln Gly Met Pro
                260                 265                 270

Gly Val Gly Glu Lys Gly Glu Pro Gly Lys Pro Gly Pro Arg Gly Lys
            275                 280                 285

Pro Gly Lys Asp Gly Asp Lys Gly Glu Lys Gly Ser Pro Gly Phe Pro
    290                 295                 300

Gly Glu Pro Gly Tyr Pro Gly Leu Ile Gly Arg Gln Gly Pro Gln Gly
305                 310                 315                 320

Glu Lys Gly Glu Ala Gly Pro Pro Gly Pro Pro Gly Ile Val Ile Gly
                325                 330                 335

Thr Gly Pro Leu Gly Glu Lys Gly Glu Arg Gly Tyr Pro Gly Thr Pro
                340                 345                 350

Gly Pro Arg Gly Glu Pro Gly Pro Lys Gly Phe Pro Gly Leu Pro Gly
            355                 360                 365

Gln Pro Gly Pro Pro Gly Leu Pro Val Pro Gly Gln Ala Gly Ala Pro
        370                 375                 380

Gly Phe Pro Gly Glu Arg Gly Glu Lys Gly Asp Arg Gly Phe Pro Gly
385                 390                 395                 400
```

-continued

```
Thr Ser Leu Pro Gly Pro Ser Gly Arg Asp Gly Leu Pro Gly Pro Pro
                405                 410                 415
Gly Ser Pro Gly Pro Pro Gly Gln Pro Gly Tyr Thr Asn Gly Ile Val
            420                 425                 430
Glu Cys Gln Pro Gly Pro Pro Gly Asp Gln Gly Pro Pro Gly Ile Pro
            435                 440                 445
Gly Gln Pro Gly Phe Ile Gly Glu Ile Gly Glu Lys Gly Gln Lys Gly
            450                 455                 460
Glu Ser Cys Leu Ile Cys Asp Ile Asp Gly Tyr Arg Gly Pro Pro Gly
465                 470                 475                 480
Pro Gln Gly Pro Pro Gly Glu Ile Gly Phe Pro Gly Gln Pro Gly Ala
                485                 490                 495
Lys Gly Asp Arg Gly Leu Pro Gly Arg Asp Gly Val Ala Gly Val Pro
            500                 505                 510
Gly Pro Gln Gly Thr Pro Gly Leu Ile Gly Gln Pro Gly Ala Lys Gly
            515                 520                 525
Glu Pro Gly Glu Phe Tyr Phe Asp Leu Arg Leu Lys Gly Asp Lys Gly
            530                 535                 540
Asp Pro Gly Phe Pro Gly Gln Pro Gly Met Thr Gly Arg Ala Gly Ser
545                 550                 555                 560
Pro Gly Arg Asp Gly His Pro Gly Leu Pro Gly Pro Lys Gly Ser Pro
                565                 570                 575
Gly Ser Val Gly Leu Lys Gly Glu Arg Gly Pro Pro Gly Gly Val Gly
            580                 585                 590
Phe Pro Gly Ser Arg Gly Asp Thr Gly Pro Pro Gly Pro Pro Gly Tyr
            595                 600                 605
Gly Pro Ala Gly Pro Ile Gly Asp Lys Gly Gln Ala Gly Phe Pro Gly
            610                 615                 620
Gly Pro Gly Ser Pro Gly Leu Pro Gly Pro Lys Gly Glu Pro Gly Lys
625                 630                 635                 640
Ile Val Pro Leu Pro Gly Pro Pro Gly Ala Glu Gly Leu Pro Gly Ser
                645                 650                 655
Pro Gly Phe Pro Gly Pro Gln Gly Asp Arg Gly Phe Pro Gly Thr Pro
            660                 665                 670
Gly Arg Pro Gly Leu Pro Gly Glu Lys Gly Ala Val Gly Gln Pro Gly
            675                 680                 685
Ile Gly Phe Pro Gly Pro Pro Gly Pro Lys Gly Val Asp Gly Leu Pro
            690                 695                 700
Gly Asp Met Gly Pro Pro Gly Thr Pro Gly Arg Pro Gly Phe Asn Gly
705                 710                 715                 720
Leu Pro Gly Asn Pro Gly Val Gln Gly Gln Lys Gly Glu Pro Gly Val
                725                 730                 735
Gly Leu Pro Gly Leu Lys Gly Leu Pro Gly Leu Pro Gly Ile Pro Gly
            740                 745                 750
Thr Pro Gly Glu Lys Gly Ser Ile Gly Val Pro Gly Val Pro Gly Glu
            755                 760                 765
His Gly Ala Ile Gly Pro Pro Gly Leu Gln Gly Ile Arg Gly Glu Pro
            770                 775                 780
Gly Pro Pro Gly Leu Pro Gly Ser Val Gly Ser Pro Gly Val Pro Gly
785                 790                 795                 800
Ile Gly Pro Pro Gly Ala Arg Gly Pro Pro Gly Gly Gln Gly Pro Pro
                805                 810                 815
Gly Leu Ser Gly Pro Pro Gly Ile Lys Gly Glu Lys Gly Phe Pro Gly
```

-continued

```
                820                 825                 830
Phe Pro Gly Leu Asp Met Pro Gly Pro Lys Gly Asp Lys Gly Ala Gln
            835                 840                 845
Gly Leu Pro Gly Ile Thr Gly Gln Ser Gly Leu Pro Gly Leu Pro Gly
        850                 855                 860
Gln Gln Gly Ala Pro Gly Ile Pro Gly Phe Pro Gly Ser Lys Gly Glu
865                 870                 875                 880
Met Gly Val Met Gly Thr Pro Gly Gln Pro Gly Ser Pro Gly Pro Val
                885                 890                 895
Gly Ala Pro Gly Leu Pro Gly Glu Lys Gly Asp His Gly Phe Pro Gly
            900                 905                 910
Ser Ser Gly Pro Arg Gly Asp Pro Gly Leu Lys Gly Asp Lys Gly Asp
        915                 920                 925
Val Gly Leu Pro Gly Lys Pro Gly Ser Met Asp Lys Val Asp Met Gly
    930                 935                 940
Ser Met Lys Gly Gln Lys Gly Asp Gln Gly Glu Lys Gly Gln Ile Gly
945                 950                 955                 960
Pro Ile Gly Glu Lys Gly Ser Arg Gly Asp Pro Gly Thr Pro Gly Val
                965                 970                 975
Pro Gly Lys Asp Gly Gln Ala Gly Gln Pro Gly Gln Pro Gly Pro Lys
            980                 985                 990
Gly Asp Pro Gly Ile Ser Gly Thr Pro Gly Ala Pro Gly Leu Pro Gly
        995                 1000                1005
Pro Lys Gly Ser Val Gly Gly Met Gly Leu Pro Gly Thr Pro Gly
    1010                1015                1020
Glu Lys Gly Val Pro Gly Ile Pro Gly Pro Gln Gly Ser Pro Gly
    1025                1030                1035
Leu Pro Gly Asp Lys Gly Ala Lys Gly Glu Lys Gly Gln Ala Gly
    1040                1045                1050
Pro Pro Gly Ile Gly Ile Pro Gly Leu Arg Gly Glu Lys Gly Asp
    1055                1060                1065
Gln Gly Ile Ala Gly Phe Pro Gly Ser Pro Gly Glu Lys Gly Glu
    1070                1075                1080
Lys Gly Ser Ile Gly Ile Pro Gly Met Pro Gly Ser Pro Gly Leu
    1085                1090                1095
Lys Gly Ser Pro Gly Ser Val Gly Tyr Pro Gly Ser Pro Gly Leu
    1100                1105                1110
Pro Gly Glu Lys Gly Asp Lys Gly Leu Pro Gly Leu Asp Gly Ile
    1115                1120                1125
Pro Gly Val Lys Gly Glu Ala Gly Leu Pro Gly Thr Pro Gly Pro
    1130                1135                1140
Thr Gly Pro Ala Gly Gln Lys Gly Glu Pro Gly Ser Asp Gly Ile
    1145                1150                1155
Pro Gly Ser Ala Gly Glu Lys Gly Glu Pro Gly Leu Pro Gly Arg
    1160                1165                1170
Gly Phe Pro Gly Phe Pro Gly Ala Lys Gly Asp Lys Gly Ser Lys
    1175                1180                1185
Gly Glu Val Gly Phe Pro Gly Leu Ala Gly Ser Pro Gly Ile Pro
    1190                1195                1200
Gly Ser Lys Gly Glu Gln Gly Phe Met Gly Pro Pro Gly Pro Gln
    1205                1210                1215
Gly Gln Pro Gly Leu Pro Gly Ser Pro Gly His Ala Thr Glu Gly
    1220                1225                1230
```

```
Pro Lys Gly Asp Arg Gly Pro Gln Gly Gln Pro Gly Leu Pro Gly
    1235            1240                1245

Leu Pro Gly Pro Met Gly Pro Pro Gly Leu Pro Gly Ile Asp Gly
    1250            1255                1260

Val Lys Gly Asp Lys Gly Asn Pro Gly Trp Pro Gly Ala Pro Gly
    1265            1270                1275

Val Pro Gly Pro Lys Gly Asp Pro Gly Phe Gln Gly Met Pro Gly
    1280            1285                1290

Ile Gly Gly Ser Pro Gly Ile Thr Gly Ser Lys Gly Asp Met Gly
    1295            1300                1305

Pro Pro Gly Val Pro Gly Phe Gln Gly Pro Lys Gly Leu Pro Gly
    1310            1315                1320

Leu Gln Gly Ile Lys Gly Asp Gln Gly Asp Gln Gly Val Pro Gly
    1325            1330                1335

Ala Lys Gly Leu Pro Gly Pro Pro Gly Pro Pro Gly Pro Tyr Asp
    1340            1345                1350

Ile Ile Lys Gly Glu Pro Gly Leu Pro Gly Pro Glu Gly Pro Pro
    1355            1360                1365

Gly Leu Lys Gly Leu Gln Gly Leu Pro Gly Pro Lys Gly Gln Gln
    1370            1375                1380

Gly Val Thr Gly Leu Val Gly Ile Pro Gly Pro Pro Gly Ile Pro
    1385            1390                1395

Gly Phe Asp Gly Ala Pro Gly Gln Lys Gly Glu Met Gly Pro Ala
    1400            1405                1410

Gly Pro Thr Gly Pro Arg Gly Phe Pro Gly Pro Pro Gly Pro Asp
    1415            1420                1425

Gly Leu Pro Gly Ser Met Gly Pro Pro Gly Thr Pro Ser Val Asp
    1430            1435                1440

His Gly Phe Leu Val Thr Arg His Ser Gln Thr Ile Asp Asp Pro
    1445            1450                1455

Gln Cys Pro Ser Gly Thr Lys Ile Leu Tyr His Gly Tyr Ser Leu
    1460            1465                1470

Leu Tyr Val Gln Gly Asn Glu Arg Ala His Gly Gln Asp Leu Gly
    1475            1480                1485

Thr Ala Gly Ser Cys Leu Arg Lys Phe Ser Thr Met Pro Phe Leu
    1490            1495                1500

Phe Cys Asn Ile Asn Asn Val Cys Asn Phe Ala Ser Arg Asn Asp
    1505            1510                1515

Tyr Ser Tyr Trp Leu Ser Thr Pro Glu Pro Met Pro Met Ser Met
    1520            1525                1530

Ala Pro Ile Thr Gly Glu Asn Ile Arg Pro Phe Ile Ser Arg Cys
    1535            1540                1545

Ala Val Cys Glu Ala Pro Ala Met Val Met Ala Val His Ser Gln
    1550            1555                1560

Thr Ile Gln Ile Pro Pro Cys Pro Ser Gly Trp Ser Ser Leu Trp
    1565            1570                1575

Ile Gly Tyr Ser Phe Val Met His Thr Ser Ala Gly Ala Glu Gly
    1580            1585                1590

Ser Gly Gln Ala Leu Ala Ser Pro Gly Ser Cys Leu Glu Glu Phe
    1595            1600                1605

Arg Ser Ala Pro Phe Ile Glu Cys His Gly Arg Gly Thr Cys Asn
    1610            1615                1620
```

-continued

```
Tyr Tyr Ala Asn Ala Tyr Ser Phe Trp Leu Ala Thr Ile Glu Arg
    1625            1630                1635

Ser Glu Met Phe Lys Lys Pro Thr Pro Ser Thr Leu Lys Ala Gly
1640                1645                1650

Glu Leu Arg Thr His Val Ser Arg Cys Gln Val Cys Met Arg Arg
    1655                1660                1665

Thr

<210> SEQ ID NO 61
<211> LENGTH: 1838
<212> TYPE: PRT
<213> ORGANISM: Homo sapiens
<300> PUBLICATION INFORMATION:
<308> DATABASE ACCESSION NUMBER: UniProt / P20908
<309> DATABASE ENTRY DATE: 2015-07-22
<313> RELEVANT RESIDUES IN SEQ ID NO: (1)..(1838)

<400> SEQUENCE: 61

Met Asp Val His Thr Arg Trp Lys Ala Arg Ser Ala Leu Arg Pro Gly
1               5                   10                  15

Ala Pro Leu Leu Pro Pro Leu Leu Leu Leu Leu Trp Ala Pro Pro
                20                  25                  30

Pro Ser Arg Ala Ala Gln Pro Ala Asp Leu Leu Lys Val Leu Asp Phe
            35                  40                  45

His Asn Leu Pro Asp Gly Ile Thr Lys Thr Thr Gly Phe Cys Ala Thr
        50                  55                  60

Arg Arg Ser Ser Lys Gly Pro Asp Val Ala Tyr Arg Val Thr Lys Asp
65                  70                  75                  80

Ala Gln Leu Ser Ala Pro Thr Lys Gln Leu Tyr Pro Ala Ser Ala Phe
                85                  90                  95

Pro Glu Asp Phe Ser Ile Leu Thr Thr Val Lys Ala Lys Lys Gly Ser
            100                 105                 110

Gln Ala Phe Leu Val Ser Ile Tyr Asn Glu Gln Gly Ile Gln Gln Ile
        115                 120                 125

Gly Leu Glu Leu Gly Arg Ser Pro Val Phe Leu Tyr Glu Asp His Thr
    130                 135                 140

Gly Lys Pro Gly Pro Glu Asp Tyr Pro Leu Phe Arg Gly Ile Asn Leu
145                 150                 155                 160

Ser Asp Gly Lys Trp His Arg Ile Ala Leu Ser Val His Lys Lys Asn
                165                 170                 175

Val Thr Leu Ile Leu Asp Cys Lys Lys Lys Thr Thr Lys Phe Leu Asp
            180                 185                 190

Arg Ser Asp His Pro Met Ile Asp Ile Asn Gly Ile Ile Val Phe Gly
        195                 200                 205

Thr Arg Ile Leu Asp Glu Glu Val Phe Glu Gly Asp Ile Gln Gln Leu
    210                 215                 220

Leu Phe Val Ser Asp His Arg Ala Ala Tyr Asp Tyr Cys Glu His Tyr
225                 230                 235                 240

Ser Pro Asp Cys Asp Thr Ala Val Pro Asp Thr Pro Gln Ser Gln Asp
                245                 250                 255

Pro Asn Pro Asp Glu Tyr Tyr Thr Glu Gly Asp Gly Glu Gly Glu Thr
            260                 265                 270

Tyr Tyr Tyr Glu Tyr Pro Tyr Tyr Glu Asp Pro Glu Asp Leu Gly Lys
        275                 280                 285

Glu Pro Thr Pro Ser Lys Lys Pro Val Glu Ala Ala Lys Glu Thr Thr
    290                 295                 300
```

-continued

```
Glu Val Pro Glu Glu Leu Thr Pro Thr Pro Thr Glu Ala Ala Pro Met
305                 310                 315                 320

Pro Glu Thr Ser Glu Gly Ala Gly Lys Glu Glu Asp Val Gly Ile Gly
            325                 330                 335

Asp Tyr Asp Tyr Val Pro Ser Glu Asp Tyr Tyr Thr Pro Ser Pro Tyr
        340                 345                 350

Asp Asp Leu Thr Tyr Gly Glu Gly Glu Glu Asn Pro Asp Gln Pro Thr
            355                 360                 365

Asp Pro Gly Ala Gly Ala Glu Ile Pro Thr Ser Thr Ala Asp Thr Ser
        370                 375                 380

Asn Ser Ser Asn Pro Ala Pro Pro Gly Glu Gly Ala Asp Asp Leu
385                 390                 395                 400

Glu Gly Glu Phe Thr Glu Glu Thr Ile Arg Asn Leu Asp Glu Asn Tyr
                405                 410                 415

Tyr Asp Pro Tyr Tyr Asp Pro Thr Ser Ser Pro Ser Glu Ile Gly Pro
            420                 425                 430

Gly Met Pro Ala Asn Gln Asp Thr Ile Tyr Glu Gly Ile Gly Gly Pro
            435                 440                 445

Arg Gly Glu Lys Gly Gln Lys Gly Glu Pro Ala Ile Ile Glu Pro Gly
450                 455                 460

Met Leu Ile Glu Gly Pro Pro Gly Pro Glu Gly Pro Ala Gly Leu Pro
465                 470                 475                 480

Gly Pro Pro Gly Thr Met Gly Pro Thr Gly Gln Val Gly Asp Pro Gly
                485                 490                 495

Glu Arg Gly Pro Pro Gly Arg Pro Gly Leu Pro Gly Ala Asp Gly Leu
            500                 505                 510

Pro Gly Pro Pro Gly Thr Met Leu Met Leu Pro Phe Arg Phe Gly Gly
            515                 520                 525

Gly Gly Asp Ala Gly Ser Lys Gly Pro Met Val Ser Ala Gln Glu Ser
530                 535                 540

Gln Ala Gln Ala Ile Leu Gln Gln Ala Arg Leu Ala Leu Arg Gly Pro
545                 550                 555                 560

Ala Gly Pro Met Gly Leu Thr Gly Arg Pro Gly Pro Val Gly Pro Pro
                565                 570                 575

Gly Ser Gly Gly Leu Lys Gly Glu Pro Gly Asp Val Gly Pro Gln Gly
            580                 585                 590

Pro Arg Gly Val Gln Gly Pro Pro Gly Pro Ala Gly Lys Pro Gly Arg
            595                 600                 605

Arg Gly Arg Ala Gly Ser Asp Gly Ala Arg Gly Met Pro Gly Gln Thr
610                 615                 620

Gly Pro Lys Gly Asp Arg Gly Phe Asp Gly Leu Ala Gly Leu Pro Gly
625                 630                 635                 640

Glu Lys Gly His Arg Gly Asp Pro Gly Pro Ser Gly Pro Pro Gly Pro
                645                 650                 655

Pro Gly Asp Asp Gly Glu Arg Gly Asp Asp Gly Glu Val Gly Pro Arg
            660                 665                 670

Gly Leu Pro Gly Glu Pro Gly Pro Arg Gly Leu Leu Gly Pro Lys Gly
            675                 680                 685

Pro Pro Gly Pro Pro Gly Pro Gly Val Thr Gly Met Asp Gly Gln
690                 695                 700

Pro Gly Pro Lys Gly Asn Val Gly Pro Gln Gly Glu Pro Gly Pro Pro
705                 710                 715                 720
```

```
Gly Gln Gln Gly Asn Pro Gly Ala Gln Gly Leu Pro Gly Pro Gln Gly
            725                 730                 735

Ala Ile Gly Pro Pro Gly Glu Lys Gly Pro Leu Gly Lys Pro Gly Leu
        740                 745                 750

Pro Gly Met Pro Gly Ala Asp Gly Pro Pro Gly His Pro Gly Lys Glu
            755                 760                 765

Gly Pro Pro Gly Glu Lys Gly Gln Gly Pro Pro Gly Pro Gln Gly
        770                 775                 780

Pro Ile Gly Tyr Pro Gly Pro Arg Gly Val Lys Gly Ala Asp Gly Ile
785                 790                 795                 800

Arg Gly Leu Lys Gly Thr Lys Gly Glu Lys Gly Glu Asp Gly Phe Pro
                805                 810                 815

Gly Phe Lys Gly Asp Met Gly Ile Lys Gly Asp Arg Gly Glu Ile Gly
            820                 825                 830

Pro Pro Gly Pro Arg Gly Glu Asp Gly Pro Glu Gly Pro Lys Gly Arg
        835                 840                 845

Gly Gly Pro Asn Gly Asp Pro Gly Pro Leu Gly Pro Pro Gly Glu Lys
    850                 855                 860

Gly Lys Leu Gly Val Pro Gly Leu Pro Gly Tyr Pro Gly Arg Gln Gly
865                 870                 875                 880

Pro Lys Gly Ser Ile Gly Phe Pro Gly Phe Pro Gly Ala Asn Gly Glu
            885                 890                 895

Lys Gly Gly Arg Gly Thr Pro Gly Lys Pro Gly Pro Arg Gly Gln Arg
            900                 905                 910

Gly Pro Thr Gly Pro Arg Gly Glu Arg Gly Pro Arg Gly Ile Thr Gly
            915                 920                 925

Lys Pro Gly Pro Lys Gly Asn Ser Gly Gly Asp Gly Pro Ala Gly Pro
930                 935                 940

Pro Gly Glu Arg Gly Pro Asn Gly Pro Gln Gly Pro Thr Gly Phe Pro
945                 950                 955                 960

Gly Pro Lys Gly Pro Pro Gly Pro Pro Gly Lys Asp Gly Leu Pro Gly
            965                 970                 975

His Pro Gly Gln Arg Gly Glu Thr Gly Phe Gln Gly Lys Thr Gly Pro
            980                 985                 990

Pro Gly Pro Pro Gly Val Val Gly Pro Gln Gly Pro Thr Gly Glu Thr
        995                 1000                1005

Gly Pro Met Gly Glu Arg Gly His Pro Gly Pro Pro Gly Pro Pro
    1010                1015                1020

Gly Glu Gln Gly Leu Pro Gly Leu Ala Gly Lys Glu Gly Thr Lys
    1025                1030                1035

Gly Asp Pro Gly Pro Ala Gly Leu Pro Gly Lys Asp Gly Pro Pro
    1040                1045                1050

Gly Leu Arg Gly Phe Pro Gly Asp Arg Gly Leu Pro Gly Pro Val
    1055                1060                1065

Gly Ala Leu Gly Leu Lys Gly Asn Glu Gly Pro Pro Gly Pro Pro
    1070                1075                1080

Gly Pro Ala Gly Ser Pro Gly Glu Arg Gly Pro Ala Gly Ala Ala
    1085                1090                1095

Gly Pro Ile Gly Ile Pro Gly Arg Pro Gly Pro Gln Gly Pro Pro
    1100                1105                1110

Gly Pro Ala Gly Glu Lys Gly Ala Pro Gly Glu Lys Gly Pro Gln
    1115                1120                1125

Gly Pro Ala Gly Arg Asp Gly Leu Gln Gly Pro Val Gly Leu Pro
```

-continued

```
            1130                1135                1140

Gly Pro Ala Gly Pro Val Gly Pro Pro Gly Glu Asp Gly Asp Lys
    1145                1150                1155

Gly Glu Ile Gly Glu Pro Gly Gln Lys Gly Ser Lys Gly Asp Lys
    1160                1165                1170

Gly Glu Gln Gly Pro Pro Gly Pro Thr Gly Pro Gln Gly Pro Ile
    1175                1180                1185

Gly Gln Pro Gly Pro Ser Gly Ala Asp Gly Glu Pro Gly Pro Arg
    1190                1195                1200

Gly Gln Gln Gly Leu Phe Gly Gln Lys Gly Asp Glu Gly Pro Arg
    1205                1210                1215

Gly Phe Pro Gly Pro Pro Gly Pro Val Gly Leu Gln Gly Leu Pro
    1220                1225                1230

Gly Pro Pro Gly Glu Lys Gly Glu Thr Gly Asp Val Gly Gln Met
    1235                1240                1245

Gly Pro Pro Gly Pro Pro Gly Pro Arg Gly Pro Ser Gly Ala Pro
    1250                1255                1260

Gly Ala Asp Gly Pro Gln Gly Pro Pro Gly Gly Ile Gly Asn Pro
    1265                1270                1275

Gly Ala Val Gly Glu Lys Gly Glu Pro Gly Glu Ala Gly Glu Pro
    1280                1285                1290

Gly Leu Pro Gly Glu Gly Gly Pro Pro Gly Pro Lys Gly Glu Arg
    1295                1300                1305

Gly Glu Lys Gly Glu Ser Gly Pro Ser Gly Ala Ala Gly Pro Pro
    1310                1315                1320

Gly Pro Lys Gly Pro Pro Gly Asp Asp Gly Pro Lys Gly Ser Pro
    1325                1330                1335

Gly Pro Val Gly Phe Pro Gly Asp Pro Gly Pro Pro Gly Glu Pro
    1340                1345                1350

Gly Pro Ala Gly Gln Asp Gly Pro Pro Gly Asp Lys Gly Asp Asp
    1355                1360                1365

Gly Glu Pro Gly Gln Thr Gly Ser Pro Gly Pro Thr Gly Glu Pro
    1370                1375                1380

Gly Pro Ser Gly Pro Pro Gly Lys Arg Gly Pro Pro Gly Pro Ala
    1385                1390                1395

Gly Pro Glu Gly Arg Gln Gly Glu Lys Gly Ala Lys Gly Glu Ala
    1400                1405                1410

Gly Leu Glu Gly Pro Pro Gly Lys Thr Gly Pro Ile Gly Pro Gln
    1415                1420                1425

Gly Ala Pro Gly Lys Pro Gly Pro Asp Gly Leu Arg Gly Ile Pro
    1430                1435                1440

Gly Pro Val Gly Glu Gln Gly Leu Pro Gly Ser Pro Gly Pro Asp
    1445                1450                1455

Gly Pro Pro Gly Pro Met Gly Pro Pro Gly Leu Pro Gly Leu Lys
    1460                1465                1470

Gly Asp Ser Gly Pro Lys Gly Glu Lys Gly His Pro Gly Leu Ile
    1475                1480                1485

Gly Leu Ile Gly Pro Pro Gly Glu Gln Gly Glu Lys Gly Asp Arg
    1490                1495                1500

Gly Leu Pro Gly Pro Gln Gly Ser Ser Gly Pro Lys Gly Glu Gln
    1505                1510                1515

Gly Ile Thr Gly Pro Ser Gly Pro Ile Gly Pro Pro Gly Pro Pro
    1520                1525                1530
```

Gly Leu Pro Gly Pro Pro Gly Pro Lys Gly Ala Lys Gly Ser Ser
1535                1540                1545

Gly Pro Thr Gly Pro Lys Gly Glu Ala Gly His Pro Gly Pro Pro
1550                1555                1560

Gly Pro Pro Gly Pro Pro Gly Glu Val Ile Gln Pro Leu Pro Ile
1565                1570                1575

Gln Ala Ser Arg Thr Arg Arg Asn Ile Asp Ala Ser Gln Leu Leu
1580                1585                1590

Asp Asp Gly Asn Gly Glu Asn Tyr Val Asp Tyr Ala Asp Gly Met
1595                1600                1605

Glu Glu Ile Phe Gly Ser Leu Asn Ser Leu Lys Leu Glu Ile Glu
1610                1615                1620

Gln Met Lys Arg Pro Leu Gly Thr Gln Gln Asn Pro Ala Arg Thr
1625                1630                1635

Cys Lys Asp Leu Gln Leu Cys His Pro Asp Phe Pro Asp Gly Glu
1640                1645                1650

Tyr Trp Val Asp Pro Asn Gln Gly Cys Ser Arg Asp Ser Phe Lys
1655                1660                1665

Val Tyr Cys Asn Phe Thr Ala Gly Gly Ser Thr Cys Val Phe Pro
1670                1675                1680

Asp Lys Lys Ser Glu Gly Ala Arg Ile Thr Ser Trp Pro Lys Glu
1685                1690                1695

Asn Pro Gly Ser Trp Phe Ser Glu Phe Lys Arg Gly Lys Leu Leu
1700                1705                1710

Ser Tyr Val Asp Ala Glu Gly Asn Pro Val Gly Val Val Gln Met
1715                1720                1725

Thr Phe Leu Arg Leu Leu Ser Ala Ser Ala His Gln Asn Val Thr
1730                1735                1740

Tyr His Cys Tyr Gln Ser Val Ala Trp Gln Asp Ala Ala Thr Gly
1745                1750                1755

Ser Tyr Asp Lys Ala Leu Arg Phe Leu Gly Ser Asn Asp Glu Glu
1760                1765                1770

Met Ser Tyr Asp Asn Asn Pro Tyr Ile Arg Ala Leu Val Asp Gly
1775                1780                1785

Cys Ala Thr Lys Lys Gly Tyr Gln Lys Thr Val Leu Glu Ile Asp
1790                1795                1800

Thr Pro Lys Val Glu Gln Val Pro Ile Val Asp Ile Met Phe Asn
1805                1810                1815

Asp Phe Gly Glu Ala Ser Gln Lys Phe Gly Phe Glu Val Gly Pro
1820                1825                1830

Ala Cys Phe Met Gly
     1835

<210> SEQ ID NO 62
<211> LENGTH: 223
<212> TYPE: PRT
<213> ORGANISM: Homo sapiens
<300> PUBLICATION INFORMATION:
<308> DATABASE ACCESSION NUMBER: UniProt / P16410
<309> DATABASE ENTRY DATE: 2015-07-22
<313> RELEVANT RESIDUES IN SEQ ID NO: (1)..(223)

<400> SEQUENCE: 62

Met Ala Cys Leu Gly Phe Gln Arg His Lys Ala Gln Leu Asn Leu Ala
1               5                   10                  15

-continued

```
Thr Arg Thr Trp Pro Cys Thr Leu Leu Phe Leu Leu Phe Ile Pro
                20                  25                  30

Val Phe Cys Lys Ala Met His Val Ala Gln Pro Ala Val Val Leu Ala
            35                  40                  45

Ser Ser Arg Gly Ile Ala Ser Phe Val Cys Glu Tyr Ala Ser Pro Gly
        50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 63
<211> LENGTH: 339
<212> TYPE: PRT
<213> ORGANISM: Homo sapiens
<300> PUBLICATION INFORMATION:
<308> DATABASE ACCESSION NUMBER: UniProt / O94905
<309> DATABASE ENTRY DATE: 2015-07-22
<313> RELEVANT RESIDUES IN SEQ ID NO: (1)..(339)

<400> SEQUENCE: 63

Met Ala Gln Leu Gly Ala Val Val Ala Ala Ser Ser Phe Phe Cys
1               5                   10                  15

Ala Ser Leu Phe Ser Ala Val His Lys Ile Glu Glu Gly His Ile Gly
            20                  25                  30

Val Tyr Tyr Arg Gly Gly Ala Leu Leu Thr Ser Thr Ser Gly Pro Gly
        35                  40                  45

Phe His Leu Met Leu Pro Phe Ile Thr Ser Tyr Lys Ser Val Gln Thr
    50                  55                  60

Thr Leu Gln Thr Asp Glu Val Lys Asn Val Pro Cys Gly Thr Ser Gly
65                  70                  75                  80

Gly Val Met Ile Tyr Phe Asp Arg Ile Glu Val Val Asn Phe Leu Val
                85                  90                  95

Pro Asn Ala Val Tyr Asp Ile Val Lys Asn Tyr Thr Ala Asp Tyr Asp
            100                 105                 110

Lys Ala Leu Ile Phe Asn Lys Ile His His Glu Leu Asn Gln Phe Cys
        115                 120                 125

Ser Val His Thr Leu Gln Glu Val Tyr Ile Glu Leu Phe Asp Gln Ile
    130                 135                 140

Asp Glu Asn Leu Lys Leu Ala Leu Gln Gln Asp Leu Thr Ser Met Ala
```

```
                145                 150                 155                 160
        Pro Gly Leu Val Ile Gln Ala Val Arg Val Thr Lys Pro Asn Ile Pro
                        165                 170                 175

Glu Ala Ile Arg Arg Asn Tyr Glu Leu Met Glu Ser Glu Lys Thr Lys
                        180                 185                 190

Leu Leu Ile Ala Ala Gln Lys Gln Lys Val Val Glu Lys Glu Ala Glu
                        195                 200                 205

Thr Glu Arg Lys Lys Ala Leu Ile Glu Ala Lys Val Ala Gln Val
            210                 215                 220

Ala Glu Ile Thr Tyr Gly Gln Lys Val Met Glu Lys Thr Glu Lys
        225                 230                 235                 240

Lys Ile Ser Glu Ile Glu Asp Ala Ala Phe Leu Ala Arg Glu Lys Ala
                        245                 250                 255

Lys Ala Asp Ala Glu Cys Tyr Thr Ala Met Lys Ile Ala Glu Ala Asn
                        260                 265                 270

Lys Leu Lys Leu Thr Pro Glu Tyr Leu Gln Leu Met Lys Tyr Lys Ala
                        275                 280                 285

Ile Ala Ser Asn Ser Lys Ile Tyr Phe Gly Lys Asp Ile Pro Asn Met
            290                 295                 300

Phe Met Asp Ser Ala Gly Ser Val Ser Lys Gln Phe Glu Gly Leu Ala
        305                 310                 315                 320

Asp Lys Leu Ser Phe Gly Leu Asp Glu Pro Leu Gly Thr Ala Thr
                        325                 330                 335

Lys Glu Asn

<210> SEQ ID NO 64
<211> LENGTH: 2386
<212> TYPE: PRT
<213> ORGANISM: Homo sapiens
<300> PUBLICATION INFORMATION:
<308> DATABASE ACCESSION NUMBER: UniProt / P02751
<309> DATABASE ENTRY DATE: 2015-07-22
<313> RELEVANT RESIDUES IN SEQ ID NO: (1)..(2386)

<400> SEQUENCE: 64

Met Leu Arg Gly Pro Gly Pro Gly Leu Leu Leu Leu Ala Val Gln Cys
        1               5                   10                  15

Leu Gly Thr Ala Val Pro Ser Thr Gly Ala Ser Lys Ser Lys Arg Gln
                        20                  25                  30

Ala Gln Gln Met Val Gln Pro Gln Ser Pro Val Ala Val Ser Gln Ser
                        35                  40                  45

Lys Pro Gly Cys Tyr Asp Asn Gly Lys His Tyr Gln Ile Asn Gln Gln
                        50                  55                  60

Trp Glu Arg Thr Tyr Leu Gly Asn Ala Leu Val Cys Thr Cys Tyr Gly
        65                  70                  75                  80

Gly Ser Arg Gly Phe Asn Cys Glu Ser Lys Pro Glu Ala Glu Glu Thr
                        85                  90                  95

Cys Phe Asp Lys Tyr Thr Gly Asn Thr Tyr Arg Val Gly Asp Thr Tyr
                        100                 105                 110

Glu Arg Pro Lys Asp Ser Met Ile Trp Asp Cys Thr Cys Ile Gly Ala
                        115                 120                 125

Gly Arg Gly Arg Ile Ser Cys Thr Ile Ala Asn Arg Cys His Glu Gly
                        130                 135                 140

Gly Gln Ser Tyr Lys Ile Gly Asp Thr Trp Arg Arg Pro His Glu Thr
        145                 150                 155                 160
```

-continued

```
Gly Gly Tyr Met Leu Glu Cys Val Cys Leu Gly Asn Gly Lys Gly Glu
                165                 170                 175
Trp Thr Cys Lys Pro Ile Ala Glu Lys Cys Phe Asp His Ala Ala Gly
            180                 185                 190
Thr Ser Tyr Val Val Gly Glu Thr Trp Glu Lys Pro Tyr Gln Gly Trp
        195                 200                 205
Met Met Val Asp Cys Thr Cys Leu Gly Glu Gly Ser Gly Arg Ile Thr
    210                 215                 220
Cys Thr Ser Arg Asn Arg Cys Asn Asp Gln Asp Thr Arg Thr Ser Tyr
225                 230                 235                 240
Arg Ile Gly Asp Thr Trp Ser Lys Lys Asp Asn Arg Gly Asn Leu Leu
                245                 250                 255
Gln Cys Ile Cys Thr Gly Asn Gly Arg Gly Glu Trp Lys Cys Glu Arg
            260                 265                 270
His Thr Ser Val Gln Thr Thr Ser Ser Gly Ser Gly Pro Phe Thr Asp
        275                 280                 285
Val Arg Ala Ala Val Tyr Gln Pro Gln Pro His Pro Gln Pro Pro Pro
    290                 295                 300
Tyr Gly His Cys Val Thr Asp Ser Gly Val Val Tyr Ser Val Gly Met
305                 310                 315                 320
Gln Trp Leu Lys Thr Gln Gly Asn Lys Gln Met Leu Cys Thr Cys Leu
                325                 330                 335
Gly Asn Gly Val Ser Cys Gln Glu Thr Ala Val Thr Gln Thr Tyr Gly
            340                 345                 350
Gly Asn Ser Asn Gly Glu Pro Cys Val Leu Pro Phe Thr Tyr Asn Gly
        355                 360                 365
Arg Thr Phe Tyr Ser Cys Thr Thr Glu Gly Arg Gln Asp Gly His Leu
    370                 375                 380
Trp Cys Ser Thr Thr Ser Asn Tyr Glu Gln Asp Gln Lys Tyr Ser Phe
385                 390                 395                 400
Cys Thr Asp His Thr Val Leu Val Gln Thr Arg Gly Gly Asn Ser Asn
                405                 410                 415
Gly Ala Leu Cys His Phe Pro Phe Leu Tyr Asn Asn His Asn Tyr Thr
            420                 425                 430
Asp Cys Thr Ser Glu Gly Arg Arg Asp Asn Met Lys Trp Cys Gly Thr
        435                 440                 445
Thr Gln Asn Tyr Asp Ala Asp Gln Lys Phe Gly Phe Cys Pro Met Ala
    450                 455                 460
Ala His Glu Glu Ile Cys Thr Thr Asn Glu Gly Val Met Tyr Arg Ile
465                 470                 475                 480
Gly Asp Gln Trp Asp Lys Gln His Asp Met Gly His Met Met Arg Cys
                485                 490                 495
Thr Cys Val Gly Asn Gly Arg Gly Glu Trp Thr Cys Ile Ala Tyr Ser
            500                 505                 510
Gln Leu Arg Asp Gln Cys Ile Val Asp Ile Thr Tyr Asn Val Asn
        515                 520                 525
Asp Thr Phe His Lys Arg His Glu Glu Gly His Met Leu Asn Cys Thr
    530                 535                 540
Cys Phe Gly Gln Gly Arg Gly Arg Trp Lys Cys Asp Pro Val Asp Gln
545                 550                 555                 560
Cys Gln Asp Ser Glu Thr Gly Thr Phe Tyr Gln Ile Gly Asp Ser Trp
                565                 570                 575
Glu Lys Tyr Val His Gly Val Arg Tyr Gln Cys Tyr Cys Tyr Gly Arg
```

-continued

```
                580                 585                 590
Gly Ile Gly Glu Trp His Cys Gln Pro Leu Gln Thr Tyr Pro Ser Ser
            595                 600                 605
Ser Gly Pro Val Glu Val Phe Ile Thr Glu Thr Pro Ser Gln Pro Asn
            610                 615                 620
Ser His Pro Ile Gln Trp Asn Ala Pro Gln Pro Ser His Ile Ser Lys
625                 630                 635                 640
Tyr Ile Leu Arg Trp Arg Pro Lys Asn Ser Val Gly Arg Trp Lys Glu
                645                 650                 655
Ala Thr Ile Pro Gly His Leu Asn Ser Tyr Thr Ile Lys Gly Leu Lys
            660                 665                 670
Pro Gly Val Val Tyr Glu Gly Gln Leu Ile Ser Ile Gln Gln Tyr Gly
            675                 680                 685
His Gln Glu Val Thr Arg Phe Asp Phe Thr Thr Thr Ser Thr Ser Thr
            690                 695                 700
Pro Val Thr Ser Asn Thr Val Thr Gly Glu Thr Thr Pro Phe Ser Pro
705                 710                 715                 720
Leu Val Ala Thr Ser Glu Ser Val Thr Glu Ile Thr Ala Ser Ser Phe
                725                 730                 735
Val Val Ser Trp Val Ser Ala Ser Asp Thr Val Ser Gly Phe Arg Val
            740                 745                 750
Glu Tyr Glu Leu Ser Glu Gly Asp Glu Pro Gln Tyr Leu Asp Leu
            755                 760                 765
Pro Ser Thr Ala Thr Ser Val Asn Ile Pro Asp Leu Leu Pro Gly Arg
            770                 775                 780
Lys Tyr Ile Val Asn Val Tyr Gln Ile Ser Glu Asp Gly Glu Gln Ser
785                 790                 795                 800
Leu Ile Leu Ser Thr Ser Gln Thr Thr Ala Pro Asp Ala Pro Pro Asp
                805                 810                 815
Thr Thr Val Asp Gln Val Asp Asp Thr Ser Ile Val Val Arg Trp Ser
            820                 825                 830
Arg Pro Gln Ala Pro Ile Thr Gly Tyr Arg Ile Val Tyr Ser Pro Ser
            835                 840                 845
Val Glu Gly Ser Ser Thr Glu Leu Asn Leu Pro Glu Thr Ala Asn Ser
            850                 855                 860
Val Thr Leu Ser Asp Leu Gln Pro Gly Val Gln Tyr Asn Ile Thr Ile
865                 870                 875                 880
Tyr Ala Val Glu Glu Asn Gln Glu Ser Thr Pro Val Val Ile Gln Gln
                885                 890                 895
Glu Thr Thr Gly Thr Pro Arg Ser Asp Thr Val Pro Ser Pro Arg Asp
            900                 905                 910
Leu Gln Phe Val Glu Val Thr Asp Val Lys Val Thr Ile Met Trp Thr
            915                 920                 925
Pro Pro Glu Ser Ala Val Thr Gly Tyr Arg Val Asp Val Ile Pro Val
            930                 935                 940
Asn Leu Pro Gly Glu His Gly Gln Arg Leu Pro Ile Ser Arg Asn Thr
945                 950                 955                 960
Phe Ala Glu Val Thr Gly Leu Ser Pro Gly Val Thr Tyr Tyr Phe Lys
                965                 970                 975
Val Phe Ala Val Ser His Gly Arg Glu Ser Lys Pro Leu Thr Ala Gln
            980                 985                 990
Gln Thr Thr Lys Leu Asp Ala Pro  Thr Asn Leu Gln Phe  Val Asn Glu
            995                  1000                 1005
```

```
Thr Asp Ser Thr Val Leu Val Arg Trp Thr Pro Pro Arg Ala Gln
    1010            1015                1020

Ile Thr Gly Tyr Arg Leu Thr Val Gly Leu Thr Arg Arg Gly Gln
    1025            1030                1035

Pro Arg Gln Tyr Asn Val Gly Pro Ser Val Ser Lys Tyr Pro Leu
    1040            1045                1050

Arg Asn Leu Gln Pro Ala Ser Glu Tyr Thr Val Ser Leu Val Ala
    1055            1060                1065

Ile Lys Gly Asn Gln Glu Ser Pro Lys Ala Thr Gly Val Phe Thr
    1070            1075                1080

Thr Leu Gln Pro Gly Ser Ser Ile Pro Pro Tyr Asn Thr Glu Val
    1085            1090                1095

Thr Glu Thr Thr Ile Val Ile Thr Trp Thr Pro Ala Pro Arg Ile
    1100            1105                1110

Gly Phe Lys Leu Gly Val Arg Pro Ser Gln Gly Gly Glu Ala Pro
    1115            1120                1125

Arg Glu Val Thr Ser Asp Ser Gly Ser Ile Val Val Ser Gly Leu
    1130            1135                1140

Thr Pro Gly Val Glu Tyr Val Tyr Thr Ile Gln Val Leu Arg Asp
    1145            1150                1155

Gly Gln Glu Arg Asp Ala Pro Ile Val Asn Lys Val Val Thr Pro
    1160            1165                1170

Leu Ser Pro Pro Thr Asn Leu His Leu Glu Ala Asn Pro Asp Thr
    1175            1180                1185

Gly Val Leu Thr Val Ser Trp Glu Arg Ser Thr Thr Pro Asp Ile
    1190            1195                1200

Thr Gly Tyr Arg Ile Thr Thr Thr Pro Thr Asn Gly Gln Gln Gly
    1205            1210                1215

Asn Ser Leu Glu Glu Val Val His Ala Asp Gln Ser Ser Cys Thr
    1220            1225                1230

Phe Asp Asn Leu Ser Pro Gly Leu Glu Tyr Asn Val Ser Val Tyr
    1235            1240                1245

Thr Val Lys Asp Asp Lys Glu Ser Val Pro Ile Ser Asp Thr Ile
    1250            1255                1260

Ile Pro Ala Val Pro Pro Pro Thr Asp Leu Arg Phe Thr Asn Ile
    1265            1270                1275

Gly Pro Asp Thr Met Arg Val Thr Trp Ala Pro Pro Pro Ser Ile
    1280            1285                1290

Asp Leu Thr Asn Phe Leu Val Arg Tyr Ser Pro Val Lys Asn Glu
    1295            1300                1305

Glu Asp Val Ala Glu Leu Ser Ile Ser Pro Ser Asp Asn Ala Val
    1310            1315                1320

Val Leu Thr Asn Leu Leu Pro Gly Thr Glu Tyr Val Val Ser Val
    1325            1330                1335

Ser Ser Val Tyr Glu Gln His Glu Ser Thr Pro Leu Arg Gly Arg
    1340            1345                1350

Gln Lys Thr Gly Leu Asp Ser Pro Thr Gly Ile Asp Phe Ser Asp
    1355            1360                1365

Ile Thr Ala Asn Ser Phe Thr Val His Trp Ile Ala Pro Arg Ala
    1370            1375                1380

Thr Ile Thr Gly Tyr Arg Ile Arg His His Pro Glu His Phe Ser
    1385            1390                1395
```

```
Gly Arg Pro Arg Glu Asp Arg Val Pro His Ser Arg Asn Ser Ile
1400                1405                1410

Thr Leu Thr Asn Leu Thr Pro Gly Thr Glu Tyr Val Val Ser Ile
1415                1420                1425

Val Ala Leu Asn Gly Arg Glu Glu Ser Pro Leu Leu Ile Gly Gln
1430                1435                1440

Gln Ser Thr Val Ser Asp Val Pro Arg Asp Leu Glu Val Val Ala
1445                1450                1455

Ala Thr Pro Thr Ser Leu Leu Ile Ser Trp Asp Ala Pro Ala Val
1460                1465                1470

Thr Val Arg Tyr Tyr Arg Ile Thr Tyr Gly Glu Thr Gly Gly Asn
1475                1480                1485

Ser Pro Val Gln Glu Phe Thr Val Pro Gly Ser Lys Ser Thr Ala
1490                1495                1500

Thr Ile Ser Gly Leu Lys Pro Gly Val Asp Tyr Thr Ile Thr Val
1505                1510                1515

Tyr Ala Val Thr Gly Arg Gly Asp Ser Pro Ala Ser Ser Lys Pro
1520                1525                1530

Ile Ser Ile Asn Tyr Arg Thr Glu Ile Asp Lys Pro Ser Gln Met
1535                1540                1545

Gln Val Thr Asp Val Gln Asp Asn Ser Ile Ser Val Lys Trp Leu
1550                1555                1560

Pro Ser Ser Ser Pro Val Thr Gly Tyr Arg Val Thr Thr Thr Pro
1565                1570                1575

Lys Asn Gly Pro Gly Pro Thr Lys Thr Lys Thr Ala Gly Pro Asp
1580                1585                1590

Gln Thr Glu Met Thr Ile Glu Gly Leu Gln Pro Thr Val Glu Tyr
1595                1600                1605

Val Val Ser Val Tyr Ala Gln Asn Pro Ser Gly Glu Ser Gln Pro
1610                1615                1620

Leu Val Gln Thr Ala Val Thr Asn Ile Asp Arg Pro Lys Gly Leu
1625                1630                1635

Ala Phe Thr Asp Val Asp Val Asp Ser Ile Lys Ile Ala Trp Glu
1640                1645                1650

Ser Pro Gln Gly Gln Val Ser Arg Tyr Arg Val Thr Tyr Ser Ser
1655                1660                1665

Pro Glu Asp Gly Ile His Glu Leu Phe Pro Ala Pro Asp Gly Glu
1670                1675                1680

Glu Asp Thr Ala Glu Leu Gln Gly Leu Arg Pro Gly Ser Glu Tyr
1685                1690                1695

Thr Val Ser Val Val Ala Leu His Asp Asp Met Glu Ser Gln Pro
1700                1705                1710

Leu Ile Gly Thr Gln Ser Thr Ala Ile Pro Ala Pro Thr Asp Leu
1715                1720                1725

Lys Phe Thr Gln Val Thr Pro Thr Ser Leu Ser Ala Gln Trp Thr
1730                1735                1740

Pro Pro Asn Val Gln Leu Thr Gly Tyr Arg Val Arg Val Thr Pro
1745                1750                1755

Lys Glu Lys Thr Gly Pro Met Lys Glu Ile Asn Leu Ala Pro Asp
1760                1765                1770

Ser Ser Ser Val Val Val Ser Gly Leu Met Val Ala Thr Lys Tyr
1775                1780                1785

Glu Val Ser Val Tyr Ala Leu Lys Asp Thr Leu Thr Ser Arg Pro
```

-continued

```
              1790                1795                1800
Ala Gln Gly Val Val Thr Thr Leu Glu Asn Val Ser Pro Pro Arg
              1805                1810                1815

Arg Ala Arg Val Thr Asp Ala Thr Glu Thr Thr Ile Thr Ile Ser
              1820                1825                1830

Trp Arg Thr Lys Thr Glu Thr Ile Thr Gly Phe Gln Val Asp Ala
              1835                1840                1845

Val Pro Ala Asn Gly Gln Thr Pro Ile Gln Arg Thr Ile Lys Pro
              1850                1855                1860

Asp Val Arg Ser Tyr Thr Ile Thr Gly Leu Gln Pro Gly Thr Asp
              1865                1870                1875

Tyr Lys Ile Tyr Leu Tyr Thr Leu Asn Asp Asn Ala Arg Ser Ser
              1880                1885                1890

Pro Val Val Ile Asp Ala Ser Thr Ala Ile Asp Ala Pro Ser Asn
              1895                1900                1905

Leu Arg Phe Leu Ala Thr Thr Pro Asn Ser Leu Leu Val Ser Trp
              1910                1915                1920

Gln Pro Pro Arg Ala Arg Ile Thr Gly Tyr Ile Ile Lys Tyr Glu
              1925                1930                1935

Lys Pro Gly Ser Pro Pro Arg Glu Val Val Pro Arg Pro Arg Pro
              1940                1945                1950

Gly Val Thr Glu Ala Thr Ile Thr Gly Leu Glu Pro Gly Thr Glu
              1955                1960                1965

Tyr Thr Ile Tyr Val Ile Ala Leu Lys Asn Asn Gln Lys Ser Glu
              1970                1975                1980

Pro Leu Ile Gly Arg Lys Lys Thr Asp Glu Leu Pro Gln Leu Val
              1985                1990                1995

Thr Leu Pro His Pro Asn Leu His Gly Pro Glu Ile Leu Asp Val
              2000                2005                2010

Pro Ser Thr Val Gln Lys Thr Pro Phe Val Thr His Pro Gly Tyr
              2015                2020                2025

Asp Thr Gly Asn Gly Ile Gln Leu Pro Gly Thr Ser Gly Gln Gln
              2030                2035                2040

Pro Ser Val Gly Gln Gln Met Ile Phe Glu Glu His Gly Phe Arg
              2045                2050                2055

Arg Thr Thr Pro Pro Thr Thr Ala Thr Pro Ile Arg His Arg Pro
              2060                2065                2070

Arg Pro Tyr Pro Pro Asn Val Gly Glu Glu Ile Gln Ile Gly His
              2075                2080                2085

Ile Pro Arg Glu Asp Val Asp Tyr His Leu Tyr Pro His Gly Pro
              2090                2095                2100

Gly Leu Asn Pro Asn Ala Ser Thr Gly Gln Glu Ala Leu Ser Gln
              2105                2110                2115

Thr Thr Ile Ser Trp Ala Pro Phe Gln Asp Thr Ser Glu Tyr Ile
              2120                2125                2130

Ile Ser Cys His Pro Val Gly Thr Asp Glu Glu Pro Leu Gln Phe
              2135                2140                2145

Arg Val Pro Gly Thr Ser Thr Ser Ala Thr Leu Thr Gly Leu Thr
              2150                2155                2160

Arg Gly Ala Thr Tyr Asn Val Ile Val Glu Ala Leu Lys Asp Gln
              2165                2170                2175

Gln Arg His Lys Val Arg Glu Glu Val Val Thr Val Gly Asn Ser
              2180                2185                2190
```

```
Val Asn Glu Gly Leu Asn Gln Pro Thr Asp Asp Ser Cys Phe Asp
    2195                2200                2205

Pro Tyr Thr Val Ser His Tyr Ala Val Gly Asp Glu Trp Glu Arg
    2210                2215                2220

Met Ser Glu Ser Gly Phe Lys Leu Leu Cys Gln Cys Leu Gly Phe
    2225                2230                2235

Gly Ser Gly His Phe Arg Cys Asp Ser Ser Arg Trp Cys His Asp
    2240                2245                2250

Asn Gly Val Asn Tyr Lys Ile Gly Glu Lys Trp Asp Arg Gln Gly
    2255                2260                2265

Glu Asn Gly Gln Met Met Ser Cys Thr Cys Leu Gly Asn Gly Lys
    2270                2275                2280

Gly Glu Phe Lys Cys Asp Pro His Glu Ala Thr Cys Tyr Asp Asp
    2285                2290                2295

Gly Lys Thr Tyr His Val Gly Glu Gln Trp Gln Lys Glu Tyr Leu
    2300                2305                2310

Gly Ala Ile Cys Ser Cys Thr Cys Phe Gly Gly Gln Arg Gly Trp
    2315                2320                2325

Arg Cys Asp Asn Cys Arg Arg Pro Gly Gly Glu Pro Ser Pro Glu
    2330                2335                2340

Gly Thr Thr Gly Gln Ser Tyr Asn Gln Tyr Ser Gln Arg Tyr His
    2345                2350                2355

Gln Arg Thr Asn Thr Asn Val Asn Cys Pro Ile Glu Cys Phe Met
    2360                2365                2370

Pro Leu Asp Val Gln Ala Asp Arg Glu Asp Ser Arg Glu
    2375                2380                2385

<210> SEQ ID NO 65
<211> LENGTH: 240
<212> TYPE: PRT
<213> ORGANISM: Homo sapiens
<300> PUBLICATION INFORMATION:
<308> DATABASE ACCESSION NUMBER: UniProt / P30711
<309> DATABASE ENTRY DATE: 2015-07-22
<313> RELEVANT RESIDUES IN SEQ ID NO: (1)..(240)

<400> SEQUENCE: 65

Met Gly Leu Glu Leu Tyr Leu Asp Leu Leu Ser Gln Pro Cys Arg Ala
1               5                   10                  15

Val Tyr Ile Phe Ala Lys Lys Asn Asp Ile Pro Phe Glu Leu Arg Ile
                20                  25                  30

Val Asp Leu Ile Lys Gly Gln His Leu Ser Asp Ala Phe Ala Gln Val
            35                  40                  45

Asn Pro Leu Lys Lys Val Pro Ala Leu Lys Asp Gly Asp Phe Thr Leu
        50                  55                  60

Thr Glu Ser Val Ala Ile Leu Leu Tyr Leu Thr Arg Lys Tyr Lys Val
65                  70                  75                  80

Pro Asp Tyr Trp Tyr Pro Gln Asp Leu Gln Ala Arg Ala Arg Val Asp
                85                  90                  95

Glu Tyr Leu Ala Trp Gln His Thr Thr Leu Arg Arg Ser Cys Leu Arg
                100                 105                 110

Ala Leu Trp His Lys Val Met Phe Pro Val Phe Leu Gly Glu Pro Val
            115                 120                 125

Ser Pro Gln Thr Leu Ala Ala Thr Leu Ala Glu Leu Asp Val Thr Leu
        130                 135                 140
```

```
Gln Leu Leu Glu Asp Lys Phe Leu Gln Asn Lys Ala Phe Leu Thr Gly
145                 150                 155                 160

Pro His Ile Ser Leu Ala Asp Leu Val Ala Ile Thr Glu Leu Met His
            165                 170                 175

Pro Val Gly Ala Gly Cys Gln Val Phe Glu Gly Arg Pro Lys Leu Ala
            180                 185                 190

Thr Trp Arg Gln Arg Val Glu Ala Ala Val Gly Glu Asp Leu Phe Gln
            195                 200                 205

Glu Ala His Glu Val Ile Leu Lys Ala Lys Asp Phe Pro Pro Ala Asp
            210                 215                 220

Pro Thr Ile Lys Gln Lys Leu Met Pro Trp Val Leu Ala Met Ile Arg
225                 230                 235                 240
```

<210> SEQ ID NO 66
<211> LENGTH: 644
<212> TYPE: PRT
<213> ORGANISM: Homo sapiens
<300> PUBLICATION INFORMATION:
<308> DATABASE ACCESSION NUMBER: UniProt / P04264
<309> DATABASE ENTRY DATE: 2015-07-22
<313> RELEVANT RESIDUES IN SEQ ID NO: (1)..(644)

<400> SEQUENCE: 66

```
Met Ser Arg Gln Phe Ser Ser Arg Ser Gly Tyr Arg Ser Gly Gly Gly
1               5                   10                  15

Phe Ser Ser Gly Ser Ala Gly Ile Ile Asn Tyr Gln Arg Arg Thr Thr
            20                  25                  30

Ser Ser Ser Thr Arg Arg Ser Gly Gly Gly Gly Arg Phe Ser Ser
            35                  40                  45

Cys Gly Gly Gly Gly Gly Ser Phe Gly Ala Gly Gly Gly Phe Gly Ser
    50                  55                  60

Arg Ser Leu Val Asn Leu Gly Gly Ser Lys Ser Ile Ser Ile Ser Val
65                  70                  75                  80

Ala Arg Gly Gly Gly Arg Gly Ser Gly Phe Gly Gly Gly Tyr Gly Gly
            85                  90                  95

Gly Gly Phe Gly Gly Gly Gly Phe Gly Gly Gly Gly Phe Gly Gly Gly
            100                 105                 110

Gly Ile Gly Gly Gly Gly Phe Gly Gly Phe Gly Ser Gly Gly Gly Gly
            115                 120                 125

Phe Gly Gly Gly Gly Phe Gly Gly Gly Gly Tyr Gly Gly Gly Tyr Gly
            130                 135                 140

Pro Val Cys Pro Pro Gly Gly Ile Gln Glu Val Thr Ile Asn Gln Ser
145                 150                 155                 160

Leu Leu Gln Pro Leu Asn Val Glu Ile Asp Pro Glu Ile Gln Lys Val
            165                 170                 175

Lys Ser Arg Glu Arg Glu Gln Ile Lys Ser Leu Asn Asn Gln Phe Ala
            180                 185                 190

Ser Phe Ile Asp Lys Val Arg Phe Leu Glu Gln Gln Asn Gln Val Leu
            195                 200                 205

Gln Thr Lys Trp Glu Leu Leu Gln Gln Val Asp Thr Ser Thr Arg Thr
            210                 215                 220

His Asn Leu Glu Pro Tyr Phe Glu Ser Phe Ile Asn Asn Leu Arg Arg
225                 230                 235                 240

Arg Val Asp Gln Leu Lys Ser Asp Gln Ser Arg Leu Asp Ser Glu Leu
            245                 250                 255

Lys Asn Met Gln Asp Met Val Glu Asp Tyr Arg Asn Lys Tyr Glu Asp
```

```
            260                 265                 270
Glu Ile Asn Lys Arg Thr Asn Ala Glu Asn Glu Phe Val Thr Ile Lys
            275                 280                 285

Lys Asp Val Asp Gly Ala Tyr Met Thr Lys Val Asp Leu Gln Ala Lys
290                 295                 300

Leu Asp Asn Leu Gln Gln Glu Ile Asp Phe Leu Thr Ala Leu Tyr Gln
305                 310                 315                 320

Ala Glu Leu Ser Gln Met Gln Thr Gln Ile Ser Glu Thr Asn Val Ile
                325                 330                 335

Leu Ser Met Asp Asn Asn Arg Ser Leu Asp Leu Asp Ser Ile Ile Ala
                340                 345                 350

Glu Val Lys Ala Gln Tyr Glu Asp Ile Ala Gln Lys Ser Lys Ala Glu
                355                 360                 365

Ala Glu Ser Leu Tyr Gln Ser Lys Tyr Glu Glu Leu Gln Ile Thr Ala
                370                 375                 380

Gly Arg His Gly Asp Ser Val Arg Asn Ser Lys Ile Glu Ile Ser Glu
385                 390                 395                 400

Leu Asn Arg Val Ile Gln Arg Leu Arg Ser Glu Ile Asp Asn Val Lys
                405                 410                 415

Lys Gln Ile Ser Asn Leu Gln Gln Ser Ile Ser Asp Ala Glu Gln Arg
                420                 425                 430

Gly Glu Asn Ala Leu Lys Asp Ala Lys Asn Lys Leu Asn Asp Leu Glu
                435                 440                 445

Asp Ala Leu Gln Gln Ala Lys Glu Asp Leu Ala Arg Leu Leu Arg Asp
450                 455                 460

Tyr Gln Glu Leu Met Asn Thr Lys Leu Ala Leu Asp Leu Glu Ile Ala
465                 470                 475                 480

Thr Tyr Arg Thr Leu Leu Glu Gly Glu Glu Ser Arg Met Ser Gly Glu
                485                 490                 495

Cys Ala Pro Asn Val Ser Val Ser Val Ser Thr Ser His Thr Thr Ile
                500                 505                 510

Ser Gly Gly Gly Ser Arg Gly Gly Gly Gly Gly Tyr Gly Ser Gly
                515                 520                 525

Gly Ser Ser Tyr Gly Ser Gly Gly Ser Tyr Gly Ser Gly Gly Gly
                530                 535                 540

Gly Gly Gly Gly Arg Gly Ser Tyr Gly Ser Gly Ser Ser Tyr Gly
545                 550                 555                 560

Ser Gly Gly Gly Ser Tyr Gly Ser Gly Gly Gly Gly His Gly
                565                 570                 575

Ser Tyr Gly Ser Gly Ser Ser Ser Gly Tyr Arg Gly Gly Ser Gly
                580                 585                 590

Gly Gly Gly Gly Ser Ser Gly Arg Gly Ser Gly Gly Gly Ser
                595                 600                 605

Ser Gly Gly Ser Ile Gly Gly Arg Gly Ser Ser Gly Gly Val Lys
                610                 615                 620

Ser Ser Gly Gly Ser Ser Ser Val Lys Phe Val Ser Thr Thr Tyr Ser
625                 630                 635                 640

Gly Val Thr Arg

<210> SEQ ID NO 67
<211> LENGTH: 1939
<212> TYPE: PRT
<213> ORGANISM: Homo sapiens
<300> PUBLICATION INFORMATION:
```

<308> DATABASE ACCESSION NUMBER: UniProt / P13533
<309> DATABASE ENTRY DATE: 2015-07-22
<313> RELEVANT RESIDUES IN SEQ ID NO: (1)..(1939)

<400> SEQUENCE: 67

```
Met Thr Asp Ala Gln Met Ala Asp Phe Gly Ala Ala Ala Gln Tyr Leu
1               5                   10                  15

Arg Lys Ser Glu Lys Glu Arg Leu Glu Ala Gln Thr Arg Pro Phe Asp
            20                  25                  30

Ile Arg Thr Glu Cys Phe Val Pro Asp Asp Lys Glu Glu Phe Val Lys
        35                  40                  45

Ala Lys Ile Leu Ser Arg Glu Gly Gly Lys Val Ile Ala Glu Thr Glu
50                  55                  60

Asn Gly Lys Thr Val Thr Val Lys Glu Asp Gln Val Leu Gln Gln Asn
65                  70                  75                  80

Pro Pro Lys Phe Asp Lys Ile Glu Asp Met Ala Met Leu Thr Phe Leu
                85                  90                  95

His Glu Pro Ala Val Leu Phe Asn Leu Lys Glu Arg Tyr Ala Ala Trp
            100                 105                 110

Met Ile Tyr Thr Tyr Ser Gly Leu Phe Cys Val Thr Val Asn Pro Tyr
        115                 120                 125

Lys Trp Leu Pro Val Tyr Asn Ala Glu Val Val Ala Ala Tyr Arg Gly
    130                 135                 140

Lys Lys Arg Ser Glu Ala Pro Pro His Ile Phe Ser Ile Ser Asp Asn
145                 150                 155                 160

Ala Tyr Gln Tyr Met Leu Thr Asp Arg Glu Asn Gln Ser Ile Leu Ile
                165                 170                 175

Thr Gly Glu Ser Gly Ala Gly Lys Thr Val Asn Thr Lys Arg Val Ile
            180                 185                 190

Gln Tyr Phe Ala Ser Ile Ala Ala Ile Gly Asp Arg Gly Lys Lys Asp
        195                 200                 205

Asn Ala Asn Ala Asn Lys Gly Thr Leu Glu Asp Gln Ile Ile Gln Ala
    210                 215                 220

Asn Pro Ala Leu Glu Ala Phe Gly Asn Ala Lys Thr Val Arg Asn Asp
225                 230                 235                 240

Asn Ser Ser Arg Phe Gly Lys Phe Ile Arg Ile His Phe Gly Ala Thr
                245                 250                 255

Gly Lys Leu Ala Ser Ala Asp Ile Glu Thr Tyr Leu Leu Glu Lys Ser
            260                 265                 270

Arg Val Ile Phe Gln Leu Lys Ala Glu Arg Asn Tyr His Ile Phe Tyr
        275                 280                 285

Gln Ile Leu Ser Asn Lys Lys Pro Glu Leu Leu Asp Met Leu Leu Val
    290                 295                 300

Thr Asn Asn Pro Tyr Asp Tyr Ala Phe Val Ser Gln Gly Glu Val Ser
305                 310                 315                 320

Val Ala Ser Ile Asp Asp Ser Glu Glu Leu Met Ala Thr Asp Ser Ala
                325                 330                 335

Phe Asp Val Leu Gly Phe Thr Ser Glu Glu Lys Ala Gly Val Tyr Lys
            340                 345                 350

Leu Thr Gly Ala Ile Met His Tyr Gly Asn Met Lys Phe Lys Gln Lys
        355                 360                 365

Gln Arg Glu Glu Gln Ala Glu Pro Asp Gly Thr Glu Asp Ala Asp Lys
    370                 375                 380

Ser Ala Tyr Leu Met Gly Leu Asn Ser Ala Asp Leu Leu Lys Gly Leu
```

-continued

```
            385                 390                 395                 400
        Cys His Pro Arg Val Lys Val Gly Asn Glu Tyr Val Thr Lys Gly Gln
                            405                 410                 415
        Ser Val Gln Gln Val Tyr Tyr Ser Ile Gly Ala Leu Ala Lys Ala Val
                            420                 425                 430
        Tyr Glu Lys Met Phe Asn Trp Met Val Thr Arg Ile Asn Ala Thr Leu
                            435                 440                 445
        Glu Thr Lys Gln Pro Arg Gln Tyr Phe Ile Gly Val Leu Asp Ile Ala
                        450                 455                 460
        Gly Phe Glu Ile Phe Asp Phe Asn Ser Phe Glu Gln Leu Cys Ile Asn
        465                 470                 475                 480
        Phe Thr Asn Glu Lys Leu Gln Gln Phe Phe Asn His His Met Phe Val
                            485                 490                 495
        Leu Glu Gln Glu Glu Tyr Lys Lys Glu Gly Ile Glu Trp Thr Phe Ile
                        500                 505                 510
        Asp Phe Gly Met Asp Leu Gln Ala Cys Ile Asp Leu Ile Glu Lys Pro
                        515                 520                 525
        Met Gly Ile Met Ser Ile Leu Glu Glu Glu Cys Met Phe Pro Lys Ala
                    530                 535                 540
        Thr Asp Met Thr Phe Lys Ala Lys Leu Tyr Asp Asn His Leu Gly Lys
        545                 550                 555                 560
        Ser Asn Asn Phe Gln Lys Pro Arg Asn Ile Lys Gly Lys Gln Glu Ala
                            565                 570                 575
        His Phe Ser Leu Ile His Tyr Ala Gly Thr Val Asp Tyr Asn Ile Leu
                        580                 585                 590
        Gly Trp Leu Glu Lys Asn Lys Asp Pro Leu Asn Glu Thr Val Val Ala
                    595                 600                 605
        Leu Tyr Gln Lys Ser Ser Leu Lys Leu Met Ala Thr Leu Phe Ser Ser
                    610                 615                 620
        Tyr Ala Thr Ala Asp Thr Gly Asp Ser Gly Lys Ser Lys Gly Gly Lys
        625                 630                 635                 640
        Lys Lys Gly Ser Ser Phe Gln Thr Val Ser Ala Leu His Arg Glu Asn
                            645                 650                 655
        Leu Asn Lys Leu Met Thr Asn Leu Arg Thr Thr His Pro His Phe Val
                        660                 665                 670
        Arg Cys Ile Ile Pro Asn Glu Arg Lys Ala Pro Gly Val Met Asp Asn
                    675                 680                 685
        Pro Leu Val Met His Gln Leu Arg Cys Asn Gly Val Leu Glu Gly Ile
                    690                 695                 700
        Arg Ile Cys Arg Lys Gly Phe Pro Asn Arg Ile Leu Tyr Gly Asp Phe
        705                 710                 715                 720
        Arg Gln Arg Tyr Arg Ile Leu Asn Pro Val Ala Ile Pro Glu Gly Gln
                            725                 730                 735
        Phe Ile Asp Ser Arg Lys Gly Thr Glu Lys Leu Leu Ser Ser Leu Asp
                        740                 745                 750
        Ile Asp His Asn Gln Tyr Lys Phe Gly His Thr Lys Val Phe Phe Lys
                    755                 760                 765
        Ala Gly Leu Leu Gly Leu Leu Glu Glu Met Arg Asp Glu Arg Leu Ser
                    770                 775                 780
        Arg Ile Ile Thr Arg Met Gln Ala Gln Ala Arg Gly Gln Leu Met Arg
        785                 790                 795                 800
        Ile Glu Phe Lys Lys Ile Val Glu Arg Arg Asp Ala Leu Leu Val Ile
                            805                 810                 815
```

```
Gln Trp Asn Ile Arg Ala Phe Met Gly Val Lys Asn Trp Pro Trp Met
            820                 825                 830

Lys Leu Tyr Phe Lys Ile Lys Pro Leu Leu Lys Ser Ala Glu Thr Glu
            835                 840                 845

Lys Glu Met Ala Thr Met Lys Glu Glu Phe Gly Arg Ile Lys Glu Thr
            850                 855                 860

Leu Glu Lys Ser Glu Ala Arg Arg Lys Glu Leu Glu Glu Lys Met Val
865                 870                 875                 880

Ser Leu Leu Gln Glu Lys Asn Asp Leu Gln Leu Gln Val Gln Ala Glu
                885                 890                 895

Gln Asp Asn Leu Asn Asp Ala Glu Glu Arg Cys Asp Gln Leu Ile Lys
            900                 905                 910

Asn Lys Ile Gln Leu Glu Ala Lys Val Lys Glu Met Asn Glu Arg Leu
            915                 920                 925

Glu Asp Glu Glu Glu Met Asn Ala Glu Leu Thr Ala Lys Lys Arg Lys
            930                 935                 940

Leu Glu Asp Glu Cys Ser Glu Leu Lys Lys Asp Ile Asp Asp Leu Glu
945                 950                 955                 960

Leu Thr Leu Ala Lys Val Glu Lys Glu Lys His Ala Thr Glu Asn Lys
                965                 970                 975

Val Lys Asn Leu Thr Glu Glu Met Ala Gly Leu Asp Glu Ile Ile Ala
            980                 985                 990

Lys Leu Thr Lys Glu Lys Lys Ala  Leu Gln Glu Ala His Gln Gln Ala
            995                 1000                1005

Leu Asp  Asp Leu Gln Val Glu  Glu Asp Lys Val Asn  Ser Leu Ser
    1010                1015                1020

Lys Ser  Lys Val Lys Leu Glu  Gln Gln Val Asp Asp  Leu Glu Gly
    1025                1030                1035

Ser Leu  Glu Gln Glu Lys Lys  Val Arg Met Asp Leu  Glu Arg Ala
    1040                1045                1050

Lys Arg  Lys Leu Glu Gly Asp  Leu Lys Leu Thr Gln  Glu Ser Ile
    1055                1060                1065

Met Asp  Leu Glu Asn Asp Lys  Leu Gln Leu Glu Glu  Lys Leu Lys
    1070                1075                1080

Lys Lys  Glu Phe Asp Ile Asn  Gln Gln Asn Ser Lys  Ile Glu Asp
    1085                1090                1095

Glu Gln  Val Leu Ala Leu Gln  Leu Gln Lys Lys Leu  Lys Glu Asn
    1100                1105                1110

Gln Ala  Arg Ile Glu Glu Leu  Glu Glu Glu Leu Glu  Ala Glu Arg
    1115                1120                1125

Thr Ala  Arg Ala Lys Val Glu  Lys Leu Arg Ser Asp  Leu Ser Arg
    1130                1135                1140

Glu Leu  Glu Glu Ile Ser Glu  Arg Leu Glu Glu Ala  Gly Gly Ala
    1145                1150                1155

Thr Ser  Val Gln Ile Glu Met  Asn Lys Lys Arg Glu  Ala Glu Phe
    1160                1165                1170

Gln Lys  Met Arg Arg Asp Leu  Glu Glu Ala Thr Leu  Gln His Glu
    1175                1180                1185

Ala Thr  Ala Ala Ala Leu Arg  Lys Lys His Ala Asp  Ser Val Ala
    1190                1195                1200

Glu Leu  Gly Glu Gln Ile Asp  Asn Leu Gln Arg Val  Lys Gln Lys
    1205                1210                1215
```

```
Leu Glu Lys Glu Lys Ser Glu Phe Lys Leu Glu Leu Asp Asp Val
1220                1225                1230

Thr Ser Asn Met Glu Gln Ile Ile Lys Ala Lys Ala Asn Leu Glu
    1235                1240                1245

Lys Val Ser Arg Thr Leu Glu Asp Gln Ala Asn Glu Tyr Arg Val
1250                1255                1260

Lys Leu Glu Glu Ala Gln Arg Ser Leu Asn Asp Phe Thr Thr Gln
1265                1270                1275

Arg Ala Lys Leu Gln Thr Glu Asn Gly Glu Leu Ala Arg Gln Leu
1280                1285                1290

Glu Glu Lys Glu Ala Leu Ile Ser Gln Leu Thr Arg Gly Lys Leu
1295                1300                1305

Ser Tyr Thr Gln Gln Met Glu Asp Leu Lys Arg Gln Leu Glu Glu
1310                1315                1320

Glu Gly Lys Ala Lys Asn Ala Leu Ala His Ala Leu Gln Ser Ala
1325                1330                1335

Arg His Asp Cys Asp Leu Leu Arg Glu Gln Tyr Glu Glu Glu Thr
1340                1345                1350

Glu Ala Lys Ala Glu Leu Gln Arg Val Leu Ser Lys Ala Asn Ser
1355                1360                1365

Glu Val Ala Gln Trp Arg Thr Lys Tyr Glu Thr Asp Ala Ile Gln
1370                1375                1380

Arg Thr Glu Glu Leu Glu Glu Ala Lys Lys Lys Leu Ala Gln Arg
1385                1390                1395

Leu Gln Asp Ala Glu Glu Ala Val Glu Ala Val Asn Ala Lys Cys
1400                1405                1410

Ser Ser Leu Glu Lys Thr Lys His Arg Leu Gln Asn Glu Ile Glu
1415                1420                1425

Asp Leu Met Val Asp Val Glu Arg Ser Asn Ala Ala Ala Ala Ala
1430                1435                1440

Leu Asp Lys Lys Gln Arg Asn Phe Asp Lys Ile Leu Ala Glu Trp
1445                1450                1455

Lys Gln Lys Tyr Glu Glu Ser Gln Ser Glu Leu Glu Ser Ser Gln
1460                1465                1470

Lys Glu Ala Arg Ser Leu Ser Thr Glu Leu Phe Lys Leu Lys Asn
1475                1480                1485

Ala Tyr Glu Glu Ser Leu Glu His Leu Glu Thr Phe Lys Arg Glu
1490                1495                1500

Asn Lys Asn Leu Gln Glu Glu Ile Ser Asp Leu Thr Glu Gln Leu
1505                1510                1515

Gly Glu Gly Gly Lys Asn Val His Glu Leu Glu Lys Val Arg Lys
1520                1525                1530

Gln Leu Glu Val Glu Lys Leu Glu Leu Gln Ser Ala Leu Glu Glu
1535                1540                1545

Ala Glu Ala Ser Leu Glu His Glu Glu Gly Lys Ile Leu Arg Ala
1550                1555                1560

Gln Leu Glu Phe Asn Gln Ile Lys Ala Glu Ile Glu Arg Lys Leu
1565                1570                1575

Ala Glu Lys Asp Glu Glu Met Glu Gln Ala Lys Arg Asn His Gln
1580                1585                1590

Arg Val Val Asp Ser Leu Gln Thr Ser Leu Asp Ala Glu Thr Arg
1595                1600                1605

Ser Arg Asn Glu Val Leu Arg Val Lys Lys Lys Met Glu Gly Asp
```

```
                1610                1615                1620

Leu Asn Glu Met Glu Ile Gln Leu Ser His Ala Asn Arg Met Ala
    1625                1630                1635

Ala Glu Ala Gln Lys Gln Val Lys Ser Leu Gln Ser Leu Leu Lys
    1640                1645                1650

Asp Thr Gln Ile Gln Leu Asp Asp Ala Val Arg Ala Asn Asp Asp
    1655                1660                1665

Leu Lys Glu Asn Ile Ala Ile Val Glu Arg Arg Asn Asn Leu Leu
    1670                1675                1680

Gln Ala Glu Leu Glu Glu Leu Arg Ala Val Val Glu Gln Thr Glu
    1685                1690                1695

Arg Ser Arg Lys Leu Ala Glu Gln Glu Leu Ile Glu Thr Ser Glu
    1700                1705                1710

Arg Val Gln Leu Leu His Ser Gln Asn Thr Ser Leu Ile Asn Gln
    1715                1720                1725

Lys Lys Lys Met Glu Ser Asp Leu Thr Gln Leu Gln Ser Glu Val
    1730                1735                1740

Glu Glu Ala Val Gln Glu Cys Arg Asn Ala Glu Glu Lys Ala Lys
    1745                1750                1755

Lys Ala Ile Thr Asp Ala Ala Met Met Ala Glu Glu Leu Lys Lys
    1760                1765                1770

Glu Gln Asp Thr Ser Ala His Leu Glu Arg Met Lys Lys Asn Met
    1775                1780                1785

Glu Gln Thr Ile Lys Asp Leu Gln His Arg Leu Asp Glu Ala Glu
    1790                1795                1800

Gln Ile Ala Leu Lys Gly Gly Lys Lys Gln Leu Gln Lys Leu Glu
    1805                1810                1815

Ala Arg Val Arg Glu Leu Glu Gly Glu Leu Glu Ala Glu Gln Lys
    1820                1825                1830

Arg Asn Ala Glu Ser Val Lys Gly Met Arg Lys Ser Glu Arg Arg
    1835                1840                1845

Ile Lys Glu Leu Thr Tyr Gln Thr Glu Glu Asp Lys Lys Asn Leu
    1850                1855                1860

Leu Arg Leu Gln Asp Leu Val Asp Lys Leu Gln Leu Lys Val Lys
    1865                1870                1875

Ala Tyr Lys Arg Gln Ala Glu Glu Ala Glu Glu Gln Ala Asn Thr
    1880                1885                1890

Asn Leu Ser Lys Phe Arg Lys Val Gln His Glu Leu Asp Glu Ala
    1895                1900                1905

Glu Glu Arg Ala Asp Ile Ala Glu Ser Gln Val Asn Lys Leu Arg
    1910                1915                1920

Ala Lys Ser Arg Asp Ile Gly Ala Lys Gln Lys Met His Asp Glu
    1925                1930                1935

Glu

<210> SEQ ID NO 68
<211> LENGTH: 1935
<212> TYPE: PRT
<213> ORGANISM: Homo sapiens
<300> PUBLICATION INFORMATION:
<308> DATABASE ACCESSION NUMBER: UniProt / P12883
<309> DATABASE ENTRY DATE: 2015-07-22
<313> RELEVANT RESIDUES IN SEQ ID NO: (1)..(1935)

<400> SEQUENCE: 68
```

```
Met Gly Asp Ser Glu Met Ala Val Phe Gly Ala Ala Pro Tyr Leu
1               5                   10                  15

Arg Lys Ser Glu Lys Glu Arg Leu Glu Ala Gln Thr Arg Pro Phe Asp
            20                  25                  30

Leu Lys Lys Asp Val Phe Val Pro Asp Asp Lys Gln Glu Phe Val Lys
        35                  40                  45

Ala Lys Ile Val Ser Arg Glu Gly Lys Val Thr Ala Glu Thr Glu
50                  55                  60

Tyr Gly Lys Thr Val Thr Val Lys Glu Asp Gln Val Met Gln Gln Asn
65                  70                  75                  80

Pro Pro Lys Phe Asp Lys Ile Glu Asp Met Ala Met Leu Thr Phe Leu
                85                  90                  95

His Glu Pro Ala Val Leu Tyr Asn Leu Lys Asp Arg Tyr Gly Ser Trp
            100                 105                 110

Met Ile Tyr Thr Tyr Ser Gly Leu Phe Cys Val Thr Val Asn Pro Tyr
            115                 120                 125

Lys Trp Leu Pro Val Tyr Thr Pro Glu Val Val Ala Ala Tyr Arg Gly
        130                 135                 140

Lys Lys Arg Ser Glu Ala Pro Pro His Ile Phe Ser Ile Ser Asp Asn
145                 150                 155                 160

Ala Tyr Gln Tyr Met Leu Thr Asp Arg Glu Asn Gln Ser Ile Leu Ile
                165                 170                 175

Thr Gly Glu Ser Gly Ala Gly Lys Thr Val Asn Thr Lys Arg Val Ile
            180                 185                 190

Gln Tyr Phe Ala Val Ile Ala Ala Ile Gly Asp Arg Ser Lys Lys Asp
        195                 200                 205

Gln Ser Pro Gly Lys Gly Thr Leu Glu Asp Gln Ile Ile Gln Ala Asn
    210                 215                 220

Pro Ala Leu Glu Ala Phe Gly Asn Ala Lys Thr Val Arg Asn Asp Asn
225                 230                 235                 240

Ser Ser Arg Phe Gly Lys Phe Ile Arg Ile His Phe Gly Ala Thr Gly
            245                 250                 255

Lys Leu Ala Ser Ala Asp Ile Glu Thr Tyr Leu Leu Glu Lys Ser Arg
            260                 265                 270

Val Ile Phe Gln Leu Lys Ala Glu Arg Asp Tyr His Ile Phe Tyr Gln
        275                 280                 285

Ile Leu Ser Asn Lys Lys Pro Glu Leu Leu Asp Met Leu Leu Ile Thr
    290                 295                 300

Asn Asn Pro Tyr Asp Tyr Ala Phe Ile Ser Gln Gly Glu Thr Thr Val
305                 310                 315                 320

Ala Ser Ile Asp Asp Ala Glu Glu Leu Met Ala Thr Asp Asn Ala Phe
            325                 330                 335

Asp Val Leu Gly Phe Thr Ser Glu Glu Lys Asn Ser Met Tyr Lys Leu
        340                 345                 350

Thr Gly Ala Ile Met His Phe Gly Asn Met Lys Phe Lys Leu Lys Gln
            355                 360                 365

Arg Glu Glu Gln Ala Glu Pro Asp Gly Thr Glu Glu Ala Asp Lys Ser
370                 375                 380

Ala Tyr Leu Met Gly Leu Asn Ser Ala Asp Leu Leu Lys Gly Leu Cys
385                 390                 395                 400

His Pro Arg Val Lys Val Gly Asn Glu Tyr Val Thr Lys Gly Gln Asn
            405                 410                 415

Val Gln Gln Val Ile Tyr Ala Thr Gly Ala Leu Ala Lys Ala Val Tyr
```

-continued

```
            420                 425                 430
Glu Arg Met Phe Asn Trp Met Val Thr Arg Ile Asn Ala Thr Leu Glu
            435                 440                 445
Thr Lys Gln Pro Arg Gln Tyr Phe Ile Gly Val Leu Asp Ile Ala Gly
            450                 455                 460
Phe Glu Ile Phe Asp Phe Asn Ser Phe Glu Gln Leu Cys Ile Asn Phe
465                 470                 475                 480
Thr Asn Glu Lys Leu Gln Gln Phe Phe Asn His His Met Phe Val Leu
                    485                 490                 495
Glu Gln Glu Glu Tyr Lys Lys Glu Gly Ile Glu Trp Thr Phe Ile Asp
                    500                 505                 510
Phe Gly Met Asp Leu Gln Ala Cys Ile Asp Leu Ile Glu Lys Pro Met
                    515                 520                 525
Gly Ile Met Ser Ile Leu Glu Glu Glu Cys Met Phe Pro Lys Ala Thr
                    530                 535                 540
Asp Met Thr Phe Lys Ala Lys Leu Phe Asp Asn His Leu Gly Lys Ser
545                 550                 555                 560
Ala Asn Phe Gln Lys Pro Arg Asn Ile Lys Gly Lys Pro Glu Ala His
                    565                 570                 575
Phe Ser Leu Ile His Tyr Ala Gly Ile Val Asp Tyr Asn Ile Ile Gly
                    580                 585                 590
Trp Leu Gln Lys Asn Lys Asp Pro Leu Asn Glu Thr Val Val Gly Leu
                    595                 600                 605
Tyr Gln Lys Ser Ser Leu Lys Leu Leu Ser Thr Leu Phe Ala Asn Tyr
                    610                 615                 620
Ala Gly Ala Asp Ala Pro Ile Glu Lys Gly Lys Gly Lys Ala Lys Lys
625                 630                 635                 640
Gly Ser Ser Phe Gln Thr Val Ser Ala Leu His Arg Glu Asn Leu Asn
                    645                 650                 655
Lys Leu Met Thr Asn Leu Arg Ser Thr His Pro His Phe Val Arg Cys
                    660                 665                 670
Ile Ile Pro Asn Glu Thr Lys Ser Pro Gly Val Met Asp Asn Pro Leu
                    675                 680                 685
Val Met His Gln Leu Arg Cys Asn Gly Val Leu Glu Gly Ile Arg Ile
                    690                 695                 700
Cys Arg Lys Gly Phe Pro Asn Arg Ile Leu Tyr Gly Asp Phe Arg Gln
705                 710                 715                 720
Arg Tyr Arg Ile Leu Asn Pro Ala Ala Ile Pro Glu Gly Gln Phe Ile
                    725                 730                 735
Asp Ser Arg Lys Gly Ala Glu Lys Leu Leu Ser Ser Leu Asp Ile Asp
                    740                 745                 750
His Asn Gln Tyr Lys Phe Gly His Thr Lys Val Phe Phe Lys Ala Gly
                    755                 760                 765
Leu Leu Gly Leu Leu Glu Glu Met Arg Asp Glu Arg Leu Ser Arg Ile
                    770                 775                 780
Ile Thr Arg Ile Gln Ala Gln Ser Arg Gly Val Leu Ala Arg Met Glu
785                 790                 795                 800
Tyr Lys Lys Leu Leu Glu Arg Arg Asp Ser Leu Leu Val Ile Gln Trp
                    805                 810                 815
Asn Ile Arg Ala Phe Met Gly Val Lys Asn Trp Pro Trp Met Lys Leu
                    820                 825                 830
Tyr Phe Lys Ile Lys Pro Leu Leu Lys Ser Ala Glu Arg Glu Lys Glu
                    835                 840                 845
```

-continued

Met Ala Ser Met Lys Glu Glu Phe Thr Arg Leu Lys Glu Ala Leu Glu
       850                 855                 860

Lys Ser Glu Ala Arg Arg Lys Glu Leu Glu Glu Lys Met Val Ser Leu
865                 870                 875                 880

Leu Gln Glu Lys Asn Asp Leu Gln Leu Gln Val Gln Ala Glu Gln Asp
            885                 890                 895

Asn Leu Ala Asp Ala Glu Glu Arg Cys Asp Gln Leu Ile Lys Asn Lys
            900                 905                 910

Ile Gln Leu Glu Ala Lys Val Lys Glu Met Asn Glu Arg Leu Glu Asp
        915                 920                 925

Glu Glu Glu Met Asn Ala Glu Leu Thr Ala Lys Lys Arg Lys Leu Glu
    930                 935                 940

Asp Glu Cys Ser Glu Leu Lys Arg Asp Ile Asp Asp Leu Glu Leu Thr
945                 950                 955                 960

Leu Ala Lys Val Glu Lys Glu Lys His Ala Thr Glu Asn Lys Val Lys
                965                 970                 975

Asn Leu Thr Glu Glu Met Ala Gly Leu Asp Glu Ile Ile Ala Lys Leu
            980                 985                 990

Thr Lys Glu Lys Lys Ala Leu Gln Glu Ala His Gln Gln Ala Leu Asp
        995                 1000                1005

Asp Leu Gln Ala Glu Glu Asp Lys Val Asn Thr Leu Thr Lys Ala
    1010                1015                1020

Lys Val Lys Leu Glu Gln Gln Val Asp Asp Leu Glu Gly Ser Leu
    1025                1030                1035

Glu Gln Glu Lys Lys Val Arg Met Asp Leu Glu Arg Ala Lys Arg
    1040                1045                1050

Lys Leu Glu Gly Asp Leu Lys Leu Thr Gln Glu Ser Ile Met Asp
    1055                1060                1065

Leu Glu Asn Asp Lys Gln Gln Leu Asp Glu Arg Leu Lys Lys Lys
    1070                1075                1080

Asp Phe Glu Leu Asn Ala Leu Asn Ala Arg Ile Glu Asp Glu Gln
    1085                1090                1095

Ala Leu Gly Ser Gln Leu Gln Lys Lys Leu Lys Glu Leu Gln Ala
    1100                1105                1110

Arg Ile Glu Glu Leu Glu Glu Glu Leu Glu Ala Glu Arg Thr Ala
    1115                1120                1125

Arg Ala Lys Val Glu Lys Leu Arg Ser Asp Leu Ser Arg Glu Leu
    1130                1135                1140

Glu Glu Ile Ser Glu Arg Leu Glu Glu Ala Gly Gly Ala Thr Ser
    1145                1150                1155

Val Gln Ile Glu Met Asn Lys Lys Arg Glu Ala Glu Phe Gln Lys
    1160                1165                1170

Met Arg Arg Asp Leu Glu Glu Ala Thr Leu Gln His Glu Ala Thr
    1175                1180                1185

Ala Ala Ala Leu Arg Lys Lys His Ala Asp Ser Val Ala Glu Leu
    1190                1195                1200

Gly Glu Gln Ile Asp Asn Leu Gln Arg Val Lys Gln Lys Leu Glu
    1205                1210                1215

Lys Glu Lys Ser Glu Phe Lys Leu Glu Leu Asp Asp Val Thr Ser
    1220                1225                1230

Asn Met Glu Gln Ile Ile Lys Ala Lys Ala Asn Leu Glu Lys Met
    1235                1240                1245

```
Cys Arg Thr Leu Glu Asp Gln Met Asn Glu His Arg Ser Lys Ala
    1250                1255                1260

Glu Glu Thr Gln Arg Ser Val Asn Asp Leu Thr Ser Gln Arg Ala
    1265                1270                1275

Lys Leu Gln Thr Glu Asn Gly Glu Leu Ser Arg Gln Leu Asp Glu
    1280                1285                1290

Lys Glu Ala Leu Ile Ser Gln Leu Thr Arg Gly Lys Leu Thr Tyr
    1295                1300                1305

Thr Gln Gln Leu Glu Asp Leu Lys Arg Gln Leu Glu Glu Glu Val
    1310                1315                1320

Lys Ala Lys Asn Ala Leu Ala His Ala Leu Gln Ser Ala Arg His
    1325                1330                1335

Asp Cys Asp Leu Leu Arg Glu Gln Tyr Glu Glu Glu Thr Glu Ala
    1340                1345                1350

Lys Ala Glu Leu Gln Arg Val Leu Ser Lys Ala Asn Ser Glu Val
    1355                1360                1365

Ala Gln Trp Arg Thr Lys Tyr Glu Thr Asp Ala Ile Gln Arg Thr
    1370                1375                1380

Glu Glu Leu Glu Glu Ala Lys Lys Lys Leu Ala Gln Arg Leu Gln
    1385                1390                1395

Glu Ala Glu Glu Ala Val Glu Ala Val Asn Ala Lys Cys Ser Ser
    1400                1405                1410

Leu Glu Lys Thr Lys His Arg Leu Gln Asn Glu Ile Glu Asp Leu
    1415                1420                1425

Met Val Asp Val Glu Arg Ser Asn Ala Ala Ala Ala Leu Asp
    1430                1435                1440

Lys Lys Gln Arg Asn Phe Asp Lys Ile Leu Ala Glu Trp Lys Gln
    1445                1450                1455

Lys Tyr Glu Glu Ser Gln Ser Glu Leu Glu Ser Ser Gln Lys Glu
    1460                1465                1470

Ala Arg Ser Leu Ser Thr Glu Leu Phe Lys Leu Lys Asn Ala Tyr
    1475                1480                1485

Glu Glu Ser Leu Glu His Leu Glu Thr Phe Lys Arg Glu Asn Lys
    1490                1495                1500

Asn Leu Gln Glu Glu Ile Ser Asp Leu Thr Glu Gln Leu Gly Ser
    1505                1510                1515

Ser Gly Lys Thr Ile His Glu Leu Glu Lys Val Arg Lys Gln Leu
    1520                1525                1530

Glu Ala Glu Lys Met Glu Leu Gln Ser Ala Leu Glu Glu Ala Glu
    1535                1540                1545

Ala Ser Leu Glu His Glu Glu Gly Lys Ile Leu Arg Ala Gln Leu
    1550                1555                1560

Glu Phe Asn Gln Ile Lys Ala Glu Ile Glu Arg Lys Leu Ala Glu
    1565                1570                1575

Lys Asp Glu Glu Met Glu Gln Ala Lys Arg Asn His Leu Arg Val
    1580                1585                1590

Val Asp Ser Leu Gln Thr Ser Leu Asp Ala Glu Thr Arg Ser Arg
    1595                1600                1605

Asn Glu Ala Leu Arg Val Lys Lys Lys Met Glu Gly Asp Leu Asn
    1610                1615                1620

Glu Met Glu Ile Gln Leu Ser His Ala Asn Arg Met Ala Ala Glu
    1625                1630                1635

Ala Gln Lys Gln Val Lys Ser Leu Gln Ser Leu Leu Lys Asp Thr
```

```
                    1640                1645                1650
Gln Ile Gln Leu Asp Asp Ala Val Arg Ala Asn Asp Asp Leu Lys
        1655                1660                1665
Glu Asn Ile Ala Ile Val Glu Arg Arg Asn Asn Leu Leu Gln Ala
    1670                1675                1680
Glu Leu Glu Glu Leu Arg Ala Val Val Glu Gln Thr Glu Arg Ser
1685                1690                1695
Arg Lys Leu Ala Glu Gln Glu Leu Ile Glu Thr Ser Glu Arg Val
    1700                1705                1710
Gln Leu Leu His Ser Gln Asn Thr Ser Leu Ile Asn Gln Lys Lys
        1715                1720                1725
Lys Met Asp Ala Asp Leu Ser Gln Leu Gln Thr Glu Val Glu Glu
    1730                1735                1740
Ala Val Gln Glu Cys Arg Asn Ala Glu Glu Lys Ala Lys Lys Ala
    1745                1750                1755
Ile Thr Asp Ala Ala Met Met Ala Glu Glu Leu Lys Lys Glu Gln
    1760                1765                1770
Asp Thr Ser Ala His Leu Glu Arg Met Lys Lys Asn Met Glu Gln
    1775                1780                1785
Thr Ile Lys Asp Leu Gln His Arg Leu Asp Glu Ala Glu Gln Ile
    1790                1795                1800
Ala Leu Lys Gly Gly Lys Lys Gln Leu Gln Lys Leu Glu Ala Arg
    1805                1810                1815
Val Arg Glu Leu Glu Asn Glu Leu Glu Ala Glu Gln Lys Arg Asn
    1820                1825                1830
Ala Glu Ser Val Lys Gly Met Arg Lys Ser Glu Arg Arg Ile Lys
    1835                1840                1845
Glu Leu Thr Tyr Gln Thr Glu Glu Asp Arg Lys Asn Leu Leu Arg
    1850                1855                1860
Leu Gln Asp Leu Val Asp Lys Leu Gln Leu Lys Val Lys Ala Tyr
    1865                1870                1875
Lys Arg Gln Ala Glu Glu Ala Glu Glu Gln Ala Asn Thr Asn Leu
    1880                1885                1890
Ser Lys Phe Arg Lys Val Gln His Glu Leu Asp Glu Ala Glu Glu
    1895                1900                1905
Arg Ala Asp Ile Ala Glu Ser Gln Val Asn Lys Leu Arg Ala Lys
    1910                1915                1920
Ser Arg Asp Ile Gly Thr Lys Gly Leu Asn Glu Glu
    1925                1930                1935

<210> SEQ ID NO 69
<211> LENGTH: 197
<212> TYPE: PRT
<213> ORGANISM: Homo sapiens
<300> PUBLICATION INFORMATION:
<308> DATABASE ACCESSION NUMBER: UniProt / P12829
<309> DATABASE ENTRY DATE: 2015-07-22
<313> RELEVANT RESIDUES IN SEQ ID NO: (1)..(197)

<400> SEQUENCE: 69

Met Ala Pro Lys Lys Pro Glu Pro Lys Lys Glu Ala Ala Lys Pro Ala
1               5                   10                  15

Pro Ala Pro Ala Pro Ala Pro Ala Pro Ala Pro Ala Pro Ala Pro Glu
            20                  25                  30

Ala Pro Lys Glu Pro Ala Phe Asp Pro Lys Ser Val Lys Ile Asp Phe
        35                  40                  45
```

-continued

Thr Ala Asp Gln Ile Glu Glu Phe Lys Glu Ala Phe Ser Leu Phe Asp
            50                  55                  60

Arg Thr Pro Thr Gly Glu Met Lys Ile Thr Tyr Gly Gln Cys Gly Asp
 65                  70                  75                  80

Val Leu Arg Ala Leu Gly Gln Asn Pro Thr Asn Ala Glu Val Leu Arg
                 85                  90                  95

Val Leu Gly Lys Pro Lys Pro Glu Met Asn Val Lys Met Leu Asp
                100                 105                 110

Phe Glu Thr Phe Leu Pro Ile Leu Gln His Ile Ser Arg Asn Lys Glu
                115                 120                 125

Gln Gly Thr Tyr Glu Asp Phe Val Glu Gly Leu Arg Val Phe Asp Lys
            130                 135                 140

Glu Ser Asn Gly Thr Val Met Gly Ala Glu Leu Arg His Val Leu Ala
145                 150                 155                 160

Thr Leu Gly Glu Lys Met Thr Glu Ala Glu Val Glu Gln Leu Leu Ala
                165                 170                 175

Gly Gln Glu Asp Ala Asn Gly Cys Ile Asn Tyr Glu Ala Phe Val Lys
                180                 185                 190

His Ile Met Ser Gly
            195

<210> SEQ ID NO 70
<211> LENGTH: 810
<212> TYPE: PRT
<213> ORGANISM: Homo sapiens
<300> PUBLICATION INFORMATION:
<308> DATABASE ACCESSION NUMBER: UniProt / Q06730
<309> DATABASE ENTRY DATE: 2015-07-22
<313> RELEVANT RESIDUES IN SEQ ID NO: (1)..(810)

<400> SEQUENCE: 70

Met Asn Lys Val Glu Gln Lys Ser Gln Glu Ser Val Ser Phe Lys Asp
 1               5                  10                  15

Val Thr Val Gly Phe Thr Gln Glu Glu Trp Gln His Leu Asp Pro Ser
                20                  25                  30

Gln Arg Ala Leu Tyr Arg Asp Val Met Leu Glu Asn Tyr Ser Asn Leu
             35                  40                  45

Val Ser Val Gly Tyr Cys Val His Lys Pro Glu Val Ile Phe Arg Leu
         50                  55                  60

Gln Gln Gly Glu Glu Pro Trp Lys Gln Glu Glu Phe Pro Ser Gln
 65                  70                  75                  80

Ser Phe Pro Val Trp Thr Ala Asp His Leu Lys Glu Arg Ser Gln Glu
                 85                  90                  95

Asn Gln Ser Lys His Leu Trp Glu Val Val Phe Ile Asn Asn Glu Met
                100                 105                 110

Leu Thr Lys Glu Gln Gly Asp Val Ile Gly Ile Pro Phe Asn Val Asp
            115                 120                 125

Val Ser Ser Phe Pro Ser Arg Lys Met Phe Cys Gln Cys Asp Ser Cys
        130                 135                 140

Gly Met Ser Phe Asn Thr Val Ser Glu Leu Val Ile Ser Lys Ile Asn
145                 150                 155                 160

Tyr Leu Gly Lys Lys Ser Asp Glu Phe Asn Ala Cys Gly Lys Leu Leu
                165                 170                 175

Leu Asn Ile Lys His Asp Glu Thr His Thr Gln Glu Lys Asn Glu Val
                180                 185                 190

-continued

```
Leu Lys Asn Arg Asn Thr Leu Ser His His Glu Glu Thr Leu Gln His
        195                 200                 205
Glu Lys Ile Gln Thr Leu Glu His Asn Phe Glu Tyr Ser Ile Cys Gln
    210                 215                 220
Glu Thr Leu Leu Glu Lys Ala Val Phe Asn Thr Gln Lys Arg Glu Asn
225                 230                 235                 240
Ala Glu Glu Asn Asn Cys Asp Tyr Asn Glu Phe Gly Arg Thr Leu Cys
                245                 250                 255
Asp Ser Ser Ser Leu Leu Phe His Gln Ile Ser Pro Ser Arg Asp Asn
            260                 265                 270
His Tyr Glu Phe Ser Asp Cys Glu Lys Phe Leu Cys Val Lys Ser Thr
        275                 280                 285
Leu Ser Lys Pro His Gly Val Ser Met Lys His Tyr Asp Cys Gly Glu
    290                 295                 300
Ser Gly Asn Asn Phe Arg Arg Lys Leu Cys Leu Ser His Leu Gln Lys
305                 310                 315                 320
Gly Asp Lys Gly Glu Lys His Phe Glu Cys Asn Glu Cys Gly Lys Ala
                325                 330                 335
Phe Trp Glu Lys Ser His Leu Thr Arg His Gln Arg Val His Thr Gly
            340                 345                 350
Gln Lys Pro Phe Gln Cys Asn Glu Cys Glu Lys Ala Phe Trp Asp Lys
        355                 360                 365
Ser Asn Leu Thr Lys His Gln Arg Ser His Thr Gly Glu Lys Pro Phe
    370                 375                 380
Glu Cys Asn Glu Cys Gly Lys Ala Phe Ser His Lys Ser Ala Leu Thr
385                 390                 395                 400
Leu His Gln Arg Thr His Thr Gly Glu Lys Pro Tyr Gln Cys Asn Ala
                405                 410                 415
Cys Gly Lys Thr Phe Cys Gln Lys Ser Asp Leu Thr Lys His Gln Arg
            420                 425                 430
Thr His Thr Gly Leu Lys Pro Tyr Glu Cys Tyr Glu Cys Gly Lys Ser
        435                 440                 445
Phe Arg Val Thr Ser His Leu Lys Val His Gln Arg Thr His Thr Gly
    450                 455                 460
Glu Lys Pro Phe Glu Cys Leu Glu Cys Gly Lys Ser Phe Ser Glu Lys
465                 470                 475                 480
Ser Asn Leu Thr Gln His Gln Arg Ile His Ile Gly Asp Lys Ser Tyr
                485                 490                 495
Glu Cys Asn Ala Cys Gly Lys Thr Phe Tyr His Lys Ser Leu Leu Thr
            500                 505                 510
Arg His Gln Ile Ile His Thr Gly Trp Lys Pro Tyr Glu Cys Tyr Glu
        515                 520                 525
Cys Gly Lys Thr Phe Cys Leu Lys Ser Asp Leu Thr Val His Gln Arg
    530                 535                 540
Thr His Thr Gly Gln Lys Pro Phe Ala Cys Pro Glu Cys Gly Lys Phe
545                 550                 555                 560
Phe Ser His Lys Ser Thr Leu Ser Gln His Tyr Arg Thr His Thr Gly
                565                 570                 575
Glu Lys Pro Tyr Glu Cys His Glu Cys Gly Lys Ile Phe Tyr Asn Lys
            580                 585                 590
Ser Tyr Leu Thr Lys His Asn Arg Thr His Thr Gly Glu Lys Pro Tyr
        595                 600                 605
Glu Cys Asn Glu Cys Gly Lys Ala Phe Tyr Gln Lys Ser Gln Leu Thr
```

610                 615                 620
Gln His Gln Arg Ile His Ile Gly Glu Lys Pro Tyr Lys Cys Asn Glu
625                 630                 635                 640

Cys Gly Lys Ala Phe Cys His Lys Ser Ala Leu Ile Val His Gln Arg
                645                 650                 655

Thr His Thr Gln Glu Lys Pro Tyr Lys Cys Asn Glu Cys Gly Lys Ser
                660                 665                 670

Phe Cys Val Lys Ser Gly Leu Ile Phe His Glu Arg Lys His Thr Gly
            675                 680                 685

Glu Lys Pro Tyr Glu Cys Asn Glu Cys Gly Lys Phe Phe Arg His Lys
        690                 695                 700

Ser Ser Leu Thr Val His His Arg Ala His Thr Gly Glu Lys Ser Cys
705                 710                 715                 720

Gln Cys Asn Glu Cys Gly Lys Ile Phe Tyr Arg Lys Ser Glu Leu Ala
                725                 730                 735

Gln His Gln Arg Ser His Thr Gly Glu Lys Pro Tyr Glu Cys Asn Thr
                740                 745                 750

Cys Arg Lys Thr Phe Ser Gln Lys Ser Asn Leu Ile Val His Gln Arg
            755                 760                 765

Arg His Ile Gly Glu Asn Leu Met Asn Glu Met Asp Ile Arg Asn Phe
        770                 775                 780

Gln Pro Gln Val Ser Leu His Asn Ala Ser Glu Tyr Ser His Cys Gly
785                 790                 795                 800

Glu Ser Pro Asp Asp Ile Leu Asn Val Gln
                805                 810

<210> SEQ ID NO 71
<211> LENGTH: 369
<212> TYPE: PRT
<213> ORGANISM: Homo sapiens
<300> PUBLICATION INFORMATION:
<308> DATABASE ACCESSION NUMBER: UniProt / Q8IWU4
<309> DATABASE ENTRY DATE: 2015-07-22
<313> RELEVANT RESIDUES IN SEQ ID NO: (1)..(369)

<400> SEQUENCE: 71

Met Glu Phe Leu Glu Arg Thr Tyr Leu Val Asn Asp Lys Ala Ala Lys
1               5                   10                  15

Met Tyr Ala Phe Thr Leu Glu Ser Val Glu Leu Gln Gln Lys Pro Val
                20                  25                  30

Asn Lys Asp Gln Cys Pro Arg Glu Arg Pro Glu Glu Leu Glu Ser Gly
            35                  40                  45

Gly Met Tyr His Cys His Ser Gly Ser Lys Pro Thr Glu Lys Gly Ala
    50                  55                  60

Asn Glu Tyr Ala Tyr Ala Lys Trp Lys Leu Cys Ser Ala Ser Ala Ile
65                  70                  75                  80

Cys Phe Ile Phe Met Ile Ala Glu Val Val Gly Gly His Ile Ala Gly
                85                  90                  95

Ser Leu Ala Val Val Thr Asp Ala Ala His Leu Leu Ile Asp Leu Thr
                100                 105                 110

Ser Phe Leu Leu Ser Leu Phe Ser Leu Trp Leu Ser Ser Lys Pro Pro
            115                 120                 125

Ser Lys Arg Leu Thr Phe Gly Trp His Arg Ala Glu Ile Leu Gly Ala
        130                 135                 140

Leu Leu Ser Ile Leu Cys Ile Trp Val Val Thr Gly Val Leu Val Tyr
145                 150                 155                 160

Leu Ala Cys Glu Arg Leu Leu Tyr Pro Asp Tyr Gln Ile Gln Ala Thr
            165                 170                 175

Val Met Ile Ile Val Ser Ser Cys Ala Val Ala Ala Asn Ile Val Leu
            180                 185                 190

Thr Val Val Leu His Gln Arg Cys Leu Gly His Asn His Lys Glu Val
            195                 200                 205

Gln Ala Asn Ala Ser Val Arg Ala Ala Phe Val His Ala Leu Gly Asp
210                 215                 220

Leu Phe Gln Ser Ile Ser Val Leu Ile Ser Ala Leu Ile Ile Tyr Phe
225                 230                 235                 240

Lys Pro Glu Tyr Lys Ile Ala Asp Pro Ile Cys Thr Phe Ile Phe Ser
            245                 250                 255

Ile Leu Val Leu Ala Ser Thr Ile Thr Ile Leu Lys Asp Phe Ser Ile
            260                 265                 270

Leu Leu Met Glu Gly Val Pro Lys Ser Leu Asn Tyr Ser Gly Val Lys
            275                 280                 285

Glu Leu Ile Leu Ala Val Asp Gly Val Leu Ser Val His Ser Leu His
        290                 295                 300

Ile Trp Ser Leu Thr Met Asn Gln Val Ile Leu Ser Ala His Val Ala
305                 310                 315                 320

Thr Ala Ala Ser Arg Asp Ser Gln Val Val Arg Arg Glu Ile Ala Lys
            325                 330                 335

Ala Leu Ser Lys Ser Phe Thr Met His Ser Leu Thr Ile Gln Met Glu
            340                 345                 350

Ser Pro Val Asp Gln Asp Pro Asp Cys Leu Phe Cys Glu Asp Pro Cys
            355                 360                 365

Asp

<210> SEQ ID NO 72
<211> LENGTH: 1231
<212> TYPE: PRT
<213> ORGANISM: Homo sapiens
<300> PUBLICATION INFORMATION:
<308> DATABASE ACCESSION NUMBER: UniProt / P08603
<309> DATABASE ENTRY DATE: 2015-09-16
<313> RELEVANT RESIDUES IN SEQ ID NO: (1)..(1231)

<400> SEQUENCE: 72

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
            85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val

```
            130                 135                 140
Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                    165                 170                 175

Val Cys Asn Ser Gly Tyr Lys Ile Glu Gly Asp Glu Met His Cys
                180                 185                 190

Ser Asp Asp Gly Phe Trp Ser Lys Glu Lys Pro Lys Cys Val Glu Ile
                195                 200                 205

Ser Cys Lys Ser Pro Asp Val Ile Asn Gly Ser Pro Ile Ser Gln Lys
            210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                    245                 250                 255

Arg Pro Leu Pro Ser Cys Glu Glu Lys Ser Cys Asp Asn Pro Tyr Ile
                260                 265                 270

Pro Asn Gly Asp Tyr Ser Pro Leu Arg Ile Lys His Arg Thr Gly Asp
                275                 280                 285

Glu Ile Thr Tyr Gln Cys Arg Asn Gly Phe Tyr Pro Ala Thr Arg Gly
                290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                    325                 330                 335

His Glu Asn Met Arg Arg Pro Tyr Phe Pro Val Ala Val Gly Lys Tyr
                340                 345                 350

Tyr Ser Tyr Tyr Cys Asp Glu His Phe Glu Thr Pro Ser Gly Ser Tyr
                355                 360                 365

Trp Asp His Ile His Cys Thr Gln Asp Gly Trp Ser Pro Ala Val Pro
                370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                    405                 410                 415

His Pro Gly Tyr Ala Leu Pro Lys Ala Gln Thr Thr Val Thr Cys Met
                420                 425                 430

Glu Asn Gly Trp Ser Pro Thr Pro Arg Cys Ile Arg Val Lys Thr Cys
                435                 440                 445

Ser Lys Ser Ser Ile Asp Ile Glu Asn Gly Phe Ile Ser Glu Ser Gln
                450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Thr Cys Gly Lys
                    485                 490                 495

Asp Gly Trp Ser Ala Gln Pro Thr Cys Ile Lys Ser Cys Asp Ile Pro
                500                 505                 510

Val Phe Met Asn Ala Arg Thr Lys Asn Asp Phe Thr Trp Phe Lys Leu
                515                 520                 525

Asn Asp Thr Leu Asp Tyr Glu Cys His Asp Gly Tyr Glu Ser Asn Thr
                530                 535                 540

Gly Ser Thr Thr Gly Ser Ile Val Cys Gly Tyr Asn Gly Trp Ser Asp
545                 550                 555                 560
```

```
Leu Pro Ile Cys Tyr Glu Arg Glu Cys Glu Leu Pro Lys Ile Asp Val
            565                 570                 575
His Leu Val Pro Asp Arg Lys Lys Asp Gln Tyr Lys Val Gly Glu Val
            580                 585                 590
Leu Lys Phe Ser Cys Lys Pro Gly Phe Thr Ile Val Gly Pro Asn Ser
            595                 600                 605
Val Gln Cys Tyr His Phe Gly Leu Ser Pro Asp Leu Pro Ile Cys Lys
            610                 615                 620
Glu Gln Val Gln Ser Cys Gly Pro Pro Glu Leu Leu Asn Gly Asn
625                 630                 635                 640
Val Lys Glu Lys Thr Lys Glu Gly Tyr Gly His Ser Glu Val Val Glu
            645                 650                 655
Tyr Tyr Cys Asn Pro Arg Phe Leu Met Lys Gly Pro Asn Lys Ile Gln
            660                 665                 670
Cys Val Asp Gly Glu Trp Thr Thr Leu Pro Val Cys Ile Val Glu Glu
            675                 680                 685
Ser Thr Cys Gly Asp Ile Pro Glu Leu Glu His Gly Trp Ala Gln Leu
            690                 695                 700
Ser Ser Pro Pro Tyr Tyr Tyr Gly Asp Ser Val Glu Phe Asn Cys Ser
705                 710                 715                 720
Glu Ser Phe Thr Met Ile Gly His Arg Ser Ile Thr Cys Ile His Gly
            725                 730                 735
Val Trp Thr Gln Leu Pro Gln Cys Val Ala Ile Asp Lys Leu Lys Lys
            740                 745                 750
Cys Lys Ser Ser Asn Leu Ile Ile Leu Glu Glu His Leu Lys Asn Lys
            755                 760                 765
Lys Glu Phe Asp His Asn Ser Asn Ile Arg Tyr Arg Cys Arg Gly Lys
            770                 775                 780
Glu Gly Trp Ile His Thr Val Cys Ile Asn Gly Arg Trp Asp Pro Glu
785                 790                 795                 800
Val Asn Cys Ser Met Ala Gln Ile Gln Leu Cys Pro Pro Pro Gln
            805                 810                 815
Ile Pro Asn Ser His Asn Met Thr Thr Thr Leu Asn Tyr Arg Asp Gly
            820                 825                 830
Glu Lys Val Ser Val Leu Cys Gln Glu Asn Tyr Leu Ile Gln Glu Gly
            835                 840                 845
Glu Glu Ile Thr Cys Lys Asp Gly Arg Trp Gln Ser Ile Pro Leu Cys
850                 855                 860
Val Glu Lys Ile Pro Cys Ser Gln Pro Pro Gln Ile Glu His Gly Thr
865                 870                 875                 880
Ile Asn Ser Ser Arg Ser Ser Gln Glu Ser Tyr Ala His Gly Thr Lys
            885                 890                 895
Leu Ser Tyr Thr Cys Glu Gly Gly Phe Arg Ile Ser Glu Glu Asn Glu
            900                 905                 910
Thr Thr Cys Tyr Met Gly Lys Trp Ser Ser Pro Pro Gln Cys Glu Gly
            915                 920                 925
Leu Pro Cys Lys Ser Pro Pro Glu Ile Ser His Gly Val Val Ala His
            930                 935                 940
Met Ser Asp Ser Tyr Gln Tyr Gly Glu Glu Val Thr Tyr Lys Cys Phe
945                 950                 955                 960
Glu Gly Phe Gly Ile Asp Gly Pro Ala Ile Ala Lys Cys Leu Gly Glu
            965                 970                 975
```

```
Lys Trp Ser His Pro Pro Ser Cys Ile Lys Thr Asp Cys Leu Ser Leu
            980                 985                 990

Pro Ser Phe Glu Asn Ala Ile Pro Met Gly Glu Lys Lys Asp Val Tyr
        995                 1000                1005

Lys Ala Gly Glu Gln Val Thr Tyr Thr Cys Ala Thr Tyr Tyr Lys
    1010                1015                1020

Met Asp Gly Ala Ser Asn Val Thr Cys Ile Asn Ser Arg Trp Thr
    1025                1030                1035

Gly Arg Pro Thr Cys Arg Asp Thr Ser Cys Val Asn Pro Pro Thr
    1040                1045                1050

Val Gln Asn Ala Tyr Ile Val Ser Arg Gln Met Ser Lys Tyr Pro
    1055                1060                1065

Ser Gly Glu Arg Val Arg Tyr Gln Cys Arg Ser Pro Tyr Glu Met
    1070                1075                1080

Phe Gly Asp Glu Glu Val Met Cys Leu Asn Gly Asn Trp Thr Glu
    1085                1090                1095

Pro Pro Gln Cys Lys Asp Ser Thr Gly Lys Cys Gly Pro Pro Pro
    1100                1105                1110

Pro Ile Asp Asn Gly Asp Ile Thr Ser Phe Pro Leu Ser Val Tyr
    1115                1120                1125

Ala Pro Ala Ser Ser Val Glu Tyr Gln Cys Gln Asn Leu Tyr Gln
    1130                1135                1140

Leu Glu Gly Asn Lys Arg Ile Thr Cys Arg Asn Gly Gln Trp Ser
    1145                1150                1155

Glu Pro Pro Lys Cys Leu His Pro Cys Val Ile Ser Arg Glu Ile
    1160                1165                1170

Met Glu Asn Tyr Asn Ile Ala Leu Arg Trp Thr Ala Lys Gln Lys
    1175                1180                1185

Leu Tyr Ser Arg Thr Gly Glu Ser Val Glu Phe Val Cys Lys Arg
    1190                1195                1200

Gly Tyr Arg Leu Ser Ser Arg Ser His Thr Leu Arg Thr Thr Cys
    1205                1210                1215

Trp Asp Gly Lys Leu Glu Tyr Pro Thr Cys Ala Lys Arg
    1220                1225                1230

<210> SEQ ID NO 73
<211> LENGTH: 1663
<212> TYPE: PRT
<213> ORGANISM: Homo sapiens
<300> PUBLICATION INFORMATION:
<308> DATABASE ACCESSION NUMBER: UniProt / P01024
<309> DATABASE ENTRY DATE: 2015-09-16
<313> RELEVANT RESIDUES IN SEQ ID NO: (1)..(1663)

<400> SEQUENCE: 73

Met Gly Pro Thr Ser Gly Pro Ser Leu Leu Leu Leu Leu Thr His
1               5                   10                  15

Leu Pro Leu Ala Leu Gly Ser Pro Met Tyr Ser Ile Ile Thr Pro Asn
            20                  25                  30

Ile Leu Arg Leu Glu Ser Glu Glu Thr Met Val Leu Glu Ala His Asp
        35                  40                  45

Ala Gln Gly Asp Val Pro Val Thr Val Thr Val His Asp Phe Pro Gly
    50                  55                  60

Lys Lys Leu Val Leu Ser Ser Glu Lys Thr Val Leu Thr Pro Ala Thr
65                  70                  75                  80

Asn His Met Gly Asn Val Thr Phe Thr Ile Pro Ala Asn Arg Glu Phe
```

-continued

```
                85                  90                  95
Lys Ser Glu Lys Gly Arg Asn Lys Phe Val Thr Val Gln Ala Thr Phe
            100                 105                 110
Gly Thr Gln Val Val Glu Lys Val Leu Val Ser Leu Gln Ser Gly
            115                 120                 125
Tyr Leu Phe Ile Gln Thr Asp Lys Thr Ile Tyr Thr Pro Gly Ser Thr
130             135                 140
Val Leu Tyr Arg Ile Phe Thr Val Asn His Lys Leu Leu Pro Val Gly
145                 150                 155                 160
Arg Thr Val Met Val Asn Ile Glu Asn Pro Glu Gly Ile Pro Val Lys
                165                 170                 175
Gln Asp Ser Leu Ser Ser Gln Asn Gln Leu Gly Val Leu Pro Leu Ser
                180                 185                 190
Trp Asp Ile Pro Glu Leu Val Asn Met Gly Gln Trp Lys Ile Arg Ala
                195                 200                 205
Tyr Tyr Glu Asn Ser Pro Gln Gln Val Phe Ser Thr Glu Phe Glu Val
210                 215                 220
Lys Glu Tyr Val Leu Pro Ser Phe Glu Val Ile Val Glu Pro Thr Glu
225                 230                 235                 240
Lys Phe Tyr Tyr Ile Tyr Asn Glu Lys Gly Leu Glu Val Thr Ile Thr
                245                 250                 255
Ala Arg Phe Leu Tyr Gly Lys Lys Val Glu Gly Thr Ala Phe Val Ile
                260                 265                 270
Phe Gly Ile Gln Asp Gly Glu Gln Arg Ile Ser Leu Pro Glu Ser Leu
                275                 280                 285
Lys Arg Ile Pro Ile Glu Asp Gly Ser Gly Glu Val Val Leu Ser Arg
                290                 295                 300
Lys Val Leu Leu Asp Gly Val Gln Asn Pro Arg Ala Glu Asp Leu Val
305                 310                 315                 320
Gly Lys Ser Leu Tyr Val Ser Ala Thr Val Ile Leu His Ser Gly Ser
                325                 330                 335
Asp Met Val Gln Ala Glu Arg Ser Gly Ile Pro Ile Val Thr Ser Pro
                340                 345                 350
Tyr Gln Ile His Phe Thr Lys Thr Pro Lys Tyr Phe Lys Pro Gly Met
                355                 360                 365
Pro Phe Asp Leu Met Val Phe Val Thr Asn Pro Asp Gly Ser Pro Ala
                370                 375                 380
Tyr Arg Val Pro Val Ala Val Gln Gly Glu Asp Thr Val Gln Ser Leu
385                 390                 395                 400
Thr Gln Gly Asp Gly Val Ala Lys Leu Ser Ile Asn Thr His Pro Ser
                405                 410                 415
Gln Lys Pro Leu Ser Ile Thr Val Arg Thr Lys Lys Gln Glu Leu Ser
                420                 425                 430
Glu Ala Glu Gln Ala Thr Arg Thr Met Gln Ala Leu Pro Tyr Ser Thr
                435                 440                 445
Val Gly Asn Ser Asn Asn Tyr Leu His Leu Ser Val Leu Arg Thr Glu
                450                 455                 460
Leu Arg Pro Gly Glu Thr Leu Asn Val Asn Phe Leu Leu Arg Met Asp
465                 470                 475                 480
Arg Ala His Glu Ala Lys Ile Arg Tyr Tyr Thr Tyr Leu Ile Met Asn
                485                 490                 495
Lys Gly Arg Leu Leu Lys Ala Gly Arg Gln Val Arg Glu Pro Gly Gln
                500                 505                 510
```

```
Asp Leu Val Val Leu Pro Leu Ser Ile Thr Thr Asp Phe Ile Pro Ser
            515                 520                 525

Phe Arg Leu Val Ala Tyr Tyr Thr Leu Ile Gly Ala Ser Gly Gln Arg
        530                 535                 540

Glu Val Val Ala Asp Ser Val Trp Val Asp Val Lys Asp Ser Cys Val
545                 550                 555                 560

Gly Ser Leu Val Val Lys Ser Gly Gln Ser Glu Asp Arg Gln Pro Val
                565                 570                 575

Pro Gly Gln Gln Met Thr Leu Lys Ile Glu Gly Asp His Gly Ala Arg
            580                 585                 590

Val Val Leu Val Ala Val Asp Lys Gly Val Phe Val Leu Asn Lys Lys
        595                 600                 605

Asn Lys Leu Thr Gln Ser Lys Ile Trp Asp Val Glu Lys Ala Asp
            610                 615                 620

Ile Gly Cys Thr Pro Gly Ser Gly Lys Asp Tyr Ala Gly Val Phe Ser
625                 630                 635                 640

Asp Ala Gly Leu Thr Phe Thr Ser Ser Gly Gln Gln Thr Ala Gln
                645                 650                 655

Arg Ala Glu Leu Gln Cys Pro Gln Pro Ala Ala Arg Arg Arg Arg Ser
                660                 665                 670

Val Gln Leu Thr Glu Lys Arg Met Asp Lys Val Gly Lys Tyr Pro Lys
            675                 680                 685

Glu Leu Arg Lys Cys Cys Glu Asp Gly Met Arg Glu Asn Pro Met Arg
        690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
            740                 745                 750

Glu Asp Ile Ile Ala Glu Glu Asn Ile Val Ser Arg Ser Glu Phe Pro
        755                 760                 765

Glu Ser Trp Leu Trp Asn Val Glu Asp Leu Lys Glu Pro Pro Lys Asn
            770                 775                 780

Gly Ile Ser Thr Lys Leu Met Asn Ile Phe Leu Lys Asp Ser Ile Thr
785                 790                 795                 800

Thr Trp Glu Ile Leu Ala Val Ser Met Ser Asp Lys Lys Gly Ile Cys
                805                 810                 815

Val Ala Asp Pro Phe Glu Val Thr Val Met Gln Asp Phe Phe Ile Asp
            820                 825                 830

Leu Arg Leu Pro Tyr Ser Val Val Arg Asn Glu Gln Val Glu Ile Arg
        835                 840                 845

Ala Val Leu Tyr Asn Tyr Arg Gln Asn Gln Glu Leu Lys Val Arg Val
850                 855                 860

Glu Leu Leu His Asn Pro Ala Phe Cys Ser Leu Ala Thr Thr Lys Arg
865                 870                 875                 880

Arg His Gln Gln Thr Val Thr Ile Pro Pro Lys Ser Ser Leu Ser Val
                885                 890                 895

Pro Tyr Val Ile Val Pro Leu Lys Thr Gly Leu Gln Glu Val Glu Val
            900                 905                 910

Lys Ala Ala Val Tyr His His Phe Ile Ser Asp Gly Val Arg Lys Ser
        915                 920                 925
```

```
Leu Lys Val Val Pro Glu Gly Ile Arg Met Asn Lys Thr Val Ala Val
    930                 935                 940

Arg Thr Leu Asp Pro Glu Arg Leu Gly Arg Glu Gly Val Gln Lys Glu
945                 950                 955                 960

Asp Ile Pro Pro Ala Asp Leu Ser Asp Gln Val Pro Asp Thr Glu Ser
                965                 970                 975

Glu Thr Arg Ile Leu Leu Gln Gly Thr Pro Val Ala Gln Met Thr Glu
            980                 985                 990

Asp Ala Val Asp Ala Glu Arg Leu Lys His Leu Ile Val Thr Pro Ser
        995                 1000                1005

Gly Cys Gly Glu Gln Asn Met Ile Gly Met Thr Pro Thr Val Ile
    1010                1015                1020

Ala Val His Tyr Leu Asp Glu Thr Glu Gln Trp Glu Lys Phe Gly
    1025                1030                1035

Leu Glu Lys Arg Gln Gly Ala Leu Glu Leu Ile Lys Lys Gly Tyr
    1040                1045                1050

Thr Gln Gln Leu Ala Phe Arg Gln Pro Ser Ser Ala Phe Ala Ala
    1055                1060                1065

Phe Val Lys Arg Ala Pro Ser Thr Trp Leu Thr Ala Tyr Val Val
    1070                1075                1080

Lys Val Phe Ser Leu Ala Val Asn Leu Ile Ala Ile Asp Ser Gln
    1085                1090                1095

Val Leu Cys Gly Ala Val Lys Trp Leu Ile Leu Glu Lys Gln Lys
    1100                1105                1110

Pro Asp Gly Val Phe Gln Glu Asp Ala Pro Val Ile His Gln Glu
    1115                1120                1125

Met Ile Gly Gly Leu Arg Asn Asn Asn Glu Lys Asp Met Ala Leu
    1130                1135                1140

Thr Ala Phe Val Leu Ile Ser Leu Gln Glu Ala Lys Asp Ile Cys
    1145                1150                1155

Glu Glu Gln Val Asn Ser Leu Pro Gly Ser Ile Thr Lys Ala Gly
    1160                1165                1170

Asp Phe Leu Glu Ala Asn Tyr Met Asn Leu Gln Arg Ser Tyr Thr
    1175                1180                1185

Val Ala Ile Ala Gly Tyr Ala Leu Ala Gln Met Gly Arg Leu Lys
    1190                1195                1200

Gly Pro Leu Leu Asn Lys Phe Leu Thr Thr Ala Lys Asp Lys Asn
    1205                1210                1215

Arg Trp Glu Asp Pro Gly Lys Gln Leu Tyr Asn Val Glu Ala Thr
    1220                1225                1230

Ser Tyr Ala Leu Leu Ala Leu Leu Gln Leu Lys Asp Phe Asp Phe
    1235                1240                1245

Val Pro Pro Val Val Arg Trp Leu Asn Glu Gln Arg Tyr Tyr Gly
    1250                1255                1260

Gly Gly Tyr Gly Ser Thr Gln Ala Thr Phe Met Val Phe Gln Ala
    1265                1270                1275

Leu Ala Gln Tyr Gln Lys Asp Ala Pro Asp His Gln Glu Leu Asn
    1280                1285                1290

Leu Asp Val Ser Leu Gln Leu Pro Ser Arg Ser Ser Lys Ile Thr
    1295                1300                1305

His Arg Ile His Trp Glu Ser Ala Ser Leu Leu Arg Ser Glu Glu
    1310                1315                1320

Thr Lys Glu Asn Glu Gly Phe Thr Val Thr Ala Glu Gly Lys Gly
```

1325                1330                1335

Gln Gly Thr Leu Ser Val Val Thr Met Tyr His Ala Lys Ala Lys
        1340                1345                1350

Asp Gln Leu Thr Cys Asn Lys Phe Asp Leu Lys Val Thr Ile Lys
        1355                1360                1365

Pro Ala Pro Glu Thr Glu Lys Arg Pro Gln Asp Ala Lys Asn Thr
        1370                1375                1380

Met Ile Leu Glu Ile Cys Thr Arg Tyr Arg Gly Asp Gln Asp Ala
        1385                1390                1395

Thr Met Ser Ile Leu Asp Ile Ser Met Met Thr Gly Phe Ala Pro
        1400                1405                1410

Asp Thr Asp Asp Leu Lys Gln Leu Ala Asn Gly Val Asp Arg Tyr
        1415                1420                1425

Ile Ser Lys Tyr Glu Leu Asp Lys Ala Phe Ser Asp Arg Asn Thr
        1430                1435                1440

Leu Ile Ile Tyr Leu Asp Lys Val Ser His Ser Glu Asp Asp Cys
        1445                1450                1455

Leu Ala Phe Lys Val His Gln Tyr Phe Asn Val Glu Leu Ile Gln
        1460                1465                1470

Pro Gly Ala Val Lys Val Tyr Ala Tyr Asn Leu Glu Glu Ser
        1475                1480                1485

Cys Thr Arg Phe Tyr His Pro Glu Lys Glu Asp Gly Lys Leu Asn
        1490                1495                1500

Lys Leu Cys Arg Asp Glu Leu Cys Arg Cys Ala Glu Glu Asn Cys
        1505                1510                1515

Phe Ile Gln Lys Ser Asp Asp Lys Val Thr Leu Glu Glu Arg Leu
        1520                1525                1530

Asp Lys Ala Cys Glu Pro Gly Val Asp Tyr Val Tyr Lys Thr Arg
        1535                1540                1545

Leu Val Lys Val Gln Leu Ser Asn Asp Phe Asp Glu Tyr Ile Met
        1550                1555                1560

Ala Ile Glu Gln Thr Ile Lys Ser Gly Ser Asp Glu Val Gln Val
        1565                1570                1575

Gly Gln Gln Arg Thr Phe Ile Ser Pro Ile Lys Cys Arg Glu Ala
        1580                1585                1590

Leu Lys Leu Glu Glu Lys Lys His Tyr Leu Met Trp Gly Leu Ser
        1595                1600                1605

Ser Asp Phe Trp Gly Glu Lys Pro Asn Leu Ser Tyr Ile Ile Gly
        1610                1615                1620

Lys Asp Thr Trp Val Glu His Trp Pro Glu Glu Asp Glu Cys Gln
        1625                1630                1635

Asp Glu Glu Asn Gln Lys Gln Cys Gln Asp Leu Gly Ala Phe Thr
        1640                1645                1650

Glu Ser Met Val Val Phe Gly Cys Pro Asn
        1655                1660

<210> SEQ ID NO 74
<211> LENGTH: 1463
<212> TYPE: PRT
<213> ORGANISM: Homo sapiens
<300> PUBLICATION INFORMATION:
<308> DATABASE ACCESSION NUMBER: UniProt
<309> DATABASE ENTRY DATE: 2015-09-16
<313> RELEVANT RESIDUES IN SEQ ID NO: (1)..(1463)

<400> SEQUENCE: 74

```
Met Leu Leu Ser Pro Ser Leu Leu Leu Leu Leu Gly Ala Pro
1               5                   10                  15

Arg Gly Cys Ala Glu Gly Val Ala Ala Leu Thr Pro Glu Arg Leu
            20                  25              30

Leu Glu Trp Gln Asp Lys Gly Ile Phe Val Ile Gln Ser Glu Ser Leu
        35                  40                  45

Lys Lys Cys Ile Gln Ala Gly Lys Ser Val Leu Thr Leu Glu Asn Cys
50                      55                  60

Lys Gln Ala Asn Lys His Met Leu Trp Lys Trp Val Ser Asn His Gly
65                  70              75                  80

Leu Phe Asn Ile Gly Gly Ser Gly Cys Leu Gly Leu Asn Phe Ser Ala
                85                  90                  95

Pro Glu Gln Pro Leu Ser Leu Tyr Glu Cys Asp Ser Thr Leu Val Ser
            100                 105                 110

Leu Arg Trp Arg Cys Asn Arg Lys Met Ile Thr Gly Pro Leu Gln Tyr
        115                 120                 125

Ser Val Gln Val Ala His Asp Asn Thr Val Val Ala Ser Arg Lys Tyr
130                 135                 140

Ile His Lys Trp Ile Ser Tyr Gly Ser Gly Gly Asp Ile Cys Glu
145                 150                 155                 160

Tyr Leu His Lys Asp Leu His Thr Ile Lys Gly Asn Thr His Gly Met
            165                 170                 175

Pro Cys Met Phe Pro Phe Gln Tyr Asn His Gln Trp His His Glu Cys
            180                 185                 190

Thr Arg Glu Gly Arg Glu Asp Asp Leu Leu Trp Cys Ala Thr Thr Ser
        195                 200                 205

Arg Tyr Glu Arg Asp Glu Lys Trp Gly Phe Cys Pro Asp Pro Thr Ser
210                 215                 220

Ala Glu Val Gly Cys Asp Thr Ile Trp Glu Lys Asp Leu Asn Ser His
225                 230                 235                 240

Ile Cys Tyr Gln Phe Asn Leu Leu Ser Ser Leu Ser Trp Ser Glu Ala
                245                 250                 255

His Ser Ser Cys Gln Met Gln Gly Gly Thr Leu Leu Ser Ile Thr Asp
            260                 265                 270

Glu Thr Glu Glu Asn Phe Ile Arg Glu His Met Ser Ser Lys Thr Val
        275                 280                 285

Glu Val Trp Met Gly Leu Asn Gln Leu Asp Glu His Ala Gly Trp Gln
        290                 295                 300

Trp Ser Asp Gly Thr Pro Leu Asn Tyr Leu Asn Trp Ser Pro Glu Val
305                 310                 315                 320

Asn Phe Glu Pro Phe Val Glu Asp His Cys Gly Thr Phe Ser Ser Phe
            325                 330                 335

Met Pro Ser Ala Trp Arg Ser Arg Asp Cys Glu Ser Thr Leu Pro Tyr
            340                 345                 350

Ile Cys Lys Lys Tyr Leu Asn His Ile Asp His Glu Ile Val Glu Lys
                355                 360                 365

Asp Ala Trp Lys Tyr Tyr Ala Thr His Cys Glu Pro Gly Trp Asn Pro
370                 375                 380

Tyr Asn Arg Asn Cys Tyr Lys Leu Gln Lys Glu Lys Thr Trp His
385                 390                 395                 400

Glu Ala Leu Arg Ser Cys Gln Ala Asp Asn Ser Ala Leu Ile Asp Ile
                405                 410                 415
```

```
Thr Ser Leu Ala Glu Val Glu Phe Leu Val Thr Leu Leu Gly Asp Glu
            420                 425                 430

Asn Ala Ser Glu Thr Trp Ile Gly Leu Ser Ser Asn Lys Ile Pro Val
            435                 440                 445

Ser Phe Glu Trp Ser Asn Asp Ser Ser Val Ile Phe Thr Asn Trp His
            450                 455                 460

Thr Leu Glu Pro His Ile Phe Pro Asn Arg Ser Gln Leu Cys Val Ser
465                 470                 475                 480

Ala Glu Gln Ser Glu Gly His Trp Lys Val Lys Asn Cys Glu Glu Arg
                485                 490                 495

Leu Phe Tyr Ile Cys Lys Lys Ala Gly His Val Leu Ser Asp Ala Glu
            500                 505                 510

Ser Gly Cys Gln Glu Gly Trp Glu Arg His Gly Gly Phe Cys Tyr Lys
            515                 520                 525

Ile Asp Thr Val Leu Arg Ser Phe Asp Gln Ala Ser Ser Gly Tyr Tyr
            530                 535                 540

Cys Pro Pro Ala Leu Val Thr Ile Thr Asn Arg Phe Glu Gln Ala Phe
545                 550                 555                 560

Ile Thr Ser Leu Ile Ser Ser Val Val Lys Met Lys Asp Ser Tyr Phe
                565                 570                 575

Trp Ile Ala Leu Gln Asp Gln Asn Asp Thr Gly Glu Tyr Thr Trp Lys
            580                 585                 590

Pro Val Gly Gln Lys Pro Glu Pro Val Gln Tyr Thr His Trp Asn Thr
            595                 600                 605

His Gln Pro Arg Tyr Ser Gly Gly Cys Val Ala Met Arg Gly Arg His
610                 615                 620

Pro Leu Gly Arg Trp Glu Val Lys His Cys Arg His Phe Lys Ala Met
625                 630                 635                 640

Ser Leu Cys Lys Gln Pro Val Glu Asn Gln Glu Lys Ala Glu Tyr Glu
                645                 650                 655

Glu Arg Trp Pro Phe His Pro Cys Tyr Leu Asp Trp Glu Ser Glu Pro
            660                 665                 670

Gly Leu Ala Ser Cys Phe Lys Val Phe His Ser Glu Lys Val Leu Met
            675                 680                 685

Lys Arg Thr Trp Arg Glu Ala Glu Ala Phe Cys Glu Glu Phe Gly Ala
690                 695                 700

His Leu Ala Ser Phe Ala His Ile Glu Glu Glu Asn Phe Val Asn Glu
705                 710                 715                 720

Leu Leu His Ser Lys Phe Asn Trp Thr Glu Glu Arg Gln Phe Trp Ile
                725                 730                 735

Gly Phe Asn Lys Arg Asn Pro Leu Asn Ala Gly Ser Trp Glu Trp Ser
            740                 745                 750

Asp Arg Thr Pro Val Val Ser Ser Phe Leu Asp Asn Thr Tyr Phe Gly
            755                 760                 765

Glu Asp Ala Arg Asn Cys Ala Val Tyr Lys Ala Asn Lys Thr Leu Leu
            770                 775                 780

Pro Leu His Cys Gly Ser Lys Arg Glu Trp Ile Cys Lys Ile Pro Arg
785                 790                 795                 800

Asp Val Lys Pro Lys Ile Pro Phe Trp Tyr Gln Tyr Asp Val Pro Trp
                805                 810                 815

Leu Phe Tyr Gln Asp Ala Glu Tyr Leu Phe His Thr Phe Ala Ser Glu
            820                 825                 830

Trp Leu Asn Phe Glu Phe Val Cys Ser Trp Leu His Ser Asp Leu Leu
```

```
                835                 840                 845
Thr Ile His Ser Ala His Glu Gln Glu Phe Ile His Ser Lys Ile Lys
                850                 855                 860
Ala Leu Ser Lys Tyr Gly Ala Ser Trp Trp Ile Gly Leu Gln Glu Glu
865                 870                 875                 880
Arg Ala Asn Asp Glu Phe Arg Trp Arg Asp Gly Thr Pro Val Ile Tyr
                    885                 890                 895
Gln Asn Trp Asp Thr Gly Arg Glu Arg Thr Val Asn Asn Gln Ser Gln
                    900                 905                 910
Arg Cys Gly Phe Ile Ser Ser Ile Thr Gly Leu Trp Gly Ser Glu Glu
                    915                 920                 925
Cys Ser Val Ser Met Pro Ser Ile Cys Lys Arg Lys Lys Val Trp Leu
                930                 935                 940
Ile Glu Lys Lys Lys Asp Thr Pro Lys Gln His Gly Thr Cys Pro Lys
945                 950                 955                 960
Gly Trp Leu Tyr Phe Asn Tyr Lys Cys Leu Leu Leu Asn Ile Pro Lys
                    965                 970                 975
Asp Pro Ser Ser Trp Lys Asn Trp Thr His Ala Gln His Phe Cys Ala
                980                 985                 990
Glu Glu Gly Gly Thr Leu Val Ala   Ile Glu Ser Glu Val   Glu Gln Ala
                995                 1000                1005
Phe Ile Thr Met Asn Leu Phe  Gly Gln Thr Thr Ser  Val Trp Ile
1010                1015                1020
Gly Leu  Gln Asn Asp Asp Tyr  Glu Thr Trp Leu Asn  Gly Lys Pro
1025                1030                1035
Val Val  Tyr Ser Asn Trp Ser  Pro Phe Asp Ile Ile  Asn Ile Pro
1040                1045                1050
Ser His  Asn Thr Thr Glu Val  Gln Lys His Ile Pro  Leu Cys Ala
1055                1060                1065
Leu Leu  Ser Ser Asn Pro Asn  Phe His Phe Thr Gly  Lys Trp Tyr
1070                1075                1080
Phe Glu  Asp Cys Gly Lys Glu  Gly Tyr Gly Phe Val  Cys Glu Lys
1085                1090                1095
Met Gln  Asp Thr Ser Gly His  Gly Val Asn Thr Ser  Asp Met Tyr
1100                1105                1110
Pro Met  Pro Asn Thr Leu Glu  Tyr Gly Asn Arg Thr  Tyr Lys Ile
1115                1120                1125
Ile Asn  Ala Asn Met Thr Trp  Tyr Ala Ala Ile Lys  Thr Cys Leu
1130                1135                1140
Met His  Lys Ala Gln Leu Val  Ser Ile Thr Asp Gln  Tyr His Gln
1145                1150                1155
Ser Phe  Leu Thr Val Val Leu  Asn Arg Leu Gly Tyr  Ala His Trp
1160                1165                1170
Ile Gly  Leu Phe Thr Thr Asp  Asn Gly Leu Asn Phe  Asp Trp Ser
1175                1180                1185
Asp Gly  Thr Lys Ser Ser Phe  Thr Phe Trp Lys Asp  Glu Glu Ser
1190                1195                1200
Ser Leu  Leu Gly Asp Cys Val  Phe Ala Asp Ser Asn  Gly Arg Trp
1205                1210                1215
His Ser  Thr Ala Cys Glu Ser  Phe Leu Gln Gly Ala  Ile Cys His
1220                1225                1230
Val Pro  Pro Glu Thr Arg Gln  Ser Glu His Pro Glu  Leu Cys Ser
1235                1240                1245
```

```
Glu  Thr  Ser  Ile  Pro  Trp  Ile  Lys  Phe  Lys  Ser  Asn  Cys  Tyr  Ser
     1250                1255                1260

Phe  Ser  Thr  Val  Leu  Asp  Ser  Met  Ser  Phe  Glu  Ala  Ala  His  Glu
     1265                1270                1275

Phe  Cys  Lys  Lys  Glu  Gly  Ser  Asn  Leu  Leu  Thr  Ile  Lys  Asp  Glu
     1280                1285                1290

Ala  Glu  Asn  Ala  Phe  Leu  Leu  Glu  Glu  Leu  Phe  Ala  Phe  Gly  Ser
     1295                1300                1305

Ser  Val  Gln  Met  Val  Trp  Leu  Asn  Ala  Gln  Phe  Asp  Gly  Asn  Asn
     1310                1315                1320

Glu  Thr  Ile  Lys  Trp  Phe  Asp  Gly  Thr  Pro  Thr  Asp  Gln  Ser  Asn
     1325                1330                1335

Trp  Gly  Ile  Arg  Lys  Pro  Asp  Thr  Asp  Tyr  Phe  Lys  Pro  His  His
     1340                1345                1350

Cys  Val  Ala  Leu  Arg  Ile  Pro  Glu  Gly  Leu  Trp  Gln  Leu  Ser  Pro
     1355                1360                1365

Cys  Gln  Glu  Lys  Lys  Gly  Phe  Ile  Cys  Lys  Met  Glu  Ala  Asp  Ile
     1370                1375                1380

His  Thr  Ala  Glu  Ala  Leu  Pro  Glu  Lys  Gly  Pro  Ser  His  Ser  Ile
     1385                1390                1395

Ile  Pro  Leu  Ala  Val  Val  Leu  Thr  Leu  Ile  Val  Ile  Val  Ala  Ile
     1400                1405                1410

Cys  Thr  Leu  Ser  Phe  Cys  Ile  Tyr  Lys  His  Asn  Gly  Gly  Phe  Phe
     1415                1420                1425

Arg  Arg  Leu  Ala  Gly  Phe  Arg  Asn  Pro  Tyr  Tyr  Pro  Ala  Thr  Asn
     1430                1435                1440

Phe  Ser  Thr  Val  Tyr  Leu  Glu  Glu  Asn  Ile  Leu  Ile  Ser  Asp  Leu
     1445                1450                1455

Glu  Lys  Ser  Asp  Gln
     1460
```

METHODS OF DETECTING ALLOANTIBODIES USING HLA AND NON-HLA ANTIGENS

This application is a continuation of U.S. application Ser. No. 15/273,027, filed on Sep. 22, 2016, which claims priority to U.S. Provisional Patent Application No. 62/222,614, filed on Sep. 23, 2015, which is incorporated herein by reference in its entirety.

FIELD OF THE INVENTION

The present invention is directed to materials and methods for detecting alloantibodies using both HLA and non-HLA antigens.

BACKGROUND

Transplant rejection occurs when the immune system of the recipient of a transplant, particularly antibodies produced by the recipient, attacks the transplanted organ or tissue. The recipient's immune system recognizes the transplanted organ as foreign tissue and attempts to destroy it. Rejection also occurs when the transplanted organ comprises the donor's lymphocytes or progenitor stem cells, which may generate an immune response to the recipient tissues such as graft vs. host disease. Chronic rejection is a term used to describe all long term loss of function in organ transplants associated with chronic alloreactive immune response. Long term chronic rejection usually leads to a need for a new transplanted organ about a decade after the initial transplant. Human leukocyte antigens (HLA) are one type of molecules within a transplanted organ in which the recipient's immune system attacks that causes a transplant rejection.

It is a standard practice in the transplant field to test all potential recipients against a panel of HLA antigens selected to represent a human population and the percentage of HLA alleles against which the serum is reactive is determined. In this panel reactive antibody (PRA) testing reaction of a patient's serum against a high percentage of HLA alleles present in a normal human population is predictive of a high risk of graft rejection.

Alloantibodies, particularly when donor specific, are one of the most important factors that cause both early and late graft rejection. Despite improvements in the transplantation outcomes, antibody-mediated rejection (AMR) remains substantial and it is associated with increased morbidity, mortality and costs (Colvin, ASN 18(4):1046-1056, 2007).

The presence of HLA antibodies is widely believed to be the major elements contributing to humoral graft rejections. Transplant recipients with high panel reaction antigens (PRA) are associated with early graft rejection. Elevated donor specific HLA antibodies in the organ recipients either before and/or after allograft transplantation has been associated with acute and chronic AMR and decreased long term graft survival. Despite advanced HLA typing matching programs, there has not been a major improvement in the incidence of Graft-versus-host disease (GVHD). Several studies indicate that in addition to HLA alloantibodies, transplant recipients also developed antibodies against antigens other than HLA molecules. The role of alloantibodies against non-HLA antigens is a critical element in the pathogenesis of acute and chronic allograft outcomes (Tinckam and Chandraker, CJASN 1(3):404-414, 2006).

Currently, there are no defined non-HLA alloantibody antigens. MHC class I-related chain A (MicA), a group of polymorphic non-HLA antigens expressed on endothelial cells, have been implicated in the pathogenesis of hyperacute, acute and chronic organ allograft rejections (Sumitran-Holgersson, Current Opinion Immunology. 20(5):607-13, 2008). In addition, Vimentin, Angiotensin II Type I receptor (AT1R), LG3 peptide of Perlecan and Collagen V are also considered to be non-HLA antigens (Sigdel and Sarwal, Human Immunology, 74:1486-1490, 2013). Targets for anti-endothelial cell antibody (AECA), islet cell antibodies (ICAs), anti-Liver sinusoidal endothelial cells (anti-LSECs) and Antineutrophil cytoplasmic autoantibodies (ANCA) are also considered as non-HLA antigens. The AECA, ICA, anti-LSECs and ANCA target antigens are not well defined (Hepatology, 40(5):1211-1221, 2004).

Accordingly, there remains a need in the art for improved methods of HLA typing including methods for determination of percentage of PRA which is rapid, convenient and accurate.

SUMMARY

In one aspect, described herein is a composition comprising a first collection of solid-phase substrates each coated with different purified human leukocyte antigens (HLAs) to represent the HLA antigen population of a single cell line and a second collection of solid-phase substrates coated with a different non-HLA antigen listed in Table 1 or Table 1A. In some embodiments, the different purified HLA antigens are Class I HLA antigens. In some embodiments, the different purified HLA antigens are Class II HLA antigens.

In some embodiments, the first collection comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 55, 56, 57, 58, 59, 60 or more different Class I HLA antigens. In some embodiments, the first collection comprises 2, 3, 4, 5, 6, 7, 8, 9, 10, 11, 12, 13, 14, 15, 16, 17, 18, 19, 20, 21, 22, 23, 24, 25, 26, 27, 28, 29, 30 or more different Class II HLA antigens. In some embodiments, the first collection comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 55, 56, 57, 58, 59, 60 or more different Class I HLA antigens and or Class II HLA antigens.

In some embodiments, the second collection comprises the non-HLA antigen set forth in Table 1 or 1A. In some embodiments, the second collection comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more non-HLA antigens set forth in Table 1 and/or Table 1A.

In another aspect, described herein is a kit for determining the percentage of panel reactive antibodies in serum of a subject against HLA antigens comprising a first collection of solid-phase substrates wherein each solid-phase substrate is coated with different purified HLA antigens to represent the HLA antigen population of a single cell line such that said collection simulates the distribution of HLA antigens in a normal human population and a second collection of solid phase substrates wherein each substrate is coated with different purified non-HLA antigens listed in Table 1 or Table 1A.

In another aspect, described herein is a method for determining the percentage of panel reactive antibodies in serum of a subject against human leukocyte antigens (HLA) antigens, said method comprising: contacting a first collection of solid-phase substrates subtypes and a second collection of solid-phase substrate subtypes with serum from said subject for a sufficient time for anti-HLA antibodies in said serum to bind to said HLA-antigens to form a complex, wherein each substrate subtype in the first collection is coated with different purified HLA antigens to present HLA antigens derived from a cell population of a single cell, wherein each substrate subtype of the second collection is coated with different purified non-HLA antigens listed in Table 1 or Table 1A, detecting the presence of the complex to determine the presence or absence of panel reactive antibodies, and determining the percentage of panel reactive antibodies in the serum. In some embodiments, the subject is a transplant or transfusion recipient. In some embodiments, the serum sample is collected before the subject has received a transplant or transfusion. In other embodiments, the serum sample is collected after the subject has received a transplant or transfusion. In further embodiments, the serum sample is collected both before and after the transplant or transfusion.

The method of determining the percentage of panel reactive antibodies may be carried out to monitor the risk that the recipient will reject the transplant or transfusion or develop graft versus host disease (GVHD). Thus, in one embodiment the method may further comprise the step of obtaining a base line percentage of panel reactive antibodies before the subject receives the transplant or transfusion. The methods may also comprise a step of comparing the percent of panel reactive antibodies before and after receipt of the transplant and transfusion. The monitoring may be carried out at various time points, after transplant or transfusion to determine if the subject is developing GVHD. For example, in some embodiments, the baseline percentage of panel reactive antibodies is determined between a time period ranging from 1 hour to about 1 year or longer before the subject receives the transplant or transfusion. In some embodiments, the baseline percentage of panel reactive antibodies is determined about 1 hour, about 6 hours, about 12 hours, about 1 day, about 5 days, about 1 week, about 2 weeks, about 3 weeks, about 4 weeks, about 1 months, about 2 months, about 3 months, about 4 months, about 5 months, about 6 months, about 7 months, about 8 months, about 9 months, about 10 months, about 11 months about 1 year or longer before the subject received the transplant or transfusion. In some embodiments, the percent of panel reactive antibodies is determined between a time period ranging from 1 hours to about 1 year or longer after the subject has received the transplant or transfusion. For example, in some embodiments, the percent of panel reactive antibodies is determined about 1 hour, about 6 hours, about 12 hours, about 1 day, about 5 days, about 1 week, about 2 weeks, about 3 weeks, about 4 weeks, about 1 months, about 2 months, about 3 months, about 4 months, about 5 months, about 6 months, about 7 months, about 8 months, about 9 months, about 10 months, about 11 months about 1 year or longer after the subject has received the transplant or transfusion.

In some embodiments, the detecting step comprises detecting labeled ligand bound to the complex to determine the presence or absence of panel reactive antibodies. In some embodiments, detecting of the labeled ligand is carried out by flow cytometry. In some embodiments, the detecting step comprises detecting the presence of the complex using a solid phase immunoassay or a multiplexed bead immunoassay.

The solid-phase substrate can be any solid substrate known in the art. In some embodiments, the solid-phase substrate is selected from the group consisting of microparticle, microbead, magnetic bead, ion torrent bead, flow cytometer bead and an affinity purification column. In some embodiments, the solid-phase substrate is a microbead. In some embodiments, the microbead is a latex microbead. The microbead, in some embodiments, has a diameter ranging from about 2 μm to about 15 μm, inclusive. Microbeads having a diameter of about 2 μm, 3 μm, 4 μm, 5 μm, 6 μm, 7 μm, 8 μm, 9 μm, 10 μm, 11 μm, 12 μm, 13 μm, 14 μm or 15 μm are also contemplated. In some embodiments, at least one microbead presenting Class I HLA antigens is 3 μm is diameter. In some embodiments, at least one microbead presented Class II HLA antigens is 5 μm in diameter. In some embodiments, the microbeads comprise a mixture of 3 μm microbeads presenting Class I HLA antigens and 8 μm microbeads presented Class II HLA antigens.

In some embodiments, each solid phase substrate is detectably distinguishable from other solid phase substrates within the composition. In some embodiments, the detectably distinguishable solid phase substrates are distinguishable by fluorescent labels.

In some embodiments, the different purified HLA antigens are Class I HLA antigens. In some embodiments, the HLA antigens are selected such that the HLA antigens presented on the solid phase substrate comprise Class I HLA antigens so as to simulate the distribution of Class I HLA antigens in a normal human population. In some embodiments, the first collection comprises 54 different Class I HLA antigens. In some embodiments, the 54 different Class I HLA antigens are purified from 30 different cell lines. In some embodiments, the first collection comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54 55, 56, 57, 58, 59, 60 or more different Class I HLA antigens.

In some embodiments, the different purified HLA antigens are Class II HLA antigens. In some embodiments, the first collection comprises 22 different Class II HLA antigens. In some embodiments, the first collection comprises 2, 3, 4, 5, 6, 7, 8, 9, 10, 11, 12, 13, 14, 15, 16, 17, 18, 19, 20, 21, 22, 23, 24, 25, 26, 27, 28, 29, 30 or more different Class II HLA antigens.

In some embodiments, the second collection comprises different non-HLA antigens set forth in Table 1 or 1A. In some embodiments, the second collection comprises 2, 3, 4, 5, 6, 7, 8, 9, 10, 11, 12, 13, 14, 15, 16, 17, 18, 19, 20, 21, 22, 23, 24, 25, 26, 27, 28, 29, 30 or more non-HLA antigens set forth in Table 1 and/or Table 1A. The non-HLA antigen, in some embodiments, is a fusion protein comprising at least one domain, wherein the domain is a signal peptide, a modified cytoplasmic domain, purification tag or detection tag. In some embodiments, the domain is the B2 signal peptide, HLA cytoplasmic domain, EK Tag, V5 Tag or DPD Tag.

DETAILED DESCRIPTION

Figure 1:
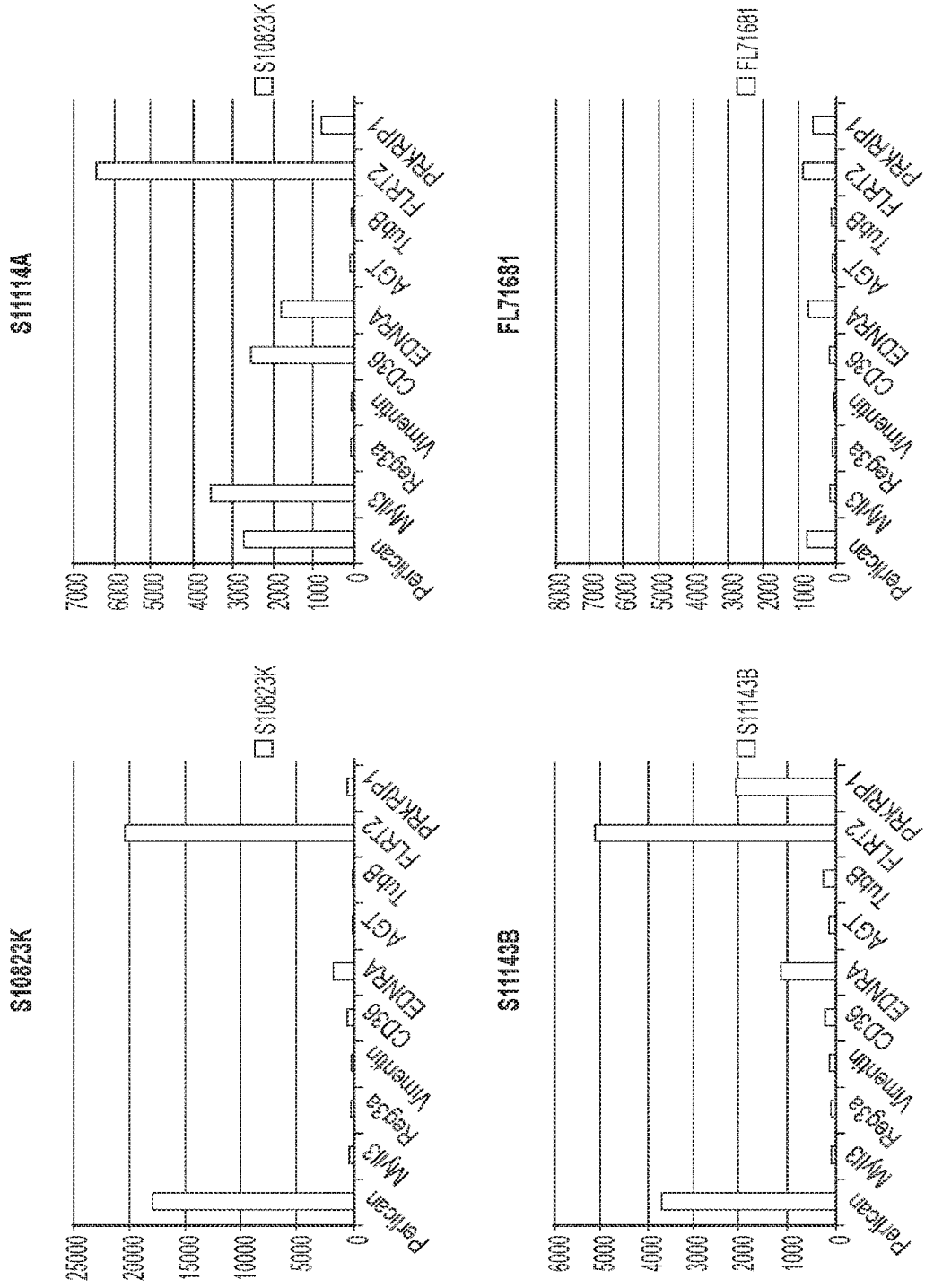
FIG. 1 describes the output data from the non-HLA multiplex assay. Four subjects (S10823K, S11114A, S11143B and FL71681) show distinct cross relativities against a panel of non-HLA antigens.

Graft rejection is when transplanted tissue is rejected by the recipient's immune system, which destroys the transplanted tissue. The rejection is an adaptive immune response via cellular immunity and humoral immunity. Chronic rejection induced by humoral response is a major cause of graft dysfunction and re-transplantation. It is well recognized that pre-existing antibodies to HLA antigens expressed by the allograft is detrimental to survival of allografts. The presence of panel-reactive antibodies (PRA) against HLA antigens before transplantation can lead to early rejection. Despite intensive HLA typing screening for HLA matching and progressive monitoring the development of anti-HLA alloantibodies, declining graft function remains a paramount clinical concern.

With the focus on the graft rejection among HLA-identical-sibling recipients, the slow decline in survival curves of HLA-identical-sibling transplants suggests that antigens other than HLA antigens may contribute to allograft rejection. Transplant recipients have also developed antibodies against targets other than HLA molecules (non-HLA antigens), such as autoimmune antigens.

The development of a solid phase platform as described in the Examples provided herein allows for large-scale antibody screening for both HLA and non-HLA antigens. As described in Example 6, antibodies to kidney-expressed non-HLA antigens have been identified in kidney allografts patients, resulting in acute kidney rejection and allograft loss. Autoantibodies are also found in patients with chronic humoral rejection.

The present inventors have discovered that the currently available methods useful for detecting HLA antibodies are not reliable and reproducible for the detection of non-HLA antibodies. For example, ELISA is the most common detection method. However, it is more suitable for a single target. Flow cytometry against panels of endothelial cells is another method, but the use of a cell based assay may result in high background and reliability reduced. As non-HLA antibodies become more relevant to antibody-mediated processes, development of reproducible assays on the multiplex global scales optimized for transplantation for these antibodies becomes important. The multi-plex assays described herein provide a reliable and reproducible method for determining the presence of both HLA and non-HLA antibodies in a single assay.

HLA Antigens

The HLA locus is highly polymorphic in nature. As disclosed in the Nomenclature for Factors of the HLA System 2000 (Hum. Immunol.; 62(4):419-68, 2001) there are 124 HLA-A alleles, 258 HLA-B alleles, 74 HLA-C alleles, 221 HLA-DRB1 alleles, 19 DRB3 alleles, 89 DRB4 alleles, 14 DRB5 alleles, 19 DQA1 alleles and 39 DQB1 alleles, with new alleles being discovered continuously, as testament to this rapid progress, a April 2007 update by the WHO nomenclature Committee for Factors of the HLA System (www.anthonynolan.com/HIG/) showed there are 545 HLA-A alleles, 895 HLA-B alleles, 307 HLA-C alleles, 8 HLA-E alleles, 12 HLA-H alleles, 9 HLA-J alleles, 6 HLA-K alleles, 4 HLA-L alleles, 4 HLA-P alleles, 3 HLA-V alleles, 3 DRA alleles, 494 DRB1 alleles, 1 DRB2 alleles, 44 DRB3 alleles, 13 DRB4 alleles, 18 DRB5 alleles, 3 DRB6 alleles, 2 DRB7 alleles, 10 DRB8 alleles, 1 DRB9 alleles, 34 DQA1 alleles, 83 DQB1 alleles, 23 DPA1, 126 DPB1 alleles, 4 DMA alleles, 7 DMB alleles, 12 DOA alleles and 9 DOB alleles.

Solid phase immunoassays for the detection and characterization of HLA-specific antibodies provide increased sensitivity and specificity, while being more efficient for time and, compared to the traditionally used cell-based methods. Multiplexed bead immunoassay (MBIA) has emerged as a powerful tool to simultaneously detect several antibodies targets in limited sample volumes. The limited sample volume and time-saving gains of the MBIA have made it an election technique for studies involving multiple factors. The invention provided herein allows for the multiplexed bead immunoassays detecting both HLA reactive antibodies and non-HLA reactive antibodies in a single assay.

Non-HLA Antigens

This invention describes the development of a multiplex solid phase platform allowing for global-scale antibody screening for both HLA and non-HLA antigens in a biological sample. For example, using such methods, in some embodiments, antibodies to kidney-expressed non-HLA antigens in the kidney allografts patients can be monitored. Some transplant recipients develop autoantibodies with acute kidney rejection and allograft loss. Autoantibodies are also found in patients with chronic humoral rejection.

The targets of humoral responses against non-HLA antigens are primarily antigens expressed on endothelial cells and epithelial cells and categorized as non-HLA alloantigens or tissue-specific autoantigens. Most of them are either patient- or graft-specific. Whether antibodies to non-HLA antigens are pathogenic and/or whether they can be used as biomarkers for transplant outcome remains unclear (J Am Soc Nephrol 22: 1168-1178, 2011). In addition, targets for anti-endothelial cell antibody (AECA), islet cell antibodies (ICAs), anti-Liver sinusoidal endothelial cells (anti-LSECs) and antineutrophil cytoplasmic autoantibodies (ANCA) are considered as non-HLA antigens. The AECA, ICA, anti-LSECs and ANCA target antigens are not defined and are subject to every research lab's definition (Hepatology, 40(5): 1211-1221, 2004).

Agrin is the most abundantly expressed glycoprotein in the glomerular basement membrane (GBM). The GBM is a basement membrane specialized in ultrafiltration and consists of various matrix molecules, including fibronectin, and collagens. The 22 kDa C-terminus Agrin fragment (CAF) is recently discovered as the biomarkers for kidney function and physical health activities (American journal of nephrology, 38(6):501-508). The presence of anti-Argrin antibodies was associated with the number of rejection episodes prior to diagnosis of transplant glomerulopathy (TGP), a symptom of kidney failure after kidney transplant (American Journal of Transplantation 2005; 5: 383-393).

Angiotensinogen (AGT) is a component of the renin-angiotensin system (RAS), a hormone system that regulates blood pressure and fluid balance. It is also known as the renin substrate, and is a non-inhibitory member of the serpin family of proteinase inhibitors. It causes vasoconstriction and a subsequent increase in blood pressure. AGT has shown very strong correlation in renal graft rejection and has been validated by customized ELISA assays in independent patient sera and their localization confirmed by immunohistochemistry (J. Proteome Res., 2010, 9 (12), pp 6715-6721).

Angiotensin II type 1 receptor (AT1R, or ATGR1) is a G protein-coupled receptor that mediates angiotensin effects and causes vasoconstriction in vascular smooth muscle. It mediates most physiologic and pathophysiologic actions of its endogenous ligand, angiotensin II, with overactivity leading to vascular remodeling and hypertension. Antibodies to AT1R are implicated in several vascular pathologies. Several studies have shown that AT1R is associated with antibody-mediated organ rejection.

Rho GDP-dissociation inhibitor 2 is a protein that, in humans, is encoded by the ARHGDIB gene. It regulates the GDP/GTP exchange reaction of the Rho proteins by inhibiting the dissociation of GDP from them, and the subsequent binding of GTP to them. By using two-dimensional Western blotting experiments, Rho GDP-dissociation inhibitor has been identified as the non-HLA antigens target in patients undergoing chronic hemodialysis.

Aurora kinase A-interacting protein (AURKA) is a cell cycle-regulated kinase that appears to be involved in microtubule formation and/or stabilization at the spindle pole during chromosome segregation. AURKA protein is found at the centrosome in interphase cells and at the spindle poles in mitosis. This gene may play a role in tumor development and progression. By comparing antibody repertoires in pre- and post-transplant sera from several cohorts of patients with and without transplant glomerulopathy, de novo increase of anti-AURKA has been identified as non-HLA antigen.

Complement C4-B is a part of the classical activation pathway. It provides a surface for interaction between the antigen-antibody complex and other complement components. It can be cleaved to release C4 anaphylatoxin, a mediator of local inflammation. Deficiency of this protein is associated with systemic lupus erythematosus. C4B has been involved with graft injuries by combined with C2a and starts cascades reactions in the antibody mediated damages.

Chromatin assembly factor 1 subunit B (CHAF1b, CAF-1, or p60) is required for the assembly of histone octamers onto newly-replicated DNA. CAF-I is composed of three protein subunits, p50, p60, and p150. The protein encoded by this gene corresponds to the p60 subunit and is required for chromatin assembly after replication. The encoded protein is differentially phosphorylated in a cell cycle-dependent manner. In addition, it is normally found in the nucleus except during mitosis, when it is released into the cytoplasm. CHAF1b-specific antibodies were predominantly detected in patients with acute myeloid leukemia (AML) one year after allogeneic bone marrow transplantation.

CXCL11 is a small cytokine belonging to the CC chemokine family. Gene expression of CXCL11 is strongly induced by IFN-γ and IFN-β, and weakly induced by IFN-α. CXCL11 has been identified independently as I-TAC. CXCL11 is thought to play a critical role in allograft rejection. It is a dominant chemokine in controlling skin intragraft inflammation. By using high-density protein arrays to identify non-HLA antibodies in chronic allograft injury (CAI) and subsequently validated a subset in a cohort of 172 serum samples collected serially post-transplantation, the authors have identified CXCL11 as the non-HLA antigens (Sigdel et al. Non-HLA antibodies to immunogenic epitopes predict the evolution of chronic renal allograft injury. JASN Apr. 1, 2012 vol. 23 no. 4 750-763).

CXCL9, also known as MIG, is a CXC inflammatory chemokine. CXCL9 plays a key role in leukocyte trafficking and induces angiostatic effects in human microvacular endothelial cells. CXCL9 enhances T lymphocyte function in alloimmune response. CXCL9 is induced by cytokines, particularly IFNγ during infection, injury, or immunoinflammatory responses. Similar to CXCL11, CLCX9 was identified as non-HLA in the bone marrow transplant patients by microarray.

Cyclophilin A or peptidylprolyl isomerase A (PPIA) is a ubiquitously distributed protein belonging to the immunophilin family PPIA was initially believed to function primarily as an intracellular protein. Recent studies have revealed that it can be secreted by cells in response to inflammatory stimuli. It has shown that extracellular PPIA stimulates pro-inflammatory signals in endothelial cells (EC) and vascular smooth muscle cells (VSMC). Similar to AURKA, by compare antibody repertoires in pre- and post-transplant sera from several cohorts of patients with and without transplant glomerulopathy, de novo increase of anti-PPIA has been identified as non-HLA antigen (Dinavah et al., Antibodies Reactive to Non-HLA Antigens in Transplant Glomerulopathy, J Am Soc Nephrol 22: 1168-1178, 2011).

Eukaryotic translation initiation factor 2A (eIF2A) is a eukaryotic initiation factor. It is required in the initiation of translation. It is an essential factor for protein synthesis. Since eIF2 is essential for translation initiation and therefore protein synthesis, defects in eIF2 are lethal. Its activity is regulated by a mechanism involving both guanine nucleotide exchange and phosphorylation. By using IgG isolated from patients with allograft rejection and look the reactivity against endothelial cell surface, eIF2A has been identified an antigen of interests for liver transplant allograft rejection.

Alpha-enolase (EOS-1), also known as phosphopyruvate hydratase, is responsible for the catalysis of the conversion of 2-phosphoglycerate (2-PG) to phosphoenolpyruvate (PEP), the ninth and penultimate step of glycolysis. Higher concentrations of ENO-1 in cerebrospinal fluid more strongly correlated to low-grade astrocytoma. Increased levels of alpha enolase have also been identified in patients who have suffered a recent myocardial infarction or cerebrovascular accident. By looking for the Anti Endothelial Cells antibody targets in the anti-neutrophil cytoplasmic antigens (ANA) associated vasculitides, ENO-1 has been identified as one of the targets.

Glutamate decarboxylase 2 or glutamic acid decarboxylase 2 (GAD2, GAD65) is an enzyme that catalyzes the decarboxylation of glutamate. It is the targets of autoantibodies in people who later develop type 1 diabetes mellitus or latent autoimmune diabetes. Autoimmunity is the term to describe an attack against native cells and tissues by the immune system. An autoimmune response against glutamic acid decarboxylase in neurons has been implicated in a rare neurological condition known as Stiff-Man syndrome. It has been proposed that a similar autoimmune response against GAD in pancreatic cells may be associated with type 1 diabetes. Circulating GAD65 can be used as a biomarker of islet damage or transplant rejection and it will facilitate in vivo studies of the pathogenesis of anti-GAD65 autoreactivity. By checking simultaneous pancreas-kidney transplant (SPKT) recipients on type 1 diabetic patients, the incidence of rejection episodes was significantly higher in pretransplantation GAD autoantibody-positive daclizumab-treated recipients compared with GAD autoantibody-negative or ATG-treated recipients (Janet al., Pretransplantation GAD-Autoantibody Status to Guide Prophylactic Antibody Induction Therapy in Simultaneous Pancreas and Kidney Transplantation. Transplantation 96(8):745-752, 2013).

Glial cell-derived neurotrophic factor, also known as GDNF is a small protein that potently promotes the survival of many types of neurons. GDNF has regenerative properties for brain cells and showed potential as treatment for Parkinson's disease—monkeys with an induced form of Parkinson's disease showed less trembling when treated with the drug, and neuronal fibers grew in part of the human brain exposed to the drug. Similar to CXCL11, GDNF is identified as non-HLA in the bone marrow transplant patients by microarray in the chronicle renal graft rejection.

Heterogeneous nuclear ribonucleoprotein K (hnRNPK) is involved in several steps of gene expression regulation. It integrates cellular signaling cascades with multiple processes of gene expression mechanisms. This protein has a role during cell cycle progression of gene expression. It is one of the major pre-mRNA-binding proteins. HNRNPK has been reported to be involved in the life cycle of different viruses by either direct interaction with viral proteins. hnRPNK has been identified by screen a coronary artery cells cDNA library against cardiac allograft vasculopathy patient serum sample as the new antigenic targets (Acevedo et al., Antibodies against heterogeneous nuclear ribonucleoprotein K in patients with cardiac allograft vasculopathy. Journal of Heart and Lung Transplantation, 30(9):1051-1059, 2011).

Intercellular adhesion molecule 1, ICAM-1, also known as CD54, binds to CD11a/CD18 (HNA5), or CD11b/CD18 (HNA4), and is known for its importance in stabilizing cell-cell interactions and facilitating leukocyte endothelial transmigration. More recently, ICAM-1 has been characterized as a site for the cellular entry of human rhinovirus. Signal-transducing functions of ICAM-1 seem to be associated primarily with proinflammatory pathways. In particular, ICAM-1 signaling seems to produce a recruitment of inflammatory immune cells such as macrophages and granulocytes. ICAM-1 is considered one of AECA. 60% of cardiac recipients have developed anti ICAM-1 IgM (Lawson et al., Anti-intercellular adhesion molecule-1 antibodies in sera of heart transplant recipients: a role in endothelial cell activation. Transplantation 2005; 80: 264-271).

Gamma-interferon inducible protein 16 (IFI16) also known as interferon-inducible myeloid differentiation transcriptional activator. IFI16 has been shown to play a role in the sensing of intracellular DNA—and has also been linked to HIV-infected helper T-cell pyroptosis. IFI16 binds nuclear viral DNA, triggering expression of antiviral cytokines in response to infection with herpesviruses. Similar to eIF2A, IgG isolated from patients with allograft rejection reacts against endothelial cell surface. IFI16 has been identified as an antigen of interest for liver transplant allograft rejection.

Interferon-gamma (IFN-gamma) is crucial for immunity against intracellular pathogens and for tumor control. However, aberrant IFN-gamma expression has been associated with a number of autoinflammatory and autoimmune diseases. It is a potent activator of macrophages, which has antiproliferative effects on transformed cells and can potentiate the antiviral and antitumor effects of the type I interferons. IFN-gamma is produced mainly by T-cells and natural killer cells activated by antigens, mitogens, or alloantigens. Similar to CXCL11, IFN-gamma is identified as non-HLA in the bone marrow transplant patients by high density microarray in the chronicle renal graft rejection.

The interleukin-2 receptor (IL-2R) is a heterotrimeric protein expressed on the surface of certain immune cells, such as lymphocytes, that binds and responds to a cytokine called IL-2. It has three subunits, generated by different combinations of three different proteins, often referred to as "chains": α (alpha) (also called IL-2Rα, CD25, or Tac antigen), β (beta) (also called IL-2Rβ, or CD122), and γ (gamma) (also called IL-2Rγ, γc, common gamma chain, or CD132); these subunits are also parts of receptors for other cytokines. The β and γ chains of the IL-2R is membranes of the type I cytokine receptor family IL-2 and its receptor have key roles in key functions of the immune system, tolerance and immunity, primarily via their direct effects on T cells. The polymorphism of alpha chain has been reported linked to multiple sclerosis, an autoimmune disease.

Interleukin-7 receptor subunit alpha (IL7R-α), also known as CD127, is the alpha-subunit of IL7 Receptor for interleukin-7 and acts as a receptor for thymic stromal lymphopoietin (TSLP). The interleukin-7 receptor a chain transmits distinct signals for proliferation and differentiation during B lymphopoiesis and is essential for the development of T Cells. There are reports indicating IL7R polymorphisms is associated with inflammatory demyelinating diseases.

Insulin (INS) is a peptide hormone produced by beta cells in the pancreas and it regulates the metabolism of carbohydrates and fats by promoting the absorption of glucose from the blood to skeletal muscles and fat tissue. Insulin also inhibits the production of glucose by the liver. Type 1 diabetes is a chronic illness characterized by the body's inability to produce insulin due to the autoimmune destruction of the beta cells in the pancreas. Anti-insulin antibodies are a cause of hypoglycemia following pancreas transplantation. In Islet cell transplantation for the treatment of Type 1 diabetes, insulin autoantibodies can be detected in Type 1 diabetes.

Far upstream element-binding protein 2 (FUBP2) binds to the dendritic targeting element and may play a role in mRNA trafficking. It may activate gene expression. FUBP2 represents a novel and frequent pro-tumorigenic mechanism promoting proliferation (tumor growth) and motility (dissemination) of human liver cancer cells. Similar to ENO-1, by looking for the Anti Endothelial Cells antibody targets in the anti-neutrophil cytoplasmic antigens (ANA) associated vasculitides, FUBP2 has been identified as one of the AECA targets.

Lamins are components of the nuclear lamina, a fibrous layer on the nucleoplasmic side of the inner nuclear membrane, which is thought to provide a framework for the nuclear envelope and may also interact with chromatin. Lamin A and C are present in equal amounts in the lamina of mammals. Lamin-A plays an important role in nuclear assembly, chromatin organization, nuclear membrane and telomere dynamics. Whereas Lamin-B1 (LMNB1) (~585 aa) is in the protein matrix over inner nuclear membrane and has been associated with aging. LMNB1 forms homodimer. There is a common polymorphism A510V (2%) in Lamin-B1, which is not that significant. The only commercial source for LMNB1 protein is from wheat germ in vitro translation system. There are some LMNB1 Elisa kits available but it aims for the antigen detection rather than for autoimmune rejection. Lamin A has been identified as one of target antigens of anti-endothelial cell and anti-vascular smooth muscle cell antibodies in patients with giant cell arteritis. Similar to Rho GDP-dissociation inhibitor, by using two-dimensional Western blotting experiments, Lamin B has been identified as the non-HLA antigens target in patients undergoing chronic hemodialysis.

Myosin comprise a family of ATP-dependent motor proteins and are best known for their role in muscle contraction and their involvement in a wide range of other eukaryotic motility processes. Cardiac myosin (CM) is a heart specific antigen implicated in allograft rejection. Pretransplant myosin autoantibodies correlated with acute cardiac transplant rejection. The expansion of alloreactive T cells was followed by an increase of cardiac myosin reactive T cells and development of anti-myosin IgG1 autoantibodies in a mouse heart transplant model mismatched for minor histocompatibility alloantigens. This supports the idea that CM released during alloimmune injury of the allograft is recognized by CD4+ T helper autoreactive cells through indirect recognition pathway and triggers the generation of autoreactive CM antibodies. Notably, mature CM is not expressed in the thymus during development which may result in incomplete negative selection (Zhang and Reed, Non-MHC antigenic targets of the humoral immune response in transplantation. Curr Opin Immunol. 2010 October; 22(5): 682-688). Since CM consists of myosin heavy chain and light chains, they may also responsible for the graft rejections.

Neuropilin-1 (NRP-1) bind many ligands and various types of co-receptors; they affect cell survival, migration, and attraction. Some of the ligands and co-receptors bound by neuropilins are vascular endothelial growth factor (VEGF) and semaphorin family members. It is a membrane-bound coreceptor to a tyrosine kinase receptor. Neuropilin expression is up-regulated in multiple tumor types, and correlates with tumor progression and prognosis in specific tumors. Neuropilins may indirectly mediate effects on tumor progression by affecting angiogenesis or directly through effects on tumor cells. (Bates et al., High diversity of non-human leukocyte antigens in transplant-associated coronary artery disease. Transplantation. 2003; 75:1347-1350.)

Nuclear and spindle-associated protein 1 (NuSap1) has been reported to function in mitotic spindle assembly, chromosome segregation, and regulation of cytokinesis. Depletion of NUSAP1 from cells led to the suppression of double strand DNA break repair via the homologous recombination and single-strand annealing pathways. NUSAP1 has recently been identified as a biomarker for aggressive prostate cancer. By testing the sera on protein array, Nusap1 is identified as one of the targets of de novo antibody after allogeneic allogeneic hematopoietic cell transplantation (HCT), Wadia et al., Antibodies specifically target AML antigen NuSAP1 after allogeneic bone marrow transplantation. Blood. 115(10): 2077-2087 2010.)

Collagen V (Col V) acts as a major risk factor after human lung transplantations. Col V is not normally expressed in healthy tissue. However, Col V is unveiled during graft injuries in lung transplants. Col V-specific T cells appear in lung transplant recipients before the clinical onset of rejection. It has been implicated in a number of autoimmune or inflammatory conditions and allograft rejection. Collagen V are associated with chronic rejection after lung transplantation (American Journal of Transplantation 2014; 14: 685-693).

The ErbB3 binding protein-1 (EBP1) or Proliferation-associated protein 2G4 (PA2G4) belongs to a family of DNA/RNA binding proteins implicated in cell growth, apoptosis and differentiation. Ebp1 is a well-conserved DNA/RNA binding protein that is implicated in cell growth, apoptosis and differentiation in many cell types. Similar to eIF2A, IgG isolated from patients with allograft rejection reacts against endothelial cell surface. EBP1 has been Identified an antigen of interests for liver transplant allograft rejection.

Peroxiredoxin 2 (PRDX2) might participate in the signaling cascades of growth factors and tumor necrosis factor-alpha by regulating the intracellular concentrations of H2O2. It is the third most abundant protein in erythrocytes. PRDX2 is an essential antioxidant enzyme that prevents the oxidative inactivation of VEGF receptor-2 in vascular endothelial cells. Proteins extracted from human umbilical vein endothelial cells (HUVEC) were separated by two-dimensional electrophoresis, and Western blotting was subsequently conducted using sera from patients with systemic vasculitis. PRDX2 has been identified as one of the anti-endothelial cell antibodies (AECA) targets in systemic vasculitis (Karasawa et al., Peroxiredoxin 2 is a novel autoantigen for anti-endothelial cell antibodies in systemic vasculitis. Clin Exp Immunol. 161(3):459-70), 2010.

Protein Kinase C-zeta plays an important role in insulin-stimulated glucose transport. It has at least two alternative transcripts, the full-length PKCζ (this protein) and an N-terminal truncated form PKMζ. PKCζ is about 67 kDa (592 aa) and located in the cytoplasmic region.

BPI fold-containing family A member 1 (BPIFA1), or palate, lung and nasal epithelium clone (PLUNC) plays a role in the innate immune responses of the upper airways. It reduces the surface tension in secretions from airway epithelia and inhibits the formation of biofilm by pathogenic Gram-negative bacteria. BPIFA1 binds bacterial lipopolysaccharide (LPS) and negatively regulates airway surface liquid homeostasis and proper clearance of mucus. It plays a role in the airway inflammatory response after exposure to irritants.

26S protease regulatory subunit 6B (PSMC4) is involved in the ATP-dependent degradation of ubiquitinated proteins. The regulatory (or ATPase) complex confers ATP dependency and substrate specificity to the 26S complex. It is a part of the immunoproteasome whose function is to process class I HLA peptides. PSMC4 has been shown to interact with an orphan member of the nuclear hormone receptor superfamily highly expressed in liver, and with gankyrin, a liver oncoprotein. Similar to PLUNC, PSMC4 is discovered as the one of the non-HLA antibodies targets from the lung transplants.

Islet cell antigen 512 also termed IA-2 is a novel autoantigen of type 1 diabetes, which has a tyrosine phosphatase-like domain. IA-2 is a major target of islet cell autoantibodies. The frequencies of autoantibodies against glutamic acid decarboxylase 65 (GAD65) and islet cell antigen (ICA) 512/IA-2 (512/IA-2) are common on the specific human leukocyte antigen (HLA) in type 1 diabetes mellitus (T1D). In pancreas transplantations, anti-GAD (Glutamic Acid Decarboxylase) and anti-IA2 (protein tyrosine phosphatase, IA-2) autoantibodies is related to the onset of rejection or graft loss. In islet transplantation, the presence of autoantibodies also correlates with a worse evolution and could be a key factor in the chronic failure of the graft (Diabetol Metab Syndr. 2009; 1: 9).

Tyrosine-protein phosphatase non-receptor type 22 (PTPN22) affects the responsiveness of T and B cell receptors, and mutations are associated with increases or decreases in risks of autoimmune diseases. PTPN22 gene has been associated with autoimmune disorders, including an increased risk of Type 1 Diabetes, rheumatoid arthritis, Systemic Lupus Erythematosus (SLE), Vitiligo and Graves' disease, but a decreased risk of Crohn's disease. PTPN22 acts as negative regulator of T-cell receptor (TCR) signaling by direct dephosphorylation of the Src family kinases LCK and FYN, ITAMs of the TCRz/CD3 complex, as well as ZAP70, VAV, VCP and other key signaling molecules. Protein tyrosine phosphatase non-receptor 22 (PTPN22) plays a central role in T cell, B cell and innate immune cell signaling. The allelic polymorphism, TPN22 R620W-variant allele, could be involved in the susceptibility to acute allograft rejection in kidney transplant patients (Transplant Proc. 2009 March; 41(2):657-9). By using PTPN22 knockout mouse, the lack of the protein tyrosine phosphatase PTPN22 improves transplant tolerance to pancreatic islets in mice (Diabetologia. 2015 Mar. 7).

Ribosomal Protein L7 (RPL7) plays a regulatory role in the translation apparatus. It is located in the cytoplasm. RPL7 has been shown to be an autoantigen in patients with systemic autoimmune diseases, such as systemic lupus erythematosus. By screening of a HUVEC cDNA library with transplant-associated coronary artery disease sera, RPL7 is identified as a candidate autoantigen associated with transplant rejection. (Clin Exp Immunol. 2001; 126:173-179).

Speedy Homologue A (SPDYA) as a member of the Speedy/RINGO family and a novel activator of cyclin-dependent kinases, was shown to promote cell cycle progression and cell survival in response to DNA damage. SPDYA is a cell cycle protein that promotes cell proliferation by activating cyclin-dependent kinase-2 (CDK2; 116953) at the G1/S phase transition. Overexpression of SPDYA in several human and mouse cell lines increased DNA replication and the rate of cell proliferation. Similar to AGT, SPYDA has shown very strong correlation in renal graft rejection and has been validated by customized ELISA assays in independent patient sera and their localization confirmed by immunohistochemistry.

Tumor necrosis factor alpha (TNF, tumor necrosis factor, TNFα, cachexin, or cachectin) is a cell signaling protein (cytokine) involved in systemic inflammation. The primary role of TNF is in the regulation of immune cells. TNF, being an endogenous pyrogen, is able to induce fever, apoptotic cell death, cachexia, inflammation and to inhibit tumorigenesis and viral replication. TNFα stimulates IL1 and GM-CSF, increases tissue damage by IL1 and induces the onset of collagenases by fibroblasts and chondrocytes. It has a role in modulating HLA class 2 expression, as well as the adhesion molecule. TNF a level more than 45 pg/mL can be taken as an immunological marker of renal transplant rejection (Saudi J Kidney Dis Transpl 2009; 20(6):1000-1004).

Regenerating Islet-derived protein 3-alpha (Reg3A) or pancreatitis-associated protein 1 (PAP1) is a pancreatic secretory protein that may be involved in cell proliferation or differentiation. PAP is activated in primary liver cancers. Elevation of PAP in patients with pancreatic cancer is not merely explainable by concomitant pancreatitis, but seems to be due to increased PAP production by the cancer cells. Elevated anti Reg3A s has been reported on simultaneous kidney-pancreas transplantation (SKP Tx) patients (2015 American Transplant Congress Abstract #446).

Receptor tyrosine-protein kinase ERBB-3, also known as HERS (human epidermal growth factor receptor 3), is a member of the epidermal growth factor receptor (EGFR/ERBB) family of receptor tyrosine kinases. The kinase-impaired ERBB3 is known to form active heterodimers with other members of the ErbB family, most notably the ligand binding-impaired ERBB2. ERBB3 binds to the ligands heregulin and NRG-2 and causes a change in conformation that allows for dimerization, phosphorylation, and activation of signal transduction. Similar to eIF2A, IgG isolated from patients with allograft rejection reacts against endothelial cell surface. ERBB3 has been Identified an antigen of interests for liver transplant allograft rejection.

Platelet glycoprotein 4, or CD36, also known as FAT (fatty acid translocase), FAT/CD36, (FAT)/CD36, SCARB3, GP88, glycoprotein IV (gpIV), and glycoprotein IIIb (gpIIIb), is an integral membrane protein found on the surface. CD36 interacts with a number of ligands, including collagen types I and IV, thrombospondin, erythrocytes, platelet-agglutinating protein p37, and long-chain fatty acids. CD36 function in long-chain fatty acid uptake. CD36 is recognized as Naka antigen. The abnormality of anti CD36 antibody has been linked to heart failure in transplant coronary artery disease (Int J Mol Med. 1998 June; 1(6): 1007-10).

Nucleolin (NCL) is a multifunctional phosphoprotein ubiquitously distributed in the nucleolus, nucleus and cytoplasm of the cell. NCL is a eukaryotic nucleolar phosphoprotein, involved in the synthesis and maturation of ribosomes. NCL may play a role in the process of transcriptional elongation. It regulates various aspects of DNA and RNA metabolism, chromatin structure, rDNA transcription, rRNA maturation, cytokinesis, nucleogenesis, cell proliferation and growth, the folding, maturation and ribosome assembly and nucleocytoplasmic transport of newly synthesized pre-RNA. Antibodies against NCL are found in many transplant patients and they seemed to be associated with kidney allografts rejection and with coronary artery disease in heart transplant recipients (Transplantation 2011; 92: 829-835).

Peroxisomal trans-2-enoyl-CoA reductase, PECR, is an enzyme responsible for the reduction of phytenoyl-CoA to phytanoyl-CoA in peroxisomes. PECR is strongly expressed in the kidney. Recently, it has been shown that anti-PECR antibodies could be associated with transplant glomerulopathy. Similar to AURKA, by compare antibody repertoires in pre- and post-transplant sera from several cohorts of patients with and without transplant glomerulopathy, de novo increase of anti-PECR has been identified as a non-HLA antigen.

E3 ubiquitin-protein ligase TRIM21, also known as Tripartite motif-containing protein 21 (TRIM21) is an intracellular antibody effector in the intracellular antibody-mediated proteolysis pathway. TRIM21, also known as Ro52 is often the target of circulating autoantibodies in autoimmune diseases. Studies showed that anti-Ro52 antibodies are associated with different clinical outcomesTRIM21 is part of the RoSSA ribonucleoprotein, which includes a single polypeptide and one of four small RNA molecules. It interacts with autoantigens in patients with Sjögren's syndrome and systemic lupus erythematosus. TRIM21 is considered as one of AECA target protein. High anti-TRIM21 was correlated to renal rejection.

Proteasome subunit alpha type-4, PSMA4, is a multicatalytic proteinase complex which is characterized by its ability to cleave peptides with Arg, Phe, Tyr, Leu, and Glu adjacent to the leaving group at neutral or slightly basic pH. Proteasome dysfunction leads to many diseases including cancer, and drugs that inhibit proteasome activity directly affect lung cancer susceptibility through its modulation of cell proliferation and apoptosis. It has been reported that proteasome subunit alpha type-4 (PSMA4) mRNA levels are increased in lung tumors, and down-regulation of PSMA4 expression decreased proteasome activity. PSMA4 has been identified on renal rejection patient as one of the non-HLA candidates (American Journal of Transplantation 2009; 9:2126-2135).

Tissue factor (F3) also called platelet tissue factor, factor III, thromboplastin, or CD142 is a protein present in subendothelial tissue and leukocytes necessary for the initiation of thrombin formation from the zymogen prothrombin. The best known function of tissue factor is its role in blood coagulation. The signaling function of F3 plays a role in angiogenesis and apoptosis. Similar to PLUNC, F3 is discovered as the one of the non-HLA antibodies targets from the lung transplants.

60 kDa SS-A/Ro ribonucleoprotein is also known as TROVE domain family, member 2 (TROVE2) functions as a RNA chaperone that binds to misfolded pre-5S ribosomal RNA and may hasten the degradation of the defective molecule. Autoantibodies directed against Ro/SSA and La/SSB autoantigens were originally identified in patients with Sjögren's syndrome and systemic lupus erythematosus (SLE). Subsequent studies showed that anti-Ro/SSA antibodies may be present in patients with other autoimmune diseases, including systemic sclerosis, idiopathic inflammatory myopathies (IIM), primary biliary cirrhosis (PBC), and rheumatoid arthritis (RA). Additionally, anti-Ro/SSA antibodies (with or without anti-La/SSB antibodies) identify pregnant women who are at increased risk of having a child with neonatal lupus syndrome. Polymorphism of TROVE2 (L10P) has linked to lung transplant by TGF-beta (Clin Rev Allergy Immunol. 2011 February; 40(1): 27-41).

Interferon-induced helicase C domain-containing protein 1 (IFIH1) plays a major role in sensing viral infection and in the activation of a cascade of antiviral responses including the induction of type I interferons and proinflammatory cytokines. IFIH1 polymorphisms have been associated with type 1 diabetes. Autoimmune disease risk variant of IFIH1 is associated with increased sensitivity to IFN-α and serologic autoimmunity in lupus patients (J Immunol. 2011 Aug. 1; 187(3):1298-303).

Tubulin is the major building block of microtubules. The tubulin family consist of alpha- and beta-tubulin. To form microtubules, the dimers of α- and β-tubulin bind to GTP and assemble onto the (+) ends of microtubules while in the GTP-bound state. Antibodies to KA1 tubulin (TUBA1B) is associated with chronic rejection after lung transplantation (J Immunol. 2008 Apr. 1; 180(7):4487-94). Similar to Rho GDP-dissociation inhibitor, by using two-dimensional Western blotting experiments, beta tubulin has been identified as the non-HLA antigens target in patients undergoing chronic hemodialysis.

Perlecan (PLC) also known as basement membrane-specific heparan sulfate proteoglycan core protein (HSPG) or heparan sulfate proteoglycan 2 (HSPG2). Perlican LG3 peptide lies inside the Endorepellin subunit which is the domain V of Perlecan. LG3 is a biomarker for breast cancer, IgA induced nephropathy, physical status, and acute allograft vascular rejection. Patients with increased anti-LG3 antibodies have correlated with accelerated organ rejection. In addition, anti-LG3 antibodies also increase deposit buildups and induce clogged arteries (American Journal of Transplantation 2013; 13: 861-874).

PRKR-interacting protein 1 protein (PRKRIP1) binds double-stranded RNA. PRKRIP1 interacts with PKR (protein kinase RNA-activated) and functions to inhibit or negatively regulate PKR activity and is associated with adipogenesis. Similar to AGT, PRKRIP1 has shown very strong correlation in renal graft rejection and has been validated by customized ELISA assays in independent patient sera and their localization confirmed by immunohistochemistry.

Endothelin receptor type A, also known as ETAR or EDNRA, is a human G protein-coupled receptor for the endothelin-1. Endothelin-1 promotes myofibroblast induction through the ETA receptor via a rac/phosphoinositide 3-kinase/Akt-dependent pathway and it is essential for the enhanced contractile phenotype of fibrotic fibroblasts. ENDRA polymorphism I136L has been linked to breast cancer. EDNRA expresses only in platelets. The presence of anti-ETAR antibodies is associated with a decrease renal transplant function during the first 12 months after transplantation (Transpl Immunol. 2014 January; 30(1):24-9).

Fibronectin (FN) is a high-molecular weight (~440 kDa) glycoprotein of the extracellular matrix that binds to membrane-spanning receptor proteins called integrins. FN plays a major role in cell adhesion, growth, migration, and differentiation, and it is important for processes such as wound healing and embryonic development. Similar to Collagen V, elevated anti FN antibodies has linked to transplant Glomerulopathy in renal graft recipients (American Journal of Transplantation 2014; 14: 685-693).

Fibronectin Leucine-rich Repeat transmembrane protein 2 (FLRT2) functions in cell adhesion and receptor signaling. FLRT2 is required in the epicardium to promote heart morphogenesis. FLRT2 is involved in mediating cell-matrix interactions. Anti-FLRT2 antibody has the potential to induce direct endothelial cell cytotoxicity. By using the human umbilical vein endothelial cells retroviral expression system, FLRT2 has been identified as one of the AECA targets on for systemic lupus erythematosus patient (Arthritis Res Ther. 2012; 14 (4): R157).

Vimentin (VIM) is a non-polymorphic intermediate filament expressed in cytosol of endothelial, vascular smooth muscle cells, activated platelets and macrophages, renal tubular cells, mesangial cells and renal stromal cells. VIM expressed in the intima and media of coronary arteries where vascular smooth muscle cells and fibroblasts locate. Autoimmune responses to VIM are associated with both acute and chronic rejection of heart and renal allografts. Anti-vimentin antibodies are an independent predictor of transplant-associated coronary artery disease and can be used to identify some of the patients who are at high risk of developing this complication (Transplantation Vol. 71, 886-892, No. 7, Apr. 15, 2009).

Glutathione S-transferase theta-1 (GSTT1) conjugate reduced glutathione to a wide number of exogenous and endogenous hydrophobic electrophiles. Individuals with a homozygous deletion of the glutathione S-transferase theta 1 (GSTT1) gene lack GSTT1 enzymatic detoxification and have high risk of acute myeloid leukemia. In liver transplant, antibodies against glutathione-S-transferaseT1 (GSTT1) expressed on the graft may induce an antibody response leading to a severe graft dysfunction. In addition, donor-specific antibodies against MICA and GSTT1 antigens could be responsible for the occurrence of antibody-mediated kidney graft rejection (Transplantation 2009; 87: 94-99).

Endoplasmic reticulum lipid raft-associated protein 2 (ERLIN2) plays a critical role in inositol 1,4,5-trisphosphate (IP3) signaling by mediating ER-associated degradation of activated IP3 receptors. Mutations in this gene are a cause of spastic paraplegia-18 (SPG18). ERLIN2 is in the prohibitin family of proteins that define lipid-raft-like domains of the ER. ERLIN2 may confer a selective growth advantage for breast cancer cells by facilitating a cytoprotective response to various cellular stresses. Similar to eIF2A, IgG isolated from patients with allograft rejection reacts against endothelial cell surface. ERLIN2 has been Identified an antigen of interests for liver transplant allograft rejection.

Complement Factor H (CFH) is a member of the regulators of complement activation family Factor H has been shown to interact with Complement component 3. A shortage (deficiency) of complement factor H can cause uncontrolled activation of the complement system. Complement factor H deficiency, a known hereditary risk factor for post-transplant thrombotic microangiopathy (TMA), may also favor development of acute allograft glomerulopathy AAG. Unopposed complement activation is a risk factor for both immune and nonimmune forms of microvascular injuries in renal allografts (Fortin et al. Am J Transplant. 2004 February; 4(2):270-3.) Atypical Hemolytic Uremic Syndrome (HUS) associated with anti-CFH autoantibodies is an uncommon illness associated with high risk of progression to end-stage renal disease (Khandelwal et al. Pediatr Transplant. 2014 August; 18(5):E134-9)

Complement C3 produced within the kidney is an important mediator of inflammatory and immunological injury. Synthesis of complement component C3 regulates acute renal transplant rejection. Patients with SLE had increased titers of anti-C3 antibodies, compared with healthy controls. C3 nephritic factors (increased C3 autoantibodies) prolong the half-life or prevent regulation of the alternative pathway C3 convertase; result in uncontrolled complement activation. They are strongly associated with renal disease with symptoms like acquired partial lipodystrophy (APLD) or C3 glomerulopathy (C3GP) (Dragon-Durey 2013, Molecular Immunology 56 (2013) 213-221)

Phospholipase A2 Receptor, a 185 kDa type I transmembrane glycoprotein expressed on glomerular podocytes, is identified as a major target antigen of the autoantibodies involved in membranous nephropathy (MN), a common cause of adult nephrotic syndrome, one of the most common glomerulonephritides involving the renal transplant. (Dai et al. 2015, Nature). Idiopathic membranous nephropathy, a common form of the nephrotic syndrome, is an antibody-mediated autoimmune glomerular disease. A majority of patients with idiopathic membranous nephropathy have antibodies against a conformation-dependent epitope in PLA2R. PLA2R is present in normal podocytes and in immune deposits in patients with idiopathic membranous nephropathy, indicating that PLA2R is a major antigen in this disease. In addition, Anti-PLA(2)R autoantibodies in serum samples from patients with membranous nephropathy were mainly IgG4.

In some embodiments, the non-HLA antigen is selected from the set of non-HLA antigens set forth in Table 1.

TABLE 1

| Non-HLA Antigen Description | Alias | Uniprot Access No. | SEQ ID NO |
|---|---|---|---|
| Agrin (CAF) | AGRN | O00468 | 1 |
| Angiotensinogen | AGT | P01019 | 2 |
| Rho GDP-dissociation inhibitor 2 | ARGHDIB | P52566 | 3 |
| Aurora kinase A-interacting protein | AURKA | Q9NWT8 | 4 |
| Complement C4-B | C4B, C4D | P0C0L5 | 5 |
| Chromatin assembly factor 1 subunit B | CHAF1b, CAF-1, p60 | Q13112 | 6 |
| C-X-C motif chemokine 11 | ITAC, CXCL11 | O14625 | 7 |
| C-X-C motif chemokine 9 | MIG, CXCL9 | Q07325 | 8 |
| Cyclophilin A | PPIA | P62937 | 9 |
| Eukaryotic translation initiation factor 2A | EIF2A | Q9BY44 | 10 |
| Alpha-enolase | ENO1 | P06733 | 11 |
| Glutamate decarboxylase 2 | GAD2, GAD65 | Q05329 | 12 |
| Glial cell line-derived neurotrophic factor | GDNF | P39905 | 13 |
| Heterogeneous nuclear ribonucleoprotein K | HNRNPK | P61978 | 14 |
| Intercellular adhesion molecule 1 | ICAM-1, CD54 | P05362 | 15 |
| gamma-interferon inducible protein 16 | IFI16 | Q16666 | 16 |
| gamma-interferon | IEN-γ | P17803 | 17 |
| Interleukin-2 receptor subunit alpha | IL2RA, CD25 | P01589 | 18 |
| Interleukin-7 receptor subunit alpha | IL7R, CD127 | P16871 | 19 |
| Insulin | INS | P01308 | 20 |
| Far upstream element-binding protein 2 | FUBP2, KHSRP | Q92945 | 21 |
| Lamin A/C | LMNA | P02545 | 22 |
| Lamin B1 | LMNB1 | P20700 | 23 |
| NEUROPHILIN-1 | NRP1, CD304 | O14786 | 24 |
| Nucleolar and spindle-associated protein 1 | NUSAP1 | Q9BXS6 | 25 |
| ERBB3 Binding protein 1 | PA2G4, EBP1 | Q9UQ80 | 26 |
| PEROXIREDOXIN 2 | PRDX2 | P32119 | 27 |
| Protein Kinase C-zeta | PKC-Z | Q05513 | 28 |
| BPI fold-containing family A member 1 | PLUNC, BPIFA1 | Q9NP55 | 29 |
| 26S protease regulatory subunit 6B | PSMC4 | P43686 | 30 |
| Islet cell antigen 512 | PTPRN, PTPIA2, ICA512 | Q16849 | 31 |
| Tyrosine-protein phosphatase non-receptor type 22 | PTPN22 | Q9Y2R2 | 32 |
| Ribosomal Protein L7 | RPL7 | P18124 | 33 |
| Speedy Homologue A | SPDYA | Q5MJ70 | 34 |
| Tumour necrosis factor alpha | TNF-α | P01375 | 35 |
| Regenerating Islet-derived protein 3-alpha | PAP-1, REG3A | Q06141 | 36 |
| Receptor tyrosine-protein kinase erbB-3 | ERBB3 | P21860 | 37 |
| Platelet glycoprotein 4 | CD36 | P16671 | 38 |
| Nucleolin | NCL | P19338 | 39 |
| Peroxisomal trans-2-enoyl-CoA reductase | PECR | Q9BY49 | 40 |
| E3 ubiquitin-protein ligase TRIM21 | TRIM21, RO52 | PI9474 | 41 |
| Proteasome subunit alpha type-4 | PSMA4 | P25789 | 42 |
| Tissue factor | F3, TFA, CD142 | P13726 | 43 |
| 60 kDa SS-A/Ro ribonucleoprotein | TROVE2, RO60 | P10155 | 44 |
| Interferon-induced helicase C domain-containing protein 1 | IFIH1 | Q9BYX4 | 45 |
| alpha Tubulin-1A | TUBA1A | Q71U36 | 46 |
| alpha Tubulin 1B | TUBA1B | P68363 | 47 |
| alpha Tubulin 1C | TUBA1C | Q9BQE3 | 48 |
| beta Tubulin | TUBB | P07437 | 49 |
| Perlecan LG3 | HSPG2 | P98160 | 50 |
| PRKR-interacting protein 1 | PRKRIP1 | Q9H875 | 51 |

TABLE 1-continued

| Non-HLA Antigen Description | Alias | Uniprot Access No. | SEQ ID NO |
|---|---|---|---|
| Endothelin Receptor type A | EDNRA, ETAR | P25101 | 52 |
| Fibronectin Leucine-rich Repeat Transmembrane protein | FLRT2 | O43155 | 53 |
| Vimentin | Vim | P08670 | 54 |
| Angiotensin II Type I receptor | AT1R, AGTR1 | P30556 | 55 |
| C-type lectin domain family 16, member A | CLEC16A | Q2KHT3 | 56 |
| Collagen I | COL1A1, COL1A2 | P02452 | 57 |
| Collagen II | COL2A1, COL2A2 | P02458 | 58 |
| Collagen III | COL3A1, COL3A2 | P02461 | 59 |
| Collagen IV | COL4A1, COL4A2 | P02462 | 60 |
| Collagen V | COL5A1, COL5A2 | P20908 | 61 |
| Cytotoxic T-lymphocyte protein 4 | CTLA4, CD152 | P16410 | 62 |
| Endoplasmic reticulum lipid raft-associated protein 2 | ERLIN2 | O94905 | 63 |
| Fibronectin | FN1 | P02751 | 64 |
| Glutathione S-transferase theta-1 | GSTT1 | P30711 | 65 |
| Keratin, type II cytoskeletal 1 | KRT1 | P04264 | 66 |
| Myosin Heavy Chain alpha MYH6 | MYH6 | P13533 | 67 |
| Myosin Heavy Chain beta MYH7 | MYH7 | P12883 | 68 |
| Myosin Light Chain MYL4 | MYL4 | P12829 | 69 |
| Zinc finger protein 33A | ZNF33A | Q06730 | 70 |
| Zinc transporter 8 | ZnT8, SLC30A8 | Q8IWU4 | 71 |
| Complement Factor H | CHF | P08603 | 72 |
| Complement C3 | C3 | P01024 | 73 |
| Phospholipase A2 Receptor | PLA2R1 | Q13018 | 74 |

In some embodiments, the non-HLA antigen is selected from the set of non-HLA antigens set forth in Table 1A.

TABLE 1 A

| Non-HLA Antigen Description | Alias | Uniprot Access No. | Publication No. |
|---|---|---|---|
| Protein Kinase C-zeta | PKC-Z | Q05513 | US 20120077689 |
| Ribosomal Protein L7 | RPL7 | P18124 | U.S. Pat. No. 7,132,245 |
| Perlecan LG3 | HSPG2 | P98160 | US20130004978 |
| Endothelin Receptor type A | EDNRA, ETAR | P25101 | U.S. Pat. No. 8,592,164 |
| Vimentin | Vim | P08670 | U.S. Pat. No. 7,132,245 |
| Angiotensin II Type I receptor | AT1R, AGTR1 | P30556 | U.S. Pat. No. 8,425,877 |
| Collagen II | COL2A1, COL2A2 | P02458 | WO2000037940 |
| Collagen V | COL5A1, COL5A2 | P20908 | U.S. Pat. No. 8,039,225 |
| Glutathione S-transferase theta-1 | GSTT1 | P30711 | US 20110039281 |
| Myosin Light Chain MYL4 | MYL4 | P12829 | US 20120077689 |
| Zinc transporter 8 | ZnT8, SLC30A8 | Q8IWU4 | US20100143374 |
| Complement Factor H | CFH | P08603 | U.S. Pat. No. 8,501,427 |
| Phospholipase-A2-Receptor | PLA2R1 | Q13018 | US 20110177534 |

Preparation of HLA and Non-HLA-Antigens

In some embodiments, the HLA antigen and/or the non-HLA antigen is a fusion protein. For example, the invention provides for transforming or transfecting host cells with a nucleic acid encoding the amino acid sequence of an HLA antigen polypeptide or a non-HLA antigen polypeptide fused with a heterologous domain selected from the group consisting of B2 signal peptide, HLA cytoplasmic domain, EK Tag, V5 Tag or DPD Tag. A nucleic acid molecule encoding the amino acid sequence of an HLA antigen polypeptide or a non-HLA antigen polypeptide may be fused with the domain and inserted into an appropriate expression vector using standard ligation techniques. Exemplary vectors include, but are not limited to, bacterial vectors, eukaryotic vectors, plasmids, cosmids, viral vectors, adenovirus vectors and adenovirus associated vectors.

The HLA antigen polypeptide and/or the non-HLA antigen polypeptide may contain a sequence encoding a "tag" or exogenous amino acid sequence, such as an oligonucleotide molecule located at the 5' or 3' end of the non-HLA polypeptide coding sequence; an oligonucleotide sequence encoding polyHis (such as hexaHis), FLAG, hemaglutinin influenza virus (HA), V5 or myc or other tags, for which commercially available antibodies exist. This tag may be fused to the non-HLA polypeptide upon expression. The term "exogenous" as used herein refers to a substance or molecule originating or produced outside of an organism. The term "exogenous gene" or "exogenous nucleic acid molecule," as used herein, refers to a nucleic acid that codes for the expression of an RNA and/or protein that has been introduced ("transformed") into a cell or a progenitor of the cell. An exogenous gene may be from a different species (and so a "heterologous" gene) or from the same species (and so a "homologous" gene), relative to the cell being transformed.

In some embodiments, the expression vectors contain sequences for cloning and expression of exogenous nucleotide sequences. Such sequences may include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

In some embodiments, the vector comprises a selectable marker gene element. A selectable marker gene element encoding a protein necessary for the survival and growth of a host cell grown in a selective culture medium may also be a component of the expression vector. Exemplary selection marker genes include those that encode proteins that complement auxotrophic deficiencies of the cell; or supply critical nutrients not available from complex media. The invention also contemplates that the HLA antigen polypeptides and/or non-HLA antigen polypeptides described herein comprise one or more of these exogenous amino acid sequences.

In some embodiments, a leader, or signal, sequence is used to direct the non-HLA antigen polypeptide (or HLA antigen polypeptide) out of the stem cell after administration. For example, a nucleotide sequence encoding the signal sequence is positioned in the coding region of the non-HLA antigen encoding nucleic acid (or HLA antigen encoding nucleic acid), or directly at the 5' end of the non-HLA antigen coding region (or HLA antigen coding region). The signal sequence may be homologous or heterologous to the non-HLA antigen polypeptide (or HLA antigen polypeptide) gene or cDNA, or chemically synthesized. The secretion of the non-HLA antigen polypeptide (or HLA antigen polypeptide) from the stem cell via the presence of a signal peptide may result in the removal of the signal peptide from the secreted non-HLA antigen polypeptide (or HLA antigen polypeptide). The signal sequence may be a component of the vector, or it may be a part of the nucleic acid molecule encoding the non-HLA antigen polypeptide (or HLA antigen polypeptide) that is inserted into the vector.

In some embodiments, the domain is a cytoplasmic domain, or traffic signal, sequence. Cytoplasmic domain sequences may be used to direct the non-HLA antigen polypeptides (or HLA antigen polypeptides) out of the cells after administration or to modify its characteristics to avoid cell signaling pathway that leads to cell death.

The vectors described herein optionally comprise a promoter operably linked to the nucleic acid encoding the non-HLA antigen polypeptide (or HLA antigen polypeptide). Promoters are untranscribed sequences located upstream to the start codon of a structural gene that control the transcription of the structural gene. Inducible promoters initiate increased levels of transcription from DNA under their control in response to some change in culture conditions, such as the presence or absence of a nutrient or a change in temperature. Alternatively, constitutive promoters initiate continual gene product production with little or no control over gene expression. A large number of promoters, recognized by a variety of potential host cells, are well known. The native non-HLA (or HLA) gene promoter sequence may be used to direct amplification and/or expression of the non-HLA (or HLA) polypeptide nucleic acid molecule. A heterologous promoter also may be used to induce greater transcription and higher yields of the non-HLA (or HLA) polypeptide expression as compared to the non-HLA (or HLA) polypeptide expression induced by the native promoter.

In addition, an enhancer sequence may be inserted into the vector to increase the transcription of a DNA encoding the non-HLA antigen polypeptide (or HLA antigen polypeptide) Enhancers are cis-acting elements of DNA, usually about 10-300 bp in length, that act on the promoter to increase transcription. Enhancer sequences available from mammalian genes include globin, elastase, albumin, alpha-fetoprotein and insulin. Exemplary viral enhancers that activate eukaryotic promoters include the SV40 enhancer, the cytomegalovirus early promoter enhancer, the polyoma enhancer, and adenovirus enhancers. While an enhancer may be spliced into the vector at a position 5' or 3' to a nucleic acid molecule encoding the non-HLA antigen polypeptide (or HLA antigen polypeptide), it is typically located at a site 5' from the promoter. The enhancer may be native to the non-HLA antigen polynucleotide sequence or may be heterologous to the non-HLA antigen polynucleotide sequence.

The transformation of an expression vector encoding a non-HLA antigen polypeptide (or HLA antigen polypeptide) into a host cell may be accomplished by well-known methods such as transfection, infection, calcium chloride, electroporation, microinjection, lipofection or the DEAE-dextran method or any other technique known in the art. These methods and other suitable methods are well known in the art, for example, in Sambrook, Molecular Cloning: A Laboratory Manual, Cold Spring Harbor Laboratory Press; 3rd ed., 2001, the disclosure of which is incorporated herein by reference in its entirety.

Expression vectors of the invention may be constructed from a starting vector such as a commercially available vector. Such vectors may or may not contain all of the desired flanking sequences. Where one or more of the desired flanking sequences are not already present in the vector, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen Company, Carlsbad, CA), pBSII (Stratagene Company, La Jolla, CA), pET15? (Novagen, Madison, WI), pGEX (Pharmacia Biotech, Piscataway, NJ), pEGFP-N2 (Clontech, Palo Alto, CA), pETL (BlueBacII; Invitrogen), pDSR-alpha (PCT Publication No. WO90/14363) and pFastBacDual (Gibco/BRL, Grand Island, NY).

Additional suitable vectors include, but are not limited to, cosmids, plasmids or modified viruses, but it will be appreciated that the vector system must be compatible with the selected host cell. Such vectors include, but are not limited to plasmids such as Bluescript® plasmid derivatives (a high copy number ColE1-based phagemid, Stratagene Cloning Systems Inc., La Jolla CA), PCR cloning plasmids designed for cloning Taq-amplified PCR products (e.g., TOPO™ TA Cloning® Kit, PCR2.1® plasmid derivatives, Invitrogen, Carlsbad, CA), and mammalian, yeast, or virus vectors such as a baculovirus expression system (pBacPAK plasmid derivatives, Clontech, Palo Alto, CA). The recombinant molecules can be introduced into host cells via transformation, transfection, infection, or other known techniques.

Host cells may be prokaryotic host cells (such as E. coli) or eukaryotic host cells (such as a yeast cell, an insect cell or a vertebrate cell). The host cell, when cultured under appropriate conditions, synthesizes a non-HLA antigen polypeptide (or HLA antigen polypeptide) described herein which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity, such as glycosylation or phosphorylation, and ease of folding into a biologically active molecule.

A number of suitable host cells are known in the art and many are available from the American Type Culture Collection (ATCC), 10801 University Boulevard, Manassas, VA 20110-2209. Examples include, but are not limited to, mammalian cells, such as Chinese hamster ovary cells (CHO) (ATCC No. CCL61) CHO DHFR-cells (Urlaub et al., Proc. Natl. Acad. Sci. USA, 97:4216-4220 (1980)), human embryonic kidney (HEK) 293 or 293T cells (ATCC No. CRL1573), Hmy2.C1R cells (ATCC No. CRL1992) or K562 cells (ATCC No. CCL243). The selection of suitable mammalian host cells and methods for transformation, culture, amplification, screening and product production and purification are known in the art. Other suitable mammalian cell lines, are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines, which are available from the ATCC. Each of these cell lines is known by and available to those skilled in the art of protein expression.

Methods of Detecting HLA- and Non-HLA-Specific Antibodies

The invention provides for methods for determining the percentage of panel reactive antibodies in a biological sample from a subject against human leukocyte antigens. In some embodiments, the method comprises contacting a first collection of solid-phase substrates subtypes and a second collection of solid-phase substrate subtypes with serum from said subject for a sufficient time for anti-HLA antibodies in said serum to bind to said HLA-antigens to form a complex, wherein each substrate subtype in the first collection is coated with different purified HLA antigens to present HLA antigens derived from a cell population of a single cell, wherein each substrate subtype of the second collection is coated with different purified non-HLA antigens listed in Table 1 or Table 1A, detecting the presence of the complex to determine the presence or absence of panel reactive antibodies, and determining the percentage of panel reactive antibodies in the serum.

The term "panel reactive antibody" as used herein refers to an antibody in the biological sample from a subject that specifically binds to an HLA antigen present on the solid-phase substrate or specifically binds to a non-HLA antigen.

The methods are carried out with solid-phase panels wherein the panel comprises substrates that present (or have immobilized) at least one or more selected HLA antigens. The invention also may be carried out with liquid-phase assays such as assays using column chromatography, affinity chromatography, thin layer chromatography, liquid-phase immunodiagnostic (LIPA) assays, liquid-phase chemiluminescent ELISA and liquid-phase immunoradiometric (IRMA) to name a few.

HLA- and non-HLA antigens described herein may be a whole protein, a truncated protein, a fragment of a protein or a peptide. Antigens may be naturally occurring, genetically engineered variants of the protein, or may be codon optimized for expression in a particular mammalian subject or host. Generally, a B-cell epitope will include at least about 5 amino acids but can be as small as 3-4 amino acids. The antigens may be recombinantly expressed and purified from cells that either endogenously express the HLA antigens at a low level or do those that do not endogenously express the HLA antigens. Furthermore, the HLA antigens may be recombinantly expressed and presented on the cell surface, and the cells would be used in the methods of the invention.

Normally, an epitope will include between about 7 and 15 amino acids, such as, 9, 10, 12 or 15 amino acids. The term "antigen" denotes both subunit antigens, (i.e., antigens which are separate and discrete from a whole organism with which the antigen is associated in nature). Antibodies such as anti-idiotype antibodies, or fragments thereof, and synthetic peptide mimotopes, that is synthetic peptides which can mimic an antigen or antigenic determinant, are also captured under the definition of antigen as used herein.

Furthermore, for purposes of the present invention, an "antigen" refers to a protein, which includes modifications, such as deletions, additions and substitutions, generally conservative in nature, to the naturally occurring sequence, so long as the protein maintains the ability to elicit an immunological response, as defined herein. These modifications may be deliberate, as through site-directed mutagenesis, or may be accidental, such as through mutations of hosts which produce the antigens. Antigens of the present invention may also be codon optimized by methods known in the art to improve their expression or immunogenicity in the host.

Exemplary solid-phase assays such as assays of the invention may use solid substrates such as microparticles, microbeads, magnetic particles such as ferromagnetic beads and paramagnetic beads, microtiter plates, membranes, filters, glass, metal, metal-alloy, anopol, polymers, nylon, plastic or microarrays such as protein chips. Microarrays may be of any material such as glass or silica. Binding on a microtiter plate may be detected using ELISA assays, RIA assays or other immunosorbent sandwich assays. Binding on a filter may be detected using immunoblotting techniques.

Methods known in the art for HLA testing include the complement-dependent lymphocytotoxicity (CDC) test in which serum from a recipient is incubated with donor or panel lymphocytes followed by incubation with complement. The level of cytotoxicity is estimated by discriminating between dead and viable cells using a dye. This method is labor intensive, requires viable cells, may be nonspecific and requires a subjective evaluation.

Pouletty et al. U.S. Pat. No. 5,223,397 discloses methods for testing HLA compatibility between a donor and a recipient comprising the steps of adding blood from the donor to a substrate having anti-HLA antibodies bound thereto and incubating for sufficient time for soluble HLA antigens present in the blood to bind to the antibodies or ligand. Blood from the recipient is then added to the solid substrate whereby any antibody specific for any HLA antigens bound to the solid substrate may become bound. The detection of an absence of antibodies from the recipient's blood to the HLA antigen is indicative of a cross-match.

Zaer et al., Transplantion 63: 48-51 (1997) discloses use of an ELISA using HLA class I molecules purified from pooled platelets to detect anti-HLA antibodies. The reference reports that in patients found to be unsensitized, the incidence of false-positive results was less for ELISA testing than for panel studies. In patients who were highly sensitized, both tests performed equally well, whereas discordant results were registered mainly in cases of mild sensitization. In such cases, the incidence of false-negative results was higher for ELISA testing than for panel studies.

Of interest to the present invention are assay methods making use of flow cytometry. Wilson et al., J. Immunol. Methods 107: 231-237 (1988) disclose the use of polyacrylamide microspheres coupled with cell membrane proteins in immunofluorescence assays for antibodies to membrane-associated antigens. The method is said to make possible the rapid flow cytometric analysis of plasma membrane antigens from cell populations that would otherwise be unsuitable for use in flow cytometry. Scillian et al., Blood 73: 2041-2048 (1989) disclose the use of immunoreactive beads in flow cytometric assays for detection of antibodies to HIV. Frengen et al., Clin. Chem. 40/3: 420-425 (1994) disclose the use of flow cytometry for particle-based immunoassays of cefetoprotein (AFP). This reference further reports the ability of serum factors to cross-link labeled mouse monoclonal antibodies of irrelevant specificity to different particle types coated with various immunoglobulins.

Flow cytometry methods using lymphocytes are also known but suffer with difficulties because of the activity of auto-antibodies. See Shroyer et al., Transplantation 59:626-630 Moreover, when using flow cytometry with lymphocytes, use of ten or more different lymphocytes tends to result in confusing signals. As a consequence, studies using lymphocytes have been limited by presenting a small panel of HLA antigens that do not effectively simulate the distribution of HLA antigens in a normal human population.

Sumitran-Karuppan et al., Transplantation 61: 1539-1545 (1996) discloses the use of magnetic beads which use an anti-HLA capture antibody to immobilize a variety of soluble HLA antigens pooled from 80 to 100 individuals on each bead. The beads can then be directly added to patient serum for efficient absorption of HLA antibodies. The reference discloses visualization of antibody binding to the antigen-coated beads using flow cytometry. The reference suggests that this development will allow testing for antibody specificity for crossmatching purposes and for the screening of panel-reactive antibodies. The methods of Sumitran-Karuppan are limited, however, because the pooling of antigens causes sensitivity to certain rare HLA antigens. Moreover, the method is not capable of detecting the percentage of PRA.

Solid-Phase Substrates

The solid-phase substrates described herein include, but are not limited to, microparticles, microbeads, magnetic beads, ion torrent beads, flow cytometry beads, beads or microspheres of any material, e.g. silica, gold, latex, polymers such as polystyrene, polysulfone and polyethyl, or hydrogel. The solid-phase substrate may also be an affinity purification column Additional exemplary microparticles are encoded with the dyes and the antigens are immobilized to the encoded microparticles. The microparticles used in the methods of the invention are commercially available from sources such from Luminex Inc., Invitrogen (Carlsbad, CA), Polysciences Inc. (Warrington, PA) and Bangs Laboratories (Fishers, IN) to name a few.

In some embodiments, the solid-phase substrate is a microbead. The microbead, in some embodiments, has a diameter ranging from about 2 μm to about 15 μm, inclusive of each endpoint of the range. Microbeads having a diameter of about 2 μm, 3 μm, 4 μm, 5 μm, 6 μm, 7 μm, 8 μm, 9 μm, 10 μm, 11 μm, 12 μm, 13 μm, 14 μm or 15 μm are also contemplated.

The solid-phase substrates described herein may comprise a detectable label or another identifying characteristic. The solid-phase substrates may comprise a single fluorescent dye or multiple fluorescent dyes. In one embodiment, the microparticles are internally labeled with fluorescent dyes and contain surface carboxyl groups for covalent attachment of biomolecules. In another embodiment, the solid-phase substrates are internally labeled with fluorescent dyes and contain a surface layer of Avidin for near covalent binding of biotin and biotinylated ligands. In another embodiment, the solid-phase substrates may comprise a combination of different dyes, such as a fluorescent and a non-fluorescent dye. For example, the microparticles may be labeled with E)-5-[2-(methoxycarbonyl)ethenyl]cytidine, which is a non-fluorescent molecule, that when subjected to ultraviolet (UV) irradiation yields a single product, 3-?-D-ribofuranosyl-2,7-dioxopyrido[2,3-d]pyrimidine, which displays a strong fluorescence signal. In another embodiment, the solid-phase substrates may comprise bar codes as an identifiable characteristic as described in U.S. Patent Publication No. US 20070037195.

In another embodiment, the solid-phase substrate may be nanocrystals or quantum dots. These nanocrystals are substances that absorb photons of light, then re-emit photons at a different wavelength (fluorophores). In addition, additional florescent labels, or secondary antibodies may be conjugated to the nanocrystals. These nanocrystals are commercially available form sources such as Invitrogen and Evident Technologies (Troy, NY).

The invention can be carried out with any system that detects the identifiable characteristic or label, such as FLOW cytometry. Detection of fluorescent labels may also be carried out using a microscope or camera that will read the image on the microparticles, such as the Bioarray BeadChip (Bioarray Solutions, Ltd., Warren, NJ). The BeadChip format combines microparticle ("bead") chemistry with semiconductor wafer processing in which binding to the microparticle is recorded using an optical microscope and camera.

Biological samples for use in the methods described herein include, but are not limited to, whole blood, blood derivatives, red blood cell concentrates, plasma, serum, fresh frozen plasma, whole blood derived platelet concentrates, apheresis platelets, pooled platelets, intravenous gamma-globulin, cryoprecipitate, cerebrospinal fluid, tissues and cells such as epithelial cells, such as those collected from the buccal cavity, stem cells, leukocytes, neutrophils and granulocytes. The biological samples may be obtained from a human donor of tissue or cells intended for transplantation or a human donor of blood or blood derivatives intended for transfusion. The biological sample may be obtained from a healthy bone marrow donor or a subject of a paternity test. The biological sample may also be obtained from a human subject that is an intended recipient of a transplant or transfusion, or the human subject that is donating the tissue or organ intended for transplantation or transfusion. Alternatively, the biological sample may be obtained directly from tissues or cells that are intended for transplantation in a human recipient. In addition, the biological sample may be obtained from blood or blood derivatives that are intended for transfusion in a human recipient. In some embodiments, the sample is obtained before the subject has received the transplant or transfusion. In some embodiments, the sample is obtained after the subject has received the transplant or transfusion. In still further embodiments, the sample is obtained both before and after the subject has received the transplant or transfusion in order to monitor success of the transplant or transfusion.

Antibodies useful for detecting the antigens described herein may be polyclonal antibodies, monoclonal antibodies, antibody fragments which retain their ability to bind their unique epitope (e.g., Fv, Fab and F(ab)$_2$ fragments), single chain antibodies and human or humanized antibodies. Antibodies may be generated by techniques standard in the art using an antigenic HLA epitope. See, e.g. Kohler et al., Nature, 256:495-497 (1975), Brodeur et al., Monoclonal Antibody Production Techniques and Applications, pp. 51-63 (Marcel Dekker, Inc., New York, 1987). Antibody molecules of the present invention include the classes of IgG (as well as subtypes IgG 1, IgG 2a, and IgG2b), IgM, IgA, IgD, and IgE.

The antibodies of the invention may be labeled for detection of binding within the biological sample. The antibodies may comprise a radioactive label such as 3H, 14C, 32P, 35S, or 125I. In addition, the labels may be a fluorescent or chemiluminescent compound, such as fluorescein isothiocyanate, phycoerythrin, rhodamine, or luciferin. The labels may be enzymes such as alkaline phosphatase, β-galactosidase, biotin and avidin or horseradish peroxidase (Bayer et al., Meth. Enz., 184:138-163 (1990)).

Specific binding of an antibody to an antigen described herein within a biological sample may be carried out using Western blot analysis with immunoblotting, immunocytochemistry, immunohistochemistry, dot blot analysis, flow cytometry, ELISA assays or RIA assays. These techniques and other approaches are conventional in the art (See Sambrook et al., Molecular Cloning: A Laboratory Manual, cold Springs Harbor Laboratories (New York, 1989).

Kits

The invention also provides for kits to carry out the methods of the invention. In particular, the invention provides for kit for determining the percentage of panel reactive antibodies in serum of a subject against HLA antigens comprising a first collection of solid-phase substrates wherein each solid-phase substrate is coated with different purified HLA antigens to represent the HLA antigen population of a single cell line such that said collection simulates the distribution of HLA antigens in a normal human population and a second collection of solid phase substrates wherein each substrate is coated with different purified non-HLA antigens listed in Table 1. The antigens provided in the kit may be conjugated to solid substrates in the kit. Alternatively, the kit comprises solid substrates and antigens and the skilled artisan can conjugate the antigens to the solid substrates allowing for optimization of the antigens used in the assay. The kits may also comprise the reagents necessary to detect and measure antibodies, such as HLA antibodies for use as a positive control.

In some embodiments, the HLA antigens comprise Class I HLA antigens (e.g., wherein the HLA antigens are selected such that the HLA antigens presented on the solid phase substrate comprise Class I HLA antigens so as to simulate the distribution of Class I HLA antigens in a normal human population). In some embodiments, the HLA antigens comprise Class II HLA antigens.

In some embodiments, the first collection comprises 54 different Class I HLA antigens, optionally purified from 30 different cell lines. In other embodiments, the first collection comprises 22 different Class II HLA antigens.

In some embodiments, the non-HLA antigens in the second collection are optionally a fusion protein comprising at least one domain, wherein the domain is a signal peptide, a modified cytoplasmic domain, purification tag or detection tag. In some embodiments, domain is the B2 signal peptide, HLA cytoplasmic domain, EK Tag, V5 Tag or DPD Tag.

The kits described herein may further comprise any components necessary to carry out the detection assays that are conventional in the art. For example, the kits may comprise buffers, loading dyes, gels such as polyacrylamide gels and molecular weight markers for preparing SDS-PAGE gels to carry out Western blots. The kits may also comprise filters, membranes blocking buffers, control buffers, isotype control antibodies, wash buffers or buffers and reagents for detection to carry out immunoblotting or dot blotting analysis such as labeled secondary antibodies. The kit may also comprise fixing reagents, blocking buffers, control buffers, wash buffers, staining dyes and detection reagents including anti-idiospecific antibodies. Furthermore, the kits may comprise the necessary reagents and tools to carryout flow cytometry, ELISA assays, RIA assays or microtoxicity assays.

Other aspects and advantages of the present invention will be understood upon consideration of the following illustrative examples.

EXAMPLES

Example 1—a Multiplex Assay on a Panel Consisting of 10 Non-HLA Antigens in One Single Test Panel consists of 10 non-HLA were incubated with 4 different patient serum. Sera are used neat. The microbeads are subsequently washed with wash buffer comprising PBS with 0.1% polysorbate 20 (TWEEN) and incubated with goat anti-human IgG antibodies conjugated with phycocrythrin (PE) for 30 minutes. The microbeads were washed two times with wash buffer and analyzed on a Luminex analyzer according to the manufacturer's instructions.

Reaction pattern is compared. Four individuals (S10823K, S11114A, S11143B and FL71681) showed distinct reaction patterns on 10 non-HLA antigens tested (FIG. 1).

Example 2—Trend Increase in Anti-Non-HLA Allosera in a Lung Transplant Recipient During $1^{st}$ Graft Rejection on a Panel Consisting of 58 Non-HLA Antigens in One Single Test Panel consists of 58 non-HLA were incubated with 4 serum samples collected from different stage of graft rejection. Sera are used neat. The microbeads are subsequently washed with wash buffer comprising PBS with 0.1% polysorbate 20 (TWEEN) and incubated with goat anti-human IgG antibodies conjugated with phycocrythrin (PE) for 30 minutes. The microbeads were washed two times with wash buffer and analyzed on a Luminex analyzer according to the manufacturer's instructions.

Figure 2:
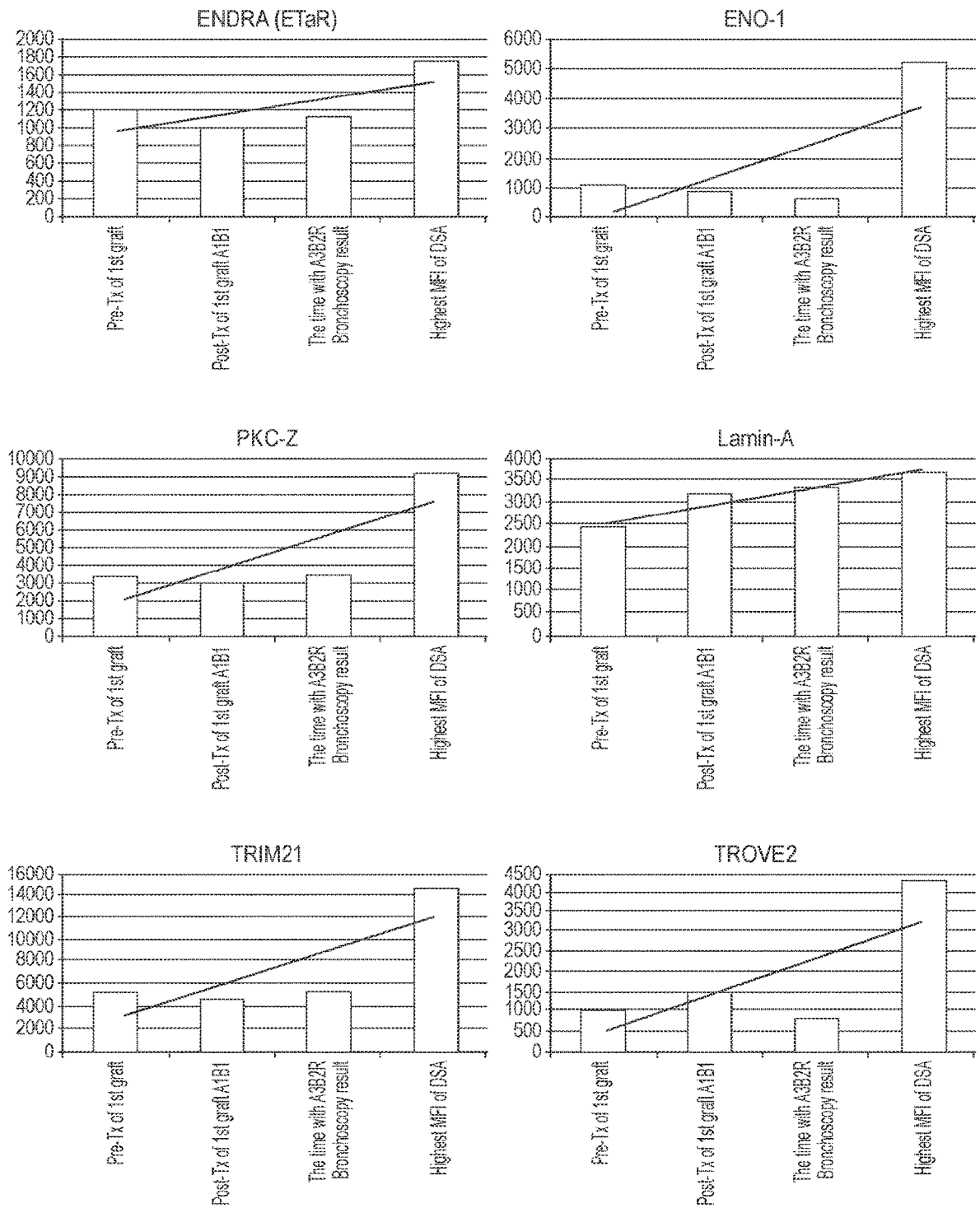
FIG. 2 describes the trend line of increase of anti-non-HLA antibodies in samples obtained from a patient undergoing 2nd lung graft in a multiplex platform.

Reaction pattern is compared on each individual non-HLA and analyzed against in a time course plot. Trend line is determined. Six non-HLA antigens show a correlation over the increasing anti-allosera activities with the graft rejection progression (FIG. 2).

Example 3—Increase of Anti-Non-HLA Allosera in Transplant Recipients During Graft Rejection on a Panel Consisting of 21 Non-HLA Antigens in One Single Test Panel consists of 21 non-HLA were incubated with serum samples collected from 13 graft recipients for graft post-transplant monitoring. Sera are collected on time course. Sera are used neat. The microbeads are subsequently washed with wash buffer comprising PBS with 0.1% polysorbate 20 (TWEEN) and incubated with goat anti-human IgG antibodies conjugated with phycocrythrin (PE) for 30 minutes. The microbeads were washed two times with wash buffer and analyzed on a Luminex analyzer according to the manufacturer's instructions.

Reaction pattern is compared on each individual non-HLA antigens and each individual graft recipient is analyzed against on a time course plot. Trend line on each non-HLA antigen over individual patient is determined. Six non-HLA antigens show a correlation over the increasing anti-allosera activities with the graft rejection progression among graft recipient monitored. See Table 2.

TABLE 2

| non-HLA Antigen | % Patient shows positive increase of non-HLA allosera during post-translation monitoring |
|---|---|
| TubA1B | 0.23 |
| Perlican | 0.69 |
| PRKRIP1 | 0.31 |
| EDNRA | 0.23 |
| ELRT2 | 0.38 |
| Vimentin | 0.15 |

Example 4—Increase Detection Sensitization by Fusion Tag in One Single Test

Enhancing antigenic polypeptide NusA-V5 binding on Luminex beads by a synthetic domain, DPD. The antigenic polypeptides NusA-V5 were fused to DPD. Mouse anti V5 antibody (1 μg) are incubated with NusA polypeptides containing microbeads. The NusA polypeptides containing microbeads are subsequently washed with wash buffer comprising PBS with 0.1% polysorbate 20 (TWEEN) and incubated with goat anti-mouse IgG antibodies conjugated with phycocrythrin (PE) for 30 minutes. The microbeads were washed two times with wash buffer and analyzed on a Luminex analyzer according to the manufacturer's instruction.

Figure 3A:
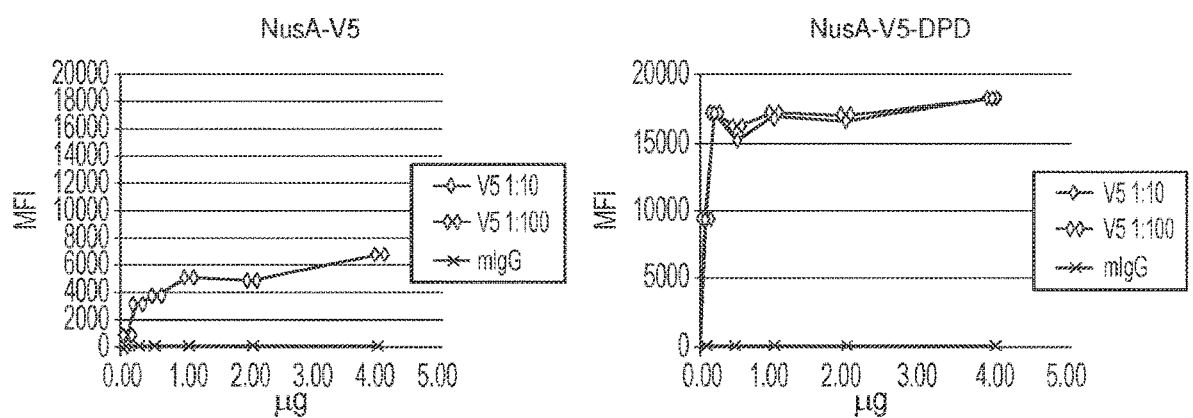
FIGS. 3A-3B describe (a) the fusion DPD tag that enhances the multiplex reactivity and (b) the structure of DPD indicates it is an alpha helix loop.
Figure 3B:
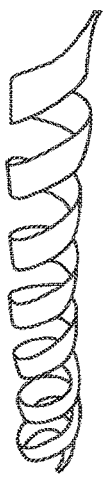

The NusA-V5 fused with DPD tag shows higher sensitivity compared with no fusion (FIG. 3).

Example 5—Box and Whiskers' Plot of Non-HLA Antigens from Two Patient Population Using a Panel of 21 Non-HLA Antigens in One Test Panel consists of 21 non-HLA were incubated with serum samples collected from graft recipients before and after transplant for graft post-transplant monitoring. Sera are collect and used neat. The microbeads are subsequently washed with wash buffer comprising PBS with 0.1% polysorbate 20 (TWEEN) and incubated with goat anti-human IgG antibodies conjugated with phycocrythrin (PE) for 30 minutes. The microbeads were washed two times with wash buffer and analyzed on a Luminex analyzer according to the manufacturer's instructions.

Figure 4:
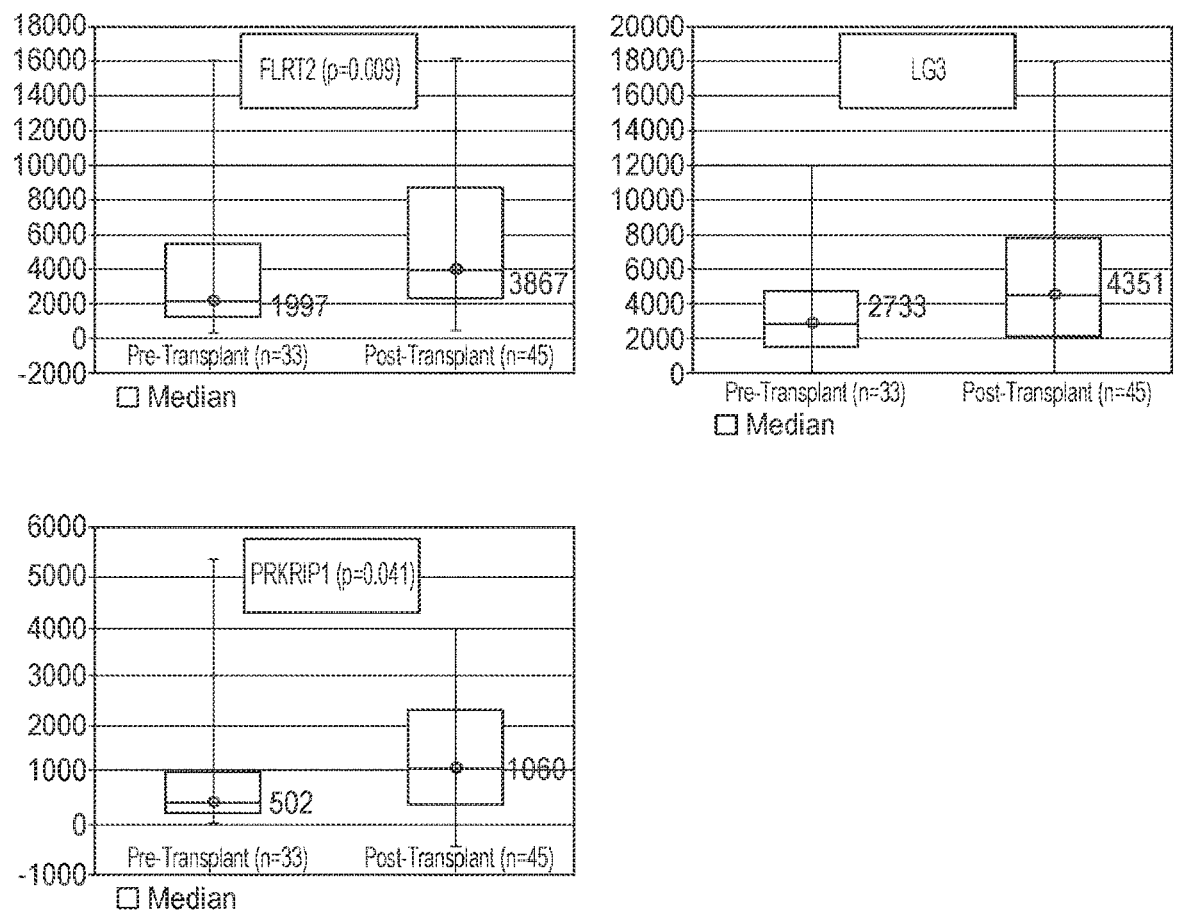
FIG. 4 describes the Box and whiskers' plot of non-HLA antigens from two patient population using a panel of 21 non-HLA antigens in one test.
Figure 5:
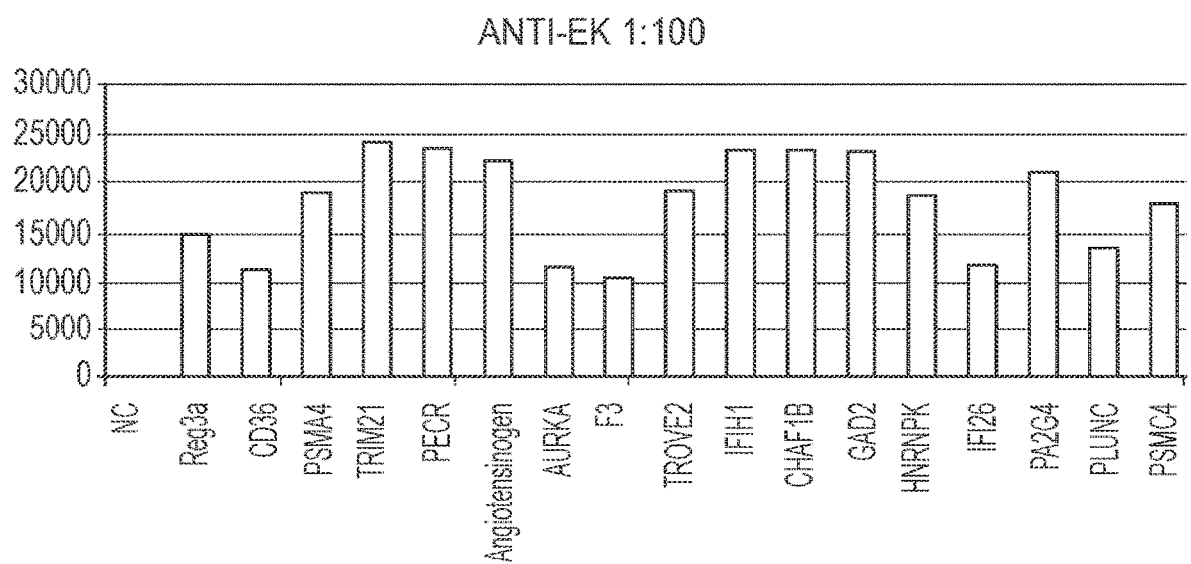
FIG. 5 describe the reactivity of non-HLA fusion proteins detected by an anti-fusion antibody on a multiplex platform.

Serum anti non-HLA alloantibodies activities are determined for 45 post-transplant allograft patients and 33 pre-transplant allograft patients. The median (line) and IQR (box top and bottom) values are shown with a Mann-Whitney Rank Sum test providing a p-value listed in the box. Three non-HLA antigens show a significance increase of de novo alloantibodies (FIG. 4).

Example 6—Antibodies to Non-HLA Antigens have been Identified in Kidney Allograft Patients Anti-vimentin IgG and IgM which target at the non-HLA antigen vimentin has been identified in a chronic kidney transplant patient under post-transplant monitoring. In addition, high titer of HLA IgM antibodies was observed (Table 3)

TABLE 3

Large scale monitoring of both nHLA and non-HLA antigens

| Monitoring time | Signals | | | |
|---|---|---|---|---|
| | Vimentin | | HLA | |
| | IgG | IgM | IgG | IgM |
| beginning | 708 | 2910 | 175 | 340 |
| 1 month | 699 | 3579 | 172 | 204 |
| 1 year | 1281 | 4537 | 141 | 367 |
| 1.5 year | 1080 | 7256 | 139 | 1025 |

Example 7

According to this example, Class I HLA antigen preparations were purified from Epstein Barr virus transformed lymphocyte cell lines according to the methods of Henderson et al., Virology 76: 152-163 (1977). Thirty of the Class I HLA antigen preparations were then selected to simulate the distribution of HLA in a normal population as set out in Table 4 and were coated by passive absorption onto 3 μm latex beads obtained from Spherotech according to the method of Cantarero et al., Anal. Biochem., 105: 373-382 (1980).

TABLE 4

| Bead No. | HLA CLASS I | Antigen Typing |
|---|---|---|
| 1 | A11 | B27, 48 |
| 2 | A2, 29 | B39, 56 |
| 3 | A1, 29 | B8, 45 |
| 4 | A2, 24 | B7, 55 |
| 5 | A2, 25 | B18, 64 |
| 6 | A26, 24 | B52, 62 |
| 7 | A31, 68 | B53 |
| 8 | A2, 11 | B13, 62 |
| 9 | A23, 33 | B45, 63 |
| 10 | A23, 34 | B44 |
| 11 | A11, 23 | B49, 52 |
| 12 | A11, 24 | B59, 60 |
| 13 | A24, 33 | B44, 51 |
| 14 | A23, 26 | B41, 72 |
| 15 | A3, 32 | B50, 56 |
| 16 | A2, 24 | B54, 67 |
| 17 | A2 | B52, 73 |
| 18 | A26, 66 | B38, 75 |
| 19 | A11, 33 | B51, 54 |
| 20 | A30 | B13, 72 |
| 21 | A30, 36 | B35, 71 |
| 22 | A69 | B35, 61 |
| 23 | A1, 32 | B60, 64 |
| 24 | A2 | B7, 46 |
| 25 | A30 | B42 |
| 26 | A2 | B8, 58 |
| 27 | A2, 3 | B58, 65 |
| 28 | A1, 36 | B37, 57 |
| 29 | A3, 68 | B7, 65 |
| 30 | A33, 36 | B53, 61 |

The reactivity of the HLA antigen on each bead was confirmed by a panel of serologically defined HLA monoclonal antibodies or by human allosera using a flow cytometry test. Each bead reacted specifically to the HLA monoclonal antibodies or allosera with the same HLA specificity.

The sensitivity of the beads was tested by mixing two beads with different typing at different percentages. A minimum of 2 to 3% of one kind of bead was found to be sufficient to detect the antigen.

Example 8

According to this example, the sensitivity of the microbeads useful with the invention was tested by carrying out a serial dilution of selected PRA sera. The results presented in Table 5 below show that most PRA sera decrease the percentage of reactivity at a 1:10 dilution measured by a cytotoxicity test while they did not decrease the percentage of reactivity at a 1:40 dilution by use of the microbeads in a flow cytometry device according to the invention.

TABLE 5

| Sera ID | Dilution | Percentage Cytotoxicity | Flow Cytometry |
| --- | --- | --- | --- |
| N21 | 1 | 40 | — |
|  | 1:10 | 10 | 41 |
|  | 1:20 | 0 | 30 |
|  | 1:40 | 0 | 41 |
|  | 1:50 | 0 | 18 |
|  | 1:160 | 0 | 16 |
| A2 | 1 | 30 |  |
|  | 1:20 | 0 | 25 |
|  | 1:40 | 0 | 26 |
|  | 1:80 | 0 | 8 |
| S193 | 1 | 25 |  |
|  | 1:10 | 31 | 28 |
|  | 1:20 | 17 | 100 |
|  | 1:40 | 10 | 100 |
|  | 1:80 | 0 | 100 |
| S176 | 1 | 54 |  |
|  | 1:10 | 24 | 40 |
|  | 1:20 | 28 | 41 |
|  | 1:40 | 10 | 40 |
|  | 1:50 | 0 | 40 |
| S199 | 1 | 100 |  |
|  | 1:10 | 10 | 97 |
|  | 1:20 | 3 | 97 |
|  | 1:40 | 10 | 97 |
|  | 1:50 | 3 | 99 |
| B73 | 1 | 65 |  |
|  | 1:10 | 27 | 54 |
|  | 1:20 | 3 | 40 |
|  | 1:40 | 3 | 43 |
|  | 1:50 | 0 | 25 |

Example 9

According to this example, an assay to detect panel reactive antibodies was carried out by mixing 10 µl of a mixture of the 30 different types of beads produced according to Example 7 with 100 µl (1:10 diluted) serum to be tested and incubating for 30 minutes at 20-25° C. with gentle rotating. The beads were then washed three times with 1 mL of wash buffer. The beads were then incubated with 100 µl of 1:100 diluted Goat anti-human IgG-PE obtained from Jackson InnumoResearch for 30 minutes. The beads were then washed twice and 1 mL of wash buffer and read on a flow cytometer (B.D. FacStar Plus). The percentage of PRA is represented by the percentage of microbeads which are positively labeled.

Figure 6:
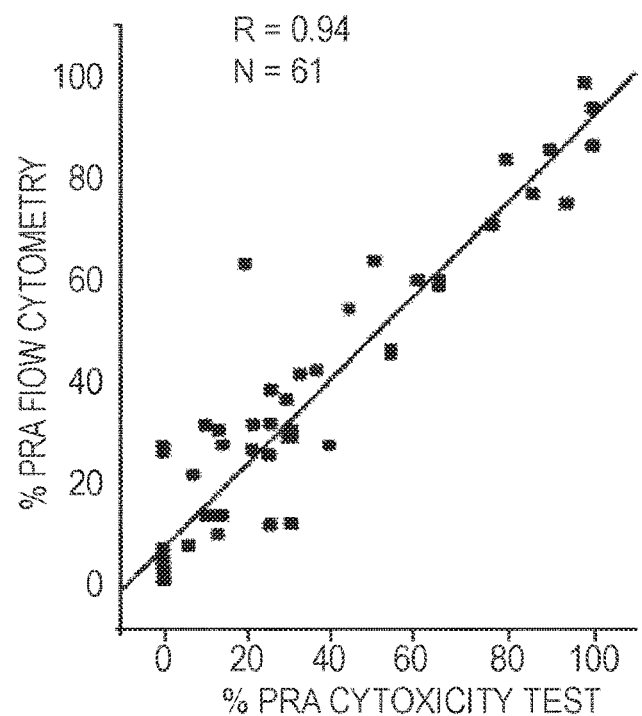
FIG. 6 depicts the correlation between the results of the method of the invention in determining the percentage PRA versus a standard cytotoxicity test for sample sera.

According to this example, 61 sera samples including 22 negative and 39 PRA patients who had panel reactive antibody activities developed by earlier transplantation or transfusion were tested with the results shown in FIG. 6 which shows the correlation of the flow cytometry results with those where the same samples were tested by complement-dependent lymphocytotoxicity. The correlation coefficient R is 0.94 for the 61 data points indicating a high degree of correlation between results obtained by flow cytometry and those obtained by a cytotoxicity test.

Example 10

According to this example, 30 Class II HLA antigen preparations as set out in Table 5 were purified from Epstein Barr virus transformed lymphocyte cell lines according to the methods of Henderson et al., Virology 76: 152-163 (1977). The antigen preparations may then be coated by passive absorption onto 5 µm latex beads obtained from Spherotech according to the method of Cantarero et al., Anal. Biochem., 105: 373-382 (1980). From this collection of Class II HLA preparations, from 15 to 30 beads may selected to simulate the distribution of the 22 Class II HLA antigens in a normal population.

TABLE 5

| Bead No. | HLA CLASS II | Antigen Typing | Typing |
| --- | --- | --- | --- |
| 1 | DR15, 9 | 53, 51 | DQ5, 9 |
| 2 | DR4, 15 | 53, 51 | DQ6, 7 |
| 3 | DR16, 4 | 53, 51 | DQ4, 5 |
| 4 | DR8, 14 | 52 | DQ4, 5 |
| 5 | DR4, 7 | 53 | DQ2, 8 |
| 6 | DR15, 18 | 51, 52 | DQ6, 4 |
| 7 | DR11, 12 | 52 | DQ5, 7 |
| 8 | DR103, 17 | 52 | DQ5, 2 |
| 9 | DR1, 13 | 52 | DQ5, 6 |
| 10 | DR9, 10 | 53 | DQ5, 9 |
| 11 | DR15, 12 | 51, 52 | DQ5, 7 |
| 12 | DR16, 14 | 51, 52 | DQ5 |
| 13 | DR13, 8 | 52 | DQ5, 6 |
| 14 | DR11, 13 | 52 | DQ5, 6 |
| 15 | DR17, 7 | 52, 53 | DQ2, 9 |
| 16 | DR15, 8 | 51 | DQ6, 8 |
| 17 | DR15, 4 | 51, 53 | DQ2, 6 |
| 18 | DR15, 17 | 51, 52 | DQ6, 2 |
| 19 | DR15, 7 | 51, 53 | DQ6, 2 |
| 20 | DR1, 7 | 53 | DQ2, 5 |
| 21 | DR15, 11 | 52 | DQ5, 6 |
| 22 | DR7, 13 | 52, 53 | DQ6, 9 |
| 23 | DR15, 13 | 51, 52 | DQ6, 2 |
| 24 | DR9, 14 | 52, 53 | DQ5, 9 |
| 25 | DR8, 9 | 53 | DQ2, 7 |
| 26 | DR17, 14 | 52 | DQ2, 5 |
| 27 | DR1, 11 | 52 | DQ5, 6 |
| 28 | DR17, 4 | 52, 53 | DQ2 |
| 29 | DR11, 4 | 52, 53 | DQ7, 8 |
| 30 | DR1, 14 | 52 | DQ5 |

Example 11

Figure 7A:
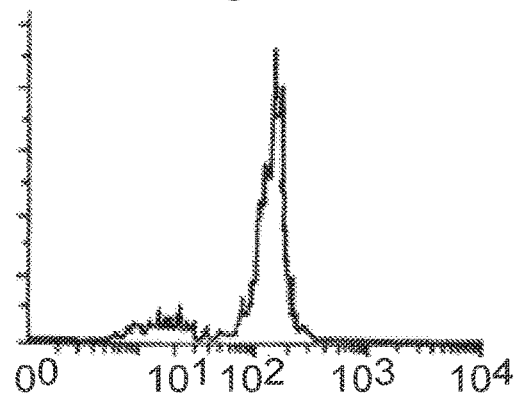
FIGS. 7A-7D depict the reaction of the mixture of Class I and Class II beads and their reaction to anti-HLA Class I antibodies (FIGS. 7A and 7B) or anti-HLA Class II antibodies (FIGS. 7C and 7D).
Figure 7C:
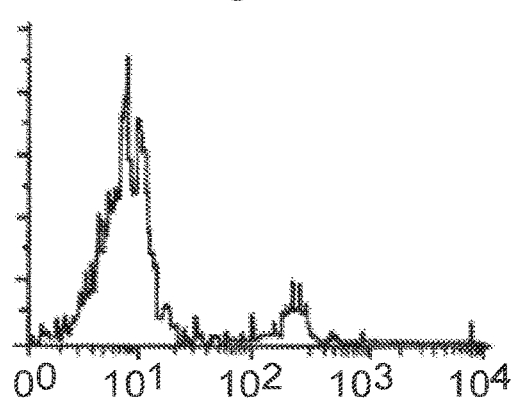
Figure 7B:
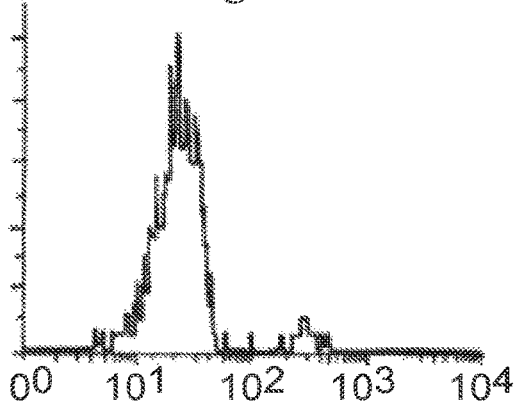
Figure 7D:
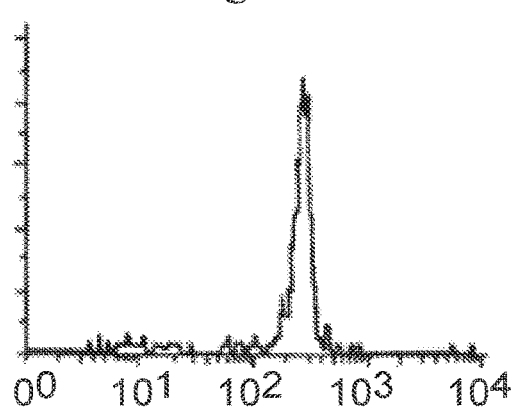

According to this example, 3 µm latex beads presenting HLA Class I antigens produced according to the methods of Example 7 and 5 µm latex beads presenting HLA Class II antigens produced according to the methods of Example 9 were mixed to perform an assay to detect the presence of antibodies specific to HLA Class I and Class II antigens. Because the beads presenting HLA Class II antigens are different in size from the HLA Class I beads, the two different sized beads can be electronically distinguished according to their sizes when analyzed on a flow cytometer as illustrated in FIGS. 7A-7D. FIG. 7A-7D depict the reaction of the mixture of Class I and Class II beads and their reaction to anti-HLA Class I antibodies (FIGS. 7A and 7B) or anti-HLA Class II antibodies (FIGS. 7C and 7D). When the Class I beads are selected by gating around the 3 µm size, the beads react to the anti-Class I antibody as illustrated in FIG. 7A. When the Class II beads are selected by gating around the 5 μm size, there is no reaction to the anti-Class I antibody as illustrated in FIG. 7B. The reaction pattern of the mixed beads to the anti-class II antibody is the reverse. When Class I beads are selected by gating around 3 μm in size, the beads do not react to the anti-Class II antibody as illustrated in FIG. 7C. When Class II antibodies are selected by gating around 5 μm in size, the Class II antigen beads react to the anti-Class II antibody as illustrated in FIG. 7D.

Numerous modifications and variations in the practice of the invention are expected to occur to those skilled in the art upon consideration of the foregoing description on the presently preferred embodiments thereof. Consequently, the only limitations which should be placed upon the scope of the present invention are those that appear in the appended claims.

What is claimed is:

1. A method for determining the presence of reactive antibodies in serum of a human subject, said method comprising:
   a. incubating the serum with:
      a first collection of solid-phase substrates comprising at least two substrates, wherein each of the at least two substrates in the first collection comprises a different Class I or Class II human leukocyte antigen (HLA) antigen, and
      a second collection of solid-phase substrates comprising at least five substrates, wherein each of the at least five substrates in the second collection comprises a different non-HLA antigen selected from the group consisting of: regenerating islet-derived protein 3-alpha (Reg3a), platelet glycoprotein 4 (CD36), proteosome subunit alpha type-4 (PSMA4), angiotensinogen, tissue factor (F3), 60 kilodalton SS-A/Ro ribonucleoprotein (TROVE2), interferon-induced helicase C domain-containing protein A (IFIHI), chromatin assembly factor 1 subunit B (CHAF 1B), glutamate decarboxylase 2 (GAD2), heterogenous nuclear ribonucleoprotein K (HNRNPK), gamma-interferon inducible protein 16 (IFI16), proliferation-associated protein 2G4 (PA2G4), bactericidal/permeability-increasing protein (BPI) fold-containing family A member 1 (PLUNC), 26S protease regulatory subunit 6B (PSMC4), fibronectin leucine-rich repeat transmembrane protein 2 (FLRT2), PRKR-interacting protein 1 (PRKRIP1), endothelin receptor type A (EDNRA), alpha-enolase (ENO-1), and lamin-A,
      wherein the first collection of solid-phase substrates and the second collection of solid-phase substrates are incubated with the serum for a sufficient time for one or more antibodies specific to the Class I and/or Class II HLA antigen(s) in said serum to bind to said HLA antigen(s) on the first collection of solid-phase substrates to form one or more first complex(es), and one or more antibodies specific for the non-HLA antigen(s) in said serum to bind to said non-HLA antigen(s) on the second collection of solid-phase substrates to form one or more second complex(es), and
   b. detecting the presence of the one or more first complex(es) and the one or more second complex(es) to determine the presence of the reactive antibodies by detecting a label bound to the one or more first complex(es) and a label bound to the one or more second complex(es).

2. The method of claim 1, wherein the detecting step is carried out by flow cytometry.

3. The method of claim 1, wherein the HLA antigens are Class I HLA antigens.

4. The method of claim 3, wherein said first collection of solid-phase substrates comprises 54 different Class HLA antigens.

5. The method of claim 1, wherein the first collection of solid-phase substrates is selected such that the HLA antigens presented thereon simulate distribution of Class I HLA antigens in a normal human population.

6. The method of claim 1, wherein the HLA antigens are Class II HLA antigens.

7. The method of claim 6, wherein said first collection of solid-phase substrates comprises 22 different Class II HLA antigens.

8. The method of claim 1, wherein at least one non-HLA antigen is a fusion protein comprising at least one domain, wherein the domain is a signal peptide, a modified cytoplasmic domain, purification tag or detection tag.

9. The method of claim 1, wherein each solid-phase substrate is detectably distinguishable from the other solid phase substrates within a collection.

10. The method of claim 9, wherein the detectably distinguishable solid-phase substrates are distinguishable by fluorescent labels.

11. The method of claim 1, wherein the subject is a transplant or transfusion recipient.

12. The method of claim 1, wherein the serum sample is collected before the subject has received a transplant or transfusion.

13. The method of claim 1, wherein the serum sample is collected after the subject has received a transplant or transfusion.

14. A method for determining the presence of reactive antibodies in serum of a human subject, said method comprising:
   a. incubating the serum with:
      a first collection of solid-phase substrates comprising at least two substrates,
         wherein each of the at least two substrates in the first collection comprises a different Class I or Class II human leukocyte antigen (HLA) antigen, and
      a second collection of solid-phase substrates comprising non-HLA antigens,
         wherein the non-HLA antigens are regenerating islet-derived protein 3-alpha (Reg3a), platelet glycoprotein 4 (CD36), proteosome subunit alpha type-4 (PSMA4), angiotensinogen, tissue factor (F3), 60 kilodalton SS-A/Ro ribonucleoprotein (TROVE2), interferon-induced helicase C domain-containing protein A (IFIHI), chromatin assembly factor 1 subunit B (CHAF 1B), glutamate decarboxylase 2 (GAD2), heterogenous nuclear ribonucleoprotein K (HNRNPK), gamma-interferon inducible protein 16 (IFI16), proliferation-associated protein 2G4 (PA2G4), bactericidal/permeability-increasing protein (BPI) fold-containing family A member 1 (PLUNC), 26S protease regulatory subunit 6B (PSMC4), fibronectin leucine-rich repeat transmembrane protein 2 (FLRT2), PRKR-interacting protein 1 (PRKRIP1), endothelin receptor type A (EDNRA), alpha-enolase (ENO-1), and lamin-A,
      wherein the first collection of solid-phase substrates and the second collection of solid-phase substrates are incubated with the serum for a sufficient time for one or more antibodies specific to the Class I and/or Class II HLA antigen(s) in said serum to bind to said HLA antigen(s) on the first collection of solid-phase substrates to form one or more first complex(es), and one or more antibodies specific for the non-HLA antigens in said serum to bind to said non-HLA antigens on the second collection of solid-phase substrates to form one or more second complex(es), and
   b. detecting the presence of the one or more first complex(es) and the one or more second complex(es) to determine the presence of the reactive antibodies by detecting a label bound to the one or more first complex(es) and a label bound to the one or more second complex(es).

\* \* \* \* \*